United States Patent
Spada et al.

(10) Patent No.: US 12,071,412 B2
(45) Date of Patent: *Aug. 27, 2024

(54) CASPASE INHIBITORS AND METHODS OF USE THEREOF

(71) Applicant: NOBO Medicine Inc., Seoul (KR)

(72) Inventors: Alfred P. Spada, Carlsbad, CA (US); Robert J. Temansky, San Diego, CA (US); Michael Mueller, San Diego, CA (US)

(73) Assignee: NOBO Medicine Inc., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/104,691

(22) Filed: Feb. 1, 2023

(65) Prior Publication Data

US 2023/0250067 A1   Aug. 10, 2023

Related U.S. Application Data

(63) Continuation of application No. 16/812,063, filed on Mar. 6, 2020, now Pat. No. 11,597,703.

(60) Provisional application No. 62/815,270, filed on Mar. 7, 2019.

(51) Int. Cl.
| | |
|---|---|
| *C07D 239/42* | (2006.01) |
| *A61P 29/00* | (2006.01) |
| *C07C 233/56* | (2006.01) |
| *C07D 213/75* | (2006.01) |
| *C07D 215/38* | (2006.01) |
| *C07D 215/40* | (2006.01) |
| *C07D 217/24* | (2006.01) |
| *C07D 239/34* | (2006.01) |
| *C07D 257/04* | (2006.01) |

(52) U.S. Cl.
CPC ............ *C07D 239/42* (2013.01); *A61P 29/00* (2018.01); *C07C 233/56* (2013.01); *C07D 213/75* (2013.01); *C07D 215/38* (2013.01); *C07D 215/40* (2013.01); *C07D 217/24* (2013.01); *C07D 239/34* (2013.01); *C07D 257/04* (2013.01)

(58) Field of Classification Search
None
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,323,907 A | 6/1994 | Kalvelage |
| 5,354,556 A | 10/1994 | Sparks et al. |
| 5,591,767 A | 1/1997 | Mohr et al. |
| 5,639,476 A | 6/1997 | Oshlack et al. |
| 5,639,480 A | 6/1997 | Bodmer et al. |
| 5,674,533 A | 10/1997 | Santus et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,840,674 A | 11/1998 | Yatvin et al. |
| 5,891,474 A | 4/1999 | Busetti et al. |
| 5,900,252 A | 5/1999 | Calanchi et al. |
| 5,922,356 A | 7/1999 | Koseki et al. |
| 5,972,366 A | 10/1999 | Haynes et al. |
| 5,972,891 A | 10/1999 | Kamei et al. |
| 5,980,945 A | 11/1999 | Ruiz |
| 5,985,307 A | 11/1999 | Hanson et al. |
| 5,993,855 A | 11/1999 | Yoshimoto et al. |
| 6,004,534 A | 12/1999 | Langer et al. |
| 6,039,975 A | 3/2000 | Shah et al. |
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger |
| 6,131,570 A | 10/2000 | Schuster et al. |
| 6,139,865 A | 10/2000 | Friend et al. |
| 6,197,350 B1 | 3/2001 | Yamagata et al. |
| 6,248,363 B1 | 6/2001 | Patel et al. |
| 6,253,872 B1 | 7/2001 | Neumann |

(Continued)

FOREIGN PATENT DOCUMENTS

| | | |
|---|---|---|
| WO | WO 2008/068615 | 6/2008 |
| WO | WO 2014/094041 | 6/2014 |

(Continued)

OTHER PUBLICATIONS

Aira et al., "Caspase 1/11 deficiency or pharmacological inhibition mitigates psoriasis-like phenotype in mice." Journal of Investigative Dermatology 139.6 (2019): 1306-1317.

Audia et al., "Caspase-1 inhibition by VX-765 administered at reperfusion in P2Y 12 receptor antagonist-treated rats provides long-term reduction in myocardial infarct size and preservation of ventricular function." Basic research in cardiology 113.5 (2018): 1-15.

Buchwald et al., "Long-term, continuous intravenous heparin administration by an implantable infusion pump in ambulatory patients with recurrent venous thrombosis," Surgery, 88:507 (1980).

(Continued)

*Primary Examiner* — Samantha L Shterengarts
(74) *Attorney, Agent, or Firm* — Harness, Dickey & Pierce, P.L.C.

(57) ABSTRACT

Provided herein are compounds of formula I, compositions comprising the compounds and method of treating various diseases with the compounds and compositions.

3 Claims, 5 Drawing Sheets

(56) References Cited

U.S. PATENT DOCUMENTS

Figure 1:
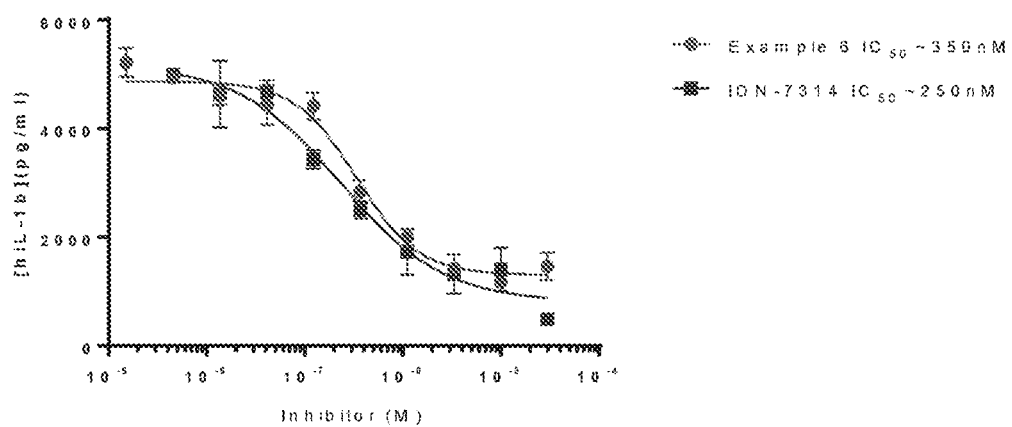

| | | |
|---|---|---|
| 6,264,970 B1 | 7/2001 | Hata et al. |
| 6,267,981 B1 | 7/2001 | Okamoto et al. |
| 6,271,359 B1 | 8/2001 | Norris et al. |
| 6,274,552 B1 | 8/2001 | Tamarkin et al. |
| 6,316,652 B1 | 11/2001 | Steliou |
| 6,376,461 B1 | 4/2002 | Igari et al. |
| 6,419,961 B1 | 7/2002 | Igari et al. |
| 6,589,548 B1 | 7/2003 | Oh et al. |
| 6,613,358 B2 | 9/2003 | Randolph et al. |
| 6,699,500 B2 | 3/2004 | Okada et al. |

FOREIGN PATENT DOCUMENTS

| | | |
|---|---|---|
| WO | WO 2017/053864 | 3/2017 |
| WO | WO 2017/076998 | 5/2017 |
| WO | WO 2020/006341 | 1/2020 |

OTHER PUBLICATIONS

Denes et al., "Caspase-1: is IL-1 just the tip of the ICEberg?." Cell death & disease 3.7 (2012): e338-e338.

Flores et al., "Caspase-1 inhibition alleviates cognitive impairment and neuropathology in an Alzheimer's disease mouse model." Nature communications 9.1 (2018): 1-14.

Goodson, Medical Applications of Controlled Release, vol. 2, pp. 115-138 (1984).

Guo et al., "Targeting inflammasome/IL-1 pathways for cancer immunotherapy." Scientific reports 6.1 (2016): 36107:1-12.

Howard et al., "IL-1-converting enzyme requires aspartic acid residues for processing of the IL-1 beta precursor at two distinct sites and does not cleave 31-kDa IL-1 alpha." The Journal of Immunology 147.9 (1991): 2964-2969.

International Search Report issued for International Application No. PCT/US2020/021324, dated Jun. 10, 2020.

Kim, R. et al., "Role for NLRP3 Inflammasome-mediated, IL-1b-Dependent Responses in Severe, Steroid-Resistant Asthma" American Journal of Respiratory and Critical Care Medicine 196. 3 (2017) 283-297.

Kostura et al., "Identification of a monocyte specific pre-interleukin 1 beta convertase activity." Proceedings of the National Academy of Sciences 86.14 (1989): 5227-5231.

Langer, "New methods of drug delivery," Science, 249:1527-1533 (1990).

McKenzie et al., "Caspase-1 inhibition prevents glial inflammasome activation and pyroptosis in models of multiple sclerosis." Proceedings of the National Academy of Sciences 115.26 (2018): E6065-E6074.

Melnikov et al., "Neutrophil-independent mechanisms of caspase-1-and IL-18-mediated ischemic acute tubular necrosis in mice." The Journal of clinical investigation 110.8 (2002): 1083-1091.

Morrison et al., "Intervention with a caspase-1 inhibitor reduces obesity-associated hyperinsulinemia, non-alcoholic steatohepatitis and hepatic fibrosis in LDLR-/-. Leiden mice." International journal of obesity 40.9 (2016): 1416-1423.

Rudolphi et al., "Pralnacasan, an inhibitor of interleukin-1β converting enzyme, reduces joint damage in two murine models of osteoarthritis." Osteoarthritis and cartilage 11.10 (2003): 738-746.

Saudek et al., "A preliminary trial of the programmable implantable medication system for insulin delivery," N. Engl. J. Med., 321:574-579 (1989).

Sefton, "Implantable pumps," CRC Crit. Ref. Biomed. Eng., 14:201 (1987).

Sleath et al., "Substrate specificity of the protease that processes human interleukin-1 beta." Journal of Biological Chemistry 265.24 (1990): 14526-14528.

Sollberger et al., "Caspase-1: the inflammasome and beyond." Innate immunity 20.2 (2014): 115-125.

Stack et al., "IL-converting enzyme/caspase-1 inhibitor VX-765 blocks the hypersensitive response to an inflammatory stimulus in monocytes from familial cold autoinflammatory syndrome patients." The Journal of Immunology 175.4 (2005): 2630-2634.

Thornberry, Nancy, "Caspases: key mediators of apoptosis." Chemistry & biology 5.5 (1998): R97-R103.

Wang et al., "Caspase-1 causes truncation and aggregation of the Parkinson's disease-associated protein α-synuclein." Proceedings of the National Academy of Sciences 113.34 (2016): 9587-9592.

Wooff et al., "Caspase-1-dependent inflammasomes mediate photoreceptor cell death in photo-oxidative damage-induced retinal degeneration." Scientific reports 10.1 (2020): 1-20.

Benjamin Southerland et al., *Journal of Cell Death*, 3(33); 33-40 (2010).

Hirokazu Ueno et al., *Bioorganic & Medicinal Chemistry Letters*, 19(1); 199-202 (2008).

Office Action from corresponding Japanese Patent Application No. 2021-552886, dated Feb. 6, 2024.

($****=p<0.0001$)

CASPASE INHIBITORS AND METHODS OF USE THEREOF

1. RELATED APPLICATIONS

This application claims priority under 35 U.S.C. § 120 to, and is a continuation of U.S. application Ser. No. 16/812,063 filed Mar. 6, 2020, which claims the benefit of the priority of U.S. Provisional Application No. 62/815,270, filed Mar. 7, 2019, the disclosure of which is incorporated herein by reference in its entirety.

2. FIELD

Provided herein are compounds that are caspase inhibitors, pharmaceutical compositions containing these compounds and methods of using such compounds and pharmaceutical compositions.

3. BACKGROUND

There are twelve known human caspases. Caspase-1, also known as interleukin converting enzyme (ICE), was the first identified human caspase. Ten caspases have been classified in two groups, based on their effects: proapoptotic caspases (caspases 2, 3, 6, 7, 8, 9 and 10) or proinflammatory caspases (caspases 1, 4 and 5). The function of two additional human caspases (12 and 14) are less well characterized Caspases are a family of cysteine protease enzymes that are key mediators in the signaling pathways for apoptosis and cell disassembly (Thornberry, Chem. Biol., 1998, 5, R97-R103). These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

The substrate specificity of human ICE has been defined with the use of peptides that span the cleavage site of the enzyme. Two features of peptide substrates are essential for catalytic recognition by the enzyme. First, there is a strong preference for aspartic acid adjacent to the cleavage site, in that any substitution of this residue in the IL-1β precursor and peptide substrates leads to a substantial reduction in the rate of catalysis (Kostura, et al., Proc. Natl. Acad. Sci., 86:5227, 1989; Sleath, et al., J. Biol. Chem., 265:14526, 1990; Howard, et al., J. Immunol., 147:2964, 1991).

Enzymatically active caspase-1 is generated from its inactive precursor, pro-caspase-1, by the action of protein complexes known as inflammasomes. The biochemical function of inflammasomes is to is to generate active caspase-1. Active caspase-1 converts the inactive precursor, pro-interleukin-1β (pro-IL-1β) to the active cytokine interleukin-1β (IL-1β), as well as pro-IL-18 to mature, active IL-1β. IL-1β is known as a master proinflammatory cytokine and is involved in multiple human diseases. IL-18 is also a proinflammatory cytokine associated with human disease. Caspase-1 also cleaves the protein gasdermin D which initiates a form of inflammatory cell death known as pyroptosis. Sollberger, G. et al., *Innate Immunity* 20, pp. 115-125 (2013) and Denes, A et al. *Cell Death Disease* 3, e338 (2012). Caspase-1 is implicated in numerous inflammatory disease conditions due to its role in regulating the production of proinflammatory cytokines and activating pyroptosis. Caspase-1 and IL-1β have been linked with autoinflammatory diseases, autoimmune diseases, CNS diseases, liver diseases, respiratory diseases, cardiovascular diseases, dermatological diseases, rheumatological diseases, kidney diseases, ophthalmological diseases and cancers. Flores, J. et al., *Nature Comm.* 9, 3916 (2018); McKenzie, B. et al., *PNAS* 115, (26), E6065-E6074 (2018); Melnikov, V. et al., *J Clin Invest.* 110, pp. 1083-1091 (2002); Wang, W. et al., *PNAS,* 113, (34) pp. 9587-9592 (2016); Morrison, M. et al., *Int J Obesity Res.* 40, pp. 1416-1423 (2016); Guo B. et al., *Sci Rep.* 6, p. 36107 (2016); Stack, J. et al., *J. Immunol.* 175, pp. 2630-2634 (2005); Kim, R. et al., Am. J. Resp. Care Med. 196, pp. 283-297 (2017); Rudolphi, K. et al., *Osteoarthritis Cartilage* 11, pp. 738-746 (2003); Audia, J. et al., *Basic Res. Cardiol.* 113, (5), pp. 32 (2018); Aira, L. et al., *J. Invest. Derm.* DOI: 10.1016/j.jid.2018.11.031 (2018), Wooff, Y. et al., *Sci. Rep.* 10, p. 2263 (2020). Therefore, inhibitors of the proinflammatory and pathogenic actions of caspase-1, capsase-4 and caspase-5 could be beneficial in the treatment of multiple human diseases.

In view of the multiple uses for caspase inhibitors, there is a constant need to develop new, more effective compounds that can selectively inhibit certain caspases.

4. SUMMARY

Provided herein are compounds, pharmaceutical compositions containing the compounds and methods of use thereof in treating diseases modulated by certain caspases, including but not limited to caspase-1, caspase-4 and/or caspase-5. In one embodiment, the compounds for use in the compositions and methods provided herein are of Formula I:

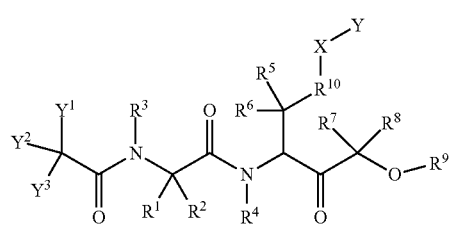

or an enantiomer or a mixture of enantiomers thereof, or a pharmaceutically acceptable salt, solvate, hydrate, co-crystal, clathrate, or polymorph thereof, wherein $R^1$, $R^2$, $R^3$, $R^4$, $R^5$, $R^6$, $R^7$, $R^8$, $R^9$, $R^{10}$, X, Y, $Y^1$, $Y^2$ and $Z^3$ are as defined elsewhere herein.

Also provided herein are pharmaceutical compositions comprising one or more compound(s) of Formula I and a pharmaceutically acceptable carrier.

In one embodiment, provided herein are methods of treating a disease or condition associated with the inflammatory caspases (i.e. caspase-1, caspae-4 and caspase-5) and/or the modulation of the inflammatory caspases, by administering a therapeutically effective amount of a compound provided herein. In certain embodiments, the conditions or diseases associated with the inflammatory caspases and/or the modulation of inflammatory caspases are selected from autoimmune diseases, inflammatory diseases, CNS diseases liver diseases, respiratory diseases, cardiovascular diseases, dermatological diseases, rheumatological diseases, kidney diseases, and cancers. In certain embodiments, the conditions or diseases associated with the inflammatory caspases and/or the modulation of inflammatory caspases are selected from autoimmune diseases, inflammatory diseases, CNS diseases liver diseases, respiratory diseases, cardiovascular diseases, dermatological diseases, rheumatological diseases, kidney diseases, ophthalmological diseases and cancers.

In one embodiment, provided herein are methods of treating a disease or condition associated with caspase-1, caspase-4 and/or caspase-5 and/or the modulation of caspase-1, caspase-4 and/or caspase-5, by administering a therapeutically effective amount of a compound herein. In certain embodiments, the conditions or diseases associated with caspase-1, caspase-4 and/or caspase-5 and/or the modulation of caspase-1, caspase-4 and/or caspase-5 are selected from autoinflammatory, autoimmune diseases, inflammatory diseases, CNS diseases, liver diseases, respiratory diseases, cardiovascular diseases, dermatological diseases, rheumatological diseases kidney diseases, and cancer. In certain embodiments, the conditions or diseases associated with caspase-1, caspase-4 and/or caspase-5 and/or the modulation of caspase-1, caspase-4 and/or caspase-5 are selected from autoinflammatory, autoimmune diseases, inflammatory diseases, CNS diseases, liver diseases, respiratory diseases, cardiovascular diseases, dermatological diseases, rheumatological diseases kidney diseases, ophthalmological diseases and cancer.

In one embodiment, the compositions described herein are useful for the treatment, prevention, or amelioration of autoinflammatory diseases, neuroinflammatory diseases, autoimmune diseases and of other inflammatory conditions. In one embodiment, the compositions described herein are useful for the treatment of liver diseases in particular, nonalcoholic steatohepatitis (NASH), nonalcoholic fatty liver disease (NAFLD), primary sclerosing cholangitis (PSC), primary biliary cirrhosis (PBC), autoimmune hepatitis (AIH) and viral hepatitis. In one embodiment, the compositions described herein are useful for the treatment of gastrointestinal diseases in particular, inflammatory bowel disease (IBD), ulcerative colitis (UC) and Crohn's disease. In one embodiment, the compositions described herein are useful for the treatment of CNS and neuroinflammatory diseases in particular multiple sclerosis (MS), Alzheimer's disease, Huntington's disease (HD), Parkinson's disease (PD) and epilepsies. The compositions described herein are useful for the treatment of cardiovascular diseases and metabolic diseases in particular myocardial infarction (MI), atherosclerosis, type 2 diabetes, and type 1 diabetes. In one embodiment, the compositions described herein are useful for the treatment of kidney diseases, in particular acute kidney injury (AKI), glomerulonephritis and lupus nephritis. In one embodiment, the compositions described herein are useful for the treatment of dermatological diseases, in particular psoriasis and acne. In one embodiment, the compositions described herein are useful for the treatment of rheumatological diseases, in particular rheumatoid arthritis (RA), osteoarthritis (OA), and gout. Exemplary specific autoimmune diseases for which a compound herein may be employed include systemic lupus erythematosus, polychondritis, scleredoma, Wegener granulomatosis, dermatomyositis, Steven-Johnson syndrome, endocrine ophthalmopathy and Graves disease.

In one embodiment, the compositions described herein are also useful for the treatment, prevention, or amelioration of asthma, steroid resistant asthma, pulmonary emphysema, and other obstructive or inflammatory diseases of the airways.

In one embodiment, the compositions described herein are also useful for the treatment, prevention, or amelioration of ophthalmological diseases such as retinal degenerative diseases such as age-related macular degeneration (AMD).

In one embodiment, the compositions described herein may be used for treatment of cancers.

In one embodiment, the present disclosure relates to the use of a compound provided herein for the treatment and/or prevention of cancers. Typically cancers include colorectal cancer (CRC), melanoma, gastric cancer (including esophageal cancer), renal cell carcinoma (RCC), breast cancer, prostate cancer, head and neck cancer, bladder cancer, hepatocellular carcinoma (HCC), ovarian cancer, cervical cancer, endometrial cancer, pancreatic cancer, neuroendocrine cancer, hematological cancers (particularly multiple myeloma, acute myeloblastic leukemia (AML), and biliary tract cancer.

In one embodiment, the compounds provide a therapy to improve the treatment of cancer having at least a partial inflammatory basis. In one embodiment, the compounds are useful for the treatment and/or prevention of cancer having at least a partial inflammatory basis. In another aspect, provided herein is a particular clinical dosage regimen for the administration of a compound for the treatment and/or prevention of cancer. In another aspect, the compound provided herein is administered with one or more therapeutic agent to a subject in need thereof (e.g., a chemotherapeutic agent), and/or the subject in certain embodiments, have received/will receive debulking procedures in addition to the administration of a compound herein.

In one embodiment, provided herein are methods of treating or preventing cancer in a human subject in need thereof comprising administering to the subject a therapeutically effective amount of a compound provided herein.

In one embodiment, provided herein is a use of a compound for the preparation of a medicament for the treatment of cancer.

In some embodiments, the compounds provided herein are used for the treatment or prevention in in cryopyrin-associated periodic syndromes (CAPS), familial Mediterranean fever (FMF), systemic onset juvenile idiopathic arthritis (SJIA), hyperimmunoglobulin D syndrome (HIDS) and tumor necrosis factor receptor-associated periodic syndrome (TRAPS), familial cold urticaria, neonatal onset multisystem inflammatory disease, SJIA and FMF, and Muckle Wells syndrome.

In practicing the methods, effective amounts of the compounds or compositions containing therapeutically effective concentrations of the compounds are administered to an individual exhibiting the symptoms of the disease or disorder to be treated. The amounts are effective to ameliorate or eliminate one or more symptoms of the disease or disorder.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

These and other aspects of the subject matter described herein will become evident upon reference to the following detailed description.

5. BRIEF DESCRIPTION OF THE DRAWINGS

FIG. 1 provides a dose response study for the compound of Example 6 and reference compound IDN-7314 for inhibition of IL-1β in THP 1 cells.

Figure 2:
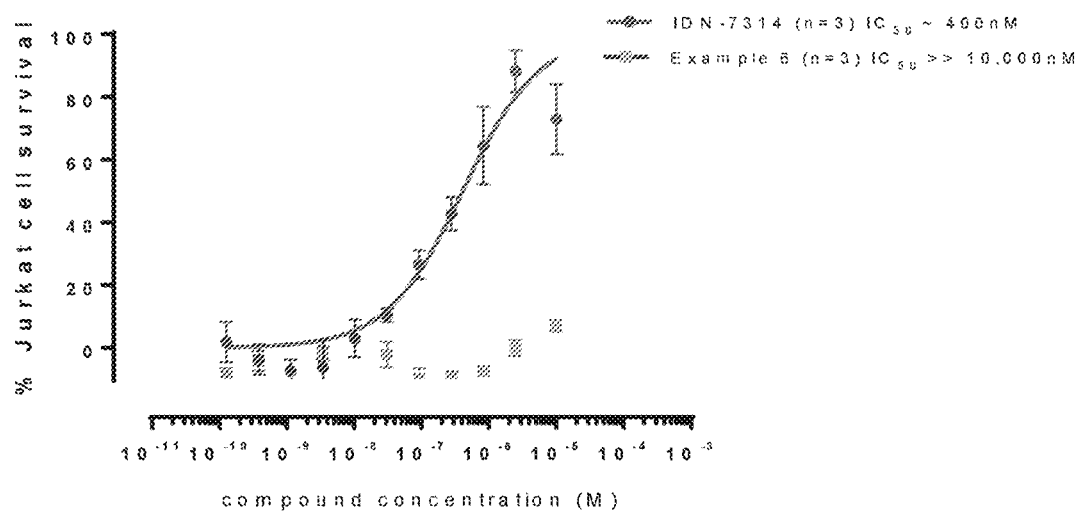

FIG. 2 provides results of a dose response study for the compound of Example 6 and reference compound IDN-7314 for Fas induced apoptosis in Jurkat cells.

Figure 3:
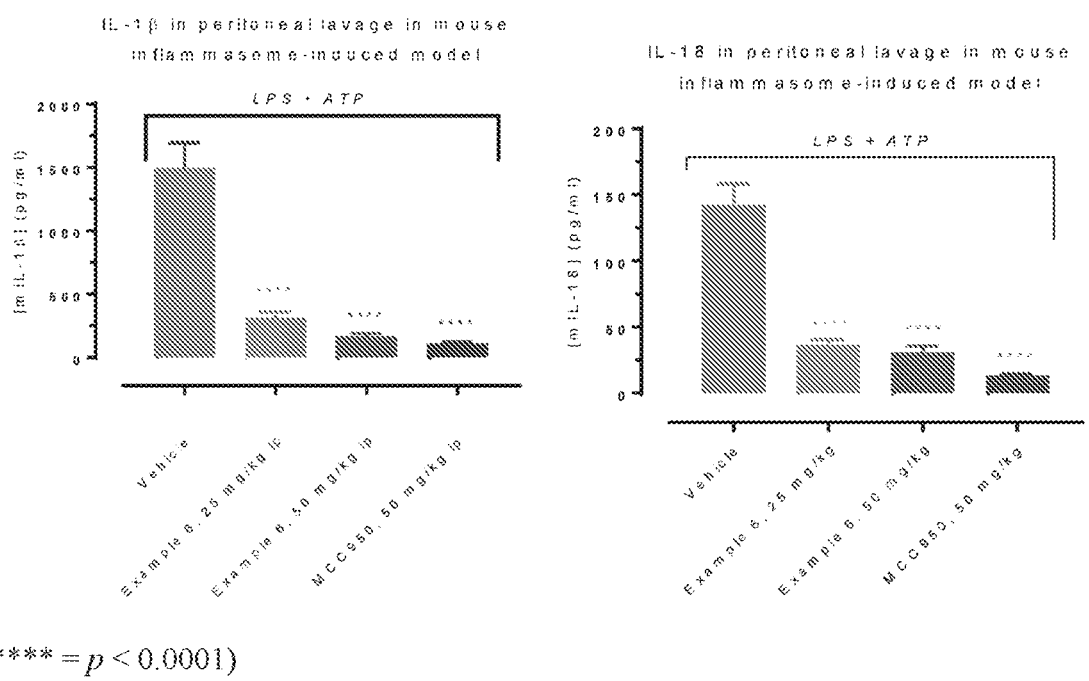

FIG. 3 demonstrates in vivo inhibition of inflammatory cytokines IL-1β and IL 18 by the compound of Example 6 and reference compound MCC950.

Figure 4:
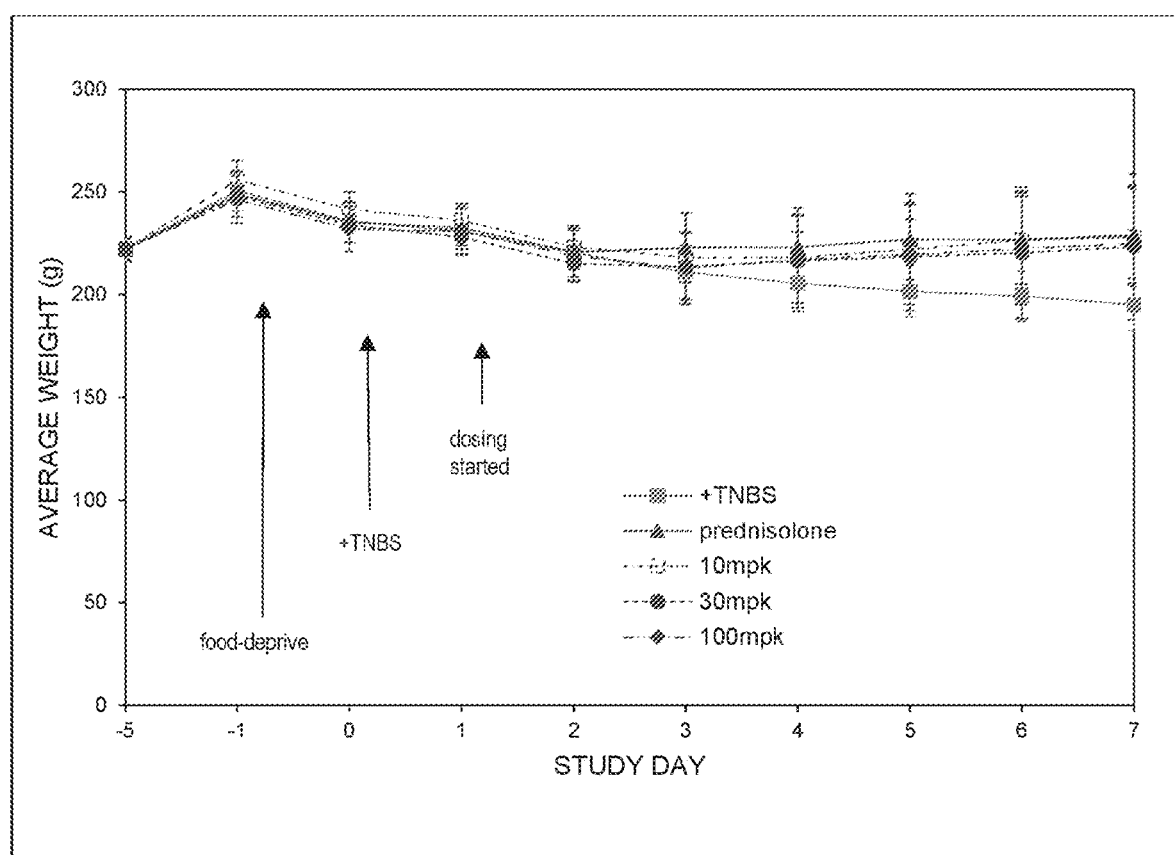

FIG. 4 provides the effect of twice daily oral administration of the compound of Example 6 and reference compounds on prevention of weight loss in a model of ulcerative colitis.

Figure 5:
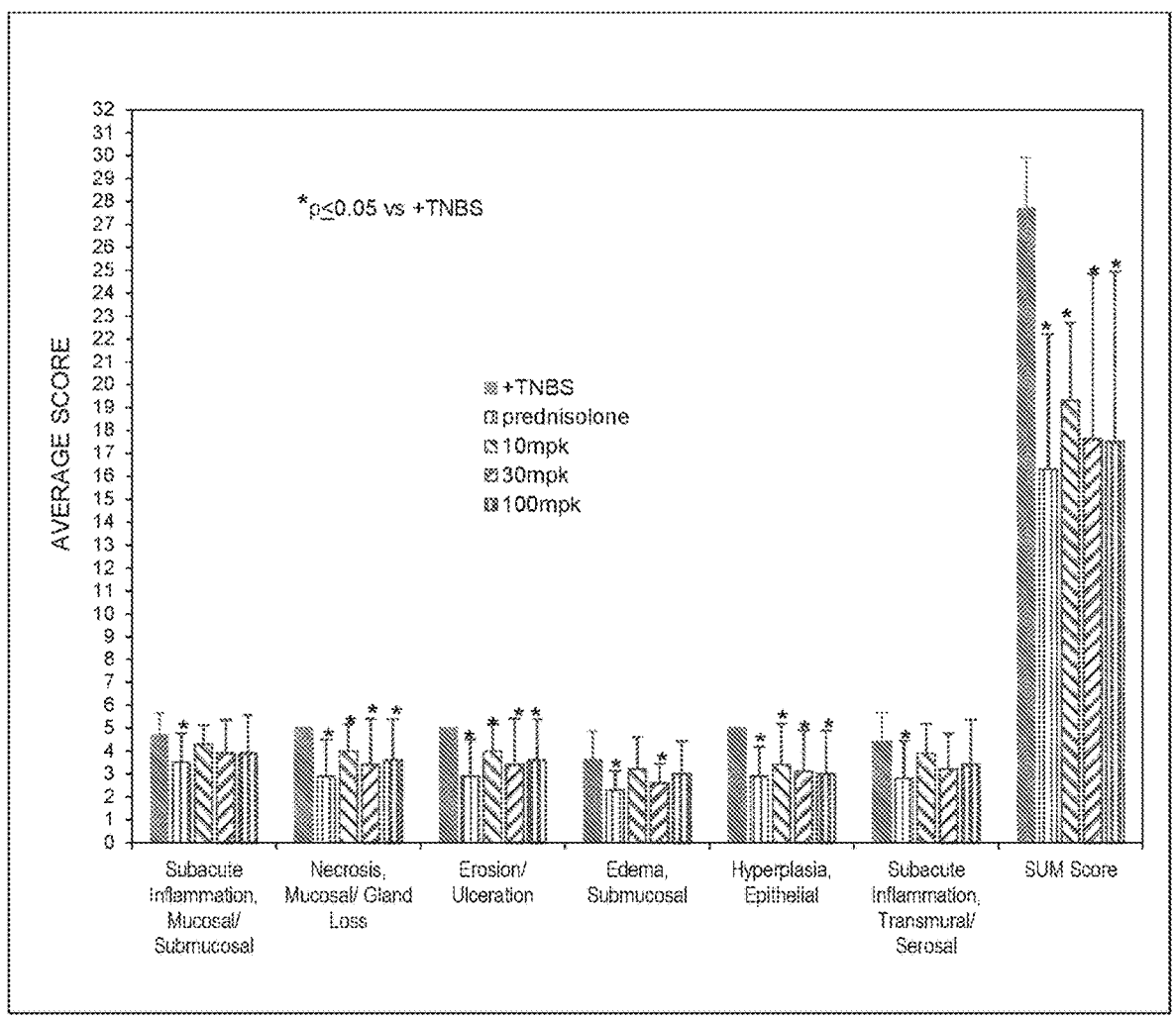

FIG. 5 provides the effect of twice daily oral administration of the compound of Example 6 and reference compounds on colon histology parameters in a model of ulcerative colitis.

6. DETAILED DESCRIPTION OF THE EMBODIMENTS

6.1. Definitions

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein, "halogen" refers to all halogens, that is, a halogen substituent can be chloro (Cl), fluoro (F), bromo (Br) or iodo (I).

"hydroxyl" or "hydroxy" refer to the group —OH.

"thio" refers to the group —SH.

As used herein, "lower alkyl" means an alkane-derived radical containing from 1 to 6 carbon atoms (unless specifically defined) that includes a straight chain alkyl or branched alkyl. As used herein, the term "alkyl" means a straight or branched $C_1$ to $C_{10}$ carbon chain such as methyl, ethyl, tert-butyl, iso-propyl, n-octyl, and the like. The straight chain or branched alkyl group is chemically feasible and attached at any available point to produce a stable compound. In embodiments, a lower alkyl is a straight or branched alkyl group containing from 1-6, 1-4, or 1-2, carbon atoms, such as methyl, ethyl, propyl, isopropyl, butyl, t-butyl, and the like. A "substituted lower alkyl" denotes lower alkyl that is optionally independently substituted, unless indicated otherwise, with one or more, for example, 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)$_2$—N(H)—R$^o$, —S(O)$_2$—N(R$^o$)—R$^o$, —C(NH)—N(H)—R$^o$, —C(NH)—N(R$^p$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^c$, —R$^f$, and —R$^g$.

"Alkylene" refer to a straight or branched divalent hydrocarbon chain consisting solely of carbon and hydrogen, containing no unsaturation. "Lower alkylene" refer to a straight or branched divalent hydrocarbon chain consisting solely of carbon and hydrogen, containing no unsaturation and having from one to six carbon atoms, e.g., methylene, ethylene, propylene, n-butylene and the like. In certain embodiment, alkylene and lower alkylene is substituted with one or more substituent described in the definition of alkyl a group above.

"Lower alkenyl" alone or in combination means a straight or branched hydrocarbon containing 2-6 carbon atoms (unless specifically defined) and at least one, 1-3, 1-2, or only one, carbon to carbon double bond. The term "alkenyl" means a straight or branched $C_1$ to $C_{10}$ carbon chain containing at least one, 1-3, 1-2, or only one, carbon to carbon double bond. Carbon to carbon double bonds can either be contained within a straight chain or branched portion. The straight chain or branched lower alkenyl group is chemically feasible and attached at any available point to provide a stable compound. Examples of lower alkenyl groups include ethenyl, propenyl, isopropenyl, butenyl, and the like. A "substituted lower alkenyl" denotes lower alkenyl that is optionally independently substituted, unless indicated otherwise, with one or more, for example, 1, 2, 3, 4 or 5, also 1, 2, or 3 substituents, attached at any available atom to produce a stable compound, wherein the substituents are selected from the group consisting of F, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)$_2$—N(H)—R$^o$, —S(O)$_2$—N(R$^o$)—R$^o$, —C(NH)—N(H)—R$^o$, —C(NH)—N(R$^p$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^f$, and —R$^g$.

"Lower alkynyl" alone or in combination means a straight or branched hydrocarbon containing 2-6 carbon atoms (unless specifically defined) containing at least one, or only one, carbon to carbon triple bond. The term "alkynyl" means a straight or branched $C_1$ to $C_{10}$ carbon chain containing at least one, or only one, carbon to carbon triple bond. The straight chain or branched lower alkynyl group is chemically feasible and attached at any available point to provide a stable compound. Examples of alkynyl groups include ethynyl, propynyl, butynyl, and the like. A "substituted lower alkynyl" denotes lower alkynyl that is optionally independently substituted, unless indicated otherwise, with one or more, for example, 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)—

OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)$_2$—N(H)—R$^o$, —S(O)$_2$—N(R$^o$)—R$^o$, —C(NH)—N(H)—R$^o$, —C(NH)—N(R$^p$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^e$, and —R$^g$.

"Cycloalkyl" refers to saturated or unsaturated, non-aromatic monocyclic, bicyclic or tricyclic carbon ring systems of 3-10, also 3-8 or 3-6, ring members per ring, such as cyclopropyl, cyclopentyl, cyclohexyl, cycloheptyl, cyclooctyl, adamantyl, cis- or trans-decalin, bicyclo[2.2.1]hept-2-ene, cyclohex-1-enyl, cyclopent-1-enyl, 1,4-cyclooctadienyl and the like. The term "(cycloalkyl)alkyl" means the above-defined alkyl group substituted with a cycloalkyl ring. Examples of such a group include (cyclohexyl)methyl, 3-(cyclopropyl)-n-propyl, 5-(cyclopentyl)hexyl, 6-(adamantyl)hexyl, and the like.

A "substituted cycloalkyl" is a cycloalkyl that is optionally independently substituted, unless indicated otherwise, with one or more, for example, 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)$_2$—N(H)—R$^o$, —S(O)$_2$—N(R$^o$)—R$^o$, —C(NH)—N(H)—R$^o$, —C(NH)—N(R$^p$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^e$, —R$^f$, and —R$^g$. For example, "C$_{3-6}$ cycloalkyl" denotes cycloalkyl containing 3-6 carbon atoms, and "C$_{3-5}$ cycloalkyl" denotes cycloalkyl containing 3-5 carbon atoms.

"Heterocycloalkyl" refers to a saturated or unsaturated non-aromatic cycloalkyl group containing from 5 to 10 atoms in which from 1 to 3 carbon atoms in the ring are replaced by heteroatoms of O, S or N, and optionally are fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which a ring carbon can be oxo substituted, i.e., the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, pyrrolidonyl, piperazinyl, dihydrobenzofuryl, and dihydroindolyl. "Nitrogen containing heterocycloalkyl" refers to heterocycloalkyl wherein at least one heteroatom is N. The term "(heterocycloalkyl)alkyl" means the above-defined alkyl group substituted with a heterocycloalkyl ring.

A "substituted heterocycloalkyl" is a heterocycloalkyl that is optionally independently substituted, unless indicated otherwise, with one or more, for example, 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)$_2$—N(H)—R$^o$, —S(O)$_2$—N(R$^o$)—R$^o$, —C(NH)—N(H)—R$^o$, —C(NH)—N(R$^p$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R$^o$)—S(O)$_2$—N(H)—R$^o$, —N(H)—S(O)$_2$—N(R$^o$)—R$^o$, —N(R$^o$)—S(O)$_2$—N(R$^o$)—R$^o$, —N(H)—R$^o$, —N(R$^o$)—R$^o$, —R$^d$, —R$^e$, —R$^f$, and —R$^g$.

"Aryl" alone or in combination refers to a monocyclic or bicyclic ring system containing aromatic hydrocarbons such as phenyl or naphthyl, which optionally can be fused with a cycloalkyl of, for example, 5-7, or, for example, 5-6, ring members. A "substituted aryl" is an aryl that optionally is independently substituted, unless indicated otherwise, with one or more, for example, 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^o$, —S—R$^o$, —O—C(O)—R$^o$, —O—C(S)—R$^o$, —C(O)—R$^o$, —C(S)—R$^o$, —C(O)—O—R$^o$, —C(S)—O—R$^o$, —S(O)—R$^o$, —S(O)$_2$—R$^o$, —C(O)—N(H)—R$^o$, —C(S)—N(H)—R$^o$, —C(O)—N(R$^o$)—R$^o$, —C(S)—N(R$^o$)—R$^o$, —S(O)$_2$—N(H)—R$^o$, —S(O)$_2$—N(R$^o$)—R$^o$, —C(NH)—N(H)—R$^o$, —C(NH)—N(R$^p$)—R$^c$, —N(H)—C(O)—R$^o$, —N(H)—C(S)—R$^o$, —N(R$^o$)—C(O)—R$^o$, —N(R$^o$)—C(S)—R$^o$, —N(H)—S(O)$_2$—R$^o$, —N(R$^o$)—S(O)$_2$—R$^o$, —N(H)—C(O)—N(H)—R$^o$, —N(H)—C(S)—N(H)—R$^o$, —N(R$^o$)—C(O)—NH$_2$, —N(R$^o$)—C(S)—NH$_2$, —N(R$^o$)—C(O)—N(H)—R$^o$, —N(R$^o$)—C(S)—N(H)—R$^o$, —N(H)—C(O)—N(R$^o$)—R$^o$, —N(H)—C(S)—N(R$^o$)—R$^o$, —N(R$^o$)—C(O)—N(R$^o$)—R$^o$, —N(R$^o$)—C(S)—N(R$^o$)—R$^o$, —N(H)—S(O)$_2$—N(H)—R$^o$, —N(R$^o$)—S(O)$_2$—NH$_2$, —N(R°)—S(O)$_2$—N(H)—R°, —N(H)—S(O)$_2$—N(R°)—R°, —N(R°)—S(O)$_2$—N(R°)—R°, —N(H)—R°, —N(R°)—R°, —R$^d$, —R$^e$, —R$^f$, and —R$^g$. In some embodiments, the substituents are selected from among one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, lower alkyl, substituted lower alkyl, cycloalkyl, substituted cycloalkyl, (cycloalkyl)alkyl, substituted (cycloalkyl)alkyl, phenyl, substituted phenyl, phenylalkyl, and substituted phenylalkyl groups. In certain embodiments, the substituents are selected from among trifluoromethyl, trichloromethyl, tribromomethyl and triiodomethyl. In some embodiments, the substituents are one or more trifluoromethyl.

The term "substituted phenyl" specifies a phenyl group substituted with one or more substituents chosen from the above-identified "aryl" substituents. In embodiments, the substituents are selected from among halogen, hydroxy, protected hydroxy, cyano, nitro, trifluoromethyl, alkyl, alkoxy, acyl, acyloxy, carboxy, protected carboxy, carboxymethyl, protected carboxymethyl, hydroxymethyl, protected hydroxymethyl, amino, protected amino, (monosubstituted)amino, protected (monosubstituted)amino, (disubstituted) amino, carboxamide, protected carboxamide, N-(lower alkyl)carboxamide, protected N-(lower alkyl)carboxamide, N,N-di(lower alkyl)carboxamide, N-((lower alkyl)sulfonyl) amino, N-(phenylsulfonyl)amino or by a substituted or unsubstituted phenyl group, such that in the latter case a biphenyl or naphthyl group results. Examples of the term "substituted phenyl" include a mono-, di-, tri- or tetra(halo)phenyl group such as 2-, 3- or 4-chlorophenyl, 2,6-dichlorophenyl, 2,5-dichlorophenyl, 3,4-dichlorophenyl, 2,3,5-trichlorophenyl, 2,3,5,6-tetrachlorophenyl, 2-, 3- or 4-bromophenyl, 2,6-dibromophenyl, 2,5-dibromophenyl, 3,4-dibromophenyl, 2,3,5-tribromophenyl, 2,3,5,6-tetrabromophenyl, 2-, 3- or 4-fluorophenyl, 2,6-difluorophenyl, 2,5-difluorophenyl, 3,4-difluorophenyl, 2,3,5-trifluorophenyl, 2,3,5,6-tetrafluorophenyl, 3-chloro-4-fluorophen land the like; a mono or di(hydroxy)phenyl group such as 2-, 3-, or 4-hydroxyphenyl, 2,4-dihydroxyphenyl, the protected-hydroxy derivatives thereof and the like; a nitrophenyl group such as 2-, 3-, or 4-nitrophenyl; a cyanophenyl group, for example, 2-, 3- or 4-cyanophenyl; a mono- or di(alkyl) phenyl group such as 2-, 3-, or 4-methylphenyl, 2,4-dimethylphenyl, 2-, 3- or 4-(isopropyl)phenyl, 2-, 3-, or 4-ethylphenyl, 2-, 3- or 4-(n-propyl)phenyl and the like; a mono or di(alkoxy)phenyl group, for example, 2,6-dimethoxyphenyl, 2-, 3- or 4-(isopropoxy)phenyl, 2-, 3- or 4-(t-butoxy) phenyl, 3-ethoxy-4-methoxyphenyl and the like; 2-, 3- or 4-trifluoromethylphenyl; a mono- or dicarboxyphenyl or (protected carboxyphenyl group such as 2-, 3- or 4-carboxyphenyl or 2,4-di(protected carboxy)phenyl; a mono- or di(hydroxymethyl)phenyl or (protected hydroxymethyl)phenyl such as 2-, 3- or 4-(protected hydroxymethyl)phenyl or 3,4-di(hydroxymethyl)phenyl; a mono- or di(aminomethyl) phenyl or (protected aminomethyl)phenyl such as 2-, 3- or 4-(aminomethyl) phenyl or 2,4-(protected aminomethyl) phenyl; or a mono- or di(N-(methylsulfonylamino))phenyl such as 2, 3 or 4-(N (methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like.

The term "arylalkyl" means an aryl groups attached to one of the above-described alkyl groups, and the term "substituted arylalkyl" means that either the aryl, or the alkyl, or both, are substituted with one or more of the above-defined substituents. Examples of "arylalkyl" substituents include, for example, phenylmethyl (benzyl), phenylethyl, phenylpropyl, phenylisopropyl and the like. Examples of "substituted phenyl" groups include 2-phenyl-1-chloroethyl, 2-(4'-methoxyphenyl)ethyl, 4-(2',6'-dihydroxy phenyl)n-hexyl, 2-(5'-cyano-3' methoxyphenyl)n-pentyl, 3-(2',6'-dimethylphenyl)n-propyl, 4-chloro-3-aminobenzyl, 6-(4'-methoxyphenyl)-3-carboxy (n-hexyl), 5-(4'-aminomethylphenyl)-3-(aminomethyl)n-pentyl, 5-phenyl-3-oxo-n-pent-1-yl, (4-hydroxynapth-2-yl)methyl, and the like.

"Heteroaryl" alone or in combination refers to a monocyclic aromatic ring structure containing 5 or 6 ring atoms, or a bicyclic aromatic group having 8 to 10 atoms, containing one or more, e.g., 1-4, 1-3 or 1-2 heteroatoms independently selected from the group consisting of 0, S, and N, which optionally can be fused with a cycloalkyl of, for example, 5-7, or, for example, 5-6, ring members. Heteroaryl also is intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups (whether substituted or unsubstituted) include, but are not limited to, pyridinyl, pyridazinyl, pyrazinyl, quinoxalyl, indolizinyl, benzo [b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, pyrrolidinyl, thiadiazolyl, oxadiazolyl, thiatriazolyl, oxatriazolyl, pyridyl, oxazinyl, triazinyl, thiadiazinyl tetrazolo, 1,5-[b]pyridazinyl and purinyl, as well as benzo-fused derivatives, for example, benzoxazolyl, benzothiazolyl, benzimidazolyl, benzofuryl and indolyl. "Nitrogen containing heteroaryl" refers to heteroaryl wherein at least one heteroatom is N. In some instances, for example when R groups of a nitrogen combine with the nitrogen to form a 5 or 7 membered nitrogen containing heteroaryl, any heteroatoms in such 5 or 7 membered heteroaryl are N. An "optionally substituted heteroaryl" is a heteroaryl that is optionally independently substituted, unless indicated otherwise, with one or more, for example, 1, 2, 3, 4 or 5, also 1, 2, or 3 substituents, attached at any available atom to produce a stable compound, wherein the substituents are selected from the group consisting of halogen, —CF$_3$, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R°, —S—R°, —O—C(O)—R°, —O—C(S)—R°, —C(O)—R°, —C(S)—R°, —C(O)—O—R°, —C(S)—O—R°, —S(O)—R°, —S(O)$_2$—R°, —C(O)—N(H)—R°, —C(S)—N(H)—R°, —C(O)—N(R°)—R°, —C(S)—N(R°)—R°, S(O)$_2$—N(H)—R°, —S(O)$_2$—N(R°)—R°, —C(NH)—N(H)—R°, —C(NH)—N(R$^p$)—R$^c$, —N(H)—C(O)—R°, —N(H)—C(S)—R°, —N(R°)—C(O)—R°, —N(R°)—C(S)—R°, —N(H)—S(O)$_2$—R°, —N(R°)—S(O)$_2$—R°, —N(H)—C(O)—N(H)—R°, —N(H)—C(S)—N(H)—R°, —N(R°)—C(O)—NH$_2$, —N(R°)—C(S)—NH$_2$, —N(R°)—C(O)—N(H)—R°, —N(R°)—C(S)—N(H)—R°, —N(H)—C(O)—N(R°)—R°, —N(H)—C(S)—N(R°)—R°, —N(R°)—C(O)—N(R°)—R°, —N(R°)—C(S)—N(R°)—R°, —N(H)—S(O)$_2$—N(H)—R°, —N(R°)—S(O)$_2$—NH$_2$, —N(R°)—S(O)$_2$—N(H)—R°, —N(H)—S(O)$_2$—N(R°)—R°, —N($R^o$)—S(O)$_2$—, —N($R^o$)—$R^o$, —N(H)—$R^o$, —N($R^o$)—$R^o$, —$R^d$, —$R^e$, —$R^f$ and —$R^g$.

Substituents for the above optionally substituted heteroaryl rings are as denoted above, e.g., for the "aryl," and "phenyl," groups. In certain embodiments, the substituents are selected from among one to three halo, trihalomethyl, amino, protected amino, amino salts, mono-substituted amino, di-substituted amino, carboxy, protected carboxy, carboxy late salts, hydroxy, protected hydroxy, salts of a hydroxy group, lower alkoxy, lower alkylthio, lower alkyl, substituted lower alkyl, cycloalkyl, substituted cycloalkyl, (cycloalkyl)alkyl, substituted (cycloalkyl)alkyl, phenyl, substituted phenyl, phenylalkyl, and substituted phenylalkyl groups.

"Pyridyl," as used herein, refers to a 6-membered aromatic ring with one "N" atom. As used herein, "pyridazinyl" refers to a 6-membered aromatic ring with two "N" atoms in the 1 and 2 positions, "pyrimidyl" refers to a 6-membered aromatic ring with two "N" atoms in the 1 and 3 positions and "pyrazinyl" refers to a 6-membered aromatic ring with two "N" atoms in the 1 and 4 positions.

Substituents for the above defined "pyridyl," "pyridazinyl," "pyrimidyl" and "pyrazinyl" groups are as denoted above, e.g., for the "aryl," "phenyl," and "heteroaryl" groups. In some embodiments, the substituents are selected from among one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, lower alkyl, substituted lower alkyl, cycloalkyl, substituted cycloalkyl, (cycloalkyl)alkyl, substituted (cycloalkyl)alkyl, phenyl, substituted phenyl, phenylalkyl, and substituted phenylalkyl groups. In certain embodiments, the substituents are selected from among trifluoromethyl, trichloromethyl, tribromomethyl and triiodomethyl. In some embodiments, the substituents are one or more trifluoromethyl.

The variables $R^o$, $R^p$, $R^c$, $R^d$, $R^e$, $R^f$ and $R^g$ as used in the description of optional substituents for alkyl, alkenyl, alkynyl, cycloalkyl, heterocycloalkyl, aryl, phenyl, napthyl and heteroaryl are defined as follows:

each $R^c$, $R^p$, and $R^c$ are independently selected from the group consisting of $R^d$, $R^e$, $R^f$, and $R^g$, or $R^p$ and $R^c$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, for example 1, 2, 3, 4 or 5, also 1, 2, or 3 substituents selected from the group consisting of halogen, —NO$_2$, —CN, —OH, —NH$_2$, —O—$R^u$, —S—$R^u$, —N(H)—$R^u$, —N($R^u$)—$R^u$, —$R^x$, and —$R^y$;

each $R^d$ is independently lower alkyl, wherein lower alkyl is optionally substituted with one or more, for example 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—$R^k$, —S—$R^k$, —O—C(O)—$R^k$, —O—C(S)—$R^k$, —C(O)—$R^k$, —C(S)—$R^k$, —C(O)—O—$R^k$, —C(S)—O—$R^k$, —S(O)—$R^k$, —S(O)$_2$—$R^k$, —C(O)—N(H)—$R^k$, —C(S)—N(H)—$R^k$, —C(O)—N($R^k$)—$R^k$, —C(S)—N($R^k$)—$R^k$, —S(O)$_2$—N(H)—$R^k$, —S(O)$_2$—N($R^k$)—$R^k$, —C(NH)—N(H)—$R^k$, —C(NH)—N($R^m$)—$R^n$, —N(H)—C(O)—$R^k$, —N(H)—C(S)—$R^k$, —N($R^k$)—C(O)—$R^k$, —N($R^k$)—C(S)—$R^k$, —N(H)—S(O)$_2$—$R^k$, —N($R^k$)—S(O)$_2$—$R^k$, —N(H)—C(O)—N(H)—$R^k$, —N(H)—C(S)—N(H)—$R^k$, —N(H)—S(O)$_2$—N(H)—$R^k$, —N($R^k$)—C(O)—NH$_2$, —N($R^k$)—C(S)—NH$_2$, —N($R^k$)—C(O)—N(H)—$R^k$, —N($R^k$)—C(S)—N(H)—$R^k$, —N(H)—C(O)—N($R^k$)—$R^k$, —N(H)—C(S)—N($R^k$)—$R^k$, —N($R^k$)—C(O)—N($R^k$)—$R^k$, —N($R^k$)—C(S)—N($R^k$)—$R^k$, —N(H)—S(O)$_2$—N(H)—$R^k$, —N($R^k$)—S(O)$_2$—NH$_2$, —N($R^k$)—S(O)$_2$—N(H)—$R^k$, —N(H)—S(O)$_2$—N($R^k$)—$R^k$, —N($R^k$)—S(O)$_2$—N($R^k$)—$R^k$, —N(H)—$R^k$, —N($R^k$)—$R^k$, —$R^i$, and —$R^j$;

each $R^e$ is independently lower alkenyl, wherein lower alkenyl is optionally substituted with one or more, for example 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—$R^k$, —S—$R^k$, —O—C(O)—$R^k$, —O—C(S)—$R^k$, —C(O)—$R^k$, —C(S)—$R^k$, —C(O)—O—$R^k$, —C(S)—O—$R^k$, —S(O)—$R^k$, —S(O)$_2$—$R^k$, —C(O)—N(H)—$R^k$, —C(S)—N(H)—$R^k$, —C(O)—N($R^k$)—$R^k$, —C(S)—N($R^k$)—$R^k$, —S(O)$_2$—N(H)—$R^k$, —S(O)$_2$—N($R^k$)—$R^k$, —C(NH)—N(H)—$R^k$, —C(NH)—N($R^m$)—$R^n$, —N(H)—C(O)—$R^k$, —N(H)—C(S)—$R^k$, —N($R^k$)—C(O)—$R^k$, —N($R^k$)—C(S)—$R^k$, —N(H)—S(O)$_2$—$R^k$, —N($R^k$)—S(O)$_2$—$R^k$, —N(H)—C(O)—N(H)—$R^i$, —N(H)—C(S)—N(H)—$R^k$, —N($R^k$)—C(O)—NH$_2$, —N($R^k$)—C(S)—NH$_2$, —N($R^k$)—C(O)—N(H)—$R^k$, —N($R^k$)—C(S)—N(H)—$R^k$, —N(H)—C(O)—N($R^k$)—$R^k$, —N(H)—C(S)—N($R^k$)—$R^k$, —N($R^k$)—C(O)—N($R^k$)—$R^k$, —N($R^k$)—C(S)—N($R^k$)—$R^k$, —N(H)—S(O)$_2$—N(H)—$R^k$, —N($R^k$)—S(O)$_2$—NH$_2$, —N($R^k$)—S(O)$_2$—N(H)—$R^k$, —N(H)—S(O)$_2$—N($R^k$)—$R^k$, —N($R^k$)—S(O)$_2$—N($R^k$)—$R^k$, —N(H)—$R^k$, —N($R^k$)—$R^k$, —$R^h$, and —$R^j$;

each $R^f$ is independently lower alkynyl, wherein lower alkynyl is optionally substituted with one or more, for example 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—$R^k$, —S—$R^k$, —O—C(O)—$R^k$, —O—C(S)—$R^k$, —C(O)—$R^k$, —C(S)—$R^k$, —C(O)—O—$R^k$, —C(S)—O—$R^k$, —S(O)—$R^k$, —S(O)$_2$—$R^k$, —C(O)—N(H)—$R^k$, —C(S)—N(H)—$R^k$, —C(O)—N($R^k$)—$R^k$, —C(S)—N($R^k$)—$R^k$, —S(O)$_2$—N(H)—$R^k$, —S(O)$_2$—N($R^k$)—$R^k$, —C(NH)—N(H)—$R^k$, —C(NH)—N($R^m$)—$R^n$, —N(H)—C(O)—$R^k$, —N(H)—C(S)—$R^k$, —N($R^k$)—C(O)—$R^k$, —N($R^k$)—C(S)—$R^k$, —N(H)—S(O)$_2$—$R^k$, —N($R^k$)—S(O)$_2$—$R^k$, —N(H)—C(O)—N(H)—$R^k$, —N(H)—C(S)—N(H)—$R^k$, —N($R^k$)—C(O)—NH$_2$, —N($R^k$)—C(S)—NH$_2$, —N($R^k$)—C(O)—N(H)—$R^k$, —N($R^k$)—C(S)—N(H)—$R^k$, —N(H)—C(O)—N($R^k$)—$R^k$, —N(H)—C(S)—N($R^k$)—$R^k$, —N($R^k$)—C(O)—N($R^k$)—$R^k$, —N($R^k$)—C(S)—N($R^k$)—$R^k$, —N(H)—S(O)$_2$—N(H)—$R^k$, —N($R^k$)—S(O)$_2$—NH$_2$, —N($R^k$)—S(O)$_2$—N(H)—$R^k$, —N(H)—S(O)$_2$—N($R^k$)—$R^k$, —N($R^k$)—S(O)$_2$—N($R^k$)—$R^k$, —N(H)—$R^k$, —N($R^k$)—$R^k$, —$R^h$, and —$R^j$;

each $R^g$ is independently selected from the group consisting of cycloalkyl, heterocycloalkyl, aryl, and heteroaryl, wherein cycloalkyl, heterocycloalkyl, aryl, and heteroaryl are optionally substituted with one or more, for example 1, 2, 3, 4 or 5, also 1, 2 or 3 substituents selected from the group consisting of halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^k$, —O—C(O)—R$^k$, —O—C(S)—R$^k$, —C(O)—R$^k$, —C(S)—R$^k$, —C(O)—O—R$^k$, —C(S)—O—R$^k$, —S(O)—R$^k$, —S(O)$_2$—R$^k$, —C(O)—N(H)—R$^k$, —C(S)—N(H)—R$^k$, —C(O)—N(R$^k$)—R$^k$, —C(S)—N(R$^k$)—R$^k$, —S(O)$_2$—N(H)—R$^k$, —S(O)$_2$—N(R$^k$)—R$^k$, —C(NH)—N(H)—R$^k$, —C(NH)—N(R$^m$)—R$^n$, —N(H)—C(O)—R$^k$, —N(H)—C(S)—R$^k$, —N(R$^k$)—C(O)—R$^k$, —N(R$^k$)—C(S)—R$^k$, —N(H)—S(O)$_2$—R$^k$, —N(R$^k$)—S(O)$_2$—R$^k$, —N(H)—C(O)—N(H)—R$^k$, —N(H)—C(S)—N(H)—R$^k$, —N(R$^k$)—C(O)—NH$_2$, —N(R$^k$)—C(S)—NH$_2$, —N(R$^k$)—C(O)—N(H)—R$^k$, —N(R$^k$)—C(S)—N(H)—R$^k$, —N(H)—C(O)—N(R$^k$)—R$^k$, —N(H)—C(S)—N(R$^k$)—R$^k$, —N(R$^k$)—C(O)—N(R$^k$)—R$^k$, —N(R$^k$)—C(S)—N(R$^k$)—R$^k$, —N(H)—S(O)$_2$—N(H)—R$^k$, —N(R$^k$)—S(O)$_2$—NH$_2$, —N(R$^k$)—S(O)$_2$—N(H)—R$^k$, —N(H)—S(O)$_2$—N(R$^k$)—R$^k$, —N(R$^k$)—S(O)$_2$—N(R$^k$)—R$^k$, —N(H)—R$^k$, —N(R$^k$)—R$^k$, —R$^h$, —R$^i$, and —R$^j$;

wherein R$^k$, R$^m$, and R$^n$ each occurrence are independently selected from the group consisting of R$^h$, R$^i$, and R$^j$, or R$^m$ and R$^n$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, for example 1, 2, 3, 4 or 5, also 1, 2, or 3 substituents selected from the group consisting of halogen, —NO$_2$, —CN, —OH, —NH$_2$, —O—R$^u$, —S—R$^u$, —N(H)—R$^u$, —NR$^u$R$^u$, —R$^x$, and —R$^v$;

wherein each R$^h$ is independently lower alkyl optionally substituted with one or more, for example 1, 2, 3, 4 or 5, also 1, 2, or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^r$, —S—R$^r$, —O—C(O)—R$^r$, —O—C(S)—R$^r$, —C(O)—R$^r$, —C(S)—R$^r$, —C(O)—O—R$^r$, —C(S)—O—R$^r$, —S(O)—R$^r$, —S(O)$_2$—R$^r$, —C(O)—N(H)—R$^r$, —C(S)—N(H)—R$^r$, —C(O)—N(R$^r$)—R$^r$, —C(S)—N(R)—R$^r$, —S(O)$_2$—N(H)—R$^r$, —S(O)$_2$—N(R$^r$)—R$^r$, —C(NH)—N(H)—R$^r$, —C(NH)—N(R$^s$)—R$^t$, —N(H)—C(O)—R$^r$, —N(H)—C(S)—R$^r$, —N(R$^r$)—C(O)—R$^r$, —N(R$^r$)—C(S)—R$^r$, —N(H)—S(O)$_2$—R$^r$, —N(R$^r$)—S(O)$_2$—R$^r$, —N(H)—C(O)—N(H)—R$^r$, —N(H)—C(S)—N(H)—R$^r$, —N(R$^r$)—C(O)—NH$_2$, —N(R$^r$)—C(S)—NH$_2$, —N(R$^r$)—C(O)—N(H)—R$^r$, —N(R$^r$)—C(S)—N(H)—R$^r$, —N(H)—C(O)—N(R$^r$)—R$^r$, —N(H)—C(S)—N(R$^r$)—R$^r$, —N(R$^r$)—C(O)—N(R$^r$)—R$^r$, —N(R$^r$)—C(S)—N(R$^r$)—R$^r$, —N(H)—S(O)$_2$—N(H)—R$^r$, —N(R$^r$)—S(O)$_2$—NH$_2$, —N(R$^r$)—S(O)$_2$—N(H)—R$^r$, —N(H)—S(O)$_2$—N(R$^r$)—R$^r$, —N(R$^r$)—S(O)$_2$—N(R$^r$)—R$^r$, —N(H)—R$^r$, —N(R$^r$)—R$^r$, and —R$^j$;

wherein each R$^i$ is independently selected from the group consisting of lower alkenyl and lower alkynyl, wherein lower alkenyl or lower alkynyl are optionally substituted with one or more, for example 1, 2, 3, 4 or 5, also 1, 2 or 3 substituents selected from the group consisting of fluoro, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^r$, —S—R$^r$, —O—C(O)—R$^r$, —O—C(S)—R$^r$, —C(O)—R$^r$, —C(S)—R$^r$, —C(O)—O—R$^r$, —C(S)—O—R$^r$, —S(O)—R$^r$, —S(O)$_2$—R$^r$, —C(O)—N(H)—R$^r$, —C(S)—N(H)—R$^r$, —C(O)—N(R$^r$)—R$^r$, —C(S)—N(R$^r$)—R$^r$, —S(O)$_2$—N(H)—R$^r$, —S(O)$_2$—N(R$^r$—R$^r$, —C(NH)—N(H)—, —C(NH)—N(R$^s$)—R$^t$, —N(H)—C(O)—R$^r$, —N(H)—C(S)—R$^r$, —N(R$^r$)—C(O)—R$^r$, —N(R$^r$)—C(S)—R$^r$, —N(H)—S(O)$_2$—R$^r$, —N(R$^r$)—S(O)$_2$—R$^r$, —N(H)—C(O)—N(H)—R$^r$, —N(H)—C(S)—N(H)—R$^r$, —N(R$^r$)—C(O)—NH$_2$, —N(R$^r$)—C(S)—NH$_2$, —N(R$^r$)—C(O)—N(H)—R$^r$, —N(R$^r$)—C(S)—N(H)—R$^r$, —N(H)—C(O)—N(R$^r$)—R$^r$, —N(H)—C(S)—N(R$^r$)—R$^r$, —N(R$^r$)—C(O)—N(R$^r$)—R$^r$, —N(R$^r$) C(S)—N(R$^r$)—R$^r$, —N(H)—S(O)$_2$—N(H)—R$^r$, —N(R$^r$)—S(O)$_2$—NH$_2$, —N(R$^r$)—S(O)$_2$—N(H)—R$^r$, —N(H)—S(O)$_2$—N(R$^r$)—R$^r$, —N(R$^r$)—S(O)$_2$—N(R$^r$)—R$^r$, —N(H)—R$^r$, —N(R$^r$)—R$^r$, and —R$^j$;

wherein each R$^j$ is independently selected from the group consisting of cycloalkyl, heterocycloalkyl, aryl, and heteroaryl, wherein cycloalkyl, heterocycloalkyl, aryl, and heteroaryl are optionally substituted with one or more, for example 1, 2, 3, 4 or 5, also 1, 2 or 3 substituents selected from the group consisting of halogen, —OH, —NH$_2$, —NO$_2$, —CN, —C(O)—OH, —C(S)—OH, —C(O)—NH$_2$, —C(S)—NH$_2$, —S(O)$_2$—NH$_2$, —N(H)—C(O)—NH$_2$, —N(H)—C(S)—NH$_2$, —N(H)—S(O)$_2$—NH$_2$, —C(NH)—NH$_2$, —O—R$^r$, —SR$^r$, —O—C(O)—R$^r$, —O—C(S)—R$^r$, —C(O)—R$^r$, —C(S)—R$^r$, —C(O)—O—R$^r$, —C(S)—O, —S(O)—R$^r$, —S(O)$_2$—R$^r$, —C(O)—N(H)—R$^r$, —C(S)—N(H)—R$^r$, —C(O)—N(R$^r$)—R$^r$, —C(S)—N(R$^r$)—R$^r$, —S(O)$_2$—N(H)—R$^r$, —S(O)$_2$—N(R)—R$^r$, —C(NH)—N(H)—R$^r$, —C(NH)—N(R$^s$)—R$^t$, —N(H)—C(O)—R$^r$, —N(H)—C(S)—R$^r$, —N(R$^r$)—C(O)—R$^r$, —N(R$^r$)—C(S)—R$^r$, —N(H)—S(O)$_2$—R$^r$, —N(R$^r$)—S(O)$_2$—R$^r$, —N(H)—C(O)—N(H)—R$^r$, —N(H)—C(S)—N(H)—R$^r$, —N(R$^r$)—C(O)—NH$_2$, —N(R$^r$)—C(S)—NH$_2$, —N(R$^r$)—C(O)—N(H)—R$^r$, —N(R$^r$)—C(S)—N(H)—R$^r$, —N(H)—C(O)—N(R$^r$)—R$^r$, —N(H)—C(S)—N(R$^r$)—R$^r$, —N(R$^r$)—C(O)—N(R$^r$)—R$^r$, —N(R$^r$)—C(S)—N(R$^r$)—R$^r$, —N(H)—S(O)$_2$—N(H)—R$^r$, —N(R$^r$)—S(O)$_2$—NH$_2$, —N(R$^r$)—S(O)$_2$—N(H)—R$^r$, —N(H)—S(O)$_2$—N(R$^r$)—R$^r$, —N(R$^r$)—S(O)$_2$—N(R$^r$)—R$^r$, —N(R$^r$)—R$^r$, cycloalkylamino, and —R$^x$;

wherein each R$^r$, R$^s$, and R$^t$ at each occurrence are independently selected from the group consisting of lower alkyl, C$_{3-6}$ alkenyl, C$_{3-6}$alkynyl, cycloalkyl, heterocycloalkyl, aryl and heteroaryl, wherein lower alkyl is optionally substituted with one or more, for example 1, 2, 3, 4 or 5, also 1, 2 or 3 substituents selected from the group consisting of R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein C$_{3-6}$ alkenyl or $C_{3-6}$ alkynyl are optionally substituted with one or more, for example 1, 2, 3, 4 or 5, also 1, 2, or 3 substituents selected from the group consisting of $R^y$, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, and wherein cycloalkyl, heterocycloalkyl, aryl, and heteroaryl are optionally substituted with one or more, for example 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, or $R^s$ and $R^t$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, for example 1, 2, 3, 4 or 5, also 1, 2, or 3 substituents selected from the group consisting of halogen, —NO$_2$, —CN, —OH, —NH$_2$, —O—$R^u$, —S—$R^u$, —N(H)—$R^u$, —N($R^u$)—$R^u$, —$R^x$, and —$R^y$;

wherein each $R^u$ is independently selected from the group consisting of lower alkyl, $C_{3-6}$ alkenyl, $C_{3-6}$ alkynyl, cycloalkyl, heterocycloalkyl, aryl, and heteroaryl, wherein lower alkyl is optionally substituted with one or more, for example 1, 2, 3, 4 or 5, also 1, 2, or 3 substituents selected from the group consisting of $R^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein $C_{3-6}$ alkenyl or $C_{3-6}$ alkynyl are optionally substituted with one or more, for example 1, 2, 3, 4 or 5, also 1, 2, or 3 substituents selected from the group consisting of $R^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and wherein cycloalkyl, heterocycloalkyl, aryl, and heteroaryl are optionally substituted with one or more, for example 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each $R^x$ is selected from the group consisting of lower alkyl, lower alkenyl and lower alkynyl, wherein lower alkyl is optionally substituted with one or more, for example 1, 2, 3, 4 or 5, also 1, 2, or 3 substituents selected from the group consisting of $R^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, and wherein lower alkenyl or lower alkynyl are optionally substituted with one or more, for example 1, 2, 3, 4 or 5, also 1, 2, or 3 substituents selected from the group consisting of $R^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

wherein each R is selected from the group consisting of cycloalkyl, heterocycloalkyl, aryl, and heteroaryl, wherein cycloalkyl, heterocycloalkyl, aryl, and heteroaryl are optionally substituted with one or more, for example 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted lower alkenyl, optionally substituted $C_{3-6}$ alkenyl, optionally substituted lower alkynyl, or optionally substituted $C_{3-6}$ alkynyl are optionally substituted with one or more, also 1, 2 or 3 groups or substituents selected from the group consisting of fluoro, —NO$_2$, —CN, —O—$R^{1a}$, —S—$R^{1a}$, —N($R^{1a}$)—$R^{1a}$, —O—C(O)—$R^{1a}$, —O—C(S)—$R^{1a}$, —C(O)—$R^{1a}$, —C(S)—$R^{1a}$, —C(O)—O—$R^{1a}$, —C(S)—O—$R^{1a}$, —C(O)—N($R^{1a}$)—$R^{1a}$, —C(S)—N($R^{1a}$)—$R^{1a}$, —S(O)$_2$—N($R^{1a}$)—$R^{1a}$, —C(NH)—N($R^{1a}$)—$R^{1a}$, —N($R^{1a}$)—C(O)—$R^{1a}$, —N($R^{1a}$)—C(S)—$R^{1a}$, N($R^{1a}$)—S(O)$_2$—$R^{1a}$, —N($R^{1a}$)—C(O)—N($R^{1a}$)—$R^{1a}$, —N($R^{1a}$)—C(S)—N($R^{1a}$)—$R^{1a}$, —N($R^{1a}$)—S(O)$_2$—N($R^{1a}$)—$R^{1a}$, —S(O)—$R^{1a}$, —S(O)$_2$—$R^{1a}$, cycloalkyl, heterocycloalkyl, aryl and heteroaryl; wherein cycloalkyl, heterocycloalkyl, aryl and heteroaryl are optionally substituted with one or more, also 1, 2 or 3 groups or substituents selected from the group consisting of halogen, —NO$_2$, —CN, —O—$R^{1a}$, —S—$R^{1a}$, —N($R^{1a}$)—$R^{1a}$, —O—C(O)—$R^{1a}$, —O—C(S)—$R^{1a}$, —C(O)—$R^{1a}$, —C(S)—$R^{1a}$, —C(O)—O—$R^{1a}$, —C(S)—O—$R^{1a}$, —C(O)—N($R^{1a}$)—$R^{1a}$, —C(S)—N($R^{1a}$)—$R^{1a}$, —S(O)$_2$—N($R^{1a}$)—$R^{1a}$, —C(NH)—N($R^{1a}$)—$R^{1a}$, —N($R^{1a}$)—C(O)—$R^{1a}$, —N($R^{1a}$)—C(S)—$R^{1a}$, —N($R^{1a}$)—S(O)$_2$—$R^{1a}$, —N($R^{1a}$)—C(O)—N($R^{1a}$)—$R^{1a}$, —N($R^{1a}$)—C(S)—N($R^{1a}$)—$R^{1a}$, —N($R^{1a}$)—S(O)$_2$—N($R^{1a}$)—$R^{1a}$, —S(O)—$R^{1a}$, —S(O)$_2$—$R^{1a}$, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$; and all occurrences of optionally substituted cycloalkyl, optionally substituted heterocycloalkyl, optionally substituted 5-7 membered heterocycloalkyl, optionally substituted aryl, optionally substituted heteroaryl, or optionally substituted 5 or 7 membered nitrogen containing heteroaryl are optionally substituted with one or more, also 1, 2, or 3 groups or substituents selected from the group consisting of halogen, —NO$_2$, —CN, —O—$R^{1a}$, —S—$R^{1a}$, —N($R^{1a}$)—$R^{1a}$, —O—C(O)—$R^{1a}$, —O—C(S)—$R^{1a}$, —C(O)—$R^{1a}$, —C(S)—$R^{1a}$, —C(O)—O—$R^{1a}$, —C(S)—O—$R^{1a}$, —C(O)—N($R^{1a}$)—$R^{1a}$, —C(S)—N($R^{1a}$)—$R^{1a}$, —S(O)$_2$—N($R^{1a}$) $R^{1a}$, —C(NH)—N($R^{1a}$)—$R^{1a}$, —N($R^{1a}$)—C(O)—$R^{1a}$, —N($R^{1a}$)—C(S)—$R^{1a}$, —N($R^{1a}$)—S(O)$_2$—$R^{1a}$, —N($R^{1a}$)—C(O)—N($R^{1a}$)—$R^{1a}$, —N($R^{1a}$)—C(S)—N($R^{1a}$)—$R^{1a}$, —N($R^{1a}$)—S(O)$_2$—N($R^{1a}$)—$R^{1a}$, —S(O)—$R^{1a}$, —S(O)$_2$—$R^{1a}$, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —$R^{1b}$; wherein $R^{1a}$ is selected from the group consisting of hydrogen, —$R^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, and wherein —R$^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —NH$_2$, lower alkoxy, fluoro substituted lower alkoxy, lower alkylthio, fluoro substituted lower alkylthio, mono-alkylamino, di-alkylamino, and cycloalkylamino.

In some embodiments, all occurrences of optionally substituted lower alkyl, optionally substituted lower alkenyl, optionally substituted C$_{3-6}$ alkenyl, optionally substituted lower alkynyl, or optionally substituted C$_{3-6}$ alkynyl are optionally substituted with one or more, also 1, 2 or 3 groups or substituents selected from the group consisting of fluoro, —CN, —O—R$^{1a}$, —S—R$^{1a}$, —N(R$^{1a}$)—R$^{1a}$, —C(O)—R$^{1a}$, —C(S)—R$^{1a}$, —C(O)—O—R$^{1a}$, —C(O)—N(R$^{1a}$)—R$^{1a}$, —C(S)—N(R$^{1a}$)—R$^{1a}$, —S(O)$_2$—N(R$^{1a}$)—R$^{1a}$, —N(R$^{1a}$)—C(O)—R$^{1a}$, —N(R$^{1a}$) C(S)—R$^{1a}$, —N(R$^{1a}$)—S(O)$_2$—R$^{1a}$, —S(O)—R$^{1a}$, —S(O)$_2$—R$^{1a}$, cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —O—R$^{1a}$, —S—R$^{1a}$, —N(R$^{1a}$)—R$^{1a}$, —C(O)—R$^{1a}$, —C(S)—R$^{1a}$, —C(O)—O—R$^{1a}$, —C(O)—N(R$^{1a}$)—R$^{1a}$, —C(S)—N(R$^{1a}$)—R$^{1a}$, —S(O)$_2$—N(R$^{1a}$)—R$^{1a}$, —N(R$^{1a}$)—C(O)—R$^{1a}$, —N(R$^{1a}$)—C(S)—R$^{1a}$, —N(R$^{1a}$)—S(O)$_2$—R$^{1a}$, —S(O)—R$^{1a}$, —S(O)$_2$—R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$; and all occurrences of optionally substituted cycloalkyl, optionally substituted heterocycloalkyl, optionally substituted 5-7 membered heterocycloalkyl, optionally substituted aryl, optionally substituted heteroaryl, or optionally substituted 5 or 7 membered nitrogen containing heteroaryl are optionally substituted with one or more, also 1, 2, or 3 groups or substituents selected from the group consisting of halogen, —CN, —O—R$^{1a}$, —S—R$^{1a}$, —N(R$^{1a}$)—R$^{1a}$, —C(O)—R$^{1a}$, —C(S)—R$^{1a}$, —C(O)—O—R$^{1a}$, —C(O)—N(R$^{1a}$)—R$^{1a}$, —C(S)—N(R$^{1a}$)—R$^{1a}$, —S(O)$_2$—N(R$^{1a}$)—R$^{1a}$, —N(R$^{1a}$)—C(O)—R$^{1a}$, —N(R$^{1a}$)—C(S)—R$^{1a}$, —N(R$^{1a}$) S(O)$_2$—R$^{1a}$, —S(O)—R$^{1a}$, —S(O)$_2$—R$^{1a}$, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$; wherein R$^{1a}$ is selected from the group consisting of hydrogen, —R$^{1b}$, and lower alkyl optionally substituted with one or more, also 1, 2 or 3 groups or substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, and —R$^{1b}$, and wherein —R$^{1b}$ is selected from the group consisting of cycloalkyl, heterocycloalkyl, aryl and heteroaryl, wherein cycloalkyl, heterocycloalkyl, aryl and heteroaryl are optionally substituted with one or more, also 1, 2 or 3 groups or substituents selected from the group consisting of halogen, —CN, —OH, —NH$_2$, lower alkoxy, fluoro substituted lower alkoxy, lower alkylthio, fluoro substituted lower alkylthio, mono-alkylamino, di-alkylamino, and cycloalkylamino.

As used herein, "lower alkoxy" denotes the group —OR$^z$, where R$^z$ is lower alkyl. "Substituted lower alkoxy" denotes lower alkoxy in which R$^z$ is lower alkyl substituted with one or more substituents as indicated herein, for example, in the description of compounds of Formula I, including descriptions of substituted cycloalkyl, heterocycloalkyl, aryl and heteroaryl, attached at any available atom to provide a stable compound. In some embodiments, substitution of lower alkoxy is with 1, 2, 3, 4, or 5 substituents, also 1, 2, or 3 substituents. For example, "fluoro substituted lower alkoxy" denotes lower alkoxy in which the lower alkyl is substituted with one or more fluoro atoms, where in some embodiments, the lower alkoxy is substituted with 1, 2, 3, 4 or 5 fluoro atoms, also 1, 2, or 3 fluoro atoms. It is understood that substitutions on alkoxy are chemically feasible and attached at any available atom to provide a stable compound.

It is understood that all possible substitutions as defined above include subsets of these substitutions, such as are indicated herein, for example, in the description of compounds of Formula I, attached at any available atom to produce a stable compound. For example, "fluoro substituted phenyl" denotes a phenyl group substituted with one or more fluoro atoms where, for example, the phenyl is substituted with 1, 2, 3, 4 or 5 fluoro atoms, e.g., 2,3,5,6-tetrafluorophenyl. It also is understood that any of the substitutions made according to the definitions above are chemically feasible and attached at any available atom to provide a stable compound.

It is to be understood that the compounds provided herein can contain chiral centers. Such chiral centers can be of either the (R) or (S) configuration, or can be a mixture thereof. Thus, the compounds provided herein can be enantiomerically pure, or be stereoisomeric or diastereomeric mixtures. As such, one of skill in the art will recognize that administration of a compound in its (R) form is equivalent, for compounds that undergo epimerization in vivo, to administration of the compound in its (S) form.

As used herein, "substantially pure" means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers can be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

In certain embodiments, the compound used in the methods provided herein is "stereochemically pure." A stereochemically pure compound or has a level of stereochemical purity that would be recognized as "pure" by those of skill in the art. In certain embodiments, "stereochemically pure" designates a compound that is substantially free of alternate isomers. In particular embodiments, the compound is 85%, 90%, 91%, 92%, 93%, 94%, 95%, 96%, 97%, 98%, 99%, 99.5% or 99.9% free of other isomers.

The singular forms "a," "an," and "the" include plural references, unless the context clearly dictates otherwise.

As used herein "subject" is an animal, such as a mammal, including human, such as a patient.

As used herein, "biological activity" refers to the in vitro or in vivo activities of a compound, or physiological responses that result upon in vivo administration of a compound, composition or other mixture. Biological activity, thus, encompasses therapeutic effects and pharmacokinetic behavior of such compounds, compositions and mixtures. Biological activities can be observed in in vitro and in vitro systems designed to test for such activities.

As used herein, "pharmaceutically acceptable derivatives" of a compound include salts, esters, acetals, ketals, orthoesters, hemiacetals, hemiketals, acids, bases, solvates, hydrates or prodrugs thereof. Such derivatives can readily be prepared by those of skill in this art using known methods for such derivatization. The compounds produced can be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and inorganic salts, such as but not limited to, sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, mesylates, and fumarates. Pharmaceutically acceptable esters include, but are not limited to, alkyl, alkenyl, alkynyl, aryl, arylalkyl, and cycloalkyl esters of acidic groups, including, but not limited to, carboxylic acids, phosphoric acids, phosphinic acids, sulfonic acids, sulfinic acids and boronic acids. Pharmaceutically acceptable solvates and hydrates are complexes of a compound with one or more solvent or water molecules, or 1 to about 100, or 1 to about 10, or one to about 2, 3 or 4, solvent or water molecules. Exemplary prodrugs include those set forth in Rautio J, Meanwell N A, di L, Hageman M J. The expanding role of prodrugs in contemporary drug design and development. Nat Rev Drug Discov. 2018; 17(8):559-587, which is incorporated by reference in its entirety As used herein, "treatment" means any manner in which a disease or disorder, or one or more of the symptoms of a disease or disorder, are ameliorated or otherwise beneficially altered. Treatment also encompasses any pharmaceutical use of the compositions herein, such as use for treating cancer.

As used herein, "prevention" means any manner in which the risk of contracting a disease or disorder, or of experiencing one or more of the symptoms of a disease or disorder, is reduced. Such risk can be reduced by, for example, between about 5% to 100%, such as by about 5, 10, 15, 20, 25, 30, 35, 40, 45, 50, 55, 60, 65, 70, 75, 80, 85, 90, 95 or 100%.

As used herein, "amelioration" or "mitigation" of the symptoms of a particular disorder by administration of a particular compound or pharmaceutical composition are used interchangeably and refers to any lessening of the symptoms, whether permanent or temporary, lasting or transient that can be attributed to or associated with administration of the compound or composition.

As used herein, "complication" refers to a condition that develops in association with a condition or disease. The complication can be as a direct result caused by the condition or disease, or can be associated with the existence of the primary condition or disease. In some embodiments, the complications of a disease can be manifested as a symptom and, in those instances, the two terms are used interchangeably herein.

As used herein, and unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

As used herein, the term "in combination" refers to the use of more than one therapies (e.g., a caspase inhibitor and other agents). The use of the term "in combination" does not restrict the order in which therapies (e.g., a caspase inhibitor and other agents) are administered to a subject with a disorder. A first therapy (e.g., a caspase inhibitor and other agents) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of other therapy (e.g., a caspase inhibitor and other agents) to a subject with a disorder.

The term "parenteral" as used herein includes administration of a compound to a subject using subcutaneous, intracutaneous, intravenous, intramuscular, intraarticular, intrasynovial, intrasternal, intrathecal, intralesional and intracranial injection or infusion techniques.

As used herein, "selective inhibitor of caspase-1, caspase-4, and/or caspase-5" means the compounds provided herein binds to caspase-1, caspase-4, and/or caspase-5 more selectively than to caspase-3, caspase 6, and/or caspase 7. In certain embodiments, the compounds provided herein have at least 2-fold higher binding affinity for caspase-1 as compared to other caspases. In certain embodiments, the compounds provided herein have at least 5-fold, 10-fold, 50-fold, 100-fold, 1000-fold or higher binding affinity for caspase-1, caspase-4, and/or caspase-5 as compared to caspase-3, caspase 6, and/or caspase 7.

The term "about," as used herein, unless otherwise indicated, refers to a value that is no more than 10% above or below the value being modified by the term. For example, the term "about 10 mg" means a range of from 9 mg to 11 mg.

As used herein, the abbreviations for any protective groups, amino acids and other compounds, are, unless indicated otherwise, in accord with their common usage, recognized abbreviations, or the IUPAC IUB Commission on Biochemical Nomenclature (see, Biochem. 1972, 11:942 944).

6.2. Caspase Inhibitor Compounds

In one embodiment, provided herein is a compound of Formula I:

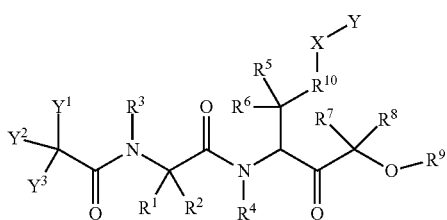

or an enantiomer or a mixture of enantiomers thereof, or a pharmaceutically acceptable salt, solvate, hydrate, co-crystal, clathrate, or polymorph thereof;
wherein
X and Y are selected as follows:
i) X is C=O; and Y is alkyl, cycloalkyl, heterocyclyl, aryl, heteroaryl, —$R^aOR^b$, or —$R^aN(R^c)(R^d)$, each of which is optionally substituted; or
ii) X is —O—, or —N($R^c$)—; Y is hydrogen, —C(O)$R^d$, optionally substituted alkyl, optionally substituted cycloalkyl, optionally substituted heterocyclyl, optionally substituted aryl, optionally substituted heteroaryl;
$R^3$, $Y^1$, $Y^2$ and $Y^3$ are selected as follows:
i) $Y^1$ together with $R^3$ forms an optionally substituted saturated or unsaturated bicyclic ring B;
$Y^2$ is absent, hydrogen or optionally substituted alkyl; and
$Y^3$ is absent, hydrogen or optionally substituted alkyl; or
ii) $R^3$ is hydrogen or optionally substituted alkyl; $Y^1$ and $Y^2$ together are =O; and $Y^3$ is —N($Z^1$)($Z^2$);
X, Y, $R^3$ and $Y^1$ are selected such that when X is O, then $Y^1$ and $R^3$ cannot form ring B;
each $R^a$ is independently alkylene or a direct bond;
$R^b$ is hydrogen, optionally substituted alkyl, optionally substituted haloalkyl, optionally substituted hydroxyalkyl, optionally substituted alkoxyalkyl, optionally substituted cycloalkyl, optionally substituted aryl, optionally substituted heteroaryl or optionally substituted heterocyclyl;
each $R^c$ is independently hydrogen or optionally substituted alkyl;
each $R^d$ is independently alkyl, aryl, cycloalkyl, heteroaryl, heterocyclyl or —$R^aOR^b$, each of which is optionally substituted;
$R^1$ and $R^2$ are selected as follows:
i) $R^1$ and $R^2$ are each independently hydrogen, optionally substituted alkyl or optionally substituted cycloalkyl; or
ii) $R^1$ and $R^2$ together with the carbon atom on which they are substituted form an optionally substituted saturated or unsaturated ring A;
$R^4$, $R^5$, $R^6$, $R^7$ and $R^8$ are each independently hydrogen or optionally substituted alkyl;
$R^9$ is aryl or heteroaryl, each optionally substituted;
$R^{10}$ is alkylene;
$Z^1$ and $Z^2$ are selected as follows:
i) $Z^1$ is hydrogen or optionally substituted alkyl; and $Z^2$ is aryl, cycloalkyl, heteroaryl or heterocyclyl, each optionally substituted; or
ii) $Z^1$ and $Z^2$ together with the nitrogen atom on which they are substituted form an optionally substituted saturated or unsaturated ring C.

In one embodiment, provided herein is a compound of Formula I or an enantiomer or a mixture of enantiomers thereof, or a pharmaceutically acceptable salt, solvate, hydrate, co-crystal, clathrate, or polymorph thereof;
wherein
X and Y are selected as follows:
i) X is C=O; and Y is alkyl, cycloalkyl, heterocyclyl, aryl, heteroaryl, —$R^aOR^b$, or —$R^aN(R^c)(R^d)$; or
ii) X is —O—, or —N($R^c$)—; Y is hydrogen, —C(O)$R^d$, alkyl, cycloalkyl, heterocyclyl, aryl, heteroaryl;
Y is optionally substituted with one to three groups $Q^1$;
$R^3$, $Y^1$, $Y^2$ and $Y^3$ are selected as follows:
i) $Y^1$ together with $R^3$ forms an optionally substituted saturated or unsaturated bicyclic ring B, where substituents on ring B, when present, are selected from one to three groups $Q^1$;
$Y^2$ is absent, hydrogen or alkyl; and
$Y^3$ is absent, hydrogen or alkyl; or
ii) $R^3$ is hydrogen or alkyl; $Y^1$ and $Y^2$ together are =O; and $Y^3$ is —N($Z^1$)($Z^2$);
X, Y, $R^3$ and $Y^1$ are selected such that when X is O, then $Y^1$ and $R^3$ cannot form ring B; each $Q^1$ is independently alkyl, halo, haloalkyl, hydroxyl, alkoxy, cycloalkyl, heterocyclyl, aryl or heteroaryl; each $Q^1$ is optionally substituted with one to three groups $Q^2$;
each $Q^2$ is independently alkyl, halo, haloalkyl, aryl or haloaryl;
each $R^a$ is independently alkylene or a direct bond;
$R^b$ is hydrogen, alkyl, haloalkyl, hydroxyalkyl, alkoxyalkyl, cycloalkyl, aryl, heteroaryl or heterocyclyl;
each $R^c$ is independently hydrogen or alkyl;
each $R^d$ is independently alkyl, aryl, cycloalkyl, heteroaryl, heterocyclyl or —$R^aOR^b$; each $R^d$ is optionally substituted with one to three groups $Q^1$;
$R^1$ and $R^2$ are selected as follows:
i) $R^1$ and $R^2$ are each independently hydrogen, alkyl or cycloalkyl; or
ii) $R^1$ and $R^2$ together with the carbon atom on which they are substituted form an optionally substituted saturated or unsaturated ring A, where the substituents on ring A, when present, are selected from one to three groups $Q^1$;
$R^4$, $R^5$, $R^6$, $R^7$ and $R^8$ are each independently hydrogen or alkyl;
$R^9$ is aryl or heteroaryl, each optionally substituted with one to four substituents $Q^1$;
$R^{10}$ is alkylene;
$Z^1$ and $Z^2$ are selected as follows:
i) $Z^1$ is hydrogen or alkyl; and $Z^2$ is aryl, cycloalkyl, heteroaryl or heterocyclyl, each optionally substituted with one to four substituents $Q^3$; or
ii) $Z^1$ and $Z^2$ together with the nitrogen atom on which they are substituted form an optionally substituted saturated or unsaturated ring C, where the substituents on ring C, when present, are selected from one to three groups $Q^3$;

each $Q^3$ is independently selected from alkyl, halo, cyano, cycloalkyl, heterocyclyl, aryl, heteroaryl, —$R^{11}OR^{12}$, —$R^{11}OR^{11}OR^{12}$, —$R^{11}N(R^{13})(R^{14})$, —$R^{11}SR^{12}$, —$R^{11}OR^{11}N(R^{13})(R^{14})$, —$R^{11}C(J)N(R^{13})(R^{14})$, —$R^{11}OR^{11}C(J)N(R^{13})(R^{14})$, —$C(J)R^{15}$ and $R^{11}S(O)_tR^{16}$; where each $Q^3$ is optionally substituted with one to three groups $Q^4$, where each $Q^4$ is independently alkyl, halo, haloalkyl, hydroxyl, alkoxy or cycloalkyl;

each $R^{11}$ is independently alkylene, alkenylene or a direct bond;

each $R^{12}$ is independently hydrogen, alkyl, haloalkyl, hydroxyalkyl, alkoxyalkyl, cycloalkyl, aryl, heteroaryl or heterocyclyl;

$R^{13}$ and $R^{14}$ are selected as follows:
i) $R^{13}$ and $R^{14}$ are each independently hydrogen, alkyl, haloalkyl, hydroxyalkyl, alkoxyalkyl, cycloalkyl, aryl, heteroaryl or heterocyclyl; or
ii) $R^{13}$ and $R^{14}$ together with the nitrogen atom on which they are substituted form a 5 or 6-membered heterocyclyl or heteroaryl ring, optionally substituted with one or two alkyl, halo, haloalkyl, hydroxyl, alkoxy or cycloalkyl;

each $R^{15}$ is independently hydroxy, alkyl, haloalkyl, alkoxy, cycloalkyl, aryl, heteroaryl, or heterocyclyl;

each $R^{16}$ is independently hydrogen, alkyl, haloalkyl, hydroxyalkyl, alkoxyalkyl, cycloalkyl, aryl, heteroaryl or heterocyclyl;

J is O or S; and t is 0-2.

In one embodiment, provided herein is a compound of Formula I, or an enantiomer or a mixture of enantiomers thereof, or a pharmaceutically acceptable salt, solvate, hydrate, co-crystal, clathrate, or polymorph thereof, wherein X and Y are selected as follows:
i) X is C=O; and Y is —$R^aOR^b$; or
ii) X is —O—; Y is hydrogen, —C(O)$R^d$, alkyl or aryl; Y is optionally substituted with one to three groups $Q^1$;

$R^3$, $Y^1$, $Y^2$ and $Y^3$ are selected as follows:
i) $Y^1$ together with $R^3$ forms an optionally substituted saturated or unsaturated ring B, where substituents on ring B, when present, are selected from one to three groups $Q^3$;
$Y^2$ is absent, hydrogen or alkyl; and
$Y^3$ is absent, hydrogen or alkyl; or
ii) $R^3$ is hydrogen or alkyl; $Y^1$ and $Y^2$ together are =O; and $Y^3$ is —$N(Z^1)(Z^2)$;

X, Y, $R^3$ and $Y^1$ are selected such that when X is O, then $Y^1$ and $R^3$ cannot form ring B;

each $Q^1$ is independently alkyl, halo, haloalkyl, hydroxyl, alkoxy, cycloalkyl, heterocyclyl, aryl or heteroaryl; each $Q^1$ is optionally substituted with one to three groups $Q^2$; each $Q^2$ is independently alkyl, halo, haloalkyl, aryl or haloaryl;

$R^a$ is alkylene or a direct bond;

$R^b$ is hydrogen, alkyl or aryl;

$R^d$ is aryl or —$R^aOR^b$;

each $R^d$ is optionally substituted with one to three groups $Q^1$;

$R^1$ and $R^2$ are selected as follows:
i) $R^1$ and $R^2$ are each independently hydrogen or alkyl; or
ii) $R^1$ and $R^2$ together with the carbon atom on which they are substituted form a cycloalkyl ring;

$R^4$, $R^5$, $R^6$, $R^7$ and $R^8$ are each independently hydrogen or alkyl;

$R^9$ is aryl or heteroaryl, each optionally substituted with one to four substituents $Q^1$;

$R^{10}$ is alkylene;

$Z^1$ is hydrogen or alkyl;

$Z^2$ is aryl or heteroaryl, each optionally substituted with one to four substituents $Q^3$;

each $Q^3$ is independently selected from alkyl, haloalkyl, haloalkoxy, halo, cyano, aryl, heteroaryl, —$R^{11}OR^{12}$, —$C(O)R^{15}$ and —$R^{11}C(O)NH_2$;

each $R^{11}$ is independently alkylene or a direct bond;

$R^{12}$ is hydrogen, alkyl or haloalkyl; and $R^{15}$ is hydroxyl or alkyl.

In one embodiment, provided herein is a compound of Formula I, or an enantiomer or a mixture of enantiomers thereof, or a pharmaceutically acceptable salt, solvate, hydrate, co-crystal, clathrate, or polymorph thereof, wherein X and Y are selected as follows:
i) X is C=O; and Y is —$R^aOR^b$; or
ii) X is —O—; Y is hydrogen, alkyl, aryl, arylalkyl, heteroarylalkyl or —C(O)$R^d$; where the alkyl and aryl groups are optionally substituted with one or two groups selected from alkyl and halo;

$R^3$, $Y^1$, $Y^2$ and $Y^3$ are selected as follows:
i) $Y^1$ together with $R^3$ forms an optionally substituted saturated or unsaturated ring B, where substituents on ring B, when present, are selected from one to three groups $Q^3$;
$Y^2$ is absent, hydrogen or alkyl; and
$Y^3$ is absent, hydrogen or alkyl; or
ii) $R^3$ is hydrogen or alkyl; $Y^1$ and $Y^2$ together are =O; and $Y^3$ is —$N(Z^1)(Z^2)$;

X, Y, $R^3$ and $Y^1$ are selected such that when X is O, then $Y^1$ and $R^3$ cannot form ring B;

$R^a$ is alkylene or a direct bond;

$R^b$ is hydrogen, alkyl or aryl;

$R^d$ is aryl or aryloxy;

$R^1$ and $R^2$ are selected as follows:
i) $R^1$ and $R^2$ are each independently hydrogen or alkyl; or
ii) $R^1$ and $R^2$ together with the carbon atom on which they are substituted form a cycloalkyl ring;

$R^4$, $R^5$, $R^6$, $R^7$ and $R^8$ are each independently hydrogen or alkyl;

$R^9$ is aryl or heteroaryl, each optionally substituted with one to four substituents selected from halo, alkyl and haloalkyl;

$R^{10}$ is alkylene;

$Z^1$ is hydrogen or alkyl;

$Z^2$ is aryl or heteroaryl, each optionally substituted with one to four substituents $Q^3$;

each $Q^3$ is independently selected from alkyl, haloalkyl, haloalkoxy, halo, cyano, aryl, heteroaryl, —$R^{11}OR^{12}$, —$C(O)R^{15}$ and —$C(O)NH_2$;

$R^{11}$ is alkylene or a direct bond;

$R^{12}$ is hydrogen, alkyl or haloalkyl; and $R^{15}$ is hydroxyl or alkyl.

In one embodiment, provided herein is a compound of Formula II:

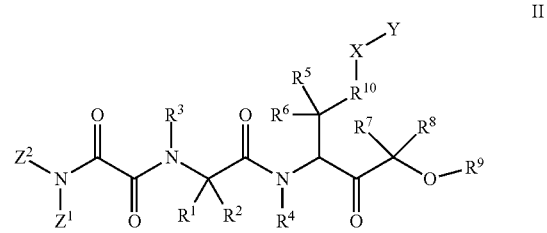

or an enantiomer or a mixture of enantiomers thereof, or a pharmaceutically acceptable salt, solvate, hydrate, co-crystal, clathrate, or polymorph thereof, wherein X and Y are selected as follows:
i) X is C=O; and Y is alkyl, cycloalkyl, heterocyclyl, aryl, heteroaryl, —$R^aOR^b$, or —$R^aN(R^c)(R^d)$; or
ii) X is —O—, or —N($R^c$)—; Y is hydrogen, —C(O)$R^d$, alkyl, cycloalkyl, heterocyclyl, aryl or heteroaryl;

Y is optionally substituted with one to three groups $Q^1$;

each $Q^1$ is independently alkyl, halo, haloalkyl, hydroxyl, alkoxy, cycloalkyl, heterocyclyl, aryl or heteroaryl; each $Q^1$ is optionally substituted with one to three groups $Q^2$;

each $Q^2$ is independently alkyl, halo, haloalkyl, aryl or haloaryl;

each $R^a$ is independently alkylene or a direct bond;

$R^b$ is hydrogen, alkyl, haloalkyl, hydroxyalkyl, alkoxyalkyl, cycloalkyl, aryl, heteroaryl or heterocyclyl;

each $R^c$ is independently hydrogen or alkyl;

each $R^d$ is independently alkyl, aryl, cycloalkyl, heteroaryl, heterocyclyl or —$R^aOR^b$;

each $R^d$ is optionally substituted with one to three groups $Q^1$;

$R^1$ and $R^2$ are selected as follows:
i) $R^1$ and $R^2$ are each independently hydrogen, alkyl or cycloalkyl; or
ii) $R^1$ and $R^2$ together with the carbon atom on which they are substituted form an optionally substituted saturated or unsaturated ring A, where substituents on ring A, when present, are selected from one to three groups $Q^1$;

$R^3$, $R^4$, $R^5$, $R^6$, $R^7$ and $R^8$ are each independently hydrogen or alkyl;

$R^9$ is aryl or heteroaryl, each optionally substituted with one to four substituents $Q^1$;

$R^{10}$ is alkylene;

$Z^1$ and $Z^2$ are selected as follows:
i) $Z^1$ is hydrogen or alkyl; and $Z^2$ is aryl, cycloalkyl, heteroaryl or heterocyclyl, each optionally substituted with one to four substituents $Q^3$; or
ii) $Z^1$ and $Z^2$ together with the nitrogen atom on which they are substituted form an optionally substituted saturated or unsaturated ring C, where the substituents on ring C, when present, are selected from one to three groups $Q^3$;

each $Q^3$ is independently selected from alkyl, halo, cyano, cycloalkyl, heterocyclyl, aryl, heteroaryl, —$R^{11}OR^{12}$, —$R^{11}OR^{11}OR^{12}$, —$R^{11}N(R^{13})(R^{14})$, —$R^{11}SR^{12}$, —$R^{11}OR^{11}N(R^{13})(R^{14})$, —$R^{11}C(J)N(R^{13})(R^{14})$, —$R^{11}OR^{11}C(J)N(R^{13})(R^{14})$, —C(J)$R^{15}$ and $R^{11}S(O)_tR^{16}$; where each $Q^3$ is optionally substituted with one to three groups $Q^4$, where each $Q^4$ is independently alkyl, halo, haloalkyl, hydroxyl, alkoxy or cycloalkyl;

each $R^{11}$ is independently alkylene, alkenylene or a direct bond;

each $R^{12}$ is independently hydrogen, alkyl, haloalkyl, hydroxyalkyl, alkoxyalkyl, cycloalkyl, aryl, heteroaryl or heterocyclyl;

$R^{13}$ and $R^{14}$ are selected as follows:
i) $R^{13}$ and $R^{14}$ are each independently hydrogen, alkyl, haloalkyl, hydroxyalkyl, alkoxyalkyl, cycloalkyl, aryl, heteroaryl or heterocyclyl; or
ii) $R^{13}$ and $R^{14}$ together with the nitrogen atom on which they are substituted form a 5 or 6-membered heterocyclyl or heteroaryl ring, optionally substituted with one or two alkyl, halo, haloalkyl, hydroxyl, alkoxy or cycloalkyl;

each $R^{15}$ is independently hydroxy, alkyl, haloalkyl, alkoxy, cycloalkyl, aryl, heteroaryl, or heterocyclyl;

each $R^{16}$ is independently hydrogen, alkyl, haloalkyl, hydroxyalkyl, alkoxyalkyl, cycloalkyl, aryl, heteroaryl or heterocyclyl;

J is O or S; and t is 0-2.

In one embodiment, provided herein is a compound of Formula II or an enantiomer or a mixture of enantiomers thereof, or a pharmaceutically acceptable salt, solvate, hydrate, co-crystal, clathrate, or polymorph thereof;

wherein

X and Y are selected as follows:
i) X is C=O; and Y is alkyl, cycloalkyl, heterocyclyl, aryl, heteroaryl, —$R^aOR^b$, or —$R^aN(R^c)(R^d)$; or
ii) X is —O—, or —N($R^c$)—; Y is hydrogen, —C(O)$R^d$, alkyl, cycloalkyl, heterocyclyl, aryl or heteroaryl;

Y is optionally substituted with one to three groups $Q^1$;

each $Q^1$ is independently alkyl, halo, haloalkyl, hydroxyl, alkoxy, cycloalkyl, heterocyclyl, aryl, heteroaryl; each $Q^1$ is optionally substituted with one to three groups $Q^2$;

each $Q^2$ is independently alkyl, halo, haloalkyl, aryl or haloaryl;

each $R^a$ is independently alkylene or a direct bond;

$R^b$ is hydrogen, alkyl, haloalkyl, hydroxyalkyl, alkoxyalkyl, cycloalkyl, aryl, heteroaryl or heterocyclyl;

each $R^c$ is independently hydrogen or alkyl;

each $R^d$ is independently alkyl, aryl, cycloalkyl, heteroaryl, heterocyclyl or —$R^aOR^b$;

each $R^d$ is optionally substituted with one to three groups $Q^1$;

$R^1$ and $R^2$ are selected as follows:
i) $R^1$ and $R^2$ are each independently hydrogen, alkyl or cycloalkyl; or
ii) $R^1$ and $R^2$ together with the carbon atom on which they are substituted form an optionally substituted saturated or unsaturated ring A, where substituents on ring A, when present, are selected from one to three groups $Q^1$;

$R^3$, $R^4$, $R^5$, $R^6$, $R^7$ and $R^8$ are each independently hydrogen or alkyl;

$R^9$ is aryl or heteroaryl, each optionally substituted with one to four substituents $Q^1$;

$R^{10}$ is alkylene;

$Z^1$ is hydrogen or alkyl;

$Z^2$ is aryl, cycloalkyl, heteroaryl or heterocyclyl, each optionally substituted with one to four substituents $Q^3$;

each $Q^3$ is independently selected from alkyl, halo, cyano, cycloalkyl, heterocyclyl, aryl, heteroaryl, —$R^{11}OR^{12}$, —$R^{11}OR^{11}OR^{12}$, —$R^{11}N(R^{13})(R^{14})$, —$R^{11}SR^{12}$, —$R^{11}OR^{11}N(R^{13})(R^{14})$, —$R^{11}C(J)N(R^{13})(R^{14})$, —$R^{11}OR^{11}C(J)N(R^{13})(R^{14})$, —C(J)$R^{15}$ and $R^{11}S(O)_tR^{16}$; where each $Q^3$ is optionally substituted with one to three groups $Q^4$, where each $Q^4$ is independently alkyl, halo, haloalkyl, hydroxyl, alkoxy or cycloalkyl;

each $R^{11}$ is independently alkylene, alkenylene or a direct bond;

each $R^{12}$ is independently hydrogen, alkyl, haloalkyl, hydroxyalkyl, alkoxyalkyl, cycloalkyl, aryl, heteroaryl or heterocyclyl;

$R^{13}$ and $R^{14}$ are selected as follows:
i) $R^{13}$ and $R^{14}$ are each independently hydrogen, alkyl, haloalkyl, hydroxyalkyl, alkoxyalkyl, cycloalkyl, aryl, heteroaryl or heterocyclyl; or
ii) $R^{13}$ and $R^{14}$ together with the nitrogen atom on which they are substituted form a 5 or 6-membered heterocyclyl or heteroaryl ring, optionally substituted with one or two alkyl, halo, haloalkyl, hydroxyl, alkoxy or cycloalkyl;
each $R^{15}$ is independently hydroxy, alkyl, haloalkyl, alkoxy, cycloalkyl, aryl, heteroaryl, or heterocyclyl;
each $R^{16}$ is independently hydrogen, alkyl, haloalkyl, hydroxyalkyl, alkoxyalkyl, cycloalkyl, aryl, heteroaryl or heterocyclyl;
J is O or S; and
t is 0-2.

In one embodiment, provided herein is a compound of Formula II, or an enantiomer or a mixture of enantiomers thereof, or a pharmaceutically acceptable salt, solvate, hydrate, co-crystal, clathrate, or polymorph thereof, wherein
X and Y are selected as follows:
i) X is C=O; and Y is —$R^aOR^b$; or
ii) X is —O—; Y is hydrogen, —C(O)$R^d$, alkyl or aryl;
Y is optionally substituted with one to three groups $Q^1$;
each $Q^1$ is independently alkyl, halo, haloalkyl, hydroxyl, alkoxy, cycloalkyl, heterocyclyl, aryl or heteroaryl;
each $Q^1$ is optionally substituted with one to three groups $Q^2$; each $Q^2$ is independently alkyl, halo, haloalkyl, aryl or haloaryl;
each $R^a$ is independently alkylene or a direct bond;
each $R^b$ is independently hydrogen, alkyl or aryl;
$R^d$ is aryl or —$R^aOR^b$;
each $R^d$ is optionally substituted with one to three groups $Q^1$;
$R^1$ and $R^2$ are selected as follows:
i) $R^1$ and $R^2$ are each independently hydrogen or alkyl; or
ii) $R^1$ and $R^2$ together with the carbon atom on which they are substituted form a cycloalkyl ring;
$R^3$, $R^4$, $R^5$, $R^6$, $R^7$ and $R^8$ are each independently hydrogen or alkyl;
$R^9$ is aryl or heteroaryl, each optionally substituted with one to four substituents $Q^1$;
$R^{10}$ is alkylene;
$Z^1$ is hydrogen or alkyl;
$Z^2$ is aryl or heteroaryl, each optionally substituted with one to four substituents $Q^3$;
each $Q^3$ is independently selected from alkyl, haloalkyl, haloalkoxy, halo, cyano, aryl, heteroaryl, —$R^{11}OR^{12}$, —C(O)$R^{15}$ and —$R^{11}$C(O)NH$_2$;
each $R^{11}$ is independently alkylene or a direct bond;
$R^{12}$ is hydrogen, alkyl or haloalkyl; and
$R^{15}$ is hydroxyl or alkyl.

In one embodiment, provided herein is a compound of Formula II, or an enantiomer or a mixture of enantiomers thereof, or a pharmaceutically acceptable salt, solvate, hydrate, co-crystal, clathrate, or polymorph thereof, wherein
X and Y are selected as follows:
i) X is C=O; and Y is —$R^aOR^b$; or
ii) X is —O—; Y is hydrogen, alkyl, aryl, arylalkyl, heteroarylalkyl or —C(O)$R^d$; where the alkyl and aryl groups are optionally substituted with one or two groups selected from alkyl and halo;
$R^a$ is alkylene or a direct bond;
$R^b$ is hydrogen, alkyl or aryl;
$R^d$ is aryl or aryloxy;
$R^1$ and $R^2$ are selected as follows:
i) $R^1$ and $R^2$ are each independently hydrogen or alkyl; or
ii) $R^1$ and $R^2$ together with the carbon atom on which they are substituted form a cycloalkyl ring;
$R^3$, $R^4$, $R^5$, $R^6$, $R^7$ and $R^8$ are each independently hydrogen or alkyl;

$R^9$ is aryl or heteroaryl, each optionally substituted with one to four substituents selected from halo, alkyl and haloalkyl;
$R^{10}$ is alkylene;
$Z^1$ is hydrogen or alkyl;
$Z^2$ is aryl or heteroaryl, each optionally substituted with one to four substituents $Q^3$;
each $Q^3$ is independently selected from alkyl, haloalkyl, haloalkoxy, halo, cyano, aryl, heteroaryl, —$R^{11}OR^{12}$, —C(O)$R^{15}$ and —C(O)NH$_2$;
each $R^{11}$ is independently alkylene or a direct bond;
$R^{12}$ is hydrogen, alkyl or haloalkyl; and
$R^{15}$ is hydroxyl or alkyl.

In one embodiment, provided herein is a compound of Formula III $$\text{III}$$

or an enantiomer or a mixture of enantiomers thereof, or a pharmaceutically acceptable salt, solvate, hydrate, co-crystal, clathrate, or polymorph thereof,
wherein
X and Y are selected as follows:
i) X is C=O; and Y is alkyl, cycloalkyl, heterocyclyl, aryl, heteroaryl, —$R^aOR^b$, or —$R^aN(R^c)(R^d)$; or
ii) X is —O—, or —N($R^c$)—; Y is hydrogen, —C(O)$R^d$, alkyl, cycloalkyl, heterocyclyl, aryl or heteroaryl;
Y is optionally substituted with one to three groups $Q^1$;
each $Q^1$ is independently alkyl, halo, haloalkyl, hydroxyl, alkoxy, cycloalkyl, heterocyclyl, aryl or heteroaryl;
each $Q^1$ is optionally substituted with one to three groups $Q^2$; each $Q^2$ is independently alkyl, halo, haloalkyl, aryl or haloaryl;
each $R^a$ is independently alkylene or a direct bond;
$R^b$ is hydrogen, alkyl, haloalkyl, hydroxyalkyl, alkoxyalkyl, cycloalkyl, aryl, heteroaryl or heterocyclyl;
each $R^c$ is independently hydrogen or alkyl;
each $R^d$ is independently alkyl, aryl, cycloalkyl, heteroaryl, heterocyclyl or —$R^aOR^b$;
each $R^d$ is optionally substituted with one to three groups $Q^1$;
$R^1$ and $R^2$ are selected as follows:
i) $R^1$ and $R^2$ are each independently hydrogen, alkyl or cycloalkyl; or
ii) $R^1$ and $R^2$ together with the carbon atom on which they are substituted form an optionally substituted saturated or unsaturated ring A, where substituents on ring A, when present, are selected from one to three groups $Q^1$;
$R^3$, $R^4$, $R^5$, $R^6$, $R^7$ and $R^8$ are each independently hydrogen or alkyl;
$R^{10}$ is alkylene;
each $Q^5$ is independently alkyl, halo or haloalkyl;
$Z^1$ is hydrogen or alkyl;
$Z^2$ is aryl, cycloalkyl, heteroaryl or heterocyclyl, each optionally substituted with one to four substituents $Q^3$;
each $Q^3$ is independently selected from alkyl, halo, cyano, cycloalkyl, heterocyclyl, aryl, heteroaryl, —$R^{11}OR^{12}$, —$R^{11}OR^{11}OR^{12}$, —$R^{11}N(R^{13})(R^{14})$, —$R^{11}SR^{12}$, —$R^{11}OR^{11}N(R^{13})(R^{14})$, —$R^{11}C(J)N(R^{13})(R^{14})$, —$R^{11}OR^{11}C(J)N(R^{13})(R^{14})$, —$C(J)R^{15}$ and $R^{11}S(O)_tR^{16}$; where each $Q^3$ is optionally substituted with one to three groups $Q^4$, where each $Q^4$ is independently alkyl, halo, haloalkyl, hydroxyl, alkoxy or cycloalkyl;

each $R^{11}$ is independently alkylene, alkenylene or a direct bond;

each $R^{12}$ is independently hydrogen, alkyl, haloalkyl, hydroxyalkyl, alkoxyalkyl, cycloalkyl, aryl, heteroaryl or heterocyclyl;

$R^{13}$ and $R^{14}$ are selected as follows:
i) $R^{13}$ and $R^{14}$ are each independently hydrogen, alkyl, haloalkyl, hydroxyalkyl, alkoxyalkyl, cycloalkyl, aryl, heteroaryl or heterocyclyl; or
ii) $R^{13}$ and $R^{14}$ together with the nitrogen atom on which they are substituted form a 5 or 6-membered heterocyclyl or heteroaryl ring, optionally substituted with one or two alkyl, halo, haloalkyl, hydroxyl, alkoxy or cycloalkyl;

each $R^{15}$ is independently hydroxy, alkyl, haloalkyl, alkoxy, cycloalkyl, aryl, heteroaryl, or heterocyclyl;

each $R^{16}$ is independently hydrogen, alkyl, haloalkyl, hydroxyalkyl, alkoxyalkyl, cycloalkyl, aryl, heteroaryl or heterocyclyl;

J is O or S;

t is 0-2; and m is 0-4.

In one embodiment, provided herein is a compound of Formula III, or an enantiomer or a mixture of enantiomers thereof, or a pharmaceutically acceptable salt, solvate, hydrate, co-crystal, clathrate, or polymorph thereof, wherein X and Y are selected as follows:
i) X is C=O; and Y is —$R^aOR^b$; or
ii) X is —O—; Y is hydrogen, alkyl, aryl, arylalkyl, heteroarylalkyl or —$C(O)R^d$; where the alkyl and aryl groups are optionally substituted with one or two groups selected from alkyl and halo;

$R^a$ is alkylene or a direct bond;

$R^b$ is hydrogen, alkyl or aryl;

each $R^d$ is independently aryl or aryloxy;

$R^1$ and $R^2$ are selected as follows:
i) $R^1$ and $R^2$ are each independently hydrogen or alkyl; or
ii) $R^1$ and $R^2$ together with the carbon atom on which they are substituted form a cycloalkyl ring;

$R^3$, $R^4$, $R^5$, $R^6$, $R^7$ and $R^8$ are each independently hydrogen or alkyl;

$Q^1$ is selected from halo, alkyl and haloalkyl;

m is 0-4;

$R^{10}$ is alkylene;

$Z^1$ is hydrogen or alkyl;

$Z^2$ is aryl or heteroaryl, each optionally substituted with one to four substituents $Q^3$;

each $Q^3$ is independently selected from alkyl, haloalkyl, haloalkoxy, halo, cyano, aryl, heteroaryl, —$R^{11}OR^{12}$, —$C(O)R^{15}$ and —$C(O)NH_2$;

$R^{11}$ is alkylene or a direct bond;

$R^{12}$ is hydrogen, alkyl or haloalkyl; and $R^{15}$ is hydroxyl or alkyl.

In one embodiment, provided herein is a compound of Formula III, or an enantiomer or a mixture of enantiomers thereof, or a pharmaceutically acceptable salt, solvate, hydrate, co-crystal, clathrate, or polymorph thereof, wherein X and Y are selected as follows:
i) X is C=O; and Y is —$R^aOR^b$; or
ii) X is —O—; Y is hydrogen, alkyl, aryl, arylalkyl, heteroarylalkyl or —$C(O)R^d$; where the alkyl and aryl groups are optionally substituted with one or two groups selected from alkyl and halo;

$R^a$ is alkylene or a direct bond;

$R^b$ is hydrogen, alkyl or aryl;

$R^d$ is aryl or aryloxy;

$R^1$ and $R^2$ are selected as follows:
i) $R^1$ and $R^2$ are each independently hydrogen or alkyl; or
ii) $R^1$ and $R^2$ together with the carbon atom on which they are substituted form a cycloalkyl ring;

$R^3$, $R^4$, $R^5$, $R^6$, $R^7$ and $R^8$ are hydrogen;

$Q^1$ is selected from halo, alkyl and haloalkyl;

m is 0-4;

$R^{10}$ is alkylene;

$R^3$, $Y^1$, $Y^2$ and $Y^3$ are selected as follows:
i) $Y^1$ together with $R^3$ forms an optionally substituted saturated or unsaturated ring B, where substituents on ring B, when present, are selected from one to three groups $Q^1$;
$Y^2$ is absent, hydrogen or alkyl; and
$Y^3$ is absent, hydrogen or alkyl; or
ii) $R^3$ is hydrogen or alkyl; $Y^1$ and $Y^2$ together are =O; and $Y^3$ is —$N(Z^1)(Z^2)$;

$Z^1$ is hydrogen or alkyl;

$Z^2$ is aryl or heteroaryl, each optionally substituted with one to four substituents $Q^3$;

each $Q^3$ is independently selected from alkyl, haloalkyl, haloalkoxy, halo, cyano, aryl, heteroaryl, —$R^{11}OR^{12}$, —$C(O)R^{15}$ and —$C(O)NH_2$;

$R^{11}$ is alkylene or a direct bond;

$R^{12}$ is hydrogen, alkyl or haloalkyl; and $R^{15}$ is hydroxyl or alkyl.

In one embodiment, provided herein is a compound of Formula IV

IV or an enantiomer or a mixture of enantiomers thereof, or a pharmaceutically acceptable salt, solvate, hydrate, co-crystal, clathrate, or polymorph thereof, wherein X and Y are selected as follows:
i) X is C=O; and Y is —$R^aOR^b$; or
ii) X is —O—; Y is hydrogen, alkyl, aryl, arylalkyl, heteroarylalkyl or —$C(O)R^d$; where the alkyl and aryl groups are optionally substituted with one or two groups selected from alkyl and halo;

$R^a$ is alkylene or a direct bond;

$R^b$ is hydrogen, alkyl or aryl;

$R^d$ is aryl or aryloxy;

$R^1$ and $R^2$ are selected as follows:
i) $R^1$ and $R^2$ are each independently hydrogen or alkyl; or
ii) $R^1$ and $R^2$ together with the carbon atom on which they are substituted form a cycloalkyl ring;

$R^3$, $R^4$, $R^5$, $R^6$, $R^7$ are hydrogen;

$Q^5$ is selected from halo, alkyl and haloalkyl;

p is 0-3;

$R^{10}$ is alkylene;

$Z^1$ is hydrogen or alkyl;

$Z^2$ is aryl or heteroaryl, each optionally substituted with one to four substituents $Q^3$;

each $Q^3$ is independently selected from alkyl, haloalkyl, haloalkoxy, halo, cyano, aryl, heteroaryl, —$R^{11}OR^{12}$, —$C(O)R^{15}$ and —$C(O)NH_2$;

$R^{11}$ is alkylene or a direct bond;

$R^{12}$ is hydrogen, alkyl or haloalkyl; and $R^{15}$ is hydroxyl or alkyl.

In one embodiment, provided herein is a compound of Formula V:

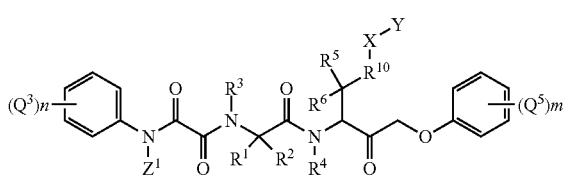

V or an enantiomer or a mixture of enantiomers thereof, or a pharmaceutically acceptable salt, solvate, hydrate, co-crystal, clathrate, or polymorph thereof, wherein X and Y are selected as follows:

i) X is C=O; and Y is alkyl, cycloalkyl, heterocyclyl, aryl, heteroaryl, —$R^aOR^b$, or —$R^aN(R^c)(R^d)$; or ii) X is —O—, or —N($R^c$)—; Y is hydrogen, —$C(O)R^d$, alkyl, cycloalkyl, heterocyclyl, aryl or heteroaryl;

Y is optionally substituted with one to three groups $Q^1$;

each $Q^1$ is independently alkyl, halo, haloalkyl, hydroxyl, alkoxy, cycloalkyl, heterocyclyl, aryl or heteroaryl; each $Q^1$ is optionally substituted with one to three groups $Q^2$; each $Q^2$ is independently alkyl, halo, haloalkyl, aryl or haloaryl;

each $R^a$ is independently alkylene or a direct bond;

$R^b$ is hydrogen, alkyl, haloalkyl, hydroxyalkyl, alkoxyalkyl, cycloalkyl, aryl, heteroaryl or heterocyclyl;

each $R^c$ is independently hydrogen or alkyl;

each $R^d$ is independently alkyl, aryl, cycloalkyl, heteroaryl, heterocyclyl or —$R^aOR^b$; each $R^d$ is optionally substituted with one to three groups $Q^1$;

$R^1$ and $R^2$ are selected as follows:

i) $R^1$ and $R^2$ are each independently hydrogen, alkyl or cycloalkyl; or ii) $R^1$ and $R^2$ together with the carbon atom on which they are substituted form an optionally substituted saturated or unsaturated ring A, where the substituents on ring A, when present, are selected from one to three groups $Q^1$;

$R^3$, $R^4$, $R^5$, $R^6$, $R^7$ and $R^8$ are each independently hydrogen or alkyl;

$R^{10}$ is alkylene;

each $Q^3$ is independently selected from alkyl, halo, cyano, cycloalkyl, heterocyclyl, aryl, heteroaryl, —$R^{11}OR^{12}$, —$R^{11}OR^{11}OR^{12}$, —$R^{11}N(R^{13})(R^{14})$, —$R^{11}SR^{12}$, —$R^{11}OR^{11}N(R^{13})(R^{14})$, —$R^{11}C(J)N(R^{13})(R^{14})$, —$R^{11}OR^{11}C(J)N(R^{13})(R^{14})$, —$C(J)R^{15}$ and $R^{11}S(O)_tR^{16}$; where each $Q^3$ is optionally substituted with one to three groups $Q^4$, where each $Q^4$ is independently alkyl, halo, haloalkyl, hydroxyl, alkoxy or cycloalkyl;

each $R^{11}$ is independently alkylene, alkenylene or a direct bond;

each $R^{12}$ is independently hydrogen, alkyl, haloalkyl, hydroxyalkyl, alkoxyalkyl, cycloalkyl, aryl, heteroaryl or heterocyclyl;

$R^{13}$ and $R^{14}$ are selected as follows:

i) $R^{13}$ and $R^{14}$ are each independently hydrogen, alkyl, haloalkyl, hydroxyalkyl, alkoxyalkyl, cycloalkyl, aryl, heteroaryl or heterocyclyl; or ii) $R^{13}$ and $R^{14}$ together with the nitrogen atom on which they are substituted form a 5 or 6-membered heterocyclyl or heteroaryl ring, optionally substituted with one or two alkyl, halo, haloalkyl, hydroxyl, alkoxy or cycloalkyl;

each $R^{15}$ is independently hydroxy, alkyl, haloalkyl, alkoxy, cycloalkyl, aryl, heteroaryl, or heterocyclyl;

each $R^{16}$ is independently hydrogen, alkyl, haloalkyl, hydroxyalkyl, alkoxyalkyl, cycloalkyl, aryl, heteroaryl or heterocyclyl;

each $Q^5$ is independently alkyl, halo or haloalkyl;

J is O or S;

t is 0-2;

m is 0-4; and n is 0-3.

In one embodiment, provided herein is a compound of Formula V, or an enantiomer or a mixture of enantiomers thereof, or a pharmaceutically acceptable salt, solvate, hydrate, co-crystal, clathrate, or polymorph thereof, wherein X and Y are selected as follows:

i) X is C=O; and Y is —$R^aOR$; or ii) X is —O—; Y is hydrogen, alkyl, aryl, arylalkyl, heteroarylalkyl or —$C(O)R^d$; where the alkyl and aryl groups are optionally substituted with one or two groups selected from alkyl and halo;

$R^a$ is alkylene or a direct bond;

$R^b$ is hydrogen, alkyl or aryl;

$R^d$ is aryl or aryloxy;

$R^1$ and $R^2$ are selected as follows:

i) $R^1$ and $R^2$ are each independently hydrogen or alkyl; or ii) $R^1$ and $R^2$ together with the carbon atom on which they are substituted form a cycloalkyl ring;

$R^3$, $R^4$, $R^5$, $R^6$, $R^7$ and $R^8$ are each independently hydrogen or alkyl;

$R^{10}$ is alkylene;

$Z^1$ is hydrogen or alkyl;

each $Q^3$ is independently selected from alkyl, haloalkyl, haloalkoxy, halo, cyano, aryl, heteroaryl, —$R^{11}OR^{12}$, —$C(O)R^{15}$ and —$C(O)NH_2$;

each $R^{11}$ is independently alkylene or a direct bond;

$R^{12}$ is hydrogen, alkyl or haloalkyl;

$R^{15}$ is hydroxyl or alkyl;

each $Q^5$ is independently alkyl, halo or haloalkyl;

m is 0-4; and n is 0-2.

In one embodiment, provided herein is a compound of Formula VI:

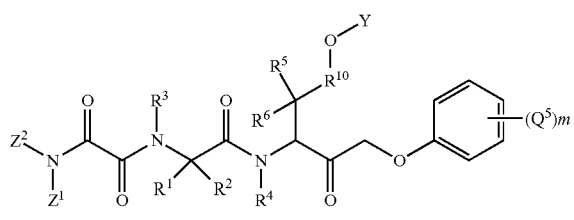

VI or an enantiomer or a mixture of enantiomers thereof, or a pharmaceutically acceptable salt, solvate, hydrate, co-crystal, clathrate, or polymorph thereof,
wherein
Y is hydrogen, —C(O)$R^d$, alkyl, cycloalkyl, heterocyclyl, aryl or heteroaryl;
Y is optionally substituted with one to three groups $Q^1$;
each $Q^1$ is independently alkyl, halo, haloalkyl, hydroxyl, alkoxy, cycloalkyl, heterocyclyl, aryl or heteroaryl; each $Q^1$ is optionally substituted with one to three groups $Q^2$; each $Q^2$ is independently alkyl, halo, haloalkyl, aryl or haloaryl;
$R^d$ is alkyl, aryl, cycloalkyl, heteroaryl, heterocyclyl or —$R^aOR^b$;
each $R^d$ is optionally substituted with one to three groups $Q^1$;
$R^a$ is alkylene or a direct bond;
$R^b$ is hydrogen, alkyl, haloalkyl, hydroxyalkyl, alkoxyalkyl, cycloalkyl, aryl, heteroaryl or heterocyclyl;
$R^1$ and $R^2$ are selected as follows:
i) $R^1$ and $R^2$ are each independently hydrogen, alkyl or cycloalkyl; or
ii) $R^1$ and $R^2$ together with the carbon atom on which they are substituted form an optionally substituted saturated or unsaturated ring A, where the substituents on ring A, when present, are selected from one to three groups $Q^1$;
$R^3$, $R^4$, $R^5$ and $R^6$ are each independently hydrogen or alkyl;
$Z^1$ is hydrogen or alkyl;
$Z^2$ is aryl, cycloalkyl, heteroaryl or heterocyclyl, each optionally substituted with one to four substituents $Q^3$;
each $Q^3$ is independently selected from alkyl, halo, cyano, cycloalkyl, heterocyclyl, aryl, heteroaryl, —$R^{11}OR^{12}$, —$R^{11}OR^{11}OR^{12}$, —$R^{11}N(R^{13})(R^{14})$, —$R^{11}SR^{12}$, —$R^{11}OR^{11}N(R^{13})(R^{14})$, —$R^{11}C(J)N(R^{13})(R^{14})$, —$R^{11}OR^{11}C(J)N(R^{13})(R^{14})$, —$C(J)R^{15}$ and $R^{11}S(O)_tR^{16}$; where each $Q^3$ is optionally substituted with one to three groups $Q^4$, where each $Q^4$ is independently alkyl, halo, haloalkyl, hydroxyl, alkoxy or cycloalkyl;
$R^{10}$ is —CH$_2$— or —CH$_2$—CH$_2$—;
each $R^{11}$ is independently alkylene, alkenylene or a direct bond;
each $R^{12}$ is independently hydrogen, alkyl, haloalkyl, hydroxyalkyl, alkoxyalkyl, cycloalkyl, aryl, heteroaryl or heterocyclyl;
$R^{13}$ and $R^{14}$ are selected as follows:
i) $R^{13}$ and $R^{14}$ are each independently hydrogen, alkyl, haloalkyl, hydroxyalkyl, alkoxyalkyl, cycloalkyl, aryl, heteroaryl or heterocyclyl; or
ii) $R^{13}$ and $R^{14}$ together with the nitrogen atom on which they are substituted form a 5 or 6-membered heterocyclyl or heteroaryl ring, optionally substituted with one or two alkyl, halo, haloalkyl, hydroxyl, alkoxy or cycloalkyl;
each $R^{15}$ is independently hydroxy, alkyl, haloalkyl, alkoxy, cycloalkyl, aryl, heteroaryl, or heterocyclyl;
each $R^{16}$ is independently hydrogen, alkyl, haloalkyl, hydroxyalkyl, alkoxyalkyl, cycloalkyl, aryl, heteroaryl or heterocyclyl;
J is O or S;
each $Q^5$ is independently alkyl, halo or haloalkyl;
t is 0-2; and
m is 0-4.
In one embodiment, provided herein is a compound of Formula VI, or an enantiomer or a mixture of enantiomers thereof, or a pharmaceutically acceptable salt, solvate, hydrate, co-crystal, clathrate, or polymorph thereof, wherein Y is hydrogen, alkyl, aryl, arylalkyl, heteroarylalkyl or —C(O)$R^d$; where the alkyl and aryl groups are optionally substituted with one or two groups selected from alkyl and halo;
$R^d$ is aryl or aryloxy;
$R^1$ and $R^2$ are selected as follows:
i) $R^1$ and $R^2$ are each independently hydrogen or alkyl; or
ii) $R^1$ and $R^2$ together with the carbon atom on which they are substituted form a cycloalkyl ring;
$R^3$, $R^4$, $R^5$ and $R^6$ are each independently hydrogen or alkyl;
$Z^1$ is hydrogen or alkyl;
$Z^2$ is aryl or heteroaryl, each optionally substituted with one to four substituents $Q^3$;
each $Q^3$ is independently selected from alkyl, haloalkyl, haloalkoxy, halo, cyano, aryl, heteroaryl, —$R^{11}OR^{12}$, —$C(O)R^{15}$ or —$C(O)NH_2$;
each $Q^5$ is independently alkyl, halo or haloalkyl;
$R^{10}$ is —CH$_2$— or —CH$_2$—CH$_2$—;
$R^{11}$ is alkylene or a direct bond;
$R^{12}$ is hydrogen, alkyl or haloalkyl;
$R^{15}$ is hydroxyl or alkyl; and
m is 0-4.
In one embodiment, provided herein is a compound of Formula VI, or an enantiomer or a mixture of enantiomers thereof, or a pharmaceutically acceptable salt, solvate, hydrate, co-crystal, clathrate, or polymorph thereof, wherein
Y is hydrogen, methyl, —C(O)$R^d$; where methyl is optionally substituted with phenyl, chlorophenyl or thienyl;
$R^d$ is phenyl or phenyloxy;
$R^1$ and $R^2$ are selected as follows:
i) $R^1$ and $R^2$ are each independently hydrogen or methyl; or
ii) $R^1$ and $R^2$ together with the carbon atom on which they are substituted form a cyclopentyl ring;
$R^3$, $R^4$, $R^5$ and $R^6$ are each independently hydrogen or methyl;
$R^{10}$ is —CH$_2$— or —CH$_2$—CH$_2$—;
$Q^5$ is fluoro, methyl or trifluoromethyl;
$Z^1$ is hydrogen;
$Z^2$ is selected from phenyl, pyridinyl, pyrimidyl, naphthyl, indazolyl, quinolinyl, isoquinolynyl and benzoisothiazolyl; each optionally substituted with one or two $Q^3$ groups, and each $Q^3$ is independently selected from chloro, fluoro, methyl, methoxy, trifluoromethoxy, —C(O)CH$_3$, cyano, —C(O)NH$_2$, benzyl and tetrazolyl; and
m is 0-4.
In one embodiment, provided herein is a compound of Formula VII:

VII or an enantiomer or a mixture of enantiomers thereof, or a pharmaceutically acceptable salt, solvate, hydrate, co-crystal, clathrate, or polymorph thereof, wherein $R^d$ is alkyl, aryl, cycloalkyl, heteroaryl, heterocyclyl or —$R^aOR^b$;

each $R^d$ is optionally substituted with one to three groups $Q^1$;

each $Q^1$ is independently alkyl, halo, haloalkyl, hydroxyl, alkoxy, cycloalkyl, heterocyclyl, aryl or heteroaryl; each $Q^1$ is optionally substituted with one to three groups $Q^2$;

each $Q^2$ is independently alkyl, halo, haloalkyl, aryl or haloaryl;

$R^a$ is alkylene or a direct bond;

$R^b$ is hydrogen, alkyl, haloalkyl, hydroxyalkyl, alkoxyalkyl, cycloalkyl, aryl, heteroaryl or heterocyclyl;

$R^1$ and $R^2$ are selected as follows:

i) $R^1$ and $R^2$ are each independently hydrogen, alkyl or cycloalkyl; or ii) $R^1$ and $R^2$ together with the carbon atom on which they are substituted form an optionally substituted saturated or unsaturated ring A, where the substituents on ring A, when present, are selected from one to three groups $Q^1$;

$R^3$, $R^4$, $R^5$ and $R^6$ are each independently hydrogen or alkyl;

$Z^1$ is hydrogen or alkyl;

$Z^2$ is aryl, cycloalkyl, heteroaryl or heterocyclyl, each optionally substituted with one to four substituents $Q^3$; or each $Q^3$ is independently selected from alkyl, halo, cyano, cycloalkyl, heterocyclyl, aryl, heteroaryl, —$R^{11}OR^{12}$, —$R^{11}OR^{11}OR^{12}$, —$R^{11}N(R^{13})(R^{14})$, —$R^{11}SR^{12}$, —$R^{11}OR^{11}N(R^{13})(R^{14})$, —$R^{11}C(J)N(R^{13})(R^{14})$, —$R^{11}OR^{11}C(J)N(R^{13})(R^{14})$, —$C(J)R^{15}$ and $R^{11}S(O)_tR^{16}$; where each $Q^3$ is optionally substituted with one to three groups $Q^4$, where each $Q^4$ is independently alkyl, halo, haloalkyl, hydroxyl, alkoxy or cycloalkyl;

$R^{10}$ is —$CH_2$— or —$CH_2$—$CH_2$—;

each $R^{11}$ is independently alkylene, alkenylene or a direct bond;

each $R^{12}$ is independently hydrogen, alkyl, haloalkyl, hydroxyalkyl, alkoxyalkyl, cycloalkyl, aryl, heteroaryl or heterocyclyl;

$R^{13}$ and $R^{14}$ are selected as follows:

i) $R^{13}$ and $R^{14}$ are each independently hydrogen, alkyl, haloalkyl, hydroxyalkyl, alkoxyalkyl, cycloalkyl, aryl, heteroaryl or heterocyclyl; or ii) $R^{13}$ and $R^{14}$ together with the nitrogen atom on which they are substituted form a 5 or 6-membered heterocyclyl or heteroaryl ring, optionally substituted with one or two alkyl, halo, haloalkyl, hydroxyl, alkoxy or cycloalkyl;

each $R^{15}$ is independently hydroxy, alkyl, haloalkyl, alkoxy, cycloalkyl, aryl, heteroaryl, or heterocyclyl;

each $R^{16}$ is independently hydrogen, alkyl, haloalkyl, hydroxyalkyl, alkoxyalkyl, cycloalkyl, aryl, heteroaryl or heterocyclyl;

each $Q^5$ is independently alkyl, halo or haloalkyl;

J is O or S;

t is 0-2; and m is 0-4.

In one embodiment, provided herein is a compound of Formula VII, or an enantiomer or a mixture of enantiomers thereof, or a pharmaceutically acceptable salt, solvate, hydrate, co-crystal, clathrate, or polymorph thereof, wherein $R^d$ is aryl or aryloxy;

$R^1$ and $R^2$ are selected as follows:

i) $R^1$ and $R^2$ are each independently hydrogen or alkyl; or ii) $R^1$ and $R^2$ together with the carbon atom on which they are substituted form a cycloalkyl ring;

$R^3$, $R^4$, $R^5$ and $R^6$ are each independently hydrogen or alkyl;

$Z^1$ is hydrogen or alkyl;

$Z^2$ is aryl or heteroaryl, each optionally substituted with one to four substituents $Q^3$;

each $Q^3$ is independently selected from alkyl, haloalkyl, haloalkoxy, halo, cyano, aryl, heteroaryl, —$R^{11}OR^{12}$, —$C(O)R^{15}$ and —$C(O)NH_2$;

$R^{10}$ is —$CH_2$— or —$CH_2$—$CH_2$—;

$R^{11}$ is alkylene or a direct bond;

$R^{12}$ is hydrogen, alkyl or haloalkyl;

$R^{15}$ is hydroxyl or alkyl;

$Q^5$ is independently alkyl, halo or haloalkyl; and m is 0-4.

In one embodiment, provided herein is a compound of Formula VII, or an enantiomer or a mixture of enantiomers thereof, or a pharmaceutically acceptable salt, solvate, hydrate, co-crystal, clathrate, or polymorph thereof, wherein each $R^d$ is independently phenyl or phenyloxy;

$R^1$ and $R^2$ are selected as follows:

i) $R^1$ and $R^2$ are each independently hydrogen or methyl; or ii) $R^1$ and $R^2$ together with the carbon atom on which they are substituted form a cyclopentyl ring;

$R^3$, $R^4$, $R^5$ and $R^6$ are each independently hydrogen or methyl;

$R^{10}$ is —$CH_2$— or —$CH_2$—$CH_2$—;

$Q^5$ is fluoro, methyl or trifluoromethyl;

$Z^1$ is hydrogen;

$Z^2$ is selected from phenyl, pyridinyl, pyrimidyl, naphthyl, indazolyl, quinolinyl, isoquinolynyl and benzoisothiazolyl; each optionally substituted with one or two $Q^3$ groups, and each $Q^3$ is independently selected from chloro, fluoro, methyl, methoxy, trifluoromethoxy, —$C(O)CH_3$, cyano, —$C(O)NH_2$, benzyl and tetrazolyl; and m is 0-4.

In one embodiment, provided herein is a compound of Formula VIII:

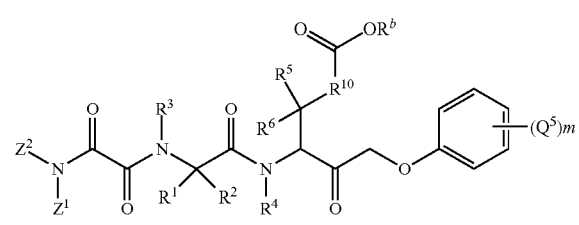

VIII or an enantiomer or a mixture of enantiomers thereof, or a pharmaceutically acceptable salt, solvate, hydrate, co-crystal, clathrate, or polymorph thereof, wherein $R^b$ is hydrogen, alkyl, haloalkyl, hydroxyalkyl, alkoxyalkyl, cycloalkyl, aryl, heteroaryl or heterocyclyl;

$R^b$ is optionally substituted with one to three groups $Q^1$;

each $Q^1$ is independently alkyl, halo, haloalkyl, hydroxyl, alkoxy, cycloalkyl, heterocyclyl, aryl or heteroaryl; each $Q^1$ is optionally substituted with one to three groups $Q^2$; each $Q^2$ is independently alkyl, halo, haloalkyl, aryl or haloaryl;

$R^1$ and $R^2$ are selected as follows:

i) $R^1$ and $R^2$ are each independently hydrogen, alkyl or cycloalkyl; or ii) $R^1$ and $R^2$ together with the carbon atom on which they are substituted form an optionally substituted saturated or unsaturated ring A, where the substituents on ring A, when present, are selected from one to three groups $Q^1$;

$R^3$, $R^4$, $R^5$ and $R^6$ are each independently hydrogen or alkyl;

$Z^1$ is hydrogen or alkyl;

$Z^2$ is aryl, cycloalkyl, heteroaryl or heterocyclyl, each optionally substituted with one to four substituents $Q^3$;

each $Q^3$ is independently selected from alkyl, halo, cyano, cycloalkyl, heterocyclyl, aryl, heteroaryl, $-R^{11}OR^{12}$, $-R^{11}OR^{11}OR^{12}$, $-R^{11}N(R^{13})(R^{14})$, $-R^{11}SR^{12}$, $-R^{11}OR^{11}N(R^{13})(R^{14})$, $-R^{11}C(J)N(R^{13})(R^{14})$, $-R^{11}OR^{11}C(J)N(R^{13})(R^{14})$, $-C(J)R^{15}$ and $R^{11}S(O)_tR^{16}$; where each $Q^3$ is optionally substituted with one to three groups $Q^4$, where each $Q^4$ is independently alkyl, halo, haloalkyl, hydroxyl, alkoxy or cycloalkyl;

$R^{10}$ is $-CH_2-$ or $-CH_2-CH_2-$;

each $R^{11}$ is independently alkylene, alkenylene or a direct bond;

each $R^{12}$ is independently hydrogen, alkyl, haloalkyl, hydroxyalkyl, alkoxyalkyl, cycloalkyl, aryl, heteroaryl or heterocyclyl;

$R^{13}$ and $R^{14}$ are selected as follows:

i) $R^{13}$ and $R^{14}$ are each independently hydrogen, alkyl, haloalkyl, hydroxyalkyl, alkoxyalkyl, cycloalkyl, aryl, heteroaryl or heterocyclyl; or ii) $R^{13}$ and $R^{14}$ together with the nitrogen atom on which they are substituted form a 5 or 6-membered heterocyclyl or heteroaryl ring, optionally substituted with one or two alkyl, halo, haloalkyl, hydroxyl, alkoxy or cycloalkyl;

each $R^{15}$ is independently hydroxy, alkyl, haloalkyl, alkoxy, cycloalkyl, aryl, heteroaryl, or heterocyclyl;

each $R^{16}$ is independently hydrogen, alkyl, haloalkyl, hydroxyalkyl, alkoxyalkyl, cycloalkyl, aryl, heteroaryl or heterocyclyl;

$Q^5$ is independently alkyl, halo or haloalkyl;

J is O or S;

m is 0-4; and t is 0-2.

In one embodiment, provided herein is a compound of Formula VIII or an enantiomer or a mixture of enantiomers thereof, or a pharmaceutically acceptable salt, solvate, hydrate, co-crystal, clathrate, or polymorph thereof; wherein $R^b$ is hydrogen;

$R^1$ and $R^2$ are selected as follows:

i) $R^1$ and $R^2$ are each independently hydrogen, alkyl or cycloalkyl; or ii) $R^1$ and $R^2$ together with the carbon atom on which they are substituted form an optionally substituted saturated or unsaturated ring A, where the substituents on ring A, when present, are selected from one to three groups $Q^1$;

each $Q^1$ is independently alkyl, halo, haloalkyl, hydroxyl, alkoxy, cycloalkyl, heterocyclyl, aryl or heteroaryl; each $Q^1$ is optionally substituted with one to three groups $Q^2$;

each $Q^2$ is independently alkyl, halo, haloalkyl, aryl or haloaryl;

$R^3$, $R^4$, $R^5$ and $R^6$ are each independently hydrogen or alkyl;

$Z^1$ is hydrogen or alkyl;

$Z^2$ is aryl, cycloalkyl, heteroaryl or heterocyclyl, each optionally substituted with one to four substituents $Q^3$;

each $Q^3$ is independently selected from alkyl, halo, cyano, cycloalkyl, heterocyclyl, aryl, heteroaryl, $-R^{11}OR^{12}$, $-R^{11}OR^{11}OR^{12}$, $-R^{11}N(R^{13})(R^{14})$, $-R^{11}SR^{12}$, $-R^{11}OR^{11}N(R^{13})(R^{14})$, $-R^{11}C(J)N(R^{13})(R^{14})$, $-R^{11}OR^{11}C(J)N(R^{13})(R^{14})$, $-C(J)R^{15}$ and $R^{11}S(O)_tR^{16}$; where each $Q^3$ is optionally substituted with one to three groups $Q^4$, where each $Q^4$ is independently alkyl, halo, haloalkyl, hydroxyl, alkoxy or cycloalkyl;

$R^{10}$ is $-CH_2-$ or $-CH_2-CH_2-$;

each $R^{11}$ is independently alkylene, alkenylene or a direct bond;

each $R^{12}$ is independently hydrogen, alkyl, haloalkyl, hydroxyalkyl, alkoxyalkyl, cycloalkyl, aryl, heteroaryl or heterocyclyl;

$R^{13}$ and $R^{14}$ are selected as follows:

i) $R^{13}$ and $R^{14}$ are each independently hydrogen, alkyl, haloalkyl, hydroxyalkyl, alkoxyalkyl, cycloalkyl, aryl, heteroaryl or heterocyclyl; or ii) $R^{13}$ and $R^{14}$ together with the nitrogen atom on which they are substituted form a 5 or 6-membered heterocyclyl or heteroaryl ring, optionally substituted with one or two alkyl, halo, haloalkyl, hydroxyl, alkoxy or cycloalkyl;

each $R^{15}$ is independently hydroxy, alkyl, haloalkyl, alkoxy, cycloalkyl, aryl, heteroaryl, or heterocyclyl;

each $R^{16}$ is independently hydrogen, alkyl, haloalkyl, hydroxyalkyl, alkoxyalkyl, cycloalkyl, aryl, heteroaryl or heterocyclyl;

$Q^5$ is independently alkyl, halo or haloalkyl;

J is O or S;

m is 0-4; and t is 0-2.

In one embodiment, provided herein is a compound of Formula VIII, or an enantiomer or a mixture of enantiomers thereof, or a pharmaceutically acceptable salt, solvate, hydrate, co-crystal, clathrate, or polymorph thereof, wherein $R^b$ is hydrogen, alkyl or aryl;

$R^1$ and $R^2$ are selected as follows:

i) $R^1$ and $R^2$ are each independently hydrogen or alkyl; or ii) $R^1$ and $R^2$ together with the carbon atom on which they are substituted form a cycloalkyl ring;

$R^3$, $R^4$, $R^5$ and $R^6$ are each independently hydrogen or alkyl;

$Z^1$ is hydrogen or alkyl;

$Z^2$ is aryl or heteroaryl, each optionally substituted with one to four substituents $Q^3$;

each $Q^3$ is independently selected from alkyl, haloalkyl, haloalkoxy, halo, cyano, aryl, heteroaryl, $-R^{11}OR^{12}$, $-C(O)R^{15}$ and $-C(O)NH_2$;

$R^{10}$ is $-CH_2-$ or $-CH_2-CH_2-$;

$R^{11}$ is alkylene or a direct bond;

$R^{12}$ is hydrogen, alkyl or haloalkyl;

$R^{15}$ is hydroxyl or alkyl;

$Q^5$ is independently alkyl, halo or haloalkyl; and m is 0-4.

In one embodiment, provided herein is a compound of Formula VIII, or an enantiomer or a mixture of enantiomers thereof, or a pharmaceutically acceptable salt, solvate, hydrate, co-crystal, clathrate, or polymorph thereof, wherein $R^b$ is hydrogen;
$R^1$ and $R^2$ are selected as follows:
i) $R^1$ and $R^2$ are each independently hydrogen or alkyl; or
ii) $R^1$ and $R^2$ together with the carbon atom on which they are substituted form a 3-5 membered cycloalkyl ring;
$R^3$, $R^4$, $R^5$ and $R^6$ are each independently hydrogen or alkyl;
$Z^1$ is hydrogen or alkyl;
$Z^2$ is aryl or heteroaryl, each optionally substituted with one to four substituents $Q^3$;
each $Q^3$ is independently selected from alkyl, haloalkyl, haloalkoxy, halo, cyano, aryl, heteroaryl, —$R^{11}OR^{12}$, —$C(O)R^{15}$ and —$C(O)NH_2$;
$R^{10}$ is —$CH_2$— or —$CH_2$—$CH_2$—;
$R^{11}$ is alkylene or a direct bond;
$R^{12}$ is hydrogen, alkyl or haloalkyl;
$R^{15}$ is hydroxyl or alkyl;
$Q^5$ is independently alkyl, halo or haloalkyl; and
m is 0-4.

In one embodiment, provided herein is a compound of Formula VIII, or an enantiomer or a mixture of enantiomers thereof, or a pharmaceutically acceptable salt, solvate, hydrate, co-crystal, clathrate, or polymorph thereof, wherein $R^b$ is hydrogen;
$R^1$ and $R^2$ are selected as follows:
i) $R^1$ and $R^2$ are each independently hydrogen or methyl; or
ii) $R^1$ and $R^2$ together with the carbon atom on which they are substituted form a cyclopentyl ring;
$R^3$, $R^4$, $R^5$ and $R^6$ are each independently hydrogen or methyl;
$R^{10}$ is —$CH_2$— or —$CH_2$—$CH_2$—;
$Q^5$ is fluoro, methyl and trifluoromethyl;
$Z^1$ is hydrogen;
$Z^2$ is selected from phenyl, pyridinyl, pyrimidyl, naphthyl, indazolyl, quinolinyl, isoquinolynyl and benzoisothiazolyl; each optionally substituted with one or two $Q^3$ groups, and each $Q^3$ is independently selected from chloro, fluoro, methyl, methoxy, trifluoromethoxy, —$C(O)CH_3$, cyano, —$C(O)NH_2$, benzyl and tetrazolyl; and
m is 0-4.

In one embodiment, provided herein is a compound of Formula IX

IX

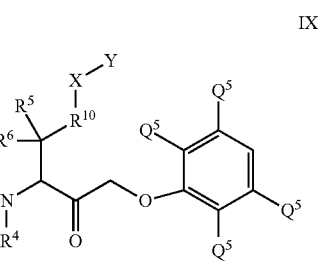

or an enantiomer or a mixture of enantiomers thereof, or a pharmaceutically acceptable salt, solvate, hydrate, co-crystal, clathrate, or polymorph thereof, wherein X and Y are selected as follows:
i) X is C=O; and Y is alkyl, cycloalkyl, heterocyclyl, aryl, heteroaryl, —$R^aOR^b$, or —$R^aN(R^c)(R^d)$; or
ii) X is —O—, or —$N(R^c)$—; Y is hydrogen, —$C(O)R^d$, alkyl, cycloalkyl, heterocyclyl, aryl or heteroaryl;
Y is optionally substituted with one to three groups $Q^1$;
each $Q^1$ is independently alkyl, halo, haloalkyl, hydroxyl, alkoxy, cycloalkyl, heterocyclyl, aryl or heteroaryl;
each $Q^1$ is optionally substituted with one to three groups $Q^2$; each $Q^2$ is independently alkyl, halo, haloalkyl, aryl or haloaryl;
each $R^a$ is independently alkylene or a direct bond;
$R^b$ is hydrogen, alkyl, haloalkyl, hydroxyalkyl, alkoxyalkyl, cycloalkyl, aryl, heteroaryl or heterocyclyl;
each $R^c$ is independently hydrogen or alkyl;
each $R^d$ is independently alkyl, aryl, cycloalkyl, heteroaryl, heterocyclyl or —$R^aOR^b$;
each $R^d$ is optionally substituted with one to three groups $Q^1$;
$R^1$ and $R^2$ are selected as follows:
i) $R^1$ and $R^2$ are each independently hydrogen, alkyl or cycloalkyl; or
ii) $R^1$ and $R^2$ together with the carbon atom on which they are substituted form an optionally substituted saturated or unsaturated ring A, where substituents on ring A, when present, are selected from one to three groups $Q^1$;
$R^3$, $R^4$, $R^5$ and $R^6$ are each independently hydrogen or alkyl;
$R^{10}$ is alkylene;
$Q^5$ is alkyl, halo or haloalkyl;
$Z^1$ is hydrogen or alkyl;
$Z^2$ is aryl, cycloalkyl, heteroaryl or heterocyclyl, each optionally substituted with one to four substituents $Q^3$;
each $Q^3$ is independently selected from alkyl, halo, cyano, cycloalkyl, heterocyclyl, aryl, heteroaryl, —$R^{11}OR^{12}$, —$R^{11}OR^{11}OR^{12}$, —$R^{11}N(R^{13})(R^{14})$, —$R^{11}SR^{12}$, —$R^{11}OR^{11}N(R^{13})(R^{14})$, —$R^{11}C(J)N(R^{13})(R^{14})$, —$R^{11}OR^{11}C(J)N(R^{13})(R^{14})$, —$C(J)R^{15}$ and $R^{11}S(O)_tR^{16}$; where each $Q^3$ is optionally substituted with one to three groups $Q^4$, where each $Q^4$ is independently alkyl, halo, haloalkyl, hydroxyl, alkoxy or cycloalkyl;
each $R^{11}$ is independently alkylene, alkenylene or a direct bond;
each $R^{12}$ is independently hydrogen, alkyl, haloalkyl, hydroxyalkyl, alkoxyalkyl, cycloalkyl, aryl, heteroaryl or heterocyclyl;
$R^{13}$ and $R^{14}$ are selected as follows:
i) $R^{13}$ and $R^{14}$ are each independently hydrogen, alkyl, haloalkyl, hydroxyalkyl, alkoxyalkyl, cycloalkyl, aryl, heteroaryl or heterocyclyl; or
ii) $R^{13}$ and $R^{14}$ together with the nitrogen atom on which they are substituted form a 5 or 6-membered heterocyclyl or heteroaryl ring, optionally substituted with one or two alkyl, halo, haloalkyl, hydroxyl, alkoxy or cycloalkyl;
each $R^{15}$ is independently hydroxy, alkyl, haloalkyl, alkoxy, cycloalkyl, aryl, heteroaryl, or heterocyclyl;
each $R^{16}$ is independently hydrogen, alkyl, haloalkyl, hydroxyalkyl, alkoxyalkyl, cycloalkyl, aryl, heteroaryl or heterocyclyl;
J is O or S;
t is 0-2; and
m is 0-4.

In one embodiment, provided herein is a compound of Formula IX, or an enantiomer or a mixture of enantiomers thereof, or a pharmaceutically acceptable salt, solvate, hydrate, co-crystal, clathrate, or polymorph thereof, wherein X and Y are selected as follows:
i) X is C=O; and Y is —$R^aOR^b$; or
ii) X is —O—; Y is hydrogen, alkyl, aryl, arylalkyl, heteroarylalkyl or —C(O)$R^d$; where the alkyl and aryl groups are optionally substituted with one or two groups selected from alkyl and halo;

$R^a$ is alkylene or a direct bond;
$R^b$ is hydrogen, alkyl or aryl;
$R^d$ is aryl or aryloxy;
$R^1$ and $R^2$ are selected as follows:
i) $R^1$ and $R^2$ are each independently hydrogen or alkyl; or
ii) $R^1$ and $R^2$ together with the carbon atom on which they are substituted form a cycloalkyl ring;
$R^3$, $R^4$, $R^5$ and $R^6$ are each independently hydrogen or alkyl;
$Q^5$ is halo;
m is 0-4;
$R^{10}$ is alkylene;
$Z^1$ is hydrogen or alkyl;
$Z^2$ is aryl or heteroaryl, each optionally substituted with one to four substituents $Q^3$;
each $Q^3$ is independently selected from alkyl, haloalkyl, haloalkoxy, halo, cyano, aryl, heteroaryl, —$R^{11}OR^{12}$, —C(O)$R^{15}$ and —C(O)NH$_2$;
$R^{11}$ is alkylene or a direct bond;
$R^{12}$ is hydrogen, alkyl or haloalkyl; and
$R^{15}$ is hydroxyl or alkyl.

In one embodiment, provided herein is a compound of Formula IX, or an enantiomer or a mixture of enantiomers thereof, or a pharmaceutically acceptable salt, solvate, hydrate, co-crystal, clathrate, or polymorph thereof, wherein
X and Y are selected as follows:
i) X is C=O; and Y is —$R^aOR^b$; or
ii) X is —O—; Y is hydrogen, alkyl, aryl, arylalkyl, heteroarylalkyl or —C(O)$R^d$; where the alkyl and aryl groups are optionally substituted with one or two groups selected from alkyl and halo;
$R^a$ is alkylene or a direct bond;
$R^b$ is hydrogen, alkyl or aryl;
$R^d$ is aryl or aryloxy;
$R^1$ and $R^2$ are selected as follows:
i) $R^1$ and $R^2$ are each independently hydrogen or alkyl; or
ii) $R^1$ and $R^2$ together with the carbon atom on which they are substituted form a cycloalkyl ring;
$R^3$, $R^4$, $R^5$ and $R^6$ are each hydrogen;
$Q^5$ is fluoro;
m is 0-4;
$R^{10}$ is alkylene;
$Z^1$ is hydrogen or alkyl;
$Z^2$ is aryl or heteroaryl, each optionally substituted with one to four substituents $Q^3$;
each $Q^3$ is independently selected from alkyl, haloalkyl, haloalkoxy, halo, cyano, aryl, heteroaryl, —$R^{11}OR^{12}$, —C(O)$R^{15}$ and —C(O)NH$_2$;
$R^{11}$ is alkylene or a direct bond;
$R^{12}$ is hydrogen, alkyl or haloalkyl; and
$R^{15}$ is hydroxyl or alkyl.

In one embodiment, provided herein is a compound of Formula X or an enantiomer or a mixture of enantiomers thereof, or a pharmaceutically acceptable salt, solvate, hydrate, co-crystal, clathrate, or polymorph thereof,
wherein
X and Y are selected as follows:
i) X is C=O; and Y is —$R^aOR^b$; or
ii) X is —O—, or —N($R^c$)—; Y is hydrogen, —C(O)$R^d$, alkyl, cycloalkyl, heterocyclyl, aryl or heteroaryl;
Y is optionally substituted with one to three groups $Q^1$;
each $Q^1$ is independently alkyl, halo, haloalkyl, hydroxyl, alkoxy, cycloalkyl, heterocyclyl, aryl or heteroaryl; each $Q^1$ is optionally substituted with one to three groups $Q^2$; each $Q^2$ is independently alkyl, halo, haloalkyl, aryl or haloaryl;
$R^a$ is alkylene or a direct bond;
$R^b$ is hydrogen, alkyl, haloalkyl, hydroxyalkyl, alkoxyalkyl, cycloalkyl, aryl, heteroaryl or heterocyclyl;
$R^c$ is hydrogen or alkyl;
$R^d$ is alkyl, aryl, cycloalkyl, heteroaryl, heterocyclyl or —$R^aOR^b$;
each $R^d$ is optionally substituted with one to three groups $Q^1$;
$R^1$ and $R^2$ are selected as follows:
i) $R^1$ and $R^2$ are each independently hydrogen, alkyl or cycloalkyl; or
ii) $R^1$ and $R^2$ together with the carbon atom on which they are substituted form an optionally substituted saturated or unsaturated ring A, where substituents on ring A, when present, are selected from one to three groups $Q^1$;
$R^{10}$ is alkylene;
$Q^5$ is alkyl, halo or haloalkyl;
$Z^1$ is hydrogen or alkyl;
$Z^2$ is aryl, cycloalkyl, heteroaryl or heterocyclyl, each optionally substituted with one to four substituents $Q^3$;
each $Q^3$ is independently selected from alkyl, halo, cyano, cycloalkyl, heterocyclyl, aryl, heteroaryl, —$R^{11}OR^{12}$, —$R^{11}OR^{11}OR^{12}$, —$R^{11}N(R^{13})(R^{14})$, —$R^{11}SR^{12}$, —$R^{11}OR^{11}N(R^{13})(R^{14})$, —$R^{11}C(J)N(R^{13})(R^{14})$, —$R^{11}OR^{11}C(J)N(R^{13})(R^{14})$, —C(J)$R^{15}$ and $R^{11}S(O)_tR^{16}$; where each $Q^3$ is optionally substituted with one to three groups $Q^4$, where each $Q^4$ is independently alkyl, halo, haloalkyl, hydroxyl, alkoxy or cycloalkyl;
each $R^{11}$ is independently alkylene, alkenylene or a direct bond;
each $R^{12}$ is independently hydrogen, alkyl, haloalkyl, hydroxyalkyl, alkoxyalkyl, cycloalkyl, aryl, heteroaryl or heterocyclyl;
$R^{13}$ and $R^{14}$ are selected as follows:
i) $R^{13}$ and $R^{14}$ are each independently hydrogen, alkyl, haloalkyl, hydroxyalkyl, alkoxyalkyl, cycloalkyl, aryl, heteroaryl or heterocyclyl; or
ii) $R^{13}$ and $R^{14}$ together with the nitrogen atom on which they are substituted form a 5 or 6-membered heterocyclyl or heteroaryl ring, optionally substituted with one or two alkyl, halo, haloalkyl, hydroxyl, alkoxy or cycloalkyl;

each $R^{15}$ is independently hydroxy, alkyl, haloalkyl, alkoxy, cycloalkyl, aryl, heteroaryl, or heterocyclyl;

each $R^{16}$ is independently hydrogen, alkyl, haloalkyl, hydroxyalkyl, alkoxyalkyl, cycloalkyl, aryl, heteroaryl or heterocyclyl;

J is O or S;

t is 0-2; and m is 0-4.

In one embodiment, provided herein is a compound of Formula X or an enantiomer or a mixture of enantiomers thereof, or a pharmaceutically acceptable salt, solvate, hydrate, co-crystal, clathrate, or polymorph thereof;

wherein

X is C=O; and Y is —OH;

$R^1$ and $R^2$ are selected as follows:

i) $R^1$ and $R^2$ are each independently hydrogen, alkyl or cycloalkyl; or ii) $R^1$ and $R^2$ together with the carbon atom on which they are substituted form a saturated or unsaturated ring A;

$R^{10}$ is alkylene;

$Q^5$ is alkyl, halo or haloalkyl;

$R^{10}$ is alkylene;

$Z^1$ is hydrogen or alkyl;

$Z^2$ is aryl or heteroaryl, each optionally substituted with one to four substituents $Q^3$; each $Q^3$ is independently selected from alkyl, haloalkyl, haloalkoxy, halo, cyano, aryl, heteroaryl, —$R^{11}OR^{12}$, —C(O)$R^{15}$ and —C(O)NH$_2$;

$R^{11}$ is alkylene or a direct bond;

$R^{12}$ is hydrogen, alkyl or haloalkyl; and $R^{15}$ is hydroxyl or alkyl.

In one embodiment, provided herein is a compound of Formula X or an enantiomer or a mixture of enantiomers thereof, or a pharmaceutically acceptable salt, solvate, hydrate, co-crystal, clathrate, or polymorph thereof;

wherein

X is C=O; and Y is —OH;

$R^1$ and $R^2$ are selected as follows:

i) $R^1$ and $R^2$ are each independently hydrogen, alkyl or cycloalkyl; or ii) $R^1$ and $R^2$ together with the carbon atom on which they are substituted form a saturated or unsaturated ring A;

$R^{10}$ is alkylene;

$Q^5$ is halo;

$R^{10}$ is alkylene;

$Z^1$ is hydrogen or alkyl;

$Z^2$ is aryl or heteroaryl, each optionally substituted with one to four substituents $Q^3$;

each $Q^3$ is independently selected from alkyl, haloalkyl, haloalkoxy, halo, cyano, aryl, heteroaryl, —$R^{11}OR^{12}$, —C(O)$R^{15}$ and —C(O)NH$_2$;

$R^{11}$ is alkylene or a direct bond;

$R^{12}$ is hydrogen, alkyl or haloalkyl; and $R^{15}$ is hydroxyl or alkyl.

In one embodiment, provided herein is a compound of Formula XI:

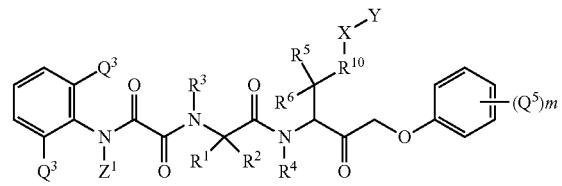

XI or an enantiomer or a mixture of enantiomers thereof, or a pharmaceutically acceptable salt, solvate, hydrate, co-crystal, clathrate, or polymorph thereof;

wherein

X and Y are selected as follows:

i) X is C=O; and Y is alkyl, cycloalkyl, heterocyclyl, aryl, heteroaryl, —$R^aOR^b$, or —$R^aN(R^c)(R^d)$; or ii) X is —O—, or —N($R^c$)—; Y is hydrogen, —C(O)$R^d$, alkyl, cycloalkyl, heterocyclyl, aryl or heteroaryl;

Y is optionally substituted with one to three groups $Q^1$;

each $Q^1$ is independently alkyl, halo, haloalkyl, hydroxyl, alkoxy, cycloalkyl, heterocyclyl, aryl or heteroaryl; each $Q^1$ is optionally substituted with one to three groups $Q^2$; each $Q^2$ is independently alkyl, halo, haloalkyl, aryl or haloaryl;

each $R^a$ is independently alkylene or a direct bond;

$R^b$ is hydrogen, alkyl, haloalkyl, hydroxyalkyl, alkoxyalkyl, cycloalkyl, aryl, heteroaryl or heterocyclyl;

each $R^c$ is independently hydrogen or alkyl;

each $R^d$ is independently alkyl, aryl, cycloalkyl, heteroaryl, heterocyclyl or —$R^aOR^b$;

each $R^d$ is optionally substituted with one to three groups $Q^1$;

$R^1$ and $R^2$ are selected as follows:

i) $R^1$ and $R^2$ are each independently hydrogen, alkyl or cycloalkyl; or ii) $R^1$ and $R^2$ together with the carbon atom on which they are substituted form an optionally substituted saturated or unsaturated ring A, where the substituents on ring A, when present, are selected from one to three groups $Q^1$;

$R^3$, $R^4$, $R^5$ and $R^6$ are each independently hydrogen or alkyl;

$R^{10}$ is alkylene;

each $Q^3$ is independently selected from alkyl, halo, cyano, cycloalkyl, heterocyclyl, aryl, heteroaryl, —$R^{11}OR^{12}$, —$R^{11}OR^{11}OR^{12}$, —$R^{11}N(R^{13})(R^{14})$, —$R^{11}SR^{12}$, —$R^{11}OR^{11}N(R^{13})(R^{14})$, —$R^{11}C(J)N(R^{13})(R^{14})$, —$R^{11}OR^{11}C(J)N(R^{13})(R^{14})$, —C(J)$R^{15}$ and $R^{11}S(O)_tR^{16}$; where each $Q^3$ is optionally substituted with one to three groups $Q^4$, where each $Q^4$ is independently alkyl, halo, haloalkyl, hydroxyl, alkoxy or cycloalkyl;

each $R^{11}$ is independently alkylene, alkenylene or a direct bond;

each $R^{12}$ is independently hydrogen, alkyl, haloalkyl, hydroxyalkyl, alkoxyalkyl, cycloalkyl, aryl, heteroaryl or heterocyclyl;

$R^{13}$ and $R^{14}$ are selected as follows:

i) $R^{13}$ and $R^{14}$ are each independently hydrogen, alkyl, haloalkyl, hydroxyalkyl, alkoxyalkyl, cycloalkyl, aryl, heteroaryl or heterocyclyl; or ii) $R^{13}$ and $R^{14}$ together with the nitrogen atom on which they are substituted form a 5 or 6-membered heterocyclyl or heteroaryl ring, optionally substituted with one or two alkyl, halo, haloalkyl, hydroxyl, alkoxy or cycloalkyl;
each $R^{15}$ is independently hydroxy, alkyl, haloalkyl, alkoxy, cycloalkyl, aryl, heteroaryl, or heterocyclyl;
each $R^{16}$ is independently hydrogen, alkyl, haloalkyl, hydroxyalkyl, alkoxyalkyl, cycloalkyl, aryl, heteroaryl or heterocyclyl;
each $Q^5$ is independently alkyl, halo or haloalkyl;
J is O or S;
t is 0-2; and
m is 0-4.

In one embodiment, provided herein is a compound of Formula XI, or an enantiomer or a mixture of enantiomers thereof, or a pharmaceutically acceptable salt, solvate, hydrate, co-crystal, clathrate, or polymorph thereof, wherein
X and Y are selected as follows:
i) X is C=O; and Y is —$R^aOR^b$; or
ii) X is —O—; Y is hydrogen, alkyl, aryl, arylalkyl, heteroarylalkyl or —C(O)$R^d$; where the alkyl and aryl groups are optionally substituted with one or two groups selected from alkyl and halo;
$R^a$ is alkylene or a direct bond;
$R^b$ is hydrogen, alkyl or aryl;
$R^d$ is aryl or aryloxy;
$R^1$ and $R^2$ are selected as follows:
i) $R^1$ and $R^2$ are each independently hydrogen or alkyl; or
ii) $R^1$ and $R^2$ together with the carbon atom on which they are substituted form a cycloalkyl ring;
$R^3$, $R^4$, $R^5$, and $R^6$ are each independently hydrogen or alkyl;
$R^{10}$ is alkylene;
$Z^1$ is hydrogen or alkyl;
each $Q^3$ is independently selected from alkyl, haloalkyl, haloalkoxy, halo, cyano, aryl, heteroaryl, —$R^{11}OR^{12}$, —C(O)$R^{15}$ and —C(O)NH$_2$;
$R^{11}$ is alkylene or a direct bond;
$R^{12}$ is hydrogen, alkyl or haloalkyl;
$R^{15}$ is hydroxyl or alkyl;
each $Q^5$ is independently alkyl, halo or haloalkyl;
m is 0-4; and
n is 0-2.

In one embodiment, provided herein is a compound of Formula XI, or an enantiomer or a mixture of enantiomers thereof, or a pharmaceutically acceptable salt, solvate, hydrate, co-crystal, clathrate, or polymorph thereof, wherein
X and Y are selected as follows:
i) X is C=O; and Y is —$R^aOR^b$; or
ii) X is —O—; Y is hydrogen, alkyl, aryl, arylalkyl, heteroarylalkyl or —C(O)$R^d$; where the alkyl and aryl groups are optionally substituted with one or two groups selected from alkyl and halo;
$R^a$ is alkylene or a direct bond;
$R^b$ is hydrogen, alkyl or aryl;
$R^d$ is aryl or aryloxy;
$R^1$ and $R^2$ are selected as follows:
i) $R^1$ and $R^2$ are each independently hydrogen or alkyl; or
ii) $R^1$ and $R^2$ together with the carbon atom on which they are substituted form a cycloalkyl ring;
$R^3$, $R^4$, $R^5$ and $R^6$ are each independently hydrogen or alkyl;
$R^{10}$ is alkylene;
$Z^1$ is hydrogen or alkyl;
each $Q^3$ is independently alkyl or halo;
each $Q^5$ is independently halo or haloalkyl;
m is 0-4; and
n is 0-2.

In one embodiment, provided herein is a compound of Formula XII:

XII or an enantiomer or a mixture of enantiomers thereof, or a pharmaceutically acceptable salt, solvate, hydrate, co-crystal, clathrate, or polymorph thereof,
wherein
X and Y are selected as follows:
i) X is C=O; and Y is alkyl, cycloalkyl, heterocyclyl, aryl, heteroaryl, —$R^aOR^b$, or —$R^aN(R^c)(R^d)$; or
ii) X is —O—, or —N($R^c$)—; Y is hydrogen, —C(O)$R^d$, alkyl, cycloalkyl, heterocyclyl, aryl or heteroaryl;
Y is optionally substituted with one to three groups $Q^1$;
each $Q^1$ is independently alkyl, halo, haloalkyl, hydroxyl, alkoxy, cycloalkyl, heterocyclyl, aryl or heteroaryl; each $Q^1$ is optionally substituted with one to three groups $Q^2$; each $Q^2$ is independently alkyl, halo, haloalkyl, aryl or haloaryl;
each $R^a$ is independently alkylene or a direct bond;
$R^b$ is hydrogen, alkyl, haloalkyl, hydroxyalkyl, alkoxyalkyl, cycloalkyl, aryl, heteroaryl or heterocyclyl;
each $R^c$ is independently hydrogen or alkyl;
each $R^d$ is independently alkyl, aryl, cycloalkyl, heteroaryl, heterocyclyl or —$R^aOR^b$;
each $R^d$ is optionally substituted with one to three groups $Q^1$;
$R^1$ and $R^2$ are selected as follows:
i) $R^1$ and $R^2$ are each independently hydrogen, alkyl or cycloalkyl; or
ii) $R^1$ and $R^2$ together with the carbon atom on which they are substituted form an optionally substituted saturated or unsaturated ring A, where the substituents on ring A, when present, are selected from one to three groups $Q^1$;
$R^3$, $R^4$, $R^5$ and $R^6$ are each independently hydrogen or alkyl;
$R^{10}$ is alkylene;
each $Q^3$ is independently selected from alkyl, halo, cyano, cycloalkyl, heterocyclyl, aryl, heteroaryl, —$R^{11}OR^{12}$, —$R^{11}OR^{11}OR^{12}$, —$R^{11}N(R^{13})(R^{14})$, —$R^{11}SR^{12}$, —$R^{11}OR^{11}N(R^{13})(R^{14})$, —$R^{11}C(J)N(R^{13})(R^{14})$, —$R^{11}OR^{11}C(J)N(R^{13})(R^{14})$, —C(J)$R^{15}$ and $R^{11}S(O)_tR^{16}$; where each $Q^3$ is optionally substituted with one to three groups $Q^4$, where each $Q^4$ is independently alkyl, halo, haloalkyl, hydroxyl, alkoxy or cycloalkyl;
each $R^{11}$ is independently alkylene, alkenylene or a direct bond;
each $R^{12}$ is independently hydrogen, alkyl, haloalkyl, hydroxyalkyl, alkoxyalkyl, cycloalkyl, aryl, heteroaryl or heterocyclyl;
$R^{13}$ and $R^{14}$ are selected as follows:
i) $R^{13}$ and $R^{14}$ are each independently hydrogen, alkyl, haloalkyl, hydroxyalkyl, alkoxyalkyl, cycloalkyl, aryl, heteroaryl or heterocyclyl; or
ii) $R^{13}$ and $R^{14}$ together with the nitrogen atom on which they are substituted form a 5 or 6-membered heterocyclyl or heteroaryl ring, optionally substituted with one or two alkyl, halo, haloalkyl, hydroxyl, alkoxy or cycloalkyl;
each $R^{15}$ is independently hydroxy, alkyl, haloalkyl, alkoxy, cycloalkyl, aryl, heteroaryl, or heterocyclyl;
each $R^{16}$ is independently hydrogen, alkyl, haloalkyl, hydroxyalkyl, alkoxyalkyl, cycloalkyl, aryl, heteroaryl or heterocyclyl;
each $Q^5$ is independently alkyl, halo or haloalkyl;
J is O or S;
t is 0-2.

In one embodiment, provided herein is a compound of Formula XII, or an enantiomer or a mixture of enantiomers thereof, or a pharmaceutically acceptable salt, solvate, hydrate, co-crystal, clathrate, or polymorph thereof, wherein
X and Y are selected as follows:
i) X is C=O; and Y is —$R^aOR^b$; or
ii) X is —O—; Y is hydrogen, alkyl, aryl, arylalkyl, heteroarylalkyl or —C(O)$R^d$; where the alkyl and aryl groups are optionally substituted with one or two groups selected from alkyl and halo;
$R^a$ is alkylene or a direct bond;
$R^b$ is hydrogen, alkyl or aryl;
each $R^d$ is aryl or aryloxy;
$R^1$ and $R^2$ are selected as follows:
i) $R^1$ and $R^2$ are each independently hydrogen or alkyl; or
ii) $R^1$ and $R^2$ together with the carbon atom on which they are substituted form a cycloalkyl ring;
$R^3$, $R^4$, $R^5$, and $R^6$ are each independently hydrogen or alkyl;
$R^{10}$ is alkylene;
$Z^1$ is hydrogen or alkyl;
each $Q^3$ is independently selected from alkyl, haloalkyl, haloalkoxy, halo, cyano, aryl, heteroaryl, —$R^{11}OR^{12}$, —C(O)$R^{15}$ and —C(O)NH$_2$;
$R^{11}$ is alkylene or a direct bond;
$R^{12}$ is hydrogen, alkyl or haloalkyl;
$R^{15}$ is hydroxyl or alkyl; and
each $Q^5$ is independently alkyl, halo or haloalkyl.

In one embodiment, provided herein is a compound of Formula XII, or an enantiomer or a mixture of enantiomers thereof, or a pharmaceutically acceptable salt, solvate, hydrate, co-crystal, clathrate, or polymorph thereof, wherein
X and Y are selected as follows:
i) X is C=O; and Y is —$R^aOR^b$; or
ii) X is —O—; Y is hydrogen, alkyl, aryl, arylalkyl, heteroarylalkyl or —C(O)$R^d$; where the alkyl and aryl groups are optionally substituted with one or two groups selected from alkyl and halo;
$R^a$ is alkylene or a direct bond;
$R^b$ is hydrogen, alkyl or aryl;
$R^d$ is aryl or aryloxy;
$R^1$ and $R^2$ are selected as follows:
i) $R^1$ and $R^2$ are each independently hydrogen or alkyl; or
ii) $R^1$ and $R^2$ together with the carbon atom on which they are substituted form a cycloalkyl ring;
$R^3$, $R^4$, $R^5$ and $R^6$ are each independently hydrogen or alkyl;
$R^{10}$ is alkylene;
$Z^1$ is hydrogen or alkyl;
each $Q^3$ is independently alkyl or halo; and
each $Q^5$ is independently halo or haloalkyl.

In one embodiment, provided herein is a compound of Formula XIII $$XIII$$

or an enantiomer or a mixture of enantiomers thereof, or a pharmaceutically acceptable salt, solvate, hydrate, co-crystal, clathrate, or polymorph thereof,
wherein
X and Y are selected as follows:
i) X is C=O; and Y is alkyl, cycloalkyl, heterocyclyl, aryl, heteroaryl, —$R^aOR^b$, or —$R^aN(R^c)(R^d)$; or
ii) X is —O—, or —N($R^c$)—; Y is hydrogen, —C(O)$R^d$, alkyl, cycloalkyl, heterocyclyl, aryl or heteroaryl;
Y is optionally substituted with one to three groups $Q^1$;
each $Q^1$ is independently alkyl, halo, haloalkyl, hydroxyl, alkoxy, cycloalkyl, heterocyclyl, aryl or heteroaryl;
each $Q^1$ is optionally substituted with one to three groups $Q^2$; each $Q^2$ is independently alkyl, halo, haloalkyl, aryl or haloaryl;
each $R^a$ is independently alkylene or a direct bond;
$R^b$ is hydrogen, alkyl, haloalkyl, hydroxyalkyl, alkoxyalkyl, cycloalkyl, aryl, heteroaryl or heterocyclyl;
each $R^c$ is independently hydrogen or alkyl;
each $R^d$ is independently alkyl, aryl, cycloalkyl, heteroaryl, heterocyclyl or —$R^aOR^b$;
each $R^d$ is optionally substituted with one to three groups $Q^1$;
$R^1$ and $R^2$ are selected as follows:
i) $R^1$ and $R^2$ are each independently hydrogen, alkyl or cycloalkyl; or
ii) $R^1$ and $R^2$ together with the carbon atom on which they are substituted form an optionally substituted saturated or unsaturated ring A, where substituents on ring A, when present, are selected from one to three groups $Q^1$;
$R^3$, $R^4$, $R^5$ and $R^6$ are each independently hydrogen or alkyl;
$R^{10}$ is alkylene;
$Q^5$ is alkyl, halo or haloalkyl;
$Z^1$ is hydrogen or alkyl;
$Z^2$ is aryl, cycloalkyl, heteroaryl or heterocyclyl, each optionally substituted with one to four substituents $Q^3$;
each $Q^3$ is independently selected from alkyl, halo, cyano, cycloalkyl, heterocyclyl, aryl, heteroaryl, —$R^{11}OR^{12}$, —$R^{11}OR^{11}OR^{12}$, —$R^{11}N(R^{13})(R^{14})$, —$R^{11}SR^{12}$, —$R^{11}OR^{11}N(R^{13})(R^{14})$, —$R^{11}C(J)N(R^{13})(R^{14})$, —$R^{11}OR^{11}C(J)N(R^{13})(R^{14})$, —C(J)$R^{15}$ and $R^{11}S(O)_tR^{16}$; where each $Q^3$ is optionally substituted with one to three groups $Q^4$, where each $Q^4$ is independently alkyl, halo, haloalkyl, hydroxyl, alkoxy or cycloalkyl;
each $R^{11}$ is independently alkylene, alkenylene or a direct bond;
each $R^{12}$ is independently hydrogen, alkyl, haloalkyl, hydroxyalkyl, alkoxyalkyl, cycloalkyl, aryl, heteroaryl or heterocyclyl;

$R^{13}$ and $R^{14}$ are selected as follows:
i) $R^{13}$ and $R^{14}$ are each independently hydrogen, alkyl, haloalkyl, hydroxyalkyl, alkoxyalkyl, cycloalkyl, aryl, heteroaryl or heterocyclyl; or
ii) $R^{13}$ and $R^{14}$ together with the nitrogen atom on which they are substituted form a 5 or 6-membered heterocyclyl or heteroaryl ring, optionally substituted with one or two alkyl, halo, haloalkyl, hydroxyl, alkoxy or cycloalkyl;

each $R^{15}$ is independently hydroxy, alkyl, haloalkyl, alkoxy, cycloalkyl, aryl, heteroaryl, or heterocyclyl;

each $R^{16}$ is independently hydrogen, alkyl, haloalkyl, hydroxyalkyl, alkoxyalkyl, cycloalkyl, aryl, heteroaryl or heterocyclyl;

J is O or S;

t is 0-2; and m is 0-4.

In one embodiment, provided herein is a compound of Formula XIII, or an enantiomer or a mixture of enantiomers thereof, or a pharmaceutically acceptable salt, solvate, hydrate, co-crystal, clathrate, or polymorph thereof, wherein X and Y are selected as follows:
i) X is C=O; and Y is —$R^aOR^b$; or
ii) X is —O—; Y is hydrogen, alkyl, aryl, arylalkyl, heteroarylalkyl or —C(O)$R^d$; where the alkyl and aryl groups are optionally substituted with one or two groups selected from alkyl and halo;
$R^a$ is alkylene or a direct bond;
$R^b$ is hydrogen, alkyl or aryl;
$R^d$ is aryl or aryloxy;
$R^1$ and $R^2$ are selected as follows:
i) $R^1$ and $R^2$ are each independently hydrogen or alkyl; or
ii) $R^1$ and $R^2$ together with the carbon atom on which they are substituted form a cycloalkyl ring;
$R^3$, $R^4$, $R^5$ and $R^6$ are hydrogen;
$Q^5$ is haloalkyl;
m is 0-4;
$R^{10}$ is alkylene;
$R^3$, $Y^1$, $Y^2$ and $Y^3$ are selected as follows:
i) $Y^1$ together with $R^3$ forms an optionally substituted saturated or unsaturated ring B, where substituents on ring B, when present, are selected from one to three groups $Q^1$;
$Y^2$ is absent, hydrogen or alkyl; and
$Y^3$ is absent, hydrogen or alkyl; or
ii) $R^3$ is hydrogen or alkyl; $Y^1$ and $Y^2$ together are =O; and $Y^3$ is —N($Z^1$)($Z^2$);
$Z^1$ is hydrogen or alkyl;
$Z^2$ is aryl or heteroaryl, each optionally substituted with one to four substituents $Q^3$;
each $Q^3$ is independently selected from alkyl, haloalkyl, haloalkoxy, halo, cyano, aryl, heteroaryl, —$R^{11}OR^{12}$, —C(O)$R^{15}$ and —C(O)NH$_2$;
$R^{11}$ is alkylene or a direct bond;
$R^{12}$ is hydrogen, alkyl or haloalkyl; and
$R^{15}$ is hydroxyl or alkyl.

In one embodiment, provided herein is a compound of Formula XIII, or an enantiomer or a mixture of enantiomers thereof, or a pharmaceutically acceptable salt, solvate, hydrate, co-crystal, clathrate, or polymorph thereof, wherein $Q^5$ is trifluoroalkyl, and the remaining variables are as described elsewhere herein.

In one embodiment, provided herein is a compound of Formula I, II, III, IV, V, VI, VII, VIII, IX, X, XI, XII or XIII or an enantiomer or a mixture of enantiomers thereof, or a pharmaceutically acceptable salt, solvate, hydrate, co-crystal, clathrate, or polymorph thereof, wherein $R^{10}$ is —CH$_2$— or —CH$_2$—CH$_2$—, and the remaining substituents are as described elsewhere herein.

In one embodiment, provided herein is a compound of Formula I, II, III, IV, V, VI, VII or VIII, IX, X, XI, XII or XIII or an enantiomer or a mixture of enantiomers thereof, or a pharmaceutically acceptable salt, solvate, hydrate, co-crystal, clathrate, or polymorph thereof, wherein $R^1$ and $R^2$ are selected as follows:
i) $R^1$ and $R^2$ are each independently hydrogen or methyl; or
ii) $R^1$ and $R^2$ together with the carbon atom on which they are substituted form a cyclopentyl ring; and the remaining substituents are as described elsewhere herein.

In one embodiment, provided herein is a compound of Formula I or II, or an enantiomer or a mixture of enantiomers thereof, or a pharmaceutically acceptable salt, solvate, hydrate, co-crystal, clathrate, or polymorph thereof, wherein $R^9$ is aryl or heteroaryl, each optionally substituted with one to four substituents selected from halo, alkyl and haloalkyl; and the remaining substituents are as described elsewhere herein.

In one embodiment, provided herein is a compound of Formula I or II, or an enantiomer or a mixture of enantiomers thereof, or a pharmaceutically acceptable salt, solvate, hydrate, co-crystal, clathrate, or polymorph thereof, wherein $R^9$ is phenyl or pyrimidinyl, each optionally substituted with one to four substituents selected from halo, alkyl and haloalkyl; and the remaining substituents are as described elsewhere herein.

In one embodiment, provided herein is a compound of Formula I, II, III, IV, VI, VII or VIII, or an enantiomer or a mixture of enantiomers thereof, or a pharmaceutically acceptable salt, solvate, hydrate, co-crystal, clathrate, or polymorph thereof, wherein $Z^2$ is selected from 6-10 membered aryl or heteroaryl; each optionally substituted with one or two $Q^3$ groups, and each $Q^3$ is independently selected from halo, alkyl, haloalkyl, arylalkyl, alkoxy, alkylcarbonyl, haloalkoxy, cyano, aryl, heteroaryl and aminocarbonyl, and the remaining substituents are as described elsewhere herein.

In one embodiment, provided herein is a compound of Formula I, II, III, IV or V, or an enantiomer or a mixture of enantiomers thereof, or a pharmaceutically acceptable salt, solvate, hydrate, co-crystal, clathrate, or polymorph thereof, wherein $R^{10}$ is —CH$_2$— or —CH$_2$—CH$_2$—; and $Z^2$ is selected from 6-10 membered aryl or heteroaryl; each optionally substituted with one or two $Q^3$ groups, and each $Q^3$ is independently selected from halo, alkyl, haloalkyl, arylalkyl, alkoxy, alkylcarbonyl, haloalkoxy, cyano, aryl, heteroaryl and aminocarbonyl, and the remaining substituents are as described elsewhere herein.

In one embodiment, provided herein is a compound of Formula I, II, III, IV or V, or an enantiomer or a mixture of enantiomers thereof, or a pharmaceutically acceptable salt, solvate, hydrate, co-crystal, clathrate, or polymorph thereof, wherein $R^{10}$ is —CH$_2$— or —CH$_2$—CH$_2$—; and $Z^2$ is selected from 6-10 membered aryl or heteroaryl; each optionally substituted with one or two $Q^3$ groups, and each $Q^3$ is independently selected from halo, alkyl, haloalkyl, arylalkyl, alkoxy, alkylcarbonyl, haloalkoxy, cyano, aryl, heteroaryl and aminocarbonyl, where the heteroaryl contains one or two heteroatoms selected from nitrogen and sulfur, and the remaining substituents are as described elsewhere herein.

In one embodiment, provided herein is a compound of Formula I, II, III, IV, VI, VII or VIII, or an enantiomer or a mixture of enantiomers thereof, or a pharmaceutically acceptable salt, solvate, hydrate, co-crystal, clathrate, or polymorph thereof, wherein $Z^2$ is selected from phenyl, pyridinyl, pyrimidyl, naphthyl, indazolyl, quinolinyl, isoquinolynyl and benzoisothiazolyl; each optionally substituted with one or two $Q^3$ groups, and each $Q^3$ is independently selected from halo, alkyl, haloalkyl, arylalkyl, alkoxy, alkylcarbonyl, haloalkoxy, cyano, aryl, heteroaryl and aminocarbonyl, and the remaining substituents are as described elsewhere herein.

In one embodiment, provided herein is a compound of Formula I, II, III or VI, or an enantiomer or a mixture of enantiomers thereof, or a pharmaceutically acceptable salt, solvate, hydrate, co-crystal, clathrate, or polymorph thereof, wherein $R^{10}$ is —$CH_2$— or —$CH_2$—$CH_2$—; and $Z^2$ is selected from phenyl, pyridinyl, pyrimidyl, naphthyl, indazolyl, quinolinyl, isoquinolynyl and benzoisothiazolyl; each optionally substituted with one or two $Q^3$ groups, and each $Q^3$ is independently selected from halo, alkyl, haloalkyl, arylalkyl, alkoxy, alkylcarbonyl, haloalkoxy, cyano, aryl, heteroaryl and aminocarbonyl, and the remaining substituents are as described elsewhere herein.

In one embodiment, provided herein is a compound of Formula I, II, III, IV, VI, VII or VIII, or an enantiomer or a mixture of enantiomers thereof, or a pharmaceutically acceptable salt, solvate, hydrate, co-crystal, clathrate, or polymorph thereof, wherein $Z^2$ is selected from phenyl, pyridinyl, pyrimidyl, naphthyl, indazolyl, quinolinyl, isoquinolynyl and benzoisothiazolyl; each optionally substituted with one or two $Q^3$ groups, and each $Q^3$ is independently selected from chloro, fluoro, methyl, methoxy, trifluoromethoxy, —C(O)CH$_3$, cyano, —C(O)NH$_2$, benzyl and tetrazolyl, and the remaining substituents are as described elsewhere herein.

In one embodiment, provided herein is a compound of Formula I, II, III or IV, or an enantiomer or a mixture of enantiomers thereof, or a pharmaceutically acceptable salt, solvate, hydrate, co-crystal, clathrate, or polymorph thereof, wherein $R^{10}$ is —$CH_2$— or —$CH_2$—$CH_2$—; and $Z^2$ is selected from phenyl, pyridinyl, pyrimidyl, naphthyl, indazolyl, quinolinyl, isoquinolynyl and benzoisothiazolyl; each optionally substituted with one or two $Q^3$ groups, and each $Q^3$ is independently selected from chloro, fluoro, methyl, methoxy, trifluoromethoxy, —C(O)CH$_3$, cyano, —C(O)NH$_2$, benzyl and tetrazolyl, and the remaining substituents are as described elsewhere herein.

In one embodiment, provided herein is a compound of Formula XIV:

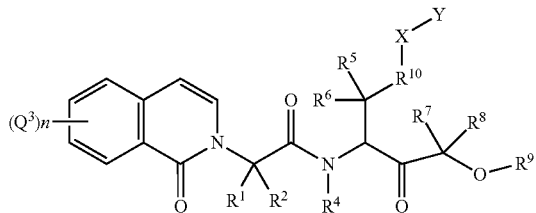

XIV or an enantiomer or a mixture of enantiomers thereof, or a pharmaceutically acceptable salt, solvate, hydrate, co-crystal, clathrate, or polymorph thereof;

wherein
X is C═O;
Y is alkyl, cycloalkyl, heterocyclyl, aryl, heteroaryl, —$R^aOR^b$, or —$R^aN(R^c)(R^d)$; each optionally substituted with one to three groups $Q^1$;
each $Q^1$ is independently alkyl, halo, haloalkyl, hydroxyl, alkoxy, cycloalkyl, heterocyclyl, aryl or heteroaryl; each $Q^1$ is optionally substituted with one to three groups $Q^2$; each $Q^2$ is independently alkyl, halo, haloalkyl, aryl or haloaryl;
each $R^a$ is independently alkylene or a direct bond;
$R^b$ is hydrogen, alkyl, haloalkyl, hydroxyalkyl, alkoxyalkyl, cycloalkyl, aryl, heteroaryl or heterocyclyl;
each $R^c$ is independently hydrogen or alkyl;
$R^d$ is alkyl, aryl, cycloalkyl, heteroaryl, heterocyclyl or —$R^aOR^b$;
each $R^d$ is optionally substituted with one to three groups $Q^1$;
$R^1$ and $R^2$ are selected as follows:
i) $R^1$ and $R^2$ are each independently hydrogen, alkyl or cycloalkyl; or
ii) $R^1$ and $R^2$ together with the carbon atom on which they are substituted form an optionally substituted saturated or unsaturated ring A, where the substituents on ring A, when present, are selected from one to three groups $Q^1$;
$R^4$, $R^5$, $R^6$, $R^7$ and $R^8$ are each independently hydrogen or alkyl;
$R^9$ is aryl or heteroaryl, each optionally substituted with one to four substituents $Q^1$;
$R^{10}$ is alkylene;
each $Q^3$ is independently selected from alkyl, halo, cyano, cycloalkyl, heterocyclyl, aryl, heteroaryl, —$R^{11}OR^{12}$, —$R^{11}OR^{11}OR^{12}$, —$R^{11}N(R^{13})(R^{14})$, —$R^{11}SR^{12}$, —$R^{11}OR^{11}N(R^{13})(R^{14})$, —$R^{11}C(J)N(R^{13})(R^{14})$, —$R^{11}OR^{11}C(J)N(R^{13})(R^{14})$, —$C(J)R^{15}$ and $R^{11}S(O)_tR^{16}$; where each $Q^3$ is optionally substituted with one to three groups $Q^4$, where each $Q^4$ is independently alkyl, halo, haloalkyl, hydroxyl, alkoxy or cycloalkyl;
each $R^{11}$ is independently alkylene, alkenylene or a direct bond;
each $R^{12}$ is independently hydrogen, alkyl, haloalkyl, hydroxyalkyl, alkoxyalkyl, cycloalkyl, aryl, heteroaryl or heterocyclyl;
$R^{13}$ and $R^{14}$ are selected as follows:
i) $R^{13}$ and $R^{14}$ are each independently hydrogen, alkyl, haloalkyl, hydroxyalkyl, alkoxyalkyl, cycloalkyl, aryl, heteroaryl or heterocyclyl; or
ii) $R^{13}$ and $R^{14}$ together with the nitrogen atom on which they are substituted form a 5 or 6-membered heterocyclyl or heteroaryl ring, optionally substituted with one or two alkyl, halo, haloalkyl, hydroxyl, alkoxy or cycloalkyl;
each $R^{15}$ is independently hydroxy, alkyl, haloalkyl, alkoxy, cycloalkyl, aryl, heteroaryl, or heterocyclyl;
each $R^{16}$ is independently hydrogen, alkyl, haloalkyl, hydroxyalkyl, alkoxyalkyl, cycloalkyl, aryl, heteroaryl or heterocyclyl;
J is O or S;
t is 0-2; and
n is 0-3.

In one embodiment, provided herein is a compound of Formula XIV or an enantiomer or a mixture of enantiomers thereof, or a pharmaceutically acceptable salt, solvate, hydrate, co-crystal, clathrate, or polymorph thereof;

wherein

X is C=O;

Y is alkyl, cycloalkyl, heterocyclyl, aryl, heteroaryl, —$R^aOR^b$, or —$R^aN(R^c)(R^d)$; each optionally substituted with one to three groups $Q^1$;

each $Q^1$ is independently alkyl, halo, haloalkyl, hydroxyl, alkoxy, cycloalkyl, heterocyclyl, aryl or heteroaryl; each $Q^1$ is optionally substituted with one to three groups $Q^2$; each $Q^2$ is independently alkyl, halo, haloalkyl, aryl or haloaryl;

each $R^a$ is independently alkylene or a direct bond;

$R^b$ is hydrogen, alkyl, haloalkyl, hydroxyalkyl, alkoxyalkyl, cycloalkyl, aryl, heteroaryl or heterocyclyl;

each $R^c$ is independently hydrogen or alkyl;

$R^d$ is alkyl, aryl, cycloalkyl, heteroaryl, heterocyclyl or —$R^aOR^b$;

each $R^d$ is optionally substituted with one to three groups $Q^1$;

$R^1$ and $R^2$ are selected as follows:

i) $R^1$ and $R^2$ are each independently hydrogen, alkyl or cycloalkyl; or ii) $R^1$ and $R^2$ together with the carbon atom on which they are substituted form an optionally substituted saturated or unsaturated ring A, where the substituents on ring A, when present, are selected from one to three groups $Q^1$;

$R^4$, $R^5$, $R^6$, $R^7$ and $R^8$ are each independently hydrogen or alkyl;

$R^9$ is aryl or heteroaryl, each optionally substituted with one to four substituents $Q^1$;

$R^{10}$ is alkylene;

each $Q^3$ is independently selected from alkyl, halo, cyano, cycloalkyl, heterocyclyl, aryl, heteroaryl, —$R^{11}OR^{12}$, —$R^{11}OR^{11}OR^{12}$, —$R^{11}N(R^{13})(R^{14})$, —$R^{11}SR^{12}$, —$R^{11}OR^{11}N(R^{13})(R^{14})$, —$R^{11}C(J)N(R^{13})(R^{14})$, —$R^{11}OR^{11}C(J)N(R^{13})(R^{14})$, —$C(J)R^{15}$ and $R^{11}S(O)_tR^{16}$; where each $Q^3$ is optionally substituted with one to three groups $Q^4$, where each $Q^4$ is independently alkyl, halo, haloalkyl, hydroxyl, alkoxy or cycloalkyl;

each $R^{11}$ is independently alkylene, alkenylene or a direct bond;

each $R^{12}$ is independently hydrogen, alkyl, haloalkyl, hydroxyalkyl, alkoxyalkyl, cycloalkyl, aryl, heteroaryl or heterocyclyl;

$R^{13}$ and $R^{14}$ are selected as follows:

i) $R^{13}$ and $R^{14}$ are each independently hydrogen, alkyl, haloalkyl, hydroxyalkyl, alkoxyalkyl, cycloalkyl, aryl, heteroaryl or heterocyclyl; or ii) $R^{13}$ and $R^{14}$ together with the nitrogen atom on which they are substituted form a 5 or 6-membered heterocyclyl or heteroaryl ring, optionally substituted with one or two alkyl, halo, haloalkyl, hydroxyl, alkoxy or cycloalkyl;

each $R^{15}$ is independently hydroxy, alkyl, haloalkyl, alkoxy, cycloalkyl, aryl, heteroaryl, heterocyclyl;

each $R^{16}$ is independently hydrogen, alkyl, haloalkyl, hydroxyalkyl, alkoxyalkyl, cycloalkyl, aryl, heteroaryl or heterocyclyl;

J is O or S;

t is 0-2; and n is 0-3.

In one embodiment, provided herein is a compound of Formula XIV or an enantiomer or a mixture of enantiomers thereof, or a pharmaceutically acceptable salt, solvate, hydrate, co-crystal, clathrate, or polymorph thereof;

wherein

X is C=O; and Y is —$R^aOR^b$;

$R^a$ is alkylene or a direct bond;

$R^b$ is hydrogen or alkyl;

$R^1$ and $R^2$ are each hydrogen;

$R^4$, $R^5$, $R^6$, $R^7$ and $R^8$ are each independently hydrogen or alkyl;

$R^9$ is aryl or heteroaryl, each optionally substituted with one to four halo;

$R^{10}$ is alkylene;

each $Q^3$ is halo; and n is 0-3.

In one embodiment, provided herein is a compound of Formula XV:

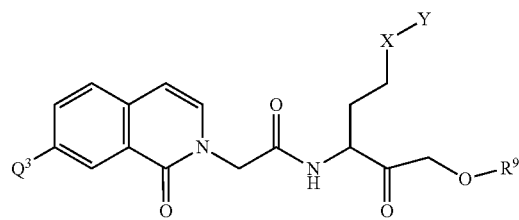

or an enantiomer or a mixture of enantiomers thereof, or a pharmaceutically acceptable salt, solvate, hydrate, co-crystal, clathrate, or polymorph thereof, where the variables are as described elsewhere herein.

In one embodiment, provided herein is a compound of Formula XV or an enantiomer or a mixture of enantiomers thereof, or a pharmaceutically acceptable salt, solvate, hydrate, co-crystal, clathrate, or polymorph thereof, wherein X is C=O; and Y is —$R^aOR^b$;

$R^a$ is alkylene or a direct bond;

$R^b$ is hydrogen or alkyl;

$R^9$ is aryl or heteroaryl, each optionally substituted with one to four halo; and $Q^3$ is halo.

In one embodiment, provided herein is a compound of Formula XVI:

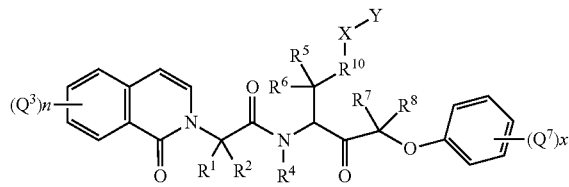

or an enantiomer or a mixture of enantiomers thereof, or a pharmaceutically acceptable salt, solvate, hydrate, co-crystal, clathrate, or polymorph thereof, where each $Q^7$ is halo, x is 0-4 and the remaining variables are as described elsewhere herein.

In one embodiment, provided herein is a compound of Formula XI or an enantiomer or a mixture of enantiomers thereof, or a pharmaceutically acceptable salt, solvate, hydrate, co-crystal, clathrate, or polymorph thereof;

wherein
X is C=O; and Y is —R$^a$OR$^b$;
R$^a$ is alkylene or a direct bond;
R$^b$ is hydrogen or alkyl;
R$^1$ and R$^2$ are each hydrogen;
R$^4$, R$^5$, R$^6$, R$^7$ and R$^8$ are each independently hydrogen or alkyl;
each Q$^7$ is halo;
R$^{10}$ is alkylene;
each Q$^3$ is halo;
x is 0-4; and
n is 0-3.

In one embodiment, provided herein is a compound of Formula XVII.

XVII or an enantiomer or a mixture of enantiomers thereof, or a pharmaceutically acceptable salt, solvate, hydrate, co-crystal, clathrate, or polymorph thereof, where each Q$^7$ is halo, x is 0-4 and the remaining variables are as described elsewhere herein.

In one embodiment, provided herein is a compound of Formula XVII or an enantiomer or a mixture of enantiomers thereof, or a pharmaceutically acceptable salt, solvate, hydrate, co-crystal, clathrate, or polymorph thereof;
wherein
Y is —R$^a$OR$^b$;
R$^a$ is alkylene or a direct bond;
R$^b$ is hydrogen or alkyl;
each Q$^7$ is halo;
each Q$^3$ is halo;
x is 0-4; and
n is 0-3.

In one embodiment, provided herein is a compound of Formula XVIII.

XVIII or an enantiomer or a mixture of enantiomers thereof, or a pharmaceutically acceptable salt, solvate, hydrate, co-crystal, clathrate, or polymorph thereof, where each Q$^7$ is halo, and the remaining variables are as described elsewhere herein.

In one embodiment, provided herein is a compound of Formula XVIII or an enantiomer or a mixture of enantiomers thereof, or a pharmaceutically acceptable salt, solvate, hydrate, co-crystal, clathrate, or polymorph thereof;
wherein
X is C=O; and Y is —R$^a$OR$^b$;
R$^a$ is alkylene or a direct bond;
R$^b$ is hydrogen or alkyl;
R$^1$ and R$^2$ are each hydrogen;
R$^4$, R$^5$ and R$^6$ are each independently hydrogen or alkyl;
each Q$^7$ is halo;
R$^{10}$ is alkylene;
each Q$^3$ is halo; and
n is 0-3.

In one embodiment, provided herein is a compound of Formula XIX:

XIX or an enantiomer or a mixture of enantiomers thereof, or a pharmaceutically acceptable salt, solvate, hydrate, co-crystal, clathrate, or polymorph thereof, where each Q$^7$ is halo, and the remaining variables are as described elsewhere herein.

In one embodiment, provided herein is a compound of Formula XIX or an enantiomer or a mixture of enantiomers thereof, or a pharmaceutically acceptable salt, solvate, hydrate, co-crystal, clathrate, or polymorph thereof;
wherein
Y is —R$^a$OR$^b$;
R$^a$ is alkylene or a direct bond;
R$^b$ is hydrogen or alkyl;
each Q$^7$ is halo; and
each Q$^3$ is halo.

In one embodiment, provided herein is a compound of Formula XIX or an enantiomer or a mixture of enantiomers thereof, or a pharmaceutically acceptable salt, solvate, hydrate, co-crystal, clathrate, or polymorph thereof;
wherein
Y is —R$^a$OR$^b$;
R$^a$ is alkylene or a direct bond;
R$^b$ is hydrogen or alkyl;
each Q$^7$ is fluoro; and
each Q$^3$ is chloro.

6.3. Methods of Treatment

The compounds provided herein are used in methods for the treatment of conditions that are associated with or modulated by caspase-1, caspase-4 and/or caspase-5.

Accordingly, in one embodiment provided herein is a method for treating or preventing a disease modulated by caspase-1, caspase-4 and/or caspase-5 in a subject comprising administering to the subject a compound provided herein.

The disease states which can be treated or prevented by the compounds and/or their pharmaceutical compositions provided herein include, but are not limited to, inflammatory diseases, autoimmune diseases, proliferative disorders, infectious diseases, and degenerative diseases.

In one embodiment, the inflammatory diseases which can be treated or prevented by the compounds and/or their pharmaceutical compositions provided herein include, but are not limited to, osteoarthritis, acute pancreatitis, chronic pancreatitis, asthma, and adult respiratory distress syndrome.

In one embodiment, the inflammatory diseases which can be treated or prevented by the compounds and/or their pharmaceutical compositions provided herein include, but are not limited to, chronic and acute diseases such as, for example, autoinflammatory diseases such as Cryopyrin-Associated Periodic Syndromes (CAPS) and neuroinflammatory diseases such as multiple sclerosis (MS), Parkinson's disease and Alzheimer's disease. Treatment of acute inflammatory diseases such as, for example, septic shock, septicemia and adult respiratory distress syndrome also are contemplated by the methods provided herein.

In one embodiment, the autoimmune diseases which can be treated or prevented by the compounds and/or their pharmaceutical compositions provided herein include, but are not limited to, glomerulonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, multiple sclerosis, inflammatory bowel disease, Crohn's disease, psoriasis, atopic dermatitis and graft vs. host disease.

In one embodiment, the diseases which can be treated or prevented by the compounds and/or their pharmaceutical compositions provided herein include, but are not limited to, destructive bone disorders, such as osteoporosis and multiple myeloma-related bone disorder.

In one embodiment, the disease which can be treated or prevented by the compounds and/or their pharmaceutical compositions provided herein include, but are not limited to, infectious diseases such as sepsis, septic shock, and Shigellosis.

In one embodiment, the degenerative diseases which can be treated or prevented by the compounds and/or their pharmaceutical compositions provided herein include, but are not limited to, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke.

Other diseases having an inflammatory or apoptotic component can be treated or prevented by the compounds provided herein. Such diseases may be systemic diseases or diseases with effects localized in the liver or other organs and may be caused by, for example, excess dietary alcohol intake or viruses, such as HBV, HCV, HGV, yellow fever virus, dengue fever virus, and Japanese encephalitis virus.

In one embodiment provided herein is a method for treating or preventing a disease in a subject comprising administering to the subject a compound provided herein, where the disease is selected from inflammation or inflammatory diseases, inflammatory bowel disease, sepsis and septic shock, degenerative diseases including Alzheimer's disease, Huntingtons' disease, Parkinsons' disease, Multiple sclerosis, amyotrophic lateral sclerosis, spinobulbar atrophy, prion disease, dementia; brain hypoxia, anoxia, hyperoxia; ischemic multifocal lesions involving the cortical or lenticulo striate branches of the MCA, ischemic lesions in the territory of the middle cerebral artery (MCA) or left cerebral hemisphere, caused by haemodynamic differences from a patent ductus arteriosus, or a more direct route involving the left common carotid; focal arterial infarction, retinal pericyte apoptosis, retinal neurons apoptosis glaucoma, retinal degenerative diseases, age related macular degeneration (AMD) retinal damages resulting from local ischemia, diabetic retinopaty, epilepsy, apoptosis during spinal cord injury, apoptosis resulting from traumatic brain injury, retinal ischemia, apoptosis during pathological situations of focal cerebral ischemia, cytotoxic T cell and natural killer cell-mediated apoptosis associated with autoimmune disease and transplant rejection, cell death of cardiac cells including heart failure, cardiomyopathy, viral infection or bacterial infection of heart, myocardial ischemia, myocardial infarct, and myocardial ischemia, coronary artery by-pass graft, mitochondrial drug toxicity e.g. as a result of chemotherapy or HIV therapy, cell death during viral infection or bacterial infection, cell death from follicle to ovocyte stages, from ovocyte to mature egg stages and sperm (for example, methods of freezing and transplanting ovarian tissue, artificial fecondation), or to preserve fertility in women and men after chemotherapy, or to preserve fertility in females and males animals, macular degenerescence and glaucoma, acute hepatitis, chronic active hepatitis, hepatitis-B, and hepatitis-C, hair loss, and said hair loss due-to male-pattern baldness, radiation, chemotherapy or emotional stress, skin damage (due to exposure to high level of radiation, heat, burns, chemicals, sun, and autoimmune diseases), cell death of bone marrow cells in myelodysplastic symdromes (MDS), pancreatisis, respiratory symdrome, or osteoarthritis, rheumatoid arthritis, psoriasis, glomerulonephritis, atheroscerosis, and graft versus host disease, disease states associated with an increase of inflammation.

In some embodiments, provided herein is a method for use of a compound herein for the treatment and/or prevention of cancers. Typical cancers include lung cancer, colorectal cancer (CRC), melanoma, gastric cancer (including esophageal cancer), renal cell carcinoma (RCC), breast cancer, prostate cancer, head and neck cancer, bladder cancer, hepatocellular carcinoma (HCC), ovarian cancer, cervical cancer, endometrial cancer, pancreatic cancer, neuroendocrine cancer, hematological cancer (particularly multiple myeloma, acute myeloblastic leukemia (AML), and biliary tract cancer.

In one embodiment, provided herein is a therapy to improve the treatment of cancer having at least a partial inflammatory basis, e.g., a cancer described herein such as lung cancer. In one embodiment, provided herein is a use of a compound herein for the treatment and/or prevention of cancer having at least a partial inflammatory basis, e.g., a cancer described herein such as lung cancer. In another aspect, provided herein is a particular clinical dosage regimen for the administration of a compound herein for the treatment and/or prevention of cancer. In another aspect the subject with cancer having at least a partial inflammatory basis, including lung cancer, is administered with one or more therapeutic agent (e.g., a chemotherapeutic agent) and/or have received/will receive debulking procedures in addition to the administration of a compound herein.

In some embodiments, the methods of treating or preventing cancer in a human subject in need thereof comprising administering to the subject a therapeutically effective amount of a compound provided herein.

Another aspect of the invention is the use of a compound herein for the preparation of a medicament for the treatment of cancer.

In some embodiments, the compounds herein are used for the treatment or prevention in in cryopyrin-associated periodic syndromes (CAPS), familial Mediterranean fever (FMF), systemic onset juvenile idiopathic arthritis (SJIA), hyperimmunoglobulin D syndrome (HIDS) and tumor necrosis factor receptor-associated periodic syndrome (TRAPS), familial cold urticaria, neonatal onset multisystem inflammatory disease, SJIA and FMF, and Muckle Wells syndrome.

In some embodiments, the compounds provided herein may be used in any of the above-mentioned methods.

6.4. Pharmaceutical Compositions

The pharmaceutical compositions provided herein contain therapeutically effective amounts of one or more of the compounds provided herein that are useful in the prevention, treatment, or amelioration of one or more conditions associated with or modulated by caspase-1, caspase-4 and/or caspase-5, or one or more symptoms of a condition associated with or modulated by caspase-1, caspase-4 and/or caspase-5, such as those described in Section 4.4, and a pharmaceutically acceptable carrier.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds provided herein are formulated into pharmaceutical compositions using techniques and procedures well known in the art (see, e.g., Remington's Pharmaceutical Sciences, 20$^{th}$ eds., Mack Publishing, Easton PA (2000)).

In the compositions, effective concentrations of one or more compounds or pharmaceutically acceptable derivatives is (are) mixed with a suitable pharmaceutical carrier or vehicle. The compounds can be derivatized as the corresponding salts, esters, acids, bases, solvates, hydrates or prodrugs prior to formulation, as described above. The concentrations of the compounds in the compositions are effective for delivery of an amount, upon administration, that treats, prevents, or ameliorates a condition or one or more of the symptoms of a condition modulated by one or more caspases as described in Section 4.4.

In one embodiment, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds can be formulated as the sole pharmaceutically active ingredient in the composition or can be combined with other active ingredients. Liposomal suspensions, including tissue-targeted liposomes, such as tumor-targeted liposomes, can also be suitable as pharmaceutically acceptable carriers. These can be prepared according to methods known to those skilled in the art. For example, liposome formulations can be prepared as known in the art. Briefly, liposomes such as multilamellar vesicles (MLV's) can be formed by drying down egg phosphatidyl choline and brain phosphatidyl serine (7:3 molar ratio) on the inside of a flask. A solution of a compound provided herein in phosphate buffered saline (PBS) lacking divalent cations is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration can be determined empirically by testing the compounds in in vitro and in vivo systems known in the art and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art.

In one embodiment, a therapeutically effective dosage should produce a serum concentration of an active ingredient of from about 0.1 ng/ml to about 50-100 µg/ml, from about 0.5 ng/ml to about 80 µg/ml, from about 1 ng/ml to about 60 µg/ml, from about 5 ng/ml to about 50 µg/ml, from about 5 ng/ml to about 40 µg/ml, from about 10 ng/ml to about 35 µg/ml, from about 10 ng/ml to about 25 µg/ml, from about 10 ng/ml to about 10 µg/ml, from about 25 ng/ml to about 10 µg/ml, from about 50 ng/ml to about 10 µg/ml, from about 50 ng/ml to about 5 g/ml, from about 100 ng/ml to about 5 µg/ml, from about 200 ng/ml to about 5 µg/ml, from about 250 ng/ml to about 5 µg/ml, from about 500 ng/ml to about 5 µg/ml, from about 1 µg/ml to about 50 µg/ml, from about 0.1 ng/ml to about 5 ng/ml, from about 1 ng/ml to about 10 ng/ml or from about 1 µg/ml to about 10 µg/ml. The pharmaceutical compositions, in certain embodiments, should provide a dosage of from about 0.001 mg to about 2000 mg of compound per kilogram of body weight per day, from about 0.002 mg to about 1000 mg of compound per kilogram of body weight per day, from about 0.005 mg to about 500 mg of compound per kilogram of body weight per day, from about 0.005 mg to about 250 mg of compound per kilogram of body weight per day, from about 0.005 mg to about 200 mg of compound per kilogram of body weight per day, from about 0.005 mg to about 100 mg of compound per kilogram of body weight per day, from about 0.001 mg to about 0.005 mg of compound per kilogram of body weight per day, from about 0.01 mg to about 100 mg of compound per kilogram of body weight per day, from about 0.02 mg to about 100 mg of compound per kilogram of body weight per day, from about 0.05 mg to about 100 mg of compound per kilogram of body weight per day, from about 0.1 mg to about 100 mg of compound per kilogram of body weight per day, from about 0.5 mg to about 100 mg of compound per kilogram of body weight per day, from about 0.75 mg to about 100 mg of compound per kilogram of body weight per day, from about 1 mg to about 100 mg of compound per kilogram of body weight per day, from about 1 mg to about 10 mg of compound per kilogram of body weight per day, from about 0.001 mg to about 5 mg of compound per kilogram of body weight per day, from about 200 mg to about 2000 mg of compound per kilogram of body weight per day, or from about 10 mg to about 100 mg of compound per kilogram of body weight per day. Pharmaceutical dosage unit forms are prepared to provide from about 1 mg to about 1000 mg, from about 1 mg to about 800 mg, from about 5 mg to about 800 mg, from about 1 mg to about 100 mg, from about 1 mg to about 50 mg, from about 5 mg to about 100 mg, from about 10 mg to about 50 mg, from about 10 mg to about 100 mg, from about 25 mg to about 50 mg, and from about 10 mg to about 500 mg of the essential active ingredient or a combination of essential ingredients per dosage unit form.

The active ingredient can be administered at once, or can be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing recurrence of a condition associated with or modulated by caspase-1, caspase-4 and/or caspase-5, such as those described in Section 4.4. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, intravitreal injection, impregnated contact lens, rectally, topically, locally, by inhalation spray, nasally, buccally, vaginally, by an implanted reservoir or via nasogastric or orogastric tube. In some embodiments, administration is by an oral route. In other embodiments, administration is by a parenteral route. For oral administration, capsules and tablets can be used. The compositions are in liquid, semi-liquid or solid form and are formulated in a manner suitable for each route of administration. In one embodiment, modes of administration include parenteral and oral modes of administration. In certain embodiments, oral administration is contemplated.

Solutions or suspensions used for parenteral, intravitreal, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds can be used. Such methods are known to those of skill in this art, and include, but are not limited to, using co-solvents, such as dimethyl sulfoxide (DMSO), using surfactants, such as TWEEN®, or dissolution in aqueous sodium bicarbonate.

Upon mixing or addition of the compound(s), the resulting mixture can be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and can be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil/water emulsions containing suitable quantities of the compounds or pharmaceutically acceptable derivatives thereof. The pharmaceutically therapeutically active compounds and derivatives thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms can be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compounds remain in the body for a long time, they can denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions Dosage forms or compositions containing active ingredient in the range of 0.001% to 100% active ingredient, 0.002% to 100% active ingredient, 0.005% to 90% active ingredient, 0.01% to 100% active ingredient, 0.05% to 100% active ingredient, 0.05% to 90% active ingredient, 0.1% to 100% active ingredient, 0.1% to 1% active ingredient, 0.1% to 0.5% active ingredient, 1% to 100% active ingredient, 1% to 99% active ingredient, 1% to 98% active ingredient, 1% to 97% active ingredient, 1% to 96% active ingredient, 1% to 95% active ingredient, 5% to 95% active ingredient, 10% to 100% active ingredient, 10% to 95% active ingredient, 15% to 95% active ingredient, 20% to 95% active ingredient, 25% to 100% active ingredient, 50% to 100% active ingredient, 50% to 95% active ingredient, 60% to 95% active ingredient or 75% to 100% active ingredient, with the balance made up from nontoxic carrier can be prepared. For oral administration, a pharmaceutically acceptable nontoxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions can contain 0.001% to 100% active ingredient, in one embodiment or 75-95% active ingredient.

The active compounds or pharmaceutically acceptable derivatives can be prepared with carriers that protect the compound against rapid elimination from the body, such as time release formulations or coatings.

The compositions can include other active compounds to obtain desired combinations of properties. The compounds provided herein, or pharmaceutically acceptable derivatives thereof as described herein, can also be advantageously administered for therapeutic or prophylactic purposes, to a subject having a condition modulated by one or more caspases, together with another pharmacological agent known in the general art to be of value in treating the same condition. It is to be understood that such combination therapy constitutes a further aspect of the compositions and methods of treatment provided herein.

Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which can be enteric coated, sugarcoated or film coated. Capsules can be hard or soft gelatin capsules, while granules and powders can be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water-soluble FD and C dyes, mixtures thereof, and water-insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emeticcoatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition can also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup can contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient can be included.

Pharmaceutically acceptable carriers included in tablets are binders, lubricants, diluents, disintegrating agents, coloring agents, flavoring agents, and wetting agents. Enteric-coated tablets, because of the entericcoating, resist the action of stomach acid and dissolve or disintegrate in the neutral or alkaline intestines. Sugarcoated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned.

Coloring agents can also be used in the above dosage forms. Flavoring and sweetening agents are used in compressed tablets, sugarcoated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil in-water or water in oil.

Elixirs are clear, sweetened, hydroalcoholic preparations. Pharmaceutically acceptable carriers used in elixirs include solvents. Syrups are concentrated aqueous solutions of a sugar, for example, sucrose, and can contain a preservative. An emulsion is a two phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, can be encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, can be diluted with a sufficient quantity of a pharmaceutically acceptable liquid carrier, e.g., water, to be easily measured for administration.

Alternatively, liquid or semisolid oral formulations can be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations can be coated as known by those of skill in the art in order to modify or sustain dissolution of the active ingredient. Thus, for example, they can be coated with a conventional enterically digestible coating, such as phenylsalicylate, waxes and cellulose acetate phthalate.

Injectables, Solutions and Emulsions

Parenteral administration, generally characterized by injection, either subcutaneously, intramuscularly, intravitreal, or intravenously, is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered can also contain minor amounts of nontoxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, intravitreal, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can either be aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl phydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit dose parenteral preparations are packaged in an ampule, a vial or a syringe with a needle. All preparations for parenteral administration must be sterile, as is known and practiced in the art.

Illustratively, intravenous, intravitreal, or intra-arterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In certain embodiments, a therapeutically effective dosage is formulated to contain a concentration of at least about 0.1% w/w up to about 90% w/w or more, or more than 1% w/w of the active compound to the treated tissue(s). The active ingredient can be administered at once, or can be divided into a number of smaller doses to be administered at intervals of time. It is understood that the precise dosage and duration of treatment is a function of the tissue being treated and can be determined empirically using known testing protocols or by extrapolation from in vivo or in vitro test data. It is to be noted that concentrations and dosage values also can vary with the age of the individual treated. It is to be further understood that for any particular subject, specific dosage regimens can be adjusted over time according to the individual need and the professional judgment of the person administering or supervising the administration of the formulations, and that the concentration ranges set forth herein are exemplary only and are not intended to limit the scope or practice of the claimed formulations.

The compound can be suspended in micronized or other suitable form or can be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and can be empirically determined.

Lyophilized Powders

Of interest herein are also lyophilized powders, which can be reconstituted for administration as solutions, emulsions and other mixtures. They also can be reconstituted and formulated as solids or gels.

The sterile, lyophilized powder is prepared by dissolving a compound provided herein, or a pharmaceutically acceptable derivative thereof, in a suitable solvent. The solvent can contain an excipient which improves the stability or other pharmacological component of the powder or reconstituted solution, prepared from the powder. Excipients that can be used include, but are not limited to, dextrose, sorbital, fructose, corn syrup, xylitol, glycerin, glucose, sucrose or other suitable agent. The solvent can also contain a buffer, such as citrate, sodium or potassium phosphate or other such buffer known to those of skill in the art at about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg or 100-500 mg) or multiple dosages of the compound. The lyophilized powder can be stored under appropriate conditions, such as at about 4 degrees Celsius to room temperature.

Reconstitution of this lyophilized powder with water for injection provides a formulation for use in parenteral administration. For reconstitution, about 1-50 mg, 5-35 mg or about 9-30 mg of lyophilized powder, is added per mL of sterile water or other suitable carrier. The precise amount depends upon the selected compound. Such amount can be empirically determined.

Topical Administration

Topical mixtures are prepared as described for the local and systemic administration. The resulting mixture can be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches, contact lens or any other formulations suitable for topical administration.

The compounds or pharmaceutically acceptable derivatives thereof can be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will have diameters of less than 50 microns or less than 10 microns.

The compounds can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, can be formulated as 0.01%-10% isotonic solutions, pH about 5-7, with appropriate salts.

Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin gelatin, carbowax (polyoxyethylene glycol) and appropriate mixtures of mono, di and triglycerides of fatty acids. Combinations of the various bases can be used. Agents to raise the melting point of suppositories include spermaceti and wax. Rectal suppositories can be prepared either by the compressed method or by molding. In certain embodiments, the weight of a rectal suppository is about 2 to 3 gm.

Tablets and capsules for rectal administration are manufactured using the same pharmaceutically acceptable substance and by the same methods as for formulations for oral administration.

Sustained Release Compositions

Active ingredients such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358 and 6,699,500 each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus, the compositions provided encompass single unit dosage forms suitable for oral administration such as, but not limited to, tablets, capsules, gel caps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug can be administered using intravenous infusion, an implantable osmotic pump, a transdermal patch, liposomes, or other modes of administration. In one embodiment, a pump can be used (see, Sefton, *CRC Crit. Ref Biomed. Eng.* 1987; 14:201, Buchwald et al., *Surgery* 1980; 88:507, Saudek et al., *N. Engl. J. Med.* 1989; 321: 574. In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, 1984, pp. 115-138. Other controlled release systems are discussed in the review by Langer (*Science* 1990; 249:1527-1533. The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Targeted Formulations

The compounds provided herein, or pharmaceutically acceptable derivatives thereof, can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, can also be suitable as pharmaceutically acceptable carriers. These can be prepared according to methods known to those skilled in the art. For example, liposome formulations can be prepared as described in U.S. Pat. No. 4,522,811. Briefly, liposomes such as multilamellar vesicles (MILV's) can be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Dosage and Unit Dosage Forms

In human therapeutics, the doctor will determine the posology which he considers most appropriate according to a preventive or curative treatment and according to the age, weight, stage of the disease and other factors specific to the subject to be treated. Generally, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. Dose rates of from about 50 to about 500 mg per day are also contemplated.

In certain embodiments, the amount of the compound or composition which will be effective in the treatment of colon cancer or prevention one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses can be extrapolated from dose-response curves derived from in vitro or animal model test systems.

Exemplary doses of a composition include milligram or microgram amounts of the chemotherapeutic agent and caspase inhibitor per kilogram of subject or sample weight (e.g., about 0.001-1000 mg/Kg, about 0.01-100 mg/Kg, about 0.01-50 mg/Kg, about 0.1-25 mg/Kg, or about 0.1-10 mg/Kg. In certain embodiments, the dosage administered to a subject is between 0.20 mg/kg and 2.00 mg/kg, or between 0.30 mg/kg and 1.50 mg/kg of the subject's body weight.

In certain embodiments, the recommended daily dose range of the caspase inhibitors described herein and, optionally, where applicable, a co-administered chemotherapeutic agent, for the conditions described herein, lies within the range of from about 0.1 mg to about 1000 mg of each of the chemotherapeutic agent and caspase inhibitor per day, given as a single once-a-day dose or as divided doses throughout a day. In one embodiment, the daily dose is administered twice daily in equally divided doses. Specifically, a daily dose range should be from about 10 mg to about 200 mg per day, more specifically, between about 10 mg and about 150 mg per day, or even more specifically between about 25 and about 100 mg per day. It sometimes is necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts can be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the compound described herein are also encompassed by the above described dosage amounts and dose frequency schedules. Further, when a subject is administered multiple dosages of a compound described herein, not all of the dosages need be the same. For example, the dosage administered to the subject can be increased to improve the prophylactic or therapeutic effect of the compound or it can be decreased to reduce one or more side effects that a particular subject is experiencing.

In one embodiment, the dosage of compounds described herein administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the compounds provided herein administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of the caspase inhibitor and, optionally, where applicable, a co-administered chemotherapeutic agent, followed by one or more maintenance doses. In such embodiments, the loading dose can be, for instance, about 60 to about 400 mg per day, or about 100 to about 200 mg per day for one day to five weeks. The loading dose can be followed by one or more maintenance doses. Each maintenance does can be, independently, about from about 10 mg to about 200 mg per day, more specifically, between about 25 mg and about 150 mg per day, or even more specifically between about 25 mg and about 80 mg per day or between about 25 mg and about 50 mg per day. Maintenance doses can be administered daily and can be administered as single doses, or as divided doses.

In certain embodiments, a dose of the caspase inhibitor and, optionally, where applicable, a co-administered chemotherapeutic agent, can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound provided herein is administered to achieve a steady-state concentration in blood or serum of the subject of from about 300 to about 4000 ng/mL, from about 400 to about 1600 ng/mL, or from about 600 to about 1200 ng/mL. Loading doses can be administered to achieve steady-state blood or serum concentrations of about 1200 to about 8000 ng/mL, or about 2000 to about 4000 ng/mL for one to five days. Maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same compound can be repeated and the administrations can be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent can be repeated and the administration can be separated by at least at least 1 day, 2 days, 3 days, 5 days, 10 days, 15 days, 30 days, 45 days, 2 months, 75 days, 3 months, or 6 months.

In certain aspects, provided herein are unit dosages comprising a compound, or a pharmaceutically acceptable derivative thereof, in a form suitable for administration. Such forms are described in detail above. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

6.5. Articles of Manufacture

The compounds or pharmaceutically acceptable derivatives can be packaged as articles of manufacture containing packaging material, a compound or pharmaceutically acceptable derivative thereof provided herein, which is used for treatment, prevention or amelioration of a condition modulation by caspases or one or more symptoms associated with the condition, and a label that indicates that the compound or pharmaceutically acceptable derivative thereof is used for treatment, prevention or amelioration of the condition or one or more symptoms of the condition.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated.

6.6. Kits

Further provided are kits for use of the compounds provided herein in methods of treatment. The kits can include a caspase inhibitor or composition thereof, and instructions providing information to a health care provider regarding usage for treating or preventing a condition modulated by one or more caspases. Instructions can be provided in printed form or in the form of an electronic medium such as a CD, or DVD, or in the form of a website address where such instructions can be obtained. A unit dose of a caspase inhibitor or composition thereof, can include a dosage such that when administered to a subject, a therapeutically or prophylactically effective plasma level of the compound or composition can be maintained in the subject for at least 1 day. In some embodiments, the compounds or composition can be included as sterile aqueous pharmaceutical compositions or dry powder (e.g., lyophilized) compositions.

6.7. Schematics for the Preparation of Compounds

The compounds provided herein can be prepared by the general processes outlined in the schemes below. In schemes 1-4, where Ar and Ar' are each aryl, and $R^1$, $R^2$, $R^3$, $Y^1$, $Y^2$ and $Y^3$ are selected as described elsewhere herein.

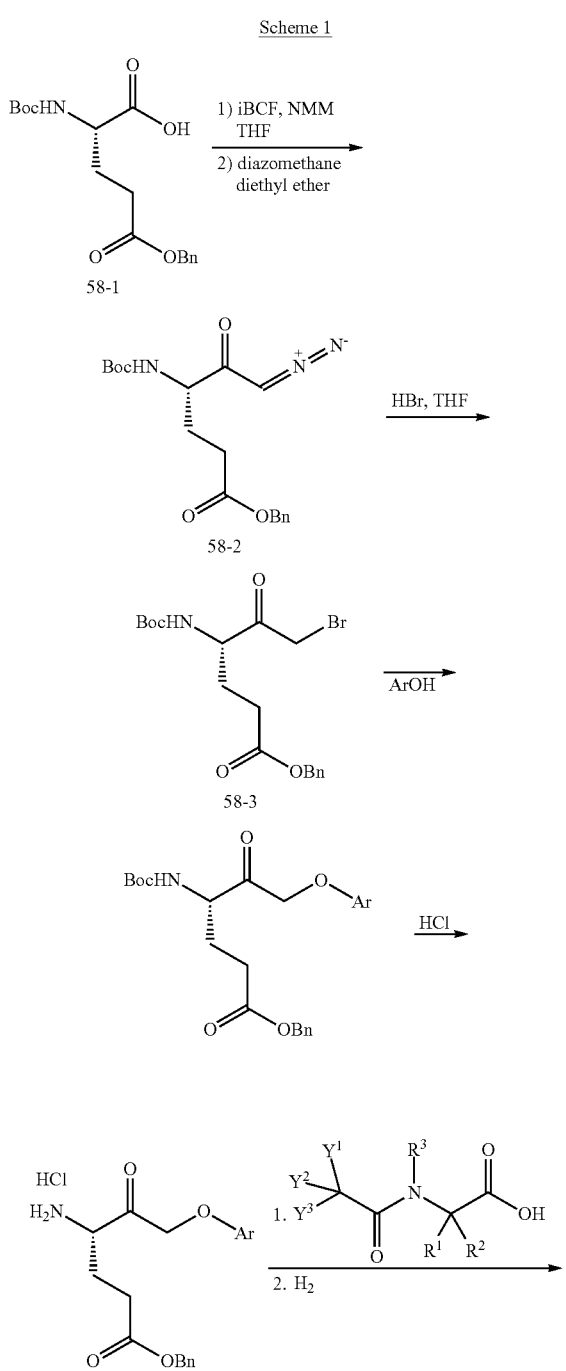

75
-continued
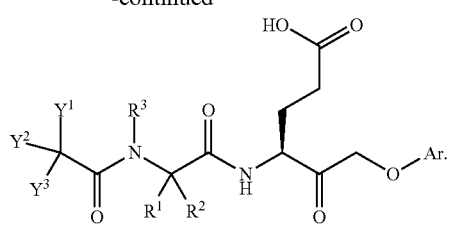
Scheme 2
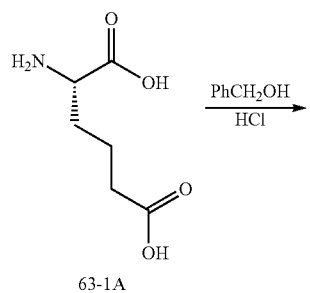
76
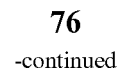
-continued
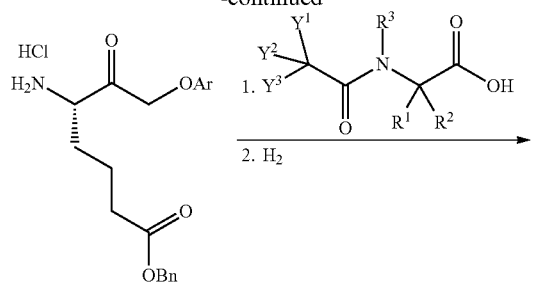
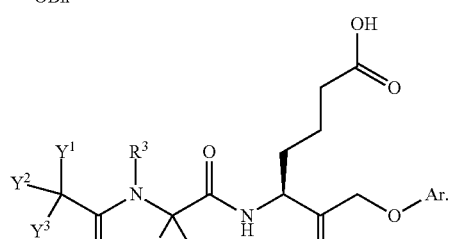
Scheme 3
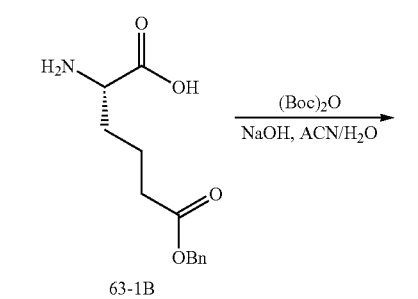
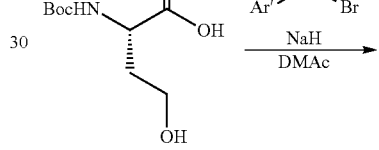
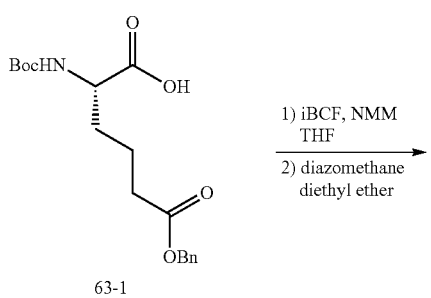
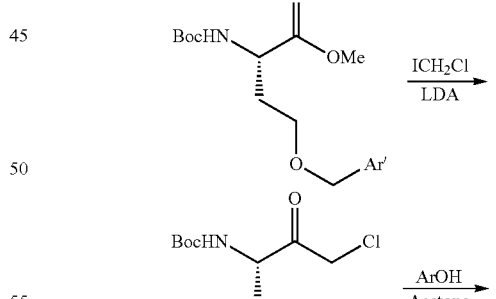
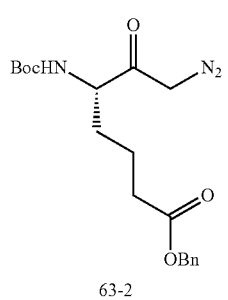
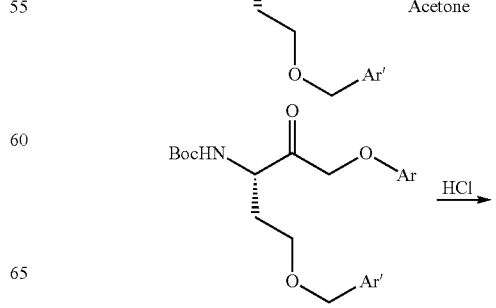

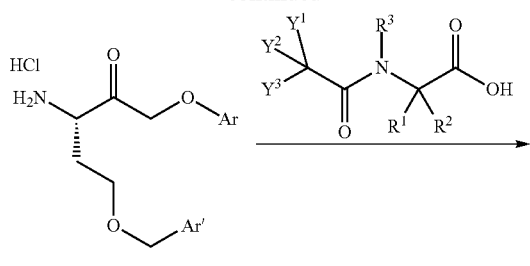
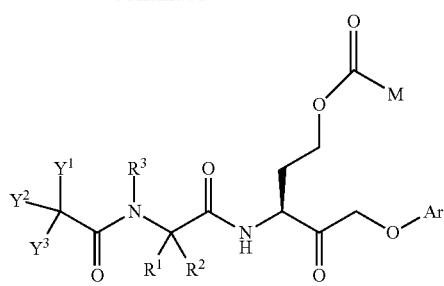

where M=lower alkylene, —OR′′′ or NR″R°, where R′′′ is optionally substituted aryl or optionally substituted heteroaryl, R″ and R° are each independently hydrogen, optionally substituted alkyl, optionally substituted aryl or optionally substituted heteroaryl, or R″ and R° together with the nitrogen atom on which they are substituted form a heterocyclic or heteroaryl ring, each of which is optionally substituted.

The following examples present certain exemplary embodiments and are intended by way of illustration and not by way of limitation.

7. EXAMPLES

The following Examples are presented by way of illustration, not limitation. One skilled in the art can modify the procedures set forth in the illustrative examples to arrive at the desired products.

Example 1

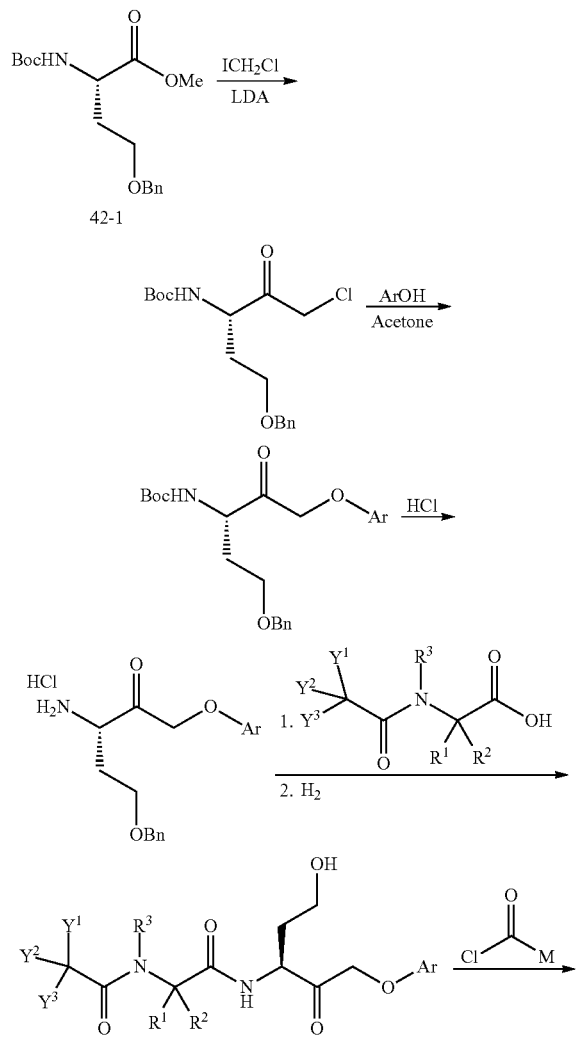

Scheme 4

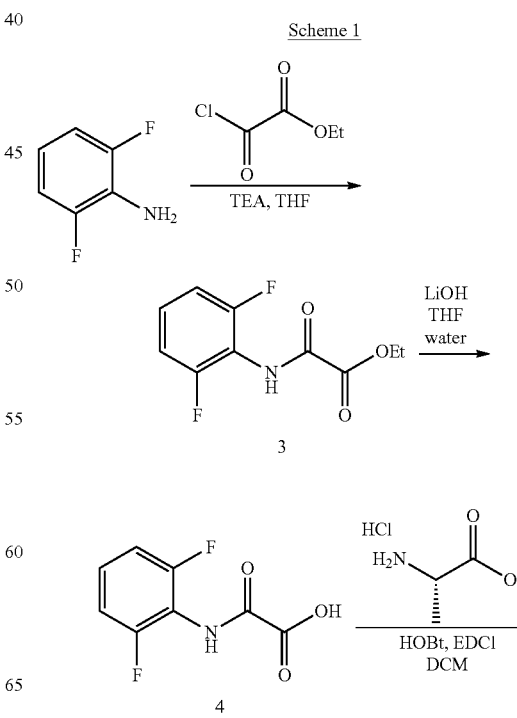

Scheme 1

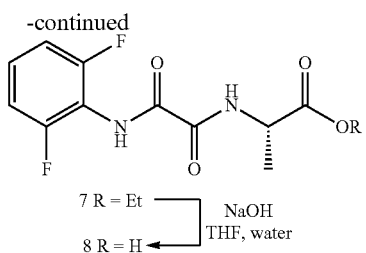

7 R = Et
8 R = H  ← NaOH, THF, water

Ethyl 2-((2,6-difluorophenyl)amino)-2-oxoacetate (3): Triethylamine (27.2 mL, 193.8 mmol, 1 equiv.) was added to a solution of 2,6-difluoroaniline (25.0 g, 193.8 mmol, 1 equiv.) in THF (1 L) at 0-5° C. Ethyl oxalyl chloride (21.6 mL, 193.8 mmol, 1 equiv.) was added dropwise over 60 minutes, while maintaining the temperature <5° C. The reaction was warmed to room temperature and stirred for 24 hours. The reaction was filtered through celite, the celite was washed with methyl t-butyl ether (500 mL) and the combined organic layers were washed with a 1N HCl (2×200 mL) and water (400 mL). The organic layer was dried over sodium sulfate, filtered and concentrated under reduced pressure to give the desired product as a beige oil (44.8 g, quantitative yield).

2-((2,6-Difluorophenyl)amino)-2-oxoacetic acid (4): 1N Lithium hydroxide (233 mL, 233 mmol, 1.2 equiv.) was added to a solution of compound 3 (44.8 g, 193.8 mmol, 1 equiv.) in THF (233 mL). After stirring at room temperature for 4 hours, the reaction was cooled to 0° C. and acidified with concentrated HCl to pH 2. The aqueous mix was saturated with sodium chloride and extracted with ethyl acetate (6×200 mL). The combined organic layers were dried over sodium sulfate, filtered and concentrated under reduced pressure to give the desired product as a white solid (18.3 g, 47% yield).

Ethyl (2-((2,6-difluorophenyl)amino)-2-oxoacetyl)-L-alaninate (7): EDC·HCl (25.9 g, 135 mmol, 1.4 equiv.) was added to a suspension of compound 4 (19.4 g, 96.5 mmol, 1.0 equiv.), HOAt (18.4 g, 135 mmol, 1.4 equiv.) in acetonitrile (1.0 L). The mixture was stirred at room temperature until all solids dissolved. L-Alanine ethyl ester hydrochloride (14.8 g, 96.5 mmol, 1.0 equiv.) and N-methylmorpholine (19.5 g, 193 mmol, 2.0 equiv) were added and the mixture was stirred at room temperature overnight. LC-MS analysis indicated that the reaction was complete. The mixture was concentrated under reduced pressure, and the wet solid was diluted in ethyl acetate (300 mL) and water (100 mL). The layers were separated, and the aqueous layer was extracted with ethyl acetate (2×50 mL). The combined organic layers were washed with saturated brine (50 mL), dried over sodium sulfate, filtered and concentrated under reduced pressure. The crude product was dissolved in dichloromethane (200 mL) and absorbed onto Celite (30 g). Purification on an Interchim automated system (330 g column) eluting with a gradient of 0 to 5% ethyl acetate in dichloromethane gave compound 7 (18.2 g, 62.8% yield) as a white solid.

(2-((2,6-Difluorophenyl)amino)-2-oxoacetyl)-L-alanine (8): 1N Lithium hydroxide (1.0 N, 71.5 mL, 71.5 mmol, 1.2 equiv.) was added to a solution of compound 7 (17.9 g, 59.6 mmol, 1.0 equiv.) in tetrahydrofuran (240 mL) at room temperature. After stirring for 48 hours, LC-MS analysis indicated that the reaction was complete. The mixture was cooled in an ice water bath and adjusted with concentrated HCl to pH=2. Saturated brine (300 mL) was added and the layers were separated. The aqueous layer was extracted with ethyl acetate (50 mL). The combined organic layers were dried over sodium sulfate, filtered and concentrated. The wet solid was mixed with 25% ethyl acetate in toluene (400 mL) at 40° C. for 30 minutes, concentrated under reduced pressure and dried under vacuum at 40° C. overnight to give compound 8 (14.1 g, 86.9% yield) as a white solid.

Scheme 2

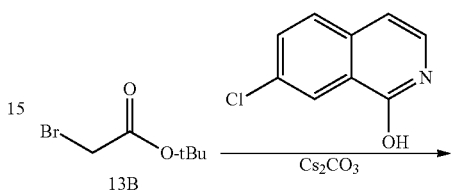

tert-Butyl 2-(7-chloro-1-oxoisoquinolin-2(1H)-yl)acetate (Compound 14B): A mixture of 7-chloroisoquinolin-1-ol (18 g, 100.2 mmol, 1.0 equiv.), cesium carbonate (65.3 g, 200 mmol, 2.0 equiv.) and t-butyl bromoacetate (29.3 g, 22 mL, 150 mmol, 1.5 equiv.) in dimethylformamide (500 mL) was stirred at 80° C. for 24 hours. The solvent was removed under reduced pressure and the residue was diluted with ethyl acetate (1000 mL) and washed with water (3×300 mL). The organic layer was dried over sodium sulfate, filtered and concentrated under reduced pressure. The resulting oil was dissolved in dichloromethane (500 mL) and absorbed onto silica gel (100 g). The material was divided into four equal portions. Each portion was purified on an Interchim HPLC system (330 g silica gel column), eluting with a gradient of 0 to 50% ethyl acetate in heptanes to give the desired product (25.8 g, 88% yield) as a white solid.

2-(7-Chloro-1-oxoisoquinolin-2(1H)-yl)acetic acid (Compound 15): A mixture of compound 14B (14.3 g, 49.1 mmol) and trifluoroacetic acid (27.9 g, 18.8 mL, 245 mmol, 5.0 equiv.) in dichloromethane (300 mL) was stirred for 48 hours at room temperature. The solvent was removed under reduced pressure. The resulting solid was triturated with methyl t-butyl ether (500 mL), suction-filtered and washed with methyl t-butyl ether (3×200 mL). The solid was dried under vacuum at room temperature overnight to give the desired product (8.1 g, 69% yield) as a white solid.

Scheme 3

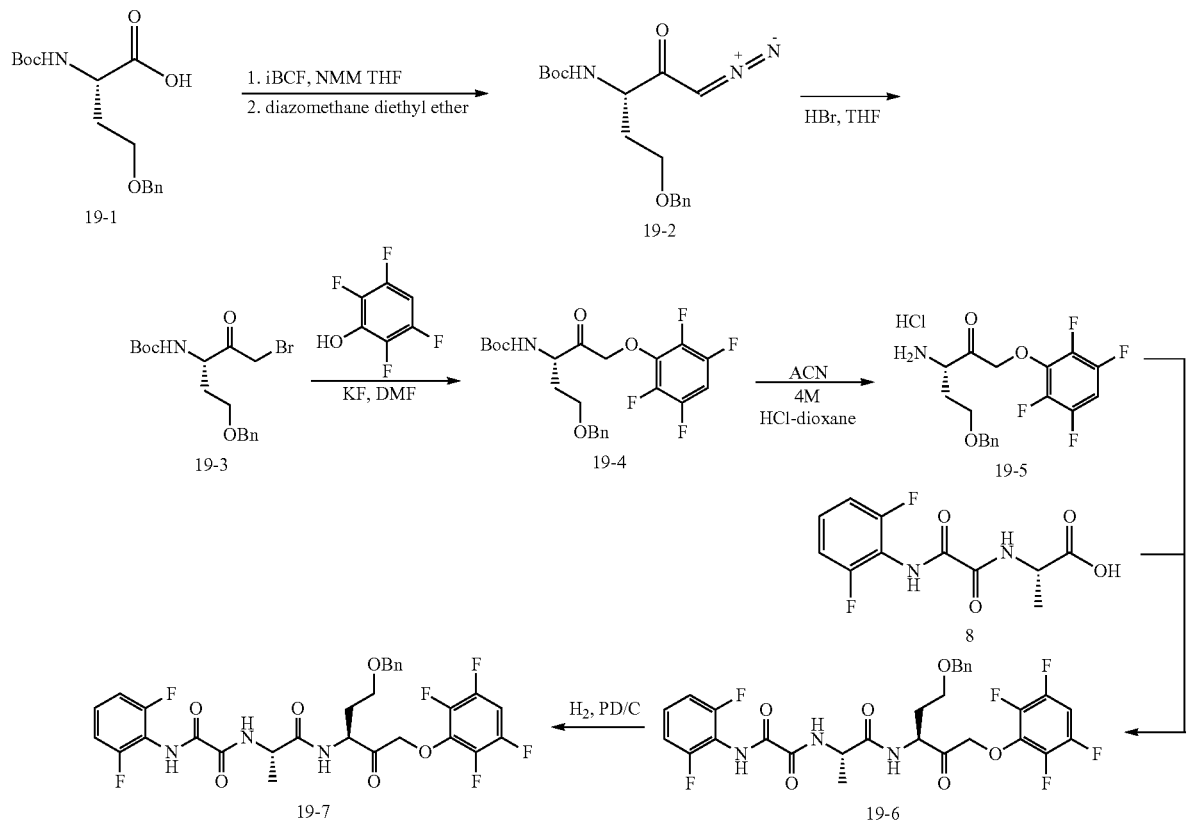

tert-Butyl (S)-(5-(benzyloxy)-1-bromo-2-oxopentan-3-yl)carbamate (19-3): Isobutyl chloroformate (6.59 mL, 50.8 mmol, 1.5 equiv.) was added dropwise to a solution of Boc-O-benzyl-L-homoserine (19-1) (10.5 g, 33.9 mmol, 1 equiv.) and N-methylmorpholine (5.96 mL, 54.2 mmol, 1.6 equiv.) in THF (113 mL) at −10° C. After stirring at −10° C. for 20 minutes, the reaction was filtered through celite and concentrated under reduced pressure to give the mixed anhydride (13.9 g) as a colorless oil, which was used subsequently.

Diazomethane preparation: A solution of N-methyl-N'-nitroso-p-toluenesulfonamide (Diazald®, 21.8 g, 101.6 mmol, 1 equiv.) in diethyl ether (113 mL) was added through an addition funnel to a mixture of potassium hydroxide (17.1 g, 304.8 mmol, 3 equiv.) in ethanol (34 mL) and water (27 mL) in an oil bath at 65° C. The receiving flask to collect the ethereal solution of diazomethane was cooled in an ice-bath and the Diazald® solution was added at such a rate as that allowed for a dropwise distillation into the receiving flask. When all of the Diazald® solution had been added, additional diethyl ether (10 mL) was added through the addition funnel until the distillate was clear (no remaining diazomethane). After cooling to room temperature, the mixture in the distillation flask was quenched slowly with acetic acid until the yellow color disappeared.

A solution of freshly prepared mixed anhydride above (13.9 g, 33.9 mmol, 1 equiv.) in diethyl ether (75 mL) was placed in a clear-seal joint flask and cooled to 0° C. in an ice bath. The freshly prepared diazomethane ethereal solution (~101.6 mmol, 3 equiv.) was added through an addition funnel dropwise while keeping it cold. The resulting mixture was stirred at 0° C. for 15 minutes, warmed to room temperature and stirred for 30 minutes. The reaction was cooled to 0° C. Meanwhile a mixture of 48% aqueous HBr (26.8 mL, 237 mmol, 7 equiv.) and acetic acid (26.8 mL) was cooled to 0° C. and added to the above reaction mixture slowly at 0° C. The mixture was stirred at 0° C. for 15 minutes, warmed to room temperature and stirred for 30 minutes. The mixture was diluted with diethyl ether (100 mL), washed with water (3×100 mL), dried over sodium sulfate, filtered and concentrated under reduced pressure. The residue was purified on an InterChim auto-chromatography system (220 g SorbTech silica gel column), eluting with a gradient of 0 to 40% ethyl acetate in heptanes to give compound 19-3 (9.0 g, 73% yield) as a colorless oil.

tert-Butyl (S)-(5-(benzyloxy)-2-oxo-1-(2,3,5,6-tetrafluorophenoxy)pentan-3-yl)carbamate (19-4): Potassium fluoride (5.46 g, 94.0 mmol, 4 equiv.) was added to a solution of compound 19-3 (9.0 g, 23.5 mmol, 1 equiv.) and 2,3,5,6-tetrafluorophenol (4.29 g, 28.8 mmol, 1.1 equiv.) in DMF (120 mL). After stirring at room temperature for 16 hours, the reaction was diluted with ethyl acetate (100 mL), washed with saturated sodium bicarbonate (100 mL) and saturated brine (100 mL). The organic layer was dried over sodium sulfate, filtered and concentrated under reduced pressure. The residue was purified on an InterChim auto-chromatography system (220 g SorbTech silica gel column), eluting with a gradient of 10 to 40% ethyl acetate in heptanes to give compound 19-4 (5.40 g, 49% yield) as a colorless oil.

(S)-3-Amino-5-(benzyloxy)-1-(2,3,5,6-tetrafluorophenoxy)pentan-2-one hydrochloride (19-5): 4M HCl in 1,4-dioxane (3.5 mL, 13.8 mmol, 1.2 equiv.) was added dropwise to a solution of compound 19-4 (5.40 g, 11.5 mmol, 1 equiv.) in acetonitrile (60 mL) at 5° C. The mixture was then warmed to room temperature and stirred overnight. LCMS indicated that the reaction was not complete. Additional 4M HCl in 1,4-dioxane (2.30 mL, 9.2 mmol, 0.8 equiv.) was added and the mixture was stirred for 6 hours at which time LCMS indicated that the reaction was complete. The mixture was concentrated under reduced pressure to give compound 19-5 (4.0 g, 86% yield) as a light yellow solid.

$N^1$—((S)-1-(((S)-5-(Benzyloxy)-2-oxo-1-(2,3,5,6-tetrafluorophenoxy)pentan-3-yl)amino)-1-oxopropan-2-yl)-$N^2$-(2,6-difluorophenyl)oxalamide (19-6, Example 1): EDC.HCl (0.907 g, 4.73 mmol, 1.1 equiv.) was added to a suspension of compound 8 (1.17 g, 4.30 mmol, 1.0 equiv.) and HOAt (0.702 g, 5.16 mmol, 1.2 equiv.) in acetonitrile (20 mL). The mixture was stirred at room temperature until all solids dissolved. Compound 19-5 (1.75 g, 4.30 mmol, 1.0 equiv.) and triethylamine (1.20 mL, 8.6 mmol, 2.0 equiv.) were added and the mixture was stirred at room temperature overnight. LC-MS analysis indicated that the reaction was complete. The mixture was diluted with ethyl acetate (40 mL) and washed with saturated sodium bicarbonate (30 mL) and saturated brine (30 mL). The organic layer was dried over sodium sulfate, filtered and concentrated under reduced pressure. The crude product was purified on an Interchim automated system (40 g column), eluting with a gradient of 10 to 70% ethyl acetate in heptanes to give compound 19-6, (Example 1) (1.90 g, 71% yield) as a light yellow solid, (Mass Spec. m/z=626.1 (M+H).

Example 2

$N^1$-(2,6-Difluorophenyl)-$N^2$—((S)-1-(((S)-5-hydroxy-2-oxo-1-(2,3,5,6-tetrafluorophenoxy)pentan-3-yl)amino)-1-oxopropan-2-yl)oxalamide (19-7, Example 2): A mixture of compound (1.30 g, 2.08 mmol, 1.0 equiv.) and 10% palladium on activated carbon (130 mg, 50% wet) in tetrahydrofuran (18 mL) and methanol (18 mL) was hydrogenated @ 45 psi for 3 hours. LC-MS analysis indicated that the reaction was complete. The mixture was filtered through Celite (20 g), which was washed with additional methanol (25 mL). The crude product was purified twice on an Interchim automated system. Two 40 g columns were used for purification. The first purification was done on a 40 g silica gel column, eluting with a gradient of 0 to 10% methanol in dichloromethane. The material was then further purified on a second 40 g silica gel column, eluting with a gradient of 30 to 90% ethyl acetate in heptanes. The product was dissolved in diethyl ether (3 mL) and precipitated by the addition of heptanes (5 mL). The solid was dried on the filter to give the desired product. The product was purified on an Interchim automated system (Teledyne ISCO—Column Gold C18 50G column), eluting with a gradient of 0 to 50% acetonitrile in water to give compound 19-7, (Example 2) (325 mg, 29% yield) as a white solid, (Mass Spec. m/z=536 (M+H).

Example 3

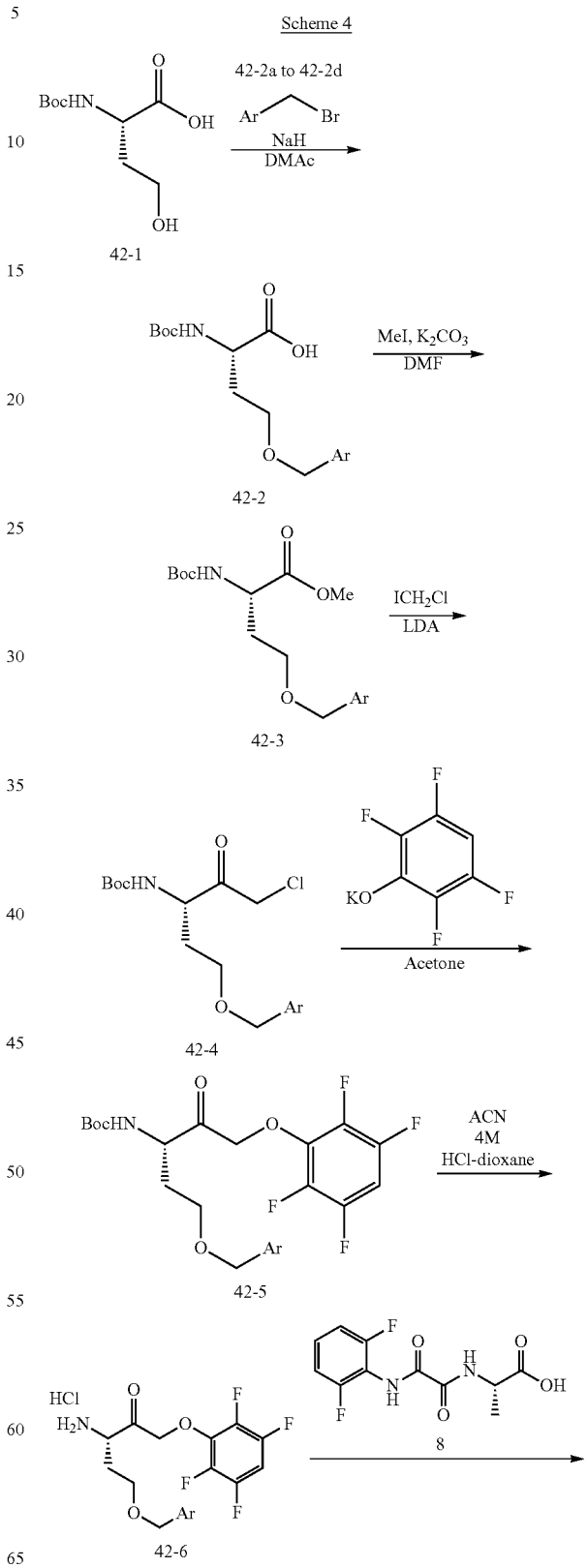

-continued

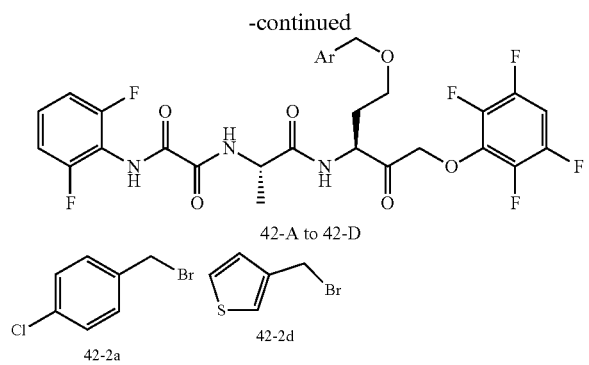

42-A to 42-D 42-2a 42-2d

N-(tert-Butoxycarbonyl)-O-(4-chlorobenzyl)-L-homoserine (42-2a): A 60% dispersion of sodium hydride in mineral oil (6.02 g, 150.5 mmol, 2.2 equiv.) was added to a solution of compound 42-1 (15.0 g, 68.4 mmol, 1 equiv.) in anhydrous N,N-dimethylacetamide (100.0 mL) at 0° C. After stirring 1.5 hours at 0° C., 4-chlorobenzyl bromide (15.465 g, 75.3 mmol, 1.1 equiv.) was added and\the reaction was stirred at room temperature for 16 hours. The reaction mixture was diluted with ice-cold water (200 mL) and extracted with diethyl ether (2×800 mL). The aqueous layer was acidified to pH 3.4 with 3M HCl (30 mL) and extracted with ethyl acetate (1 L). The organic layer was washed with saturated brine solution (1 L) and water (3×1 L), dried over sodium sulfate (150 g) and concentrated under reduced pressure. The crude material was absorbed on to celite (30 g) and purified on an Interchim automated chromatography system (Sorbtech silica gel column, 330 g), eluting with a gradient of 0 to 10% methanol in dichloromethane to give compound 42-2a (3.9 g, 16% yield) as a viscous pale yellow oil.

Methyl N-(tert-butoxycarbonyl)-O-(4-chlorobenzyl)-L-homoserinate (42-3a): Potassium carbonate (1.369 g, 9.9 mmol, 2.0 equiv.) was added to solution of compound 42-2a (1.7 g, 4.9 mmol, 1.0 equiv.) in DMF (10 mL). After stirring at room temperature for 10 minutes, methyl iodide (0.617 mL, 9.9 mmol, 2.0 equiv.) was added and the reaction was stirred at room temperature for 16 hours. The reaction mixture was diluted with ethyl acetate (500 mL) and washed with saturated brine solution (3×500 mL) and water (500 mL). The organic layer was dried over sodium sulfate (100 g) and concentrated under reduced pressure. The crude material was absorbed on to celite (4 g) and purified on an Interchim automated chromatography system (Sorbtech silica gel column, 80 g), eluting with a gradient of 0 to 60% ethyl acetate in heptanes to give compound 42-3a (1.4 g, 78% yield) as a colorless oil.

tert-Butyl (S)-(1-chloro-5-((4-chlorobenzyl)oxy)-2-oxopentan-3-yl)carbamate (42-4a): 1.6 M, n-BuLi in hexane (12.224 mL, 19.5 mmol, 5.0 equiv.) was added to diisopropylamine (3.0 mL, 21.5 mmol, 5.5 equiv.) in THF (20 mL) at −78° C. The reaction was warmed to 0° C. for 5 minutes, cooled to −78° C. and slowly added over 45 minutes to compound 42-3a (1.4 g, 3.9 mmol, 1.0 equiv.) in THF (20 mL) at −78° while maintaining the temperature <−72° C. After stirring at −78° C. for 45 minutes, acetic acid (9 mL) was added drop wise at −78° C. The reaction was diluted with saturated brine solution (800 mL) and extracted with ethyl acetate (500 mL). The organic layer was washed with saturated bicarbonate (3×500 mL) and water (250 mL). The ethyl acetate layer was dried over sodium sulfate (100 g) and concentrated under reduced pressure. The crude material was absorbed on to celite (6 g) and purified on an Interchim automated chromatography system (Sorbtech silica gel column, 80 g), eluting with a gradient of 0 to 40% ethyl acetate in heptanes to give compound 42-4a (1.0 g, 67% yield) as a light yellow oil.

Potassium salt of 2,3,5,6-tetrafluorophenol: 2,3,5,6-tetrafluorophenol (2.0 g, 12.0 mmol, 1.0 equiv.) was added to a solution of potassium hydroxide (0.68 g, 12.0 mmol, 1.0 equiv.) in methanol. After stirring at room temperature for 18 hours, the solvents were removed under reduced pressure. The residue was dried under vacuum at room temperature for 16 hours to give the potassium salt of 2,3,5,6-tetrafluorophenol (2.4 g, 97% yield) as white solid.

tert-Butyl (S)-(5-((4-chlorobenzyl)oxy)-2-oxo-1-(2,3,5,6-tetrafluorophenoxy) pentan-3-yl)carbamate (42-5a): Sodium iodide (0.6 g, 4.0 mmol, 1.5 equiv.) and the potassium salt of 2,3,5,6-tetrafluorophenol (0.813 g, 4.0 mmol, 1.5 equiv.) were added to a solution of compound 42-4a (1.0 g, 2.6 mmol, 1.0 equiv.) in acetone (12 mL). After stirring at room temperature for 20 hours, the solvents were removed under reduced pressure. The residue was diluted with ethyl acetate (500 mL) and washed with saturated brine (250 mL). The organic layer was dried over sodium sulfate, filtered and concentrated under reduced pressure. The crude material was absorbed on to celite (4 g) and purified on an Interchim automated chromatography system (Sorbtech silica gel column, 80 g), eluting with a gradient of 0 to 40% ethyl acetate in heptanes to give compound 42-5a (0.89 g, 66% yield) as a light yellow oil.

(S)-3-Amino-5-((4-chlorobenzyl)oxy)-1-(2,3,5,6-tetrafluorophenoxy)pentan-2-one hydrogen chloride (42-6a): 4M HCl in 1,4-dioxane (0.869 mL, 3.5 mmol, 2.0 equiv.) was added dropwise to a solution of compound 42-5a (0.885 g, 1.7 mmol, 1 equiv.) in acetonitrile (15 mL) at 5° C. The mixture was warmed to room temperature and stirred for 24 hours. The mixture was concentrated under reduced pressure. The residue was triturated with heptanes (3×10 mL) and decanted and dried under vacuum to give compound 42-6a (0.633 g, 81% yield) as an off-white solid.

$N^1$—((S)-1-(((S)-5-((4-Chlorobenzyl)oxy)-2-oxo-1-(2,3,5,6-tetrafluorophenoxy)pentan-3-yl)amino)-1-oxopropan-2-yl)-$N^2$-(2,6-difluorophenyl)oxalamide
(42-A, Example 3)

EDC.HCl (0.286 g, 1.5 mmol, 1.1 equiv.) was added to a suspension of compound 8 (0.369 g, 1.4 mmol, 1.0 equiv.) and HOAt (0.221 g, 1.6 mmol, 1.2 equiv.) in acetonitrile (10 mL). The mixture was stirred at room temperature until all solids dissolved. Compound 42-6a (0.6 g, 1.4 mmol, 1.0 equiv.) and triethylamine (0.378 mL, 2.7 mmol, 2.0 equiv.) were sequentially added and the mixture was stirred at room temperature for 20 hours. The mixture was diluted with ethyl acetate (250 mL) and washed with saturated sodium bicarbonate (250 mL) and saturated brine (250 mL). The organic layer was dried over sodium sulfate, filtered and concentrated under reduced pressure. The crude material was absorbed on to celite (4 g) and purified on an Interchim automated chromatography system (Sorbtech silica gel column, 80 g), eluting with a gradient of 0 to 60% ethyl acetate in heptanes to give 42-A, (Example 3) (0.59 g, 65% yield) as a white solid, (Mass Spec. m/z=660.1 (M+H).

N-(tert-Butoxycarbonyl)-O-(thiophen-3-ylmethyl)-L-homoserine (42-2d): A 60% dispersion of sodium hydride in mineral oil (4.29 g, 107.3 mmol, 2.2 equiv.) was added to a solution of compound 42-1 (10.69 g, 48.78 mmol, 1 equiv.) in anhydrous N,N-dimethylacetamide (80.0 mL) at 0° C.

After stirring for 1.5 hours at 0° C., 3-bromomethylthiophene (9.5 g, 53.6 mmol, 1.1 equiv.) was added and the reaction was stirred at room temperature for 24 hours. The reaction mixture was diluted with ice-cold water (150 mL) and extracted with ethyl acetate (2 xl L). The aqueous layer was acidified to pH 3.0, with 3M HCl (16 mL) and extracted with ethyl acetate (1 L). The organic layer was washed with saturated brine solution (1 L) and water (3×1 L), dried over sodium sulfate (150 g) and concentrated under reduced pressure. The crude material was absorbed on to celite (30 g) and purified on an Interchim automated chromatography system (Sorbtech silica gel column, 330 g), eluting with a gradient of 0 to 100% ethyl acetate in heptanes to give compound 42-2d (2.34 g, 15% yield) as a viscous pale yellow oil.

Methyl N-(tert-butoxycarbonyl)-O-(thiophen-3-ylmethyl)-L-homoserinate (42-3d): Potassium carbonate (2.05 g, 14.8 mmol, 2.0 equiv.) was added to solution of compound 42-2d (2.34 g, 7.4 mmol, 1.0 equiv.) in DMF (12 mL). After stirring at room temperature for 10 minutes, methyl iodide (0.923 mL, 14.8 mmol, 2.0 equiv.) was added and the reaction was stirred at room temperature for 24 hours. The reaction mixture was diluted with ethyl acetate (250 mL) and washed with saturated brine solution (3×250 mL) and water (250 mL). The organic layer was dried over sodium sulfate (100 g) and concentrated under reduced pressure. The crude material was absorbed on to celite (5 g) and purified on an Interchim automated chromatography system (Sorbtech silica gel column, 80 g), eluting with a gradient of 0 to 50% ethyl acetate in heptanes to give compound 42-3d (1.9 g, 77% yield) as a light yellow oil.

tert-Butyl (S)-(1-chloro-2-oxo-5-(thiophen-3-ylmethoxy)pentan-3-yl)carbamate (42-4d): 1.6 M n-BuLi in hexanes (9.5 mL, 15.2 mmol, 5.0 equiv.) was added to diisopropylamine (2.34 mL, 16.7 mmol, 5.5 equiv.) in THE (15 mL) at −78° C. The reaction was warmed to 0° C. for 5 minutes, cooled to −78° C. and slowly added over 30 minutes to compound 42-3d (1.0 g, 3.0 mmol, 1.0 equiv.) in THE (15 mL) at −78° C. After stirring at −78° C. for 25 minutes, acetic acid (6 mL) was added drop wise at −78° C. The reaction was diluted with saturated brine solution (500 mL) and extracted with ethyl acetate (500 mL). The organic layer was washed with saturated bicarbonate solution (3×500 mL) and water (250 mL). The ethyl acetate layer was dried over sodium sulfate (100 g) and concentrated under reduced pressure. The crude material was absorbed on to celite (4 g) and purified on an Interchim automated chromatography system (Sorbtech silica gel column, 80 g), eluting with a gradient of 0 to 80% ethyl acetate in heptanes to give compound 42-4d (0.938 g, 82% yield) as a light yellow oil.

tert-Butyl (S)-(2-oxo-1-(2,3,5,6-tetrafluorophenoxy)-5-(thiophen-3-ylmethoxy)pentan-3-yl)carbamate (42-5d): Sodium iodide (0.56 g, 3.7 mmol, 1.5 equiv.) and potassium salt of 2,3,5,6-tetrafluorophenol (0.763 g, 3.7 mmol, 1.5 equiv.) was added to a solution of compound 42-4d (0.938 g, 2.5 mmol, 1.0 equiv.) in acetone (10 mL). After stirring at room temperature for 18 hours, the solvents were removed under reduced pressure. The residue was diluted with ethyl acetate (500 mL) and washed with saturated brine (250 mL). The organic layer was dried over sodium sulfate (50 g), filtered and concentrated under reduced pressure. The crude material was absorbed on to celite (4 g) and purified on an Interchim automated chromatography system (Sorbtech silica gel column, 80 g), eluting with a gradient of 0 to 40% ethyl acetate in heptanes to give compound 42-5d (0.754 g, 63% yield) as a light yellow oil.

(S)-3-Amino-1-(2,3,5,6-tetrafluorophenoxy)-5-(thiophen-3-ylmethoxy)pentan-2-one hydrogen chloride (42-6d): 4M HCl in 1,4-dioxane (0.78 mL, 3.1 mmol, 2.0 equiv.) was added dropwise to a solution of compound 42-5d (0.75 g, 1.6 mmol, 1 equiv.) in acetonitrile (10 mL) at 5° C. The mixture was then warmed to room temperature and stirred for 24 hours. The mixture was concentrated under reduced pressure. The solid was triturated with heptanes (3×10 mL), decanted and dried under vacuum to give compound 42-6d (0.514 g, 79% yield) as an off-white solid.

Example 4

$N^1$-(2,6-difluorophenyl)-$N^2$—((S)-1-oxo-1-(((S)-2-oxo-1-(2,3,5,6-tetrafluorophenoxy)-5-(thiophen-3-ylmethoxy)pentan-3-yl)amino)propan-2-yl)oxalamide (42-D, Example 4): EDC.HCl (0.146 g, 0.8 mmol, 1.1 equiv.) was added to a suspension of compound 8 (0.189 g, 0.7 mmol, 1.0 equiv.) and HOAt (0.113 g, 1.0 mmol, 1.2 equiv.) in acetonitrile (8 mL). The mixture was stirred at room temperature until all solids dissolved. Compound 42-6d (0.288 g, 0.7 mmol, 1.0 equiv.) and triethylamine (0.193 mL, 1.4 mmol, 2.0 equiv.) were sequentially added and the mixture was stirred at room temperature for 20 hours. The mixture was diluted with ethyl acetate (250 mL) and washed with saturated sodium bicarbonate (250 mL) and saturated brine (250 mL). The organic layer was dried over sodium sulfate (100 g), filtered and concentrated under reduced pressure. The crude material was absorbed on to celite (3 g) and purified on an Interchim automated chromatography system (Sorbtech silica gel column, 25 g), eluting with a gradient of 0 to 90% ethyl acetate in heptanes to give 42-D, (Example 4) (0.2 g, 45% yield) as a white solid, (Mass Spec. m/z=632.1 (M+H).

Example 5

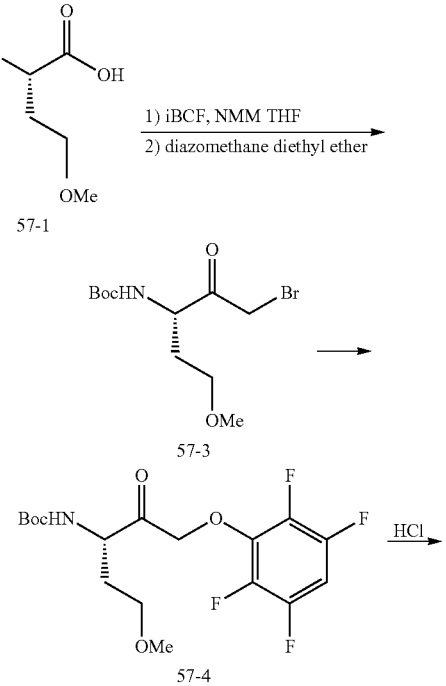

Scheme 5

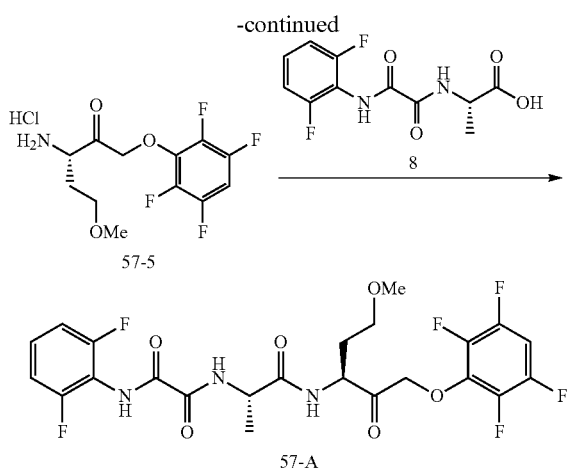

tert-Butyl (S)-(1-bromo-5-methoxy-2-oxopentan-3-yl) carbamate (57-3): Isobutyl chloroformate (0.84 mL, 6.43 mmol, 1.5 equiv.) was added dropwise to a solution of N-(tert-butoxycarbonyl)-O-methyl-L-homoserine (57-1) (1.0 g, 4.29 mmol, 1 equiv.) and N-methylmorpholine (0.75 mL, 6.86 mmol, 1.6 equiv.) in THF (18 mL) at −10° C. After stirring at −10° C. for 20 minutes, the reaction was filtered through celite and concentrated under reduced pressure to give the mixed anhydride as a colorless oil, which was used subsequently.

Diazomethane preparation: A solution of N-methyl-N'-nitroso-p-toluenesulfon-amide (Diazald®, 2.76 g, 12.87 mmol, 1 equiv.) in diethyl ether (10 mL) was added through an addition funnel to a mixture of potassium hydroxide (2.54 g, 38.6 mmol, 3 equiv.) in ethanol (6 mL) and water (5 mL) in an oil bath at 65° C. The receiving flask to collect the ethereal solution of diazomethane was cooled in an ice-bath and the Diazald® solution was added at such a rate as that allowed for a dropwise distillation into the receiving flask. When all of the Diazald® solution had been added, additional diethyl ether (3 mL) was added through the addition funnel until the distillate was clear (no remaining diazomethane). After cooling to room temperature, the mixture in the distillation flask was quenched slowly with acetic acid until the yellow color disappeared.

A solution of freshly prepared mixed anhydride above (1.37 g, 4.29 mmol, 1 equiv.) in diethyl ether (25 mL) was placed in a clear-seal joint flask and cooled to 0° C. in an ice bath. The freshly prepared diazomethane ethereal solution (~12.87 mmol, 3 equiv.) was added through an addition funnel dropwise while keeping it cold. The resulting mixture was stirred at 0° C. for 15 minutes, warmed to room temperature and stirred for 30 minutes. The reaction was cooled to 0° C. Meanwhile a mixture of 48% aqueous HBr (4.0 mL, 30.0 mmol, 7 equiv.) and acetic acid (4.0 mL) was cooled to 0° C. and added to the above reaction mixture slowly at 0° C. The mixture was stirred at 0° C. for 15 minutes, warmed to room temperature and stirred for 30 minutes. The mixture was diluted with diethyl ether (10 mL), washed with water (3×15 mL), dried over sodium sulfate, filtered and concentrated under reduced pressure. The residue was purified on an InterChim automated chromatography system (120 g SorbTech silica gel column), eluting with a gradient of 0 to 40% ethyl acetate in heptanes to give compound 57-3 (0.67 g, 50% yield) as a colorless oil.

tert-Butyl (S)-(5-methoxy-2-oxo-1-(2,3,5,6-tetrafluorophenoxy)pentan-3-yl)carbamate (57-4): Potassium fluoride (502 mg, 8.64 mmol, 4 equiv.) was added to a solution of compound 57-3 (0.67 g, 2.16 mmol, 1 equiv.) and 2,3,5,6-tetrafluorophenol (395 mg, 2.38 mmol, 1.1 equiv.) in DMF (10 mL). After stirring at room temperature for 16 hours, the reaction was diluted with ethyl acetate (15 mL), washed with saturated sodium bicarbonate (20 mL) and saturated brine (20 mL). The organic layer was dried over sodium sulfate, filtered and concentrated under reduced pressure. The residue was purified on an InterChim automated chromatography system (120 g SorbTech silica gel column), eluting with a gradient of 0 to 40% ethyl acetate in heptanes to give compound 57-4 (0.53 g, 62% yield) as a colorless oil.

(S)-3-Amino-5-methoxy-1-(2,3,5,6-tetrafluorophenoxy)pentan-2-one hydrochloride (57-5): 4M HCl in 1,4-dioxane (0.34 mL, 1.34 mmol, 1.0 equiv.) was added dropwise to a solution of compound 57-4 (0.53 g, 1.34 mmol, 1 equiv.) in acetonitrile (10 mL) at 5° C. The mixture was warmed to room temperature and stirred overnight. LCMS indicated that the reaction was not complete. Additional 4M HCl in 1,4-dioxane (0.34 mL, 1.34 mmol, 1.0 equiv.) was added and the mixture was stirred for 6 hours at which time LCMS indicated that the reaction was complete. The mixture was concentrated under reduced pressure to give compound 57-5 (0.48 g, 100% yield) as a light yellow liquid.

$N^1$-(2,6-Difluorophenyl)-$N^2$—((S)-1-(((S)-5-methoxy-2-oxo-1-(2,3,5,6-tetrafluorophenoxy)pentan-3-yl)amino)-1-oxopropan-2-yl)oxalamide (Compound 57-A, Example 5): EDC.HCl (0.305 g, 1.59 mmol, 1.1 equiv.) was added to a suspension of compound 8 (0.393 g, 1.446 mmol, 1.0 equiv.) and HOAt (0.237 g, 1.74 mmol, 1.2 equiv.) in acetonitrile (10 mL). The mixture was stirred at room temperature until all solids dissolved. Compound 57-5 (0.48 g, 1.446 mmol, 1.0 equiv.) and triethylamine (0.40 mL, 2.89 mmol, 2.0 equiv.) were sequentially added and the mixture was stirred at room temperature overnight. LC-MS analysis indicated that the reaction was complete. The mixture was diluted with ethyl acetate (20 mL) and washed with saturated sodium bicarbonate (20 mL) and saturated brine (20 mL). The organic layer was dried over sodium sulfate, filtered and concentrated under reduced pressure. The crude product was purified on an Interchim automated chromatography system (120 g column), eluting with a gradient of 0 to 60% ethyl acetate in heptanes to give 57-A, (Example 5) (0.51 g, 64% yield) as a white solid, (Mass Spec. m/z=550.1 (M+H).

Example 6

Scheme 6

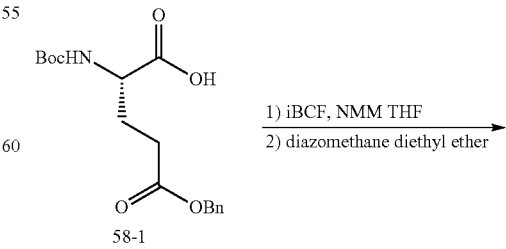

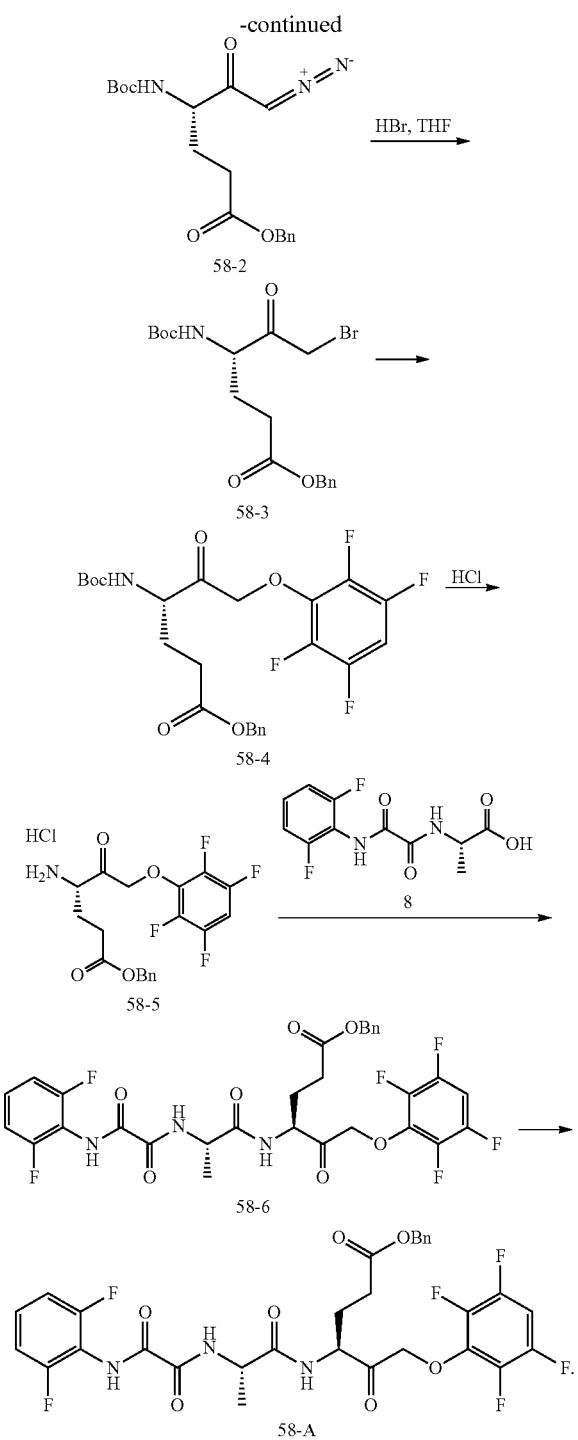

mmol, 1 equiv.) in diethyl ether (66 mL) was added through an addition funnel to a mixture of potassium hydroxide (15.12 g, 270 mmol, 3 equiv.) in ethanol (30 mL) and water (26 mL) in an oil bath at 65° C. The receiving flask to collect the ethereal solution of diazomethane was cooled in an ice-bath and the Diazald® solution was added at such a rate as that allowed for a dropwise distillation into the receiving flask. When all of the Diazald® solution had been added, additional diethyl ether (10 mL) was added through the addition funnel until the distillate was clear (no remaining diazomethane). After cooling to room temperature, the mixture in the distillation flask was quenched slowly with acetic acid until the yellow color disappeared.

A solution of freshly prepared mixed anhydride above (12.70 g, 30.0 mmol, 1 equiv.) in diethyl ether (110 mL) was placed in a clear-seal joint flask and cooled to 0° C. in an ice bath. The freshly prepared diazomethane ethereal solution (~90.0 mmol, 3 equiv.) was added through an addition funnel dropwise while keeping it cold. The resulting mixture was stirred at 0° C. for 15 minutes, warmed to room temperature and stirred for 30 minutes. The reaction was cooled to 0° C. Meanwhile a mixture of 48% aqueous HBr (24 mL, 210.0 mmol, 7 equiv.) and acetic acid (24.0 mL) was cooled to 0° C. and added to the above reaction mixture slowly at 0° C. The mixture was stirred at 0° C. for 15 minutes, warmed to room temperature and stirred for 30 minutes. The mixture was diluted with diethyl ether (80 mL), washed with water (3×100 mL), dried over sodium sulfate, filtered and concentrated under reduced pressure. The residue was purified on an InterChim automated chromatography system (220 g SorbTech silica gel column), eluting with a gradient of 0 to 40% ethyl acetate in heptanes to give compound 58-3 (8.6 g, 69% yield) as a colorless oil.

Benzyl (S)-4-((tert-butoxycarbonyl)amino)-5-oxo-6-(2,3,5,6-tetrafluorophenoxy)hexanoate (58-4): Potassium fluoride (4.83 g, 83.08 mmol, 4 equiv.) was added to a solution of compound 58-3 (8.6 g, 20.77 mmol, 1 equiv.) and 2,3,5,6-tetrafluorophenol (3.79 g, 22.85 mmol, 1.1 equiv.) in DMF (100 mL). After stirring at room temperature for 16 hours, the reaction was diluted with ethyl acetate (150 mL), washed with saturated sodium bicarbonate (200 mL) and saturated brine (200 mL). The organic layer was dried over sodium sulfate, filtered and concentrated under reduced pressure. The residue was purified on an InterChim automated chromatography system (220 g SorbTech silica gel column), eluting with a gradient of 0 to 40% ethyl acetate in heptanes to give compound 58-4 (6.13 g, 59% yield) as a colorless oil.

(S)-3-Amino-5-methoxy-1-(2,3,5,6-tetrafluorophenoxy) pentan-2-one hydrochloride (58-5): 4M HCl in 1,4-dioxane (3.1 mL, 12.3 mmol, 1.0 equiv.) was added dropwise to a solution of compound 58-4 (6.13 g, 12.28 mmol, 1 equiv.) in acetonitrile (80 mL) at 5° C. The mixture was warmed to room temperature and stirred overnight. LCMS indicated that the reaction was not complete. Additional 4M HCl in 1,4-dioxane (3.1 mL, 12.3 mmol, 1.0 equiv.) was added and the mixture was stirred for 6 hours at which time LCMS indicated that the reaction was complete. The mixture was concentrated under reduced pressure to give compound 58-5 (6.2 g, 100% yield) as a light yellow solid.

Benzyl (S)-4-((S)-2-(2-((2,6-difluorophenyl)amino)-2-oxoacetamido) propanamido)-5-oxo-6-(2,3,5,6-tetrafluorophenoxy)hexanoate (58-6): EDC.HCl (0.483 g, 2.52 mmol, 1.1 equiv.) was added to a suspension of compound 8 (0.623 g, 2.29 mmol, 1.0 equiv.) and HOAt (0.374 g, 2.75 mmol, 1.2 equiv.) in acetonitrile (15 mL). The mixture was stirred at room temperature until all solids dissolved. Compound Benzyl (S)-6-bromo-4-((tert-butoxycarbonyl)amino)-5-oxohexanoate (58-3): Isobutyl chloroformate (5.84 mL, 45.0 mmol, 1.5 equiv.) was added dropwise to a solution of (S)-5-(benzyloxy)-2-((tert-butoxycarbonyl)amino)-5-oxopentanoic acid (58-1) (10.12 g, 30.0 mmol, 1 equiv.) and N-methylmorpholine (5.28 mL, 48 mmol, 1.6 equiv.) in THF (100 mL) at −10° C. After stirring at −10° C. for 20 minutes, the reaction was filtered through celite and concentrated under reduced pressure to give the mixed anhydride as a colorless oil, which was used subsequently.

Diazomethane preparation: A solution of N-methyl-N'-nitroso-p-toluenesulfon-amide (Diazald®, 19.28 g, 90.0

58-5 (1.0 g, 2.29 mmol, 1.0 equiv.) and triethylamine (0.638 mL, 4.58 mmol, 2.0 equiv.) were sequentially added and the mixture was stirred at room temperature overnight. LC-MS analysis indicated that the reaction was complete. The mixture was diluted with ethyl acetate (30 mL) and washed with saturated sodium bicarbonate (30 mL) and saturated brine (30 mL). The organic layer was dried over sodium sulfate, filtered and concentrated under reduced pressure. The crude product was purified on an Interchim automated chromatography system (80 g column), eluting with a gradient of 0 to 60% ethyl acetate in heptanes to give compound 58-6 (0.72 g, 48% yield) as a white solid.

(S)-4-((S)-2-(2-((2,6-Difluorophenyl)amino)-2-oxoacetamido)propanamido)-5-oxo-6-(2,3,5,6-tetrafluorophenoxy)hexanoic acid (Compound 58-A, Example 6): A suspension of compound 58-6 (0.72 g, 1.10 mmol, 1 equiv.) and 10% palladium on carbon (0.072 g, 50% wet) in a mixture of THF (11 mL) and ethyl acetate (3.5 mL) was hydrogenated @25 psi for 2 hours. The reaction mixture was filtered through celite and concentrated under reduced pressure. The residue was purified on an Interchim automated chromatography system (120 g column), eluting with a gradient of 0 to 10% methanol in dichloromethane to give compound 58-A, (Example 6) (0.56 g, 90% yield) as a white solid, (Mass Spec. m/z=564.2 (M+H).

Example 7

Scheme 7

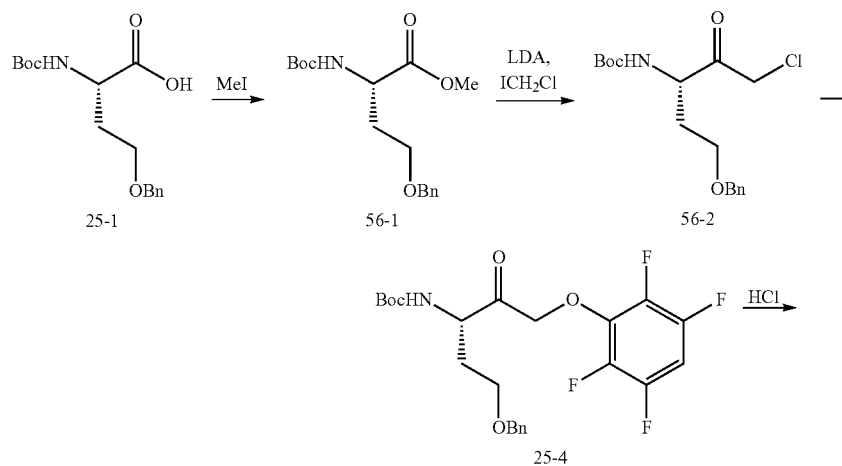

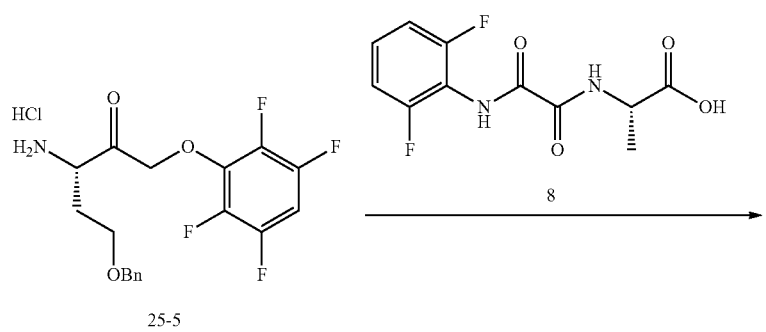

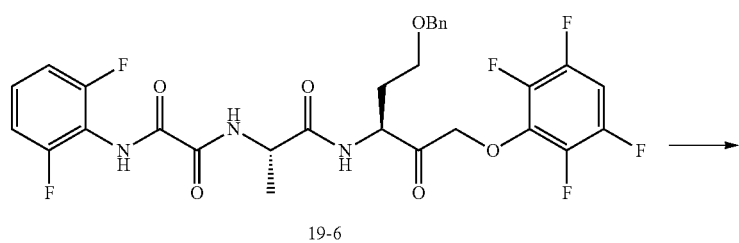

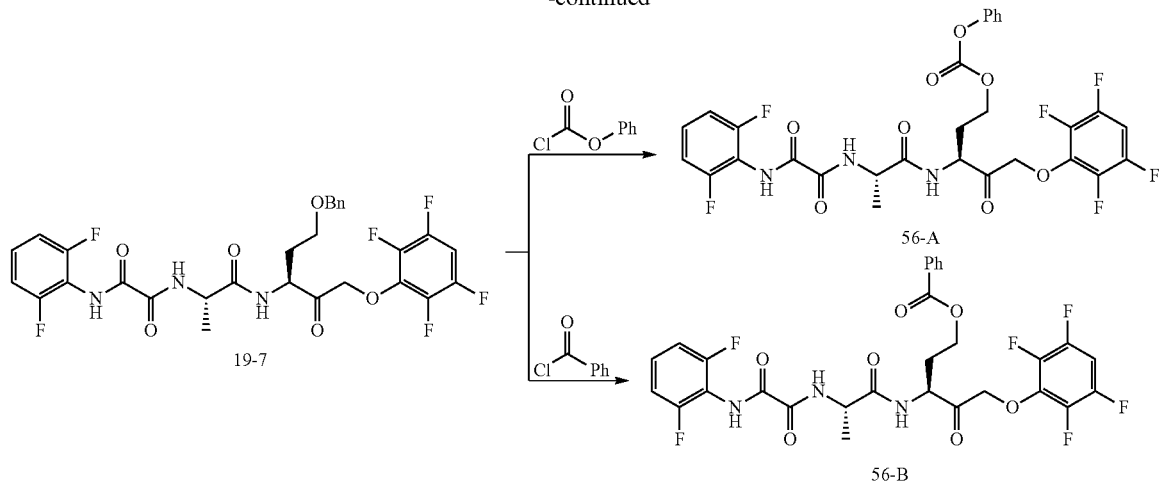

Methyl O-benzyl-N-(tert-butoxycarbonyl)-L-homoserinate (56-1): Potassium carbonate (5.53 g, 40.0 mmol, 2.0 equiv.) was added to a solution of compound 25-1 (6.18 g, 20.0 mmol, 1.0 equiv.) in DMF (25 mL). After stirring at room temperature for 15 minutes, methyl iodide (2.49 mL, 40.0 mmol, 2.0 equiv.) was added and the reaction was stirred at room temperature for 16 hours. The reaction mixture was diluted with ethyl acetate (100 mL) and washed with water (3×50 mL) and saturated brine solution (50 mL). The organic layer was dried over sodium sulfate, filtered and concentrated under reduced pressure. The crude material was purified on an Interchim automated chromatography system (Sorbtech silica gel column, 120 g), eluting with a gradient of 0 to 35% ethyl acetate in heptanes to give compound 56-1 (5.6 g, 87% yield) as a colorless oil.

tert-Butyl (S)-(5-(benzyloxy)-1-chloro-2-oxopentan-3-yl)carbamate (56-2): Chloroiodomethane (1.16 mL, 16.0 mmol, 4.0 equiv.) in tetrahydrofuran (10 mL) was added slowly to a solution compound 56-1 (1.29 g, 4.0 mmol, 1.0 equiv.) in tetrahydrofuran (20 mL) at −78° C. Fresh prepared lithium diisopropylamide solution was slowly added over 30 minutes while maintaining the temperature below −70° C. After stirring at −78° C. for 45 minutes, acetic acid (1.7 mL) in tetrahydrofuran (10 mL) was slowly added while maintaining the temperature at −65° C. After stirring at −78° C. for 10 minutes, the reaction was diluted with saturated brine (60 mL) and extracted with ethyl acetate (60 mL). The organic layer was washed with saturated bicarbonate (3×50 mL) and water (50 mL). The ethyl acetate layer was dried over sodium sulfate, filtered and concentrated under reduced pressure. The crude material was purified on an Interchim automated chromatography system (Sorbtech silica gel column, 120 g), eluting with a gradient of 0 to 20% ethyl acetate in heptanes to give compound 56-2 (0.92 g, 67% yield) as a light yellow oil.

Lithium diisopropylamide solution preparation: 1.6 M n-BuLi in hexane (12.25 mL, 20.0 mmol, 5.0 equiv.) was added to diisopropylamine (3.08 mL, 22.0 mmol, 5.5 equiv.) in THF (20 mL) at −78° C. The reaction was warmed to 0° C. for 30 minutes, cooled to −40° C.

tert-Butyl (S)-(5-(benzyloxy)-2-oxo-1-(2,3,5,6-tetrafluorophenoxy)pentan-3-yl)carbamate (25-4): Sodium iodide (605 mg, 4.03 mmol, 1.5 equiv.) and potassium 2,3,5,6-tetrafluorophenolate (823 mg, 4.03 mmol, 1.5 equiv.) were added to a solution of compound 56-2 (0.92 g, 2.69 mmol, 1.0 equiv.) in acetone (15 mL). After stirring at room temperature for 20 hours, the solvents were removed under reduced pressure. The residue was diluted with ethyl acetate (50 mL) and washed with saturated brine (50 mL). The organic layer was dried over sodium sulfate, filtered and concentrated under reduced pressure. The crude material was purified on an Interchim automated chromatography system (Sorbtech silica gel column, 80 g), eluting with a gradient of 0 to 40% ethyl acetate in heptanes to give compound 25-4 (1.10 g, 87% yield) as a light yellow oil.

(S)-3-Amino-5-(benzyloxy)-1-(2,3,5,6-tetrafluorophenoxy)pentan-2-one hydrochloride (25-5): 4M HCl in 1,4-dioxane (0.80 mL, 3.20 mmol, 1.2 equiv.) was added dropwise to a solution of compound 25-4 (1.25 g, 2.65 mmol, 1.0 equiv.) in acetonitrile (15 mL) at 5° C. The mixture was then warmed to room temperature and stirred overnight. LCMS indicated that the reaction was not complete. Additional 4M HCl in 1,4-dioxane (0.53 mL, 2.12 mmol, 0.8 equiv.) was added and the mixture was stirred for 6 hours at which time LCMS indicated that the reaction was complete. The mixture was concentrated under reduced pressure to give compound 25-5 (1.15 g, 98% yield) as a light yellow solid.

$N^1$—((S)-1-(((S)-5-(Benzyloxy)-2-oxo-1-(2,3,5,6-tetrafluorophenoxy)pentan-3-yl)amino)-1-oxopropan-2-yl)-$N^2$-(2,6-difluorophenyl)oxalamide (19-6): EDC.HCl (0.559 g, 2.92 mmol, 1.1 equiv.) was added to a suspension of compound 8 (0.721 g, 2.65 mmol, 1.0 equiv.) and HOAt (0.433 g, 3.18 mmol, 1.2 equiv.) in acetonitrile (15 mL). The mixture was stirred at room temperature until all solids dissolved. Compound 25-5 (1.08 g, 2.65 mmol, 1.0 equiv.) and triethylamine (0.74 mL, 5.3 mmol, 2.0 equiv.) were sequentially added and the mixture was stirred at room temperature overnight. LC-MS analysis indicated that the reaction was complete. The mixture was diluted with ethyl acetate (40 mL) and washed with saturated sodium bicarbonate (30 mL) and saturated brine (30 mL). The organic layer was dried over sodium sulfate, filtered and concentrated under reduced pressure. The crude product was purified on an Interchim automated system (120 g column), eluting with a gradient of 0 to 60% ethyl acetate in heptanes to give compound 19-6 (1.02 g, 62% yield) as a light yellow solid.

$N^1$-(2,6-Difluorophenyl)-$N^2$—((S)-1-(((S)-5-hydroxy-2-oxo-1-(2,3,5,6-tetrafluorophenoxy)pentan-3-yl)amino)-1-oxopropan-2-yl)oxalamide (19-7): A mixture of 19-6 (1.02 g, 1.63 mmol, 1.0 equiv.) and 10% palladium on activated carbon (102 mg, 50% wet) in tetrahydrofuran (10 mL) and methanol (10 mL) was hydrogenated @ 45 psi for 3 hours. LC-MS analysis indicated that the reaction was complete. The mixture was filtered through Celite (15 g), which was washed with additional methanol (25 mL). The crude product was purified on an Interchim automated system (120 g column), eluting with a gradient of 0 to 80% ethyl acetate in heptanes to give compound 19-7 (350 mg, 40% yield) as a white solid.

(S)-3-((S)-2-(2-((2,6-Difluorophenyl)amino)-2-oxoacetamido)propanamido)-4-oxo-5-(2,3,5,6-tetrafluorophenoxy)pentyl phenyl carbonate (56-A, Example 7): Phenyl chloroformate (0.13 mL, 1.05 mmol, 1.0 equiv.) was added at 0° C. to a solution of compound 19-7 (565 mg, 1.05 mmol, 1.0 equiv.), pyridine (0.84 mL, 10.5 mmol, 10.0 equiv.) and 4-dimethylaminopyridine (81 mg, 0.66 mmol, 0.63 equiv.) in 12 mL of dichloromethane. The reaction mixture was stirred at room temperature for 2 hours. Additional phenyl chloroformate (0.20 mL, 1.58 mmol, 1.5 equiv.) was added into the reaction. The mixture was stirred at room temperature for 2 hours, at which point LC-MS analysis indicated that the reaction was complete. The reaction mixture was washed with water (2×10 mL). The combined aqueous layers were extracted with dichloromethane (2×10 mL). The combined organic layers were washed with saturated ammonium chloride (2×10 mL) and saturated brine (10 mL). The organic layer was dried over sodium sulfate, filtered and concentrated under reduced pressure. The residue was purified on InterChim automated chromatography system (120 g, SorbTech silica gel column), eluting with a gradient of 0 to 25% ethyl acetate in dichloromethane. The product was triturated with diethyl ether (10 mL) to give the compound 56-A, (Example 7) (160 mg, 17% yield) as a yellow solid, (Mass Spec. m/z=656.2 (M+H).

Example 8

(S)-3-((S)-2-(2-((2,6-Difluorophenyl)amino)-2-oxoacetamido)propanamido)-4-oxo-5-(2,3,5,6-tetrafluorophenoxy)pentyl benzoate (56-B, Example 8): Benzoyl chloride (0.34 mL, 2.97 mmol, 2.5 equiv.) was added at 0° C. to a solution of compound 19-7 (635 mg, 1.19 mmol, 1.0 equiv.), pyridine (0.95 mL, 11.9 mmol, 10.0 equiv.) and 4-dimethylaminopyridine (91 mg, 0.75 mmol, 0.63 equiv.) in 12 mL of dichloromethane. After stirring at room temperature for 2 hours, the reaction mixture was washed with water (2×10 mL). The combined aqueous layers were extracted with dichloromethane (2×10 mL). The combined organic layers were washed with saturated ammonium chloride (2×10 mL) and saturated brine (10 mL). The organic layer was dried over sodium sulfate, filtered and concentrated under reduced pressure. The residue was purified on InterChim automated chromatography system (120 g, SorbTech silica gel column), eluting with a gradient of 0 to 25% ethyl acetate in dichloromethane. The product was triturated with diethyl ether (10 mL) to give the compound 56-B, (Example 8) (280 mg, 37% yield) as a yellow solid, (Mass Spec. m/z=640.2 (M+H).

Example 9

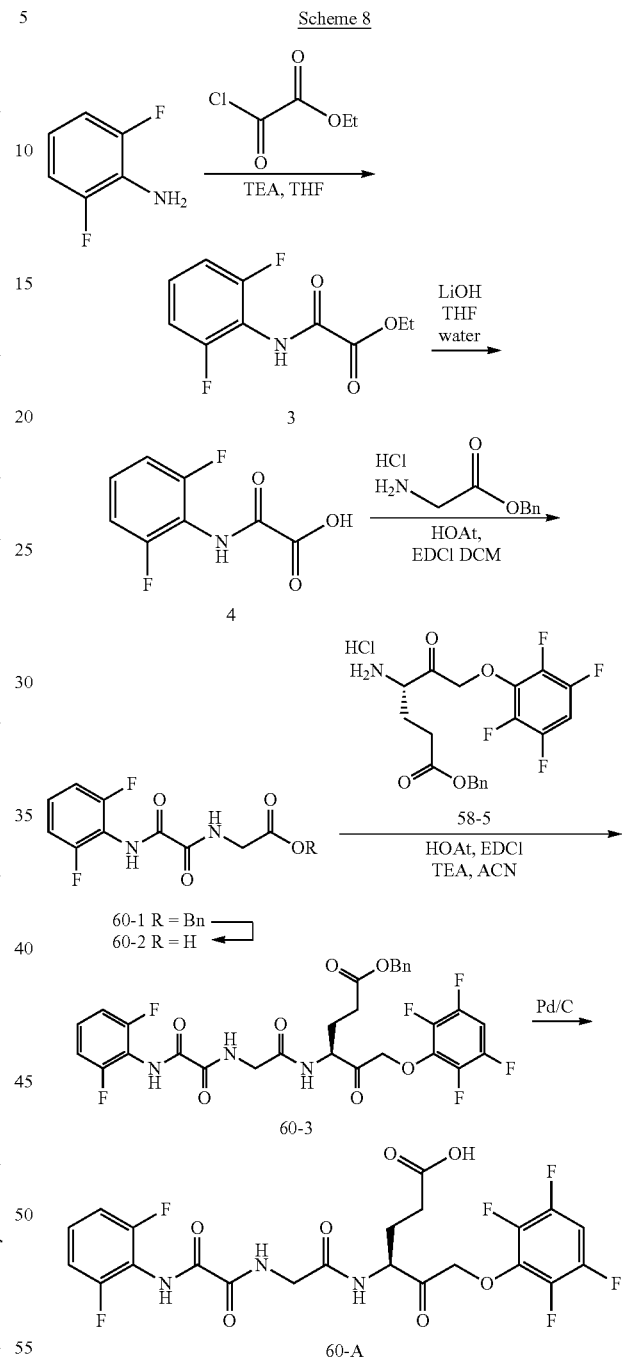

Ethyl 2-((2,6-difluorophenyl)amino)-2-oxoacetate (3): Triethylamine (27.2 mL, 193.8 mmol, 1 equiv.) was added to a solution of 2,6-difluoroaniline (25.0 g, 193.8 mmol, 1 equiv.) in THF (1 L) at 0-5° C. Ethyl oxalyl chloride (21.6 mL, 193.8 mmol, 1 equiv.) was added dropwise over 60 minutes, while maintain the temperature <5° C. The reaction was warmed to room temperature and stirred for 24 hours. The reaction was filtered through celite, the celite was washed with methyl t-butyl ether (500 mL) and the combined organic layers were washed with a 1N HCl (2×200 mL) and water (400 mL). The organic layer was dried over sodium sulfate, filtered and concentrated under reduced pressure to give the desired product as a beige oil (44.8 g, quantitative yield).

2-((2,6-Difluorophenyl)amino)-2-oxoacetic acid (4): 1N Lithium hydroxide (233 mL, 233 mmol, 1.2 equiv.) was added to a solution of compound 3 (44.8 g, 193.8 mmol, 1 equiv.) in THF (233 mL). After stirring at room temperature for 4 hours, the reaction was cooled to 0° C. and acidified with concentrated HCl to pH 2. The aqueous mix was saturated with sodium chloride and extracted with ethyl acetate (6×200 mL). The combined organic layers were dried over sodium sulfate, filtered and concentrated under reduced pressure to give the desired product as a white solid (18.3 g, 47% yield).

Benzyl (2-((2,6-difluorophenyl)amino)-2-oxoacetyl)glycinate (60-1): N'-ethylcarbodiimide hydrochloride (3.99 g, 20.83 mmol, 1.4 equiv.) was added to a suspension of compound 4 (2.99 g, 14.88 mmol, 1.0 equiv.), 1-hydroxy-7-azabenzotriazole (2.85 g, 20.83 mmol, 1.4 equiv.) in acetonitrile (200 mL). The mixture was stirred at room temperature until all solids dissolved. Benzyl glycinate hydrochloride (3.0 g, 14.88 mmol, 1.0 equiv.) and N-methylmorpholine (3.01 g, 29.76 mmol, 2.0 equiv.) were added and the mixture was stirred at room temperature overnight. LC-MS analysis indicated that the reaction was complete. The mixture was concentrated under reduced pressure and the wet solid was diluted in ethyl acetate (60 mL) and water (20 mL). The layers were separated, and the aqueous layer was extracted with ethyl acetate (2×15 mL). The combined organic layers were washed with saturated brine (100 mL), dried over sodium sulfate, filtered and concentrated under reduced pressure. The residue was purified on an InterChim automated chromatography system (220 g SorbTech silica gel column), eluting with a gradient of 0 to 5% ethyl acetate in dichloromethane. The product was further purified on an InterChim automated chromatography system (220 g SorbTech silica gel column), eluting with a gradient of 0 to 50% ethyl acetate in heptanes to give compound 60-1 (1.90 g, 37% yield) as a white solid.

(2-((2,6-difluorophenyl)amino)-2-oxoacetyl)glycine (60-2): A mixture of compound 60-1 (1.86 g, 5.34 mmol, 1.0 equiv.) and 10% palladium on activated carbon (186 mg, 50% wet) in tetrahydrofuran (11.5 mL) and ethyl acetate (3.5 mL) was hydrogenated @ 25 psi for 2 hours. LC-MS analysis indicated that the reaction was complete. The mixture was filtered through Celite (15 g) to give compound 60-1 (1.31 mg, 95% yield) as a white solid.

Benzyl (S)-4-(2-(2-((2,6-difluorophenyl)amino)-2-oxoacetamido)acetamido)-5-oxo-6-(2,3,5,6-tetrafluorophenoxy) hexanoate (60-3): N'-ethylcarbodiimide hydrochloride (0.388 g, 2.02 mmol, 1.1 equiv.) was added to a suspension of compound 60-2 (0.474 g, 1.84 mmol, 1.0 equiv.) and 1-hydroxy-7-azabenzotriazole (0.301 g, 2.21 mmol, 1.2 equiv.) in acetonitrile (15 mL). The mixture was stirred at room temperature until all solids dissolved. Compound 58-5 (0.80 g, 1.84 mmol, 1.0 equiv.) and triethylamine (0.51 mL, 3.68 mmol, 2.0 equiv.) were sequentially added and the mixture was stirred at room temperature overnight. LC-MS analysis indicated that the reaction was complete. The mixture was diluted with ethyl acetate (40 mL) and washed with saturated sodium bicarbonate (30 mL) and saturated brine (30 mL). The organic layer was dried over sodium sulfate, filtered and concentrated under reduced pressure. The crude product was purified on an Interchim automated chromatography system (120 g column), eluting with a gradient of 0 to 70% ethyl acetate in heptanes to give compound 60-3 (0.42 g, 36% yield) as a white solid.

(S)-4-(2-(2-((2,6-difluorophenyl)amino)-2-oxoacetamido)acetamido)-5-oxo-6-(2,3,5,6-tetrafluorophenoxy) hexanoic acid (60-A, Example 9): A mixture of compound 60-3 (0.42 g, 0.657 mmol, 1.0 equiv.) and 10% palladium on activated carbon (42 mg, 50% wet) in tetrahydrofuran (15 mL) and ethyl acetate (5 mL) was hydrogenated @ 25 psi for 2 hours. LC-MS analysis indicated that the reaction was complete. The mixture was filtered through Celite (15 g), which was washed with additional methanol (25 mL). The crude product was purified on an Interchim automated chromatography system (80 g column), eluting with a gradient of 0 to 10% methanol in dichloromethane. The product was triturated with diethyl ether (10 mL) to give the compound 60-A, (Example 9), (210 mg, 58% yield) as a white solid, (Mass Spec. m/z=550.1 (M+H).

Example 10

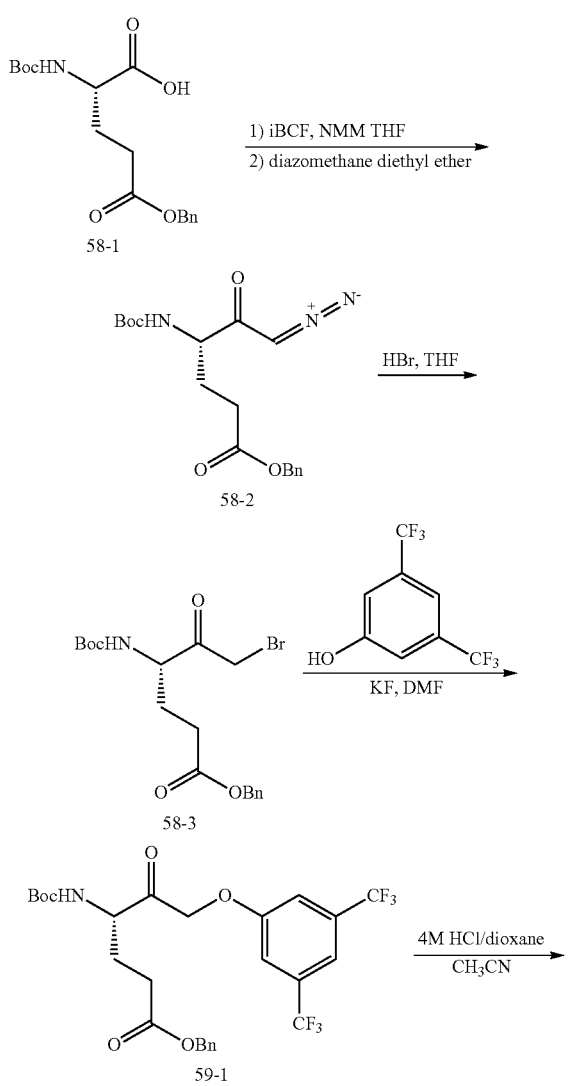

Scheme 9

-continued

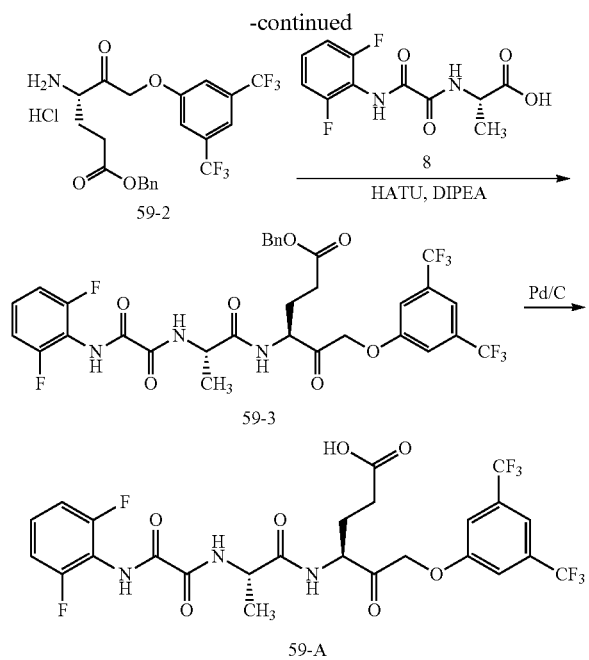

59-2

8

HATU, DIPEA 59-3

Pd/C

59-A

Benzyl (S)-6-bromo-4-((tert-butoxycarbonyl)amino)-5-oxohexanoate (58-3): Isobutyl chloroformate (5.84 mL, 45.0 mmol, 1.5 equiv.) was added dropwise to a solution of (S)-5-(benzyloxy)-2-((tert-butoxycarbonyl)amino)-5-oxopentanoic acid (58-1) (10.12 g, 30.0 mmol, 1 equiv.) and N-methylmorpholine (5.28 mL, 48 mmol, 1.6 equiv.) in THF (100 mL) at −10° C. After stirring at −10° C. for 20 minutes, the reaction was filtered through celite and concentrated under reduced pressure to give the mixed anhydride (12.7 g) as a colorless oil, which was used subsequently.

Diazomethane preparation: A solution of N-methyl-N'-nitroso-p-toluenesulfonamide (Diazald®, 19.28 g, 90.0 mmol, 1 equiv.) in diethyl ether (66 mL) was added through an addition funnel to a mixture of potassium hydroxide (15.12 g, 270 mmol, 3 equiv.) in ethanol (30 mL) and water (26 mL) in an oil bath at 65° C. The receiving flask to collect the ethereal solution of diazomethane was cooled in an ice-bath and the Diazald® solution was added at such a rate as that allowed for a dropwise distillation into the receiving flask. When all of the Diazald® solution had been added, additional diethyl ether (10 mL) was added through the addition funnel until the distillate was clear (no remaining diazomethane). After cooling to room temperature, the mixture in the distillation flask was quenched slowly with acetic acid until the yellow color disappeared.

A solution of freshly prepared mixed anhydride above (12.7 g, 30.0 mmol, 1 equiv.) in diethyl ether (110 mL) was placed in a clear-seal joint flask and cooled to 0° C. in an ice bath. The freshly prepared diazomethane ethereal solution (~90.0 mmol, 3 equiv.) was added through an addition funnel dropwise while keeping it cold. The resulting mixture was stirred at 0° C. for 15 minutes, warmed to room temperature and stirred for 30 minutes. The reaction was cooled to 0° C. Meanwhile a mixture of 48% aqueous HBr (24 mL, 210.0 mmol, 7 equiv.) and acetic acid (24.0 mL) was cooled to 0° C. and added to the above reaction mixture slowly at 0° C. The mixture was stirred at 0° C. for 15 minutes, warmed to room temperature and stirred for 30 minutes. The mixture was diluted with diethyl ether (120 mL), washed with water (3×120 mL), dried over sodium sulfate, filtered and concentrated under reduced pressure. The residue was purified on an InterChim automated chromatography system (220 g SorbTech silica gel column), eluting with a gradient of 0 to 30% ethyl acetate in heptanes to give compound 58-3 (7.26 g, 59% yield) as a white solid.

Benzyl (S)-6-(3,5-bis(trifluoromethyl)phenoxy)-4-((tert-butoxycarbonyl)amino)-5-oxohexanoate (59-1): Potassium fluoride (3.93 g, 67.6 mmol, 4 equiv.) was added to a solution of compound 58-3 (7.0 g, 16.9 mmol, 1 equiv.) and 3,5-bis(trifluoromethyl)phenol (2.8 mL, 18.6 mmol, 1.1 equiv.) in DMF (70 mL). After stirring at room temperature for 18 hours, the reaction was diluted with ethyl acetate (120 mL), washed with saturated sodium bicarbonate (180 mL) and saturated brine (180 mL). The organic layer was dried over sodium sulfate, filtered, and concentrated under reduced pressure. The residue was purified on an InterChim automated chromatography system (220 g RediSepRf silica gel column), eluting with a gradient of 0 to 25% ethyl acetate in heptanes to give compound 59-1 (6.0 g, 63% yield) as a white solid.

Benzyl (S)-4-amino-6-(3,5-bis(trifluoromethyl)phenoxy)-5-oxohexanoate hydrochloride (59-2): 4M HCl in 1,4-dioxane (2.9 mL, 11.7 mmol, 1.2 equiv.) was added dropwise to a solution of compound 59-1 (5.5 g, 9.76 mmol, 1 equiv.) in acetonitrile (100 mL) at 0 to 5° C. The mixture was warmed to room temperature and stirred for 6.5 hours. LCMS indicated that the reaction was not complete. Additional 4M HCl in 1,4-dioxane (2.0 mL, 7.8 mmol, 0.8 equiv.) was added and the mixture was stirred for 16 hours at which time LCMS indicated that the reaction was complete. The mixture was concentrated under reduced pressure to give compound 59-2 (4.6 g, 95% yield) as a white solid, which was used subsequently.

Benzyl (S)-6-(3,5-bis(trifluoromethyl)phenoxy)-4-((S)-2-(2-((2,6-difluorophenyl)amino)-2-oxoacetamido)propanamido)-5-oxohexanoate (59-3): (1-[Bis(dimethylamino)methylene]-1H-1,2,3-triazolo[4,5-b]pyridinium 3-oxid hexafluorophosphate (0.84 g, 2.2 mmol, 1.1 equiv.) was added to a solution of compound 8 (0.55 g, 2.0 mmol, 1 equiv.) in dimethylformamide (10 mL) at room temperature. After stirring at room temperature for 10 minutes, compound 59-2 (1.0 g, 2.0 mmol, 1 equiv.) and N,N-diisopropylethylamine (1.1 mL, 6.0 mmol, 3 equiv.) were sequentially added. After stirring at room temperature for 18 hours, the reaction mixture was diluted with ethyl acetate (50 mL). The organic layer was washed with water (2×30 mL), dried over sodium sulfate, filtered and concentrated under reduced pressure. The crude material was purified on an Interchim automated chromatography system (80 g RediSepRf silica gel column), eluting with a gradient of 0 to 60% ethyl acetate in heptanes. After concentrating the fractions under reduced pressure, the resulting solid was dried under vacuum at 45° C. for 18 hours to give compound 59-3 (0.72 g, 50% yield) as a yellowish solid.

(S)-6-(3,5-bis(trifluoromethyl)phenoxy)-4-((S)-2-(2-((2,6-difluorophenyl)amino)-2-oxoacetamido)propanamido)-5-oxohexanoic acid (59-A, Example 10): A suspension of compound 59-3 (0.53 g, 0.74 mmol, 1.0 equiv.) and 10% palladium on activated carbon (53 mg, 50% wet) in tetrahydrofuran (20 mL) was hydrogenated @ 25 psi for 2 hours. LC-MS analysis indicated that the reaction was complete. The mixture was filtered through Celite (15 g), which was washed with tetrahydrofuran (3×50 mL). The filtrates were concentrated under reduced pressure and the crude product was dissolved in dichloromethane (12 mL), adsorbed onto silica gel (15 g). The material was dry-loaded and purified on an Interchim automated system (40 g Sorbtech silica gel column), eluting with a gradient of 0 to 8% methanol in dichloromethane. After concentrating the fractions under reduced pressure, the resulting solid was dried under vacuum at room temperature for 18 hours to give compound 59-A, (Example 10) (0.25 g, 54% yield) as an off-white solid, (Mass Spec. m/z=628.1 (M+H).

Example 11 of compound 65-1 (0.49 g, 0.73 mmol, 1 equiv.) and 10% palladium on carbon (0.1 g, 50% wet) in THE (20 mL) and ethyl acetate (5 mL) was hydrogenated @ 20 psi for 2 hours. The reaction mixture was filtered through syringe filter and concentrated under reduced pressure. The residue was purified twice on an Interchim automated chromatography system (RediSep Gold 12 g silica gel column), eluting each time with a gradient of 0 to 5% methanol in dichloromethane to give compound 65-A, (Example 11) (140 mg, 33% yield) as a white solid, (Mass Spec. m/z=584.2 (M+H).

Example 12

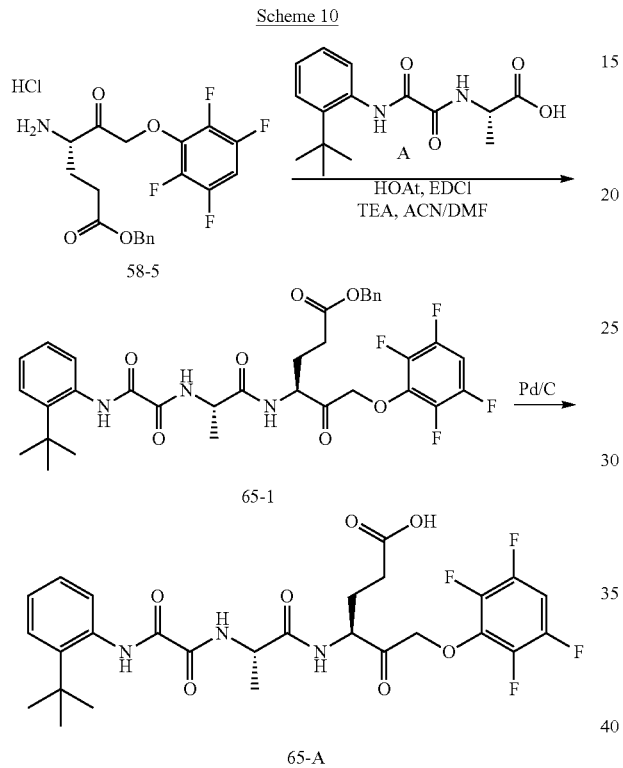

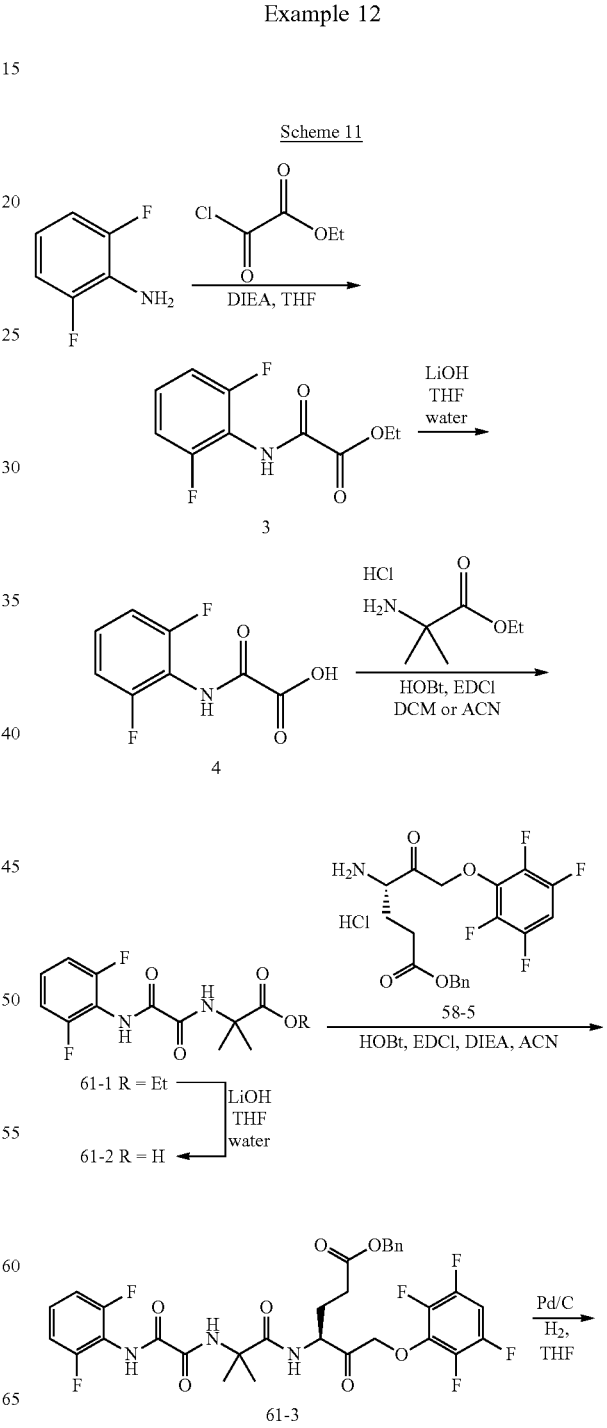

Benzyl (S)-4-((S)-2-(2-((2-(tert-butyl)phenyl)amino)-2-oxoacetamido) propanamido)-5-oxo-6-(2,3,5,6-tetrafluorophenoxy)hexanoate (65-1): 1-Hydroxy-7-azabenzotriazole (0.21 g, 1.51 mmol, 1.2 equiv.) and 1-(3-dimethylaminopropyl)-3-ethylcarbodiimide hydrochloride (0.29 g, 1.51 mmol, 1.2 equiv.) were added sequentially to a solution of (2-((2-(tert-butyl)phenyl)amino)-2-oxoacetyl)-L-alanine, compound A, (0.37 g, 1.26 mmol, 1.0 equiv.) in acetonitrile (6 mL) and DMF (3 mL) at room temperature. After stirring at room temperature for 1 hour, compound 58-5 (0.55 g, 1.26 mmol, 1.0 equiv.) and triethylamine (0.35 mL, 2.52 mmol, 2 equiv.) were sequentially added. After stirring at room temperature for 2 days, the reaction was concentrated under reduced pressure. The residue was partitioned between ethyl acetate (10 mL) and water (10 mL). Organic layer was washed with water (10 mL) and concentrated under reduced pressure. The residue was purified on an Interchim automated chromatography system (SorbTech 24 g column), eluting with a gradient of 0 to 30% ethyl acetate in hexanes to give the desired product (0.49 g, 58% yield) as a white solid.

(S)-4-((S)-2-(2-((2-(tert-Butyl)phenyl)amino)-2-oxoacetamido)propanamido)-5-oxo-6-(2,3,5,6-tetrafluorophenoxy) hexanoic acid (Compound 65-A, Example 11): A suspension

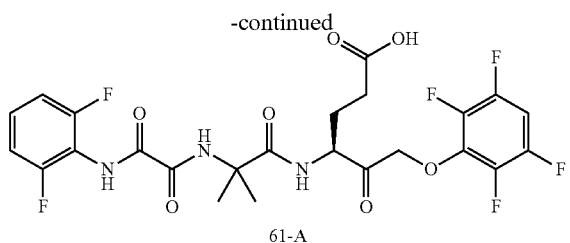

61-A 2-((2,6-Difluorophenyl)amino)-2-oxoacetic acid (4) was prepared in scheme 1. Ethyl 2-(2-((2,6-difluorophenyl) amino)-2-oxoacetamido)-2-methylpropanoate (61-1): Compound 4 (1.5 g, 7.46 mmol, 1.0 equiv.) and 1-hydroxy-7-azabenzotriazole (1.421 g, 10.44 mmol, 1.4 equiv.) were dissolved in acetonitrile (77.3 mL). 1-Ethyl-3-(3-dimethylaminopropyl)carbodiimide hydrochloride (2.002 g, 10.44 mmol, 1.4 equiv.) was added and the mixture was allowed to stir at room temperature. After 10 minutes everything had dissolved. N-methylmorpholine (1.97 mL, 17.9 mmol, 2.4 equiv.) was added, followed by ethyl 2-amino-2-methylpropanoate-hydrochloride (1.25 g, 7.46 mmol, 1.0 equiv.). After stirring at room temperature under nitrogen atmosphere for 20 hours, the reaction was warmed to 70° C. for 5 additional hours, then cooled to room temperature. Ethyl acetate (100 mL) and water (80 mL) were added and the layers separated. The aqueous layer was extracted with ethyl acetate (3×75 mL). The combined organics layers were washed with saturated brine (75 mL), dried with sodium sulfate, filtered and concentrated under reduced pressure. The residue was dissolved in dichloromethane (10 mL), adsorbed onto Celite and purified on an Interchim automated chromatography system (Sorbtech silica gel column, 80 g), eluting with a gradient of 0 to 50% ethyl acetate in dichloromethane to give compound 61-1 (0.749 g, 32% yield) as a white solid.

2-(2-((2,6-Difluorophenyl)amino)-2-oxoacetamido)-2-methylpropanoic acid (61-2): Lithium hydroxide (68.4 mg, 2.86 mmol, 1.2 equiv.) in water (2.8 mL) was added to a solution of compound 61-1 (0.748 g, 2.37 mmol, 1.0 equiv.) in tetrahydrofuran (9.3 mL). The mixture was allowed to stir at room temperature for 3 days. Additional lithium hydroxide (34.2 mg, 1.43 mmol) in water (0.7 mL) and added to the reaction mixture. After another day, additional lithium hydroxide (34.2 mg, 1.43 mmol) in water (0.4 mL) and added to the reaction mixture along with 1 mL tetrahydrofuran. After 3 more hours, the reaction was cooled to 0° C. and adjusted to pH.=2 with concentrated HCl (20 drops). The mixture was extracted with ethyl acetate (3×10 mL). The combined organics layers were dried over sodium sulfate, filtered and concentrated under reduced pressure. The residue was diluted with a 3 to 1 mixture of toluene and ethyl acetate, stirred for 30 minutes at 40° C. and concentrated under reduced pressure. The residue was dried under vacuum at 40° C. for 4 hours to give compound 61-2 (0.629 g, 92% yield) as a white solid.

Benzyl (S)-4-(2-(2-((2,6-difluorophenyl)amino)-2-oxoacetamido)-2-methylpropanamido)-5-oxo-6-(2,3,5,6-tetrafluorophenoxy)hexanoate (61-3): Compound 61-2 (0.200 g, 0.698 mmol, 1.0 equiv.) and 1-hydroxybenzotriazole hydrate (0.132 g, 0.838 mmol, 1.2 equiv.) were dissolved in acetonitrile (3.9 mL). 1-Ethyl-3-(3-dimethylaminopropyl) carbodiimide hydrochloride (0.161 g, 0.838 mmol, 1.2 equiv.) was added and the mixture was allowed to stir at room temperature under nitrogen atmosphere for 1 hour. Diisopropylethylamine (0.243 mL, 1.4 mmol, 2.0 equiv.) was added, followed by compound 58-5 (0.304 g, 0.698 mmol, 1.0 equiv.) in acetonitrile (0.4 mL). The reaction was allowed to stir at room temperature for 22 hours. Ethyl acetate (10 mL) and saturated sodium bicarbonate (5 mL) were added and the layers were separated. The aqueous layer was extracted with ethyl acetate (2×5 mL). The combined organic layers were washed with saturated brine, dried with sodium sulfate, filtered and concentrated under reduced pressure. The residue was purified on an Interchim automated chromatography system (Sorbtech silica gel column, 12 g), eluting with a gradient of 5 to 50% ethyl acetate in heptanes to give compound 61-3 (0.117 g, 25% yield) as a light yellow oil.

This procedure was repeated on 0.362 g scale of compound 61-2 to give compound 61-3 (0.160 g, 19% yield) as a light yellow oil.

(S)-4-(2-(2-((2,6-Difluorophenyl)amino)-2-oxoacetamido)-2-methylpropanamido)-5-oxo-6-(2,3,5,6-tetrafluorophenoxy)hexanoic acid (61-A, Example 12): A mixture of compound 61-3 (0.117 g, 0.175 mmol, 1.0 equiv.) and 10% Pd/C (11.2 mg, 50% wet) in tetrahydrofuran (20 mL) was hydrogenated @ 22 psi) for 2 hours. The reaction mixture was filtered through Celite, which was washed with tetrahydrofuran (25 mL). The filtrate was concentrated under reduced pressure and purified on a Büchi automated chromatography system (Sorbtech silica gel column, 12 g), eluting with a gradient of 0 to 10% methanol in dichloromethane to give 63 mg of a pink solid. This solid was triturated in dichloromethane (2 mL) to give a white solid, which was dried under vacuum overnight at 40° C. to give compound 61-A (43 mg, 42% yield) as a white powder. (RC-3-011)

This procedure was repeated on 0.180 g scale of compound 61-3 to give compound 61-A (65.0 mg, 42% yield. The two batches were combined to give 61-A, Example 12) (108 mg) as a white powder, (Mass Spec. m/z=578 (M+H).

Example 13

Scheme 12

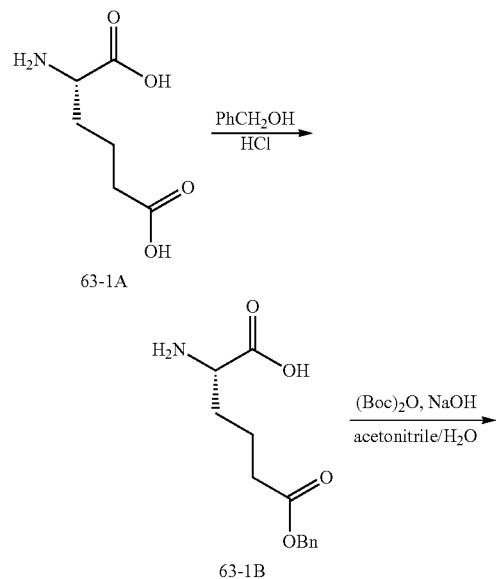

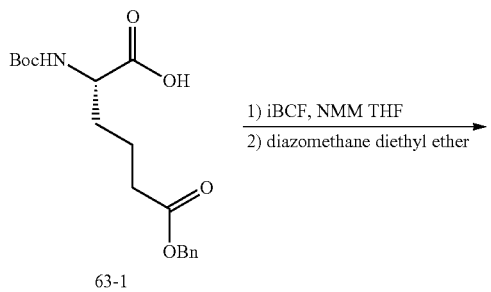

63-1

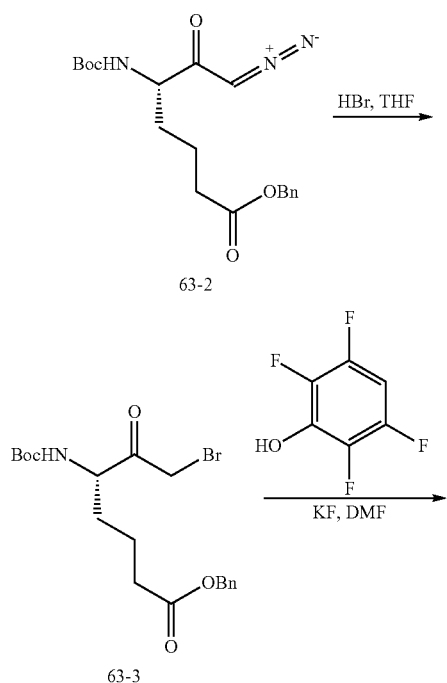

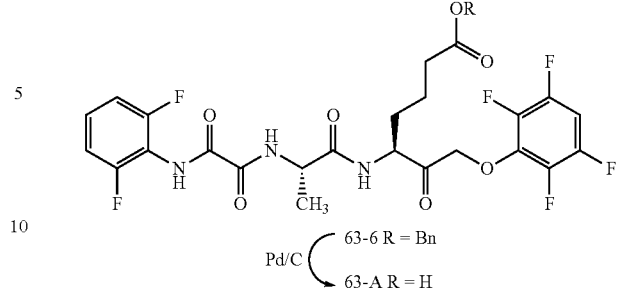

63-6 R = Bn
63-A R = H
Pd/C (S)-2-Amino-6-(benzyloxy)-6-oxohexanoic acid (63-1B): Benzyl alcohol (125 mL, 1.21 mole, 10 equiv.) was added dropwise to a suspension of L-2-aminoadipic acid (63-1A) (19.5 g, 0.12 mole, 1 equiv.) in 12M HCl (10 mL, 0.12 mole, 1 equiv.). The mixture was heated at 100° C. for 1 hour and then cooled to room temperature. Diethyl ether (700 mL) was added to the solution. The resulting solid was filtered, washed with diethyl ether (3×100 mL) and dried under vacuum at room temperature for 18 hours to give compound 63-1B (22.5 g, 65% yield) as a white solid.

(S)-6-(Benzyloxy)-2-((tert-butoxycarbonyl)amino)-6-oxohexanoic acid (63-1): Sodium hydroxide (2.5 g, 62.5 mmol, 1.2 equiv.) was added to a solution of compound 63-1B (15 g, 52.1 mmol, 1 equiv.) in the mixture of acetonitrile (200 mL) and water (200 mL). The mixture was stirred at room temperature for 15 minutes. Di-tert-butyldicarbonate (14.4 mL, 62.5 mmol, 1.2 equiv.) was added to the reaction mixture and stirred for 18 hours. LCMS analysis indicated reaction was not complete. Additional sodium hydroxide (1.04 g, 26.1 mmol, 0.5 equiv.) and di-tert-butyldicarbonate (6.0 mL, 26.1 mmol, 0.5 equiv.) were added and the mixture was stirred for 6 hours at which time LCMS analysis indicated that the reaction was complete. The acetonitrile was removed under reduced pressure. Saturated sodium bicarbonate (200 mL) was added to the aqueous solution, which was extracted with diethyl ether (3×250 mL) to remove unreacted di-tert-butyldicarbonate. The aqueous solution was cooled to 0° C. and adjusted to pH 1 with 5M hydrochloric acid (~220 mL). The mixture was extracted with ethyl acetate (3×500 mL). The combined organic layers were washed with saturated brine (3×500 mL), dried over sodium sulfate, filtered, and concentrated under reduced pressure. The resulting oil was dried under vacuum at room temperature for 18 hours to give compound 63-1 (15.7 g, 86% yield) as a yellow liquid.

Benzyl (S)-7-bromo-5-((tert-butoxycarbonyl)amino)-6-oxoheptanoate (63-3): Isobutyl chloroformate (5.84 mL, 45.0 mmol, 1.5 equiv.) was added dropwise to a solution of compound 63-1 (10.54 g, 30.0 mmol, 1 equiv.) and N-methylmorpholine (5.28 mL, 48 mmol, 1.6 equiv.) in THF (100 mL) at −10° C. After stirring at −10° C. for 20 minutes, the reaction was filtered through celite and concentrated under reduced pressure to give the mixed anhydride (12.3 g) as a yellow oil, which was used subsequently.

Diazomethane preparation: A solution of N-methyl-N'-nitroso-p-toluenesulfon-amide (Diazald®, 19.28 g, 90.0 mmol, 1 equiv.) in diethyl ether (66 mL) was added through an addition funnel to a mixture of potassium hydroxide (15.12 g, 270 mmol, 3 equiv.) in ethanol (30 mL) and water (26 mL) in an oil bath at 65° C. The receiving flask to collect the ethereal solution of diazomethane was cooled in an ice-bath and the Diazald® solution was added at such a rate as that allowed for a dropwise distillation into the receiving

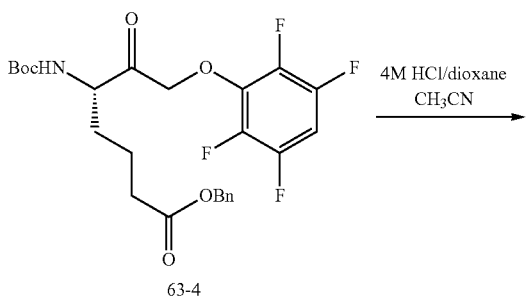

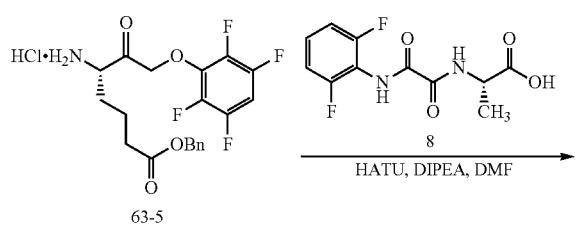

flask. When all of the Diazald® solution had been added, additional diethyl ether (10 mL) was added through the addition funnel until the distillate was clear (no remaining diazomethane). After cooling to room temperature, the mixture in the distillation flask was quenched slowly with acetic acid until the yellow color disappeared.

A solution of freshly prepared mixed anhydride above (12.7 g, 30.0 mmol, 1 equiv.) in diethyl ether (110 mL) was placed in a clear-seal joint flask and cooled to 0° C. The freshly prepared diazomethane ethereal solution (~90.0 mmol, 3 equiv.) was added through an addition funnel dropwise while keeping it cold. The resulting mixture was stirred at 0° C. for 15 minutes, warmed to room temperature and stirred for 30 minutes. The reaction was cooled to 0° C. Meanwhile a mixture of 48% aqueous HBr (24 mL, 210.0 mmol, 7 equiv.) and acetic acid (24.0 mL) was cooled to 0° C. and added to the above reaction mixture slowly at 0° C. The mixture was stirred at 0° C. for 15 minutes, warmed to room temperature and stirred for 30 minutes. The mixture was diluted with diethyl ether (120 mL), washed with water (3×120 mL), dried over sodium sulfate, filtered and concentrated under reduced pressure. The residue was purified on an InterChim automated chromatography system (220 g SorbTech silica gel column), eluting with a gradient of 0 to 25% ethyl acetate in heptanes to give compound 63-3 (4.73 g, 37% yield) as a white solid.

Benzyl (S)-5-((tert-butoxycarbonyl)amino)-6-oxo-7-(2,3,5,6-tetrafluorophenoxy)heptanoate (63-4): Potassium fluoride (2.6 g, 44 mmol, 4 equiv.) was added to a solution of compound 63-3 (4.7 g, 11 mmol, 1 equiv.) and 2,3,5,6-tetrafluorophenol (2.0 g, 12.1 mmol, 1.1 equiv.) in DMF (50 mL). After stirring at room temperature for 18 hours, the reaction was diluted with ethyl acetate (150 mL), washed with saturated sodium bicarbonate (180 mL) and saturated brine (180 mL). The organic layer was dried over sodium sulfate, filtered and concentrated under reduced pressure. The residue was purified on an InterChim automated chromatography system (120 g RediSepRf silica gel column), eluting with a gradient of 0 to 25% ethyl acetate in heptanes to give compound 63-4 (4.31 g, 77% yield) as a colorless liquid.

Benzyl (S)-5-amino-6-oxo-7-(2,3,5,6-tetrafluorophenoxy)heptanoate hydrochloride (63-5): 4M HCl in 1,4-dioxane (2.5 mL, 10.1 mmol, 1.2 equiv.) was added dropwise to a solution of compound 63-4 (4.31 g, 8.39 mmol, 1 equiv.) in acetonitrile (100 mL) at 0 to 5° C. The mixture was warmed to room temperature and stirred for 6.5 hours. LCMS indicated that the reaction was not complete. Additional 4M HCl in 1,4-dioxane (1.7 mL, 6.7 mmol, 0.8 equiv.) was added and the mixture was stirred for 18 hours at which time LCMS indicated that the reaction was complete. The mixture was concentrated under reduced pressure to give compound 63-5 (3.67 g, 97% yield) as a yellowish liquid, which was used subsequently.

Benzyl (S)-5-((S)-2-(2-((2,6-difluorophenyl)amino)-2-oxoacetamido)propanamido)-6-oxo-7-(2,3,5,6-tetrafluorophenoxy) heptanoate (63-6): Hexafluorophosphate azabenzo-triazole tetramethyluronium (HATU, 0.93 g, 2.44 mmol, 1.1 equiv.) was added to a solution of compound 8 (0.61 g, 2.22 mmol, 1 equiv.) in dimethylformamide (10 mL) at room temperature. After stirring at room temperature for 10 minutes, compound 63-5 (1.0 g, 2.22 mmol, 1 equiv.) and N,N-diisopropylethylamine (1.2 mL, 6.66 mmol, 3 equiv.) were sequentially added. After stirring at room temperature for 18 hours, the reaction mixture was diluted with ethyl acetate (60 mL). The organic layer was washed with water (2×50 mL), dried over sodium sulfate, filtered and concentrated under reduced pressure. The crude material was purified on an Interchim automated chromatography system (80 g RediSepRf silica gel column), eluting with a gradient of 0 to 50% ethyl acetate in heptanes. After concentrating the fractions under reduced pressure, the resulting solid was dried under vacuum at room temperature for 18 hours to give compound 63-6 (0.90 g, 61% yield) as a yellowish solid.

(S)-5-((S)-2-(2-((2,6-Difluorophenyl)amino)-2-oxoacetamido)propanamido)-6-oxo-7-(2,3,5,6-tetrafluorophenoxy) heptanoic acid (63-A, Example 13): A suspension of compound 63-6 (0.63 g, 0.94 mmol, 1.0 equiv.) and 10% palladium on activated carbon (63 mg, 50% wet) in tetrahydrofuran (30 mL) was hydrogenated @ 25 psi for 2 hours. LC-MS analysis indicated that the reaction was complete. The mixture was filtered through Celite (15 g), which was washed with ethyl acetate (3×70 mL). The filtrates were concentrated under reduced pressure. The crude product was dissolved in dichloromethane (20 mL) and adsorbed onto silica gel (10 g). The material was dry-loaded and purified on an Interchim automated system (40 g Sorbtech silica gel column), eluting with a gradient of 0 to 8% methanol in dichloromethane. After concentrating the fractions under reduced pressure, the resulting solid was dried under vacuum at room temperature for 18 hours to give compound 63-A, (Example 13) (0.45 g, 82% yield) as an off-white solid, (Mass Spec. m/z=578.1 (M+H).

Example 14

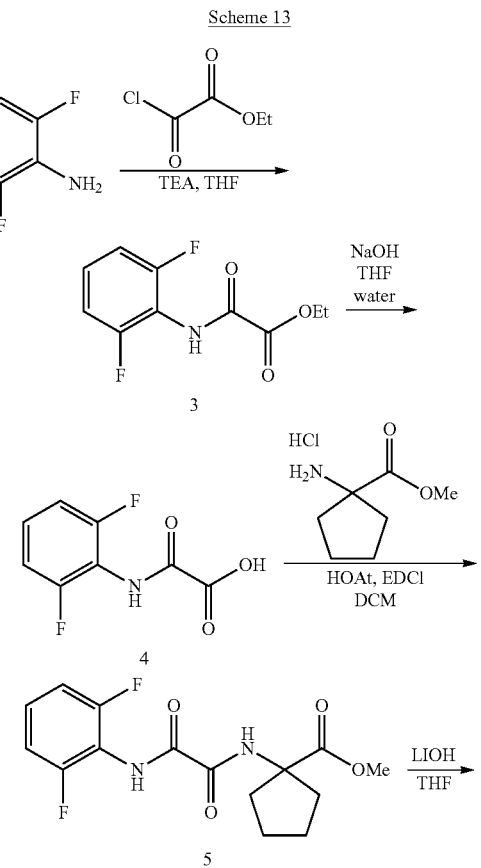

Scheme 13

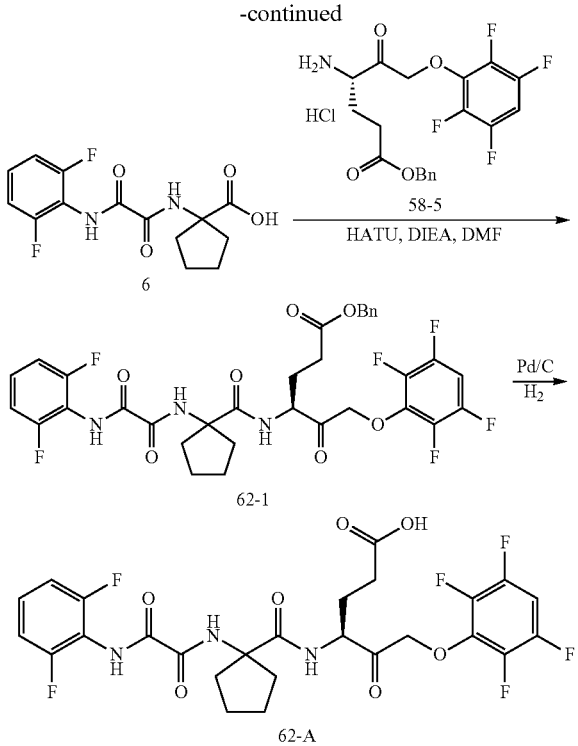

2-((2,6-Difluorophenyl)amino)-2-oxoacetic acid (4) was prepared in scheme 1.

Methyl 1-(2-((2,6-difluorophenyl)amino)-2-oxoacetamido)cyclopentane-1-carboxylate (5): Compound 4 (1.00 g, 4.97 mmol, 1.0 equiv.) and 1-hydroxy-7-azabenzotriazole (0.81 g, 5.97 mmol, 1.2 equiv.) were dissolved in anhydrous dichloromethane (50.0 mL). 1-Ethyl-3-(3-dimethylaminopropyl)carbodiimide hydrochloride (0.93 g, 5.97 mmol, 1.2 equiv.) and triethylamine (2.01 g, 19.89 mmol, 4.0 equiv.) were added sequentially and the mixture was stirred for 10 minutes. Methyl 1-aminocyclopentane-1-carboxylate hydrochloride (0.89 g, 4.97 mmol, 1.0 equiv.) was added. After stirring at room temperature for 4 days, the reaction mixture was washed with water (50 mL. The aqueous layer was extracted with dichloromethane (50 mL). The combined organic layers were dried over sodium sulfate and concentrated under reduced pressure. The residue was dissolved in dichloromethane (10 mL), adsorbed onto Celite and purified on an InterChim automated chromatography system (RediSep silica gel column, 80 g), eluting with a gradient of 0 to 50% ethyl acetate in heptanes to give compound 5 (0.356 g, 21% yield) as a white solid.

1-(2-((2,6-Difluorophenyl)amino)-2-oxoacetamido)cyclopentane-1-carboxylic acid (6): Lithium hydroxide (52.8 mg, 2.206 mmol, 2.4 equiv.) in water (2.2 mL) was added to a solution of compound 5 (0.300 g, 0.919 mmol, 1.0 equiv.) in tetrahydrofuran (10.0 mL). The mixture was stirred at room temperature for 3 hours. The reaction was cooled to 10° C., diluted with water (20 mL) and adjusted to pH=2 with aqueous 1N HCl. The resultant solid was filtered and washed with water. The solid was dried under vacuum at 40° C. for 18 hours to give compound 6 (0.160 g, 56% yield) as a white solid.

Benzyl (S)-4-(1-(2-((2,6-difluorophenyl)amino)-2-oxoacetamido) cyclopentane-1-carboxamido)-5-oxo-6-(2,3,5,6-tetrafluorophenoxy) hexanoate (62-1): [Bis(dimethylamino)methylene]-1H-1,2,3-triazolo[4,5-b]pyridinium 3-oxide hexafluorophosphate (261 mg, 1.1 equiv.) and compound 58-5 (272 mg, 0.624 mmol, 1.0 equiv.) were sequentially added to a solution of compound 6 (0.195 g, 0.624 mmol, 1.0 equiv.) in anhydrous dimethylformamide (3.0 mL). After stirring for 20 hours, the mixture was poured into saturated sodium bicarbonate (50 mL) and extracted with ethyl acetate (2×80 mL). The combined organic layers were washed with saturated brine (50 mL), dried over sodium sulfate, filtered and concentrated under reduced pressure. The residue was purified on an InterChim automated chromatography system (Sorbtech silica gel column, 2×12 g in series), eluting with a gradient of 0 to 50% ethyl acetate in heptanes to give compound 62-1 (0.178 g, 41% yield) as a white solid.

(S)-4-(1-(2-((2,6-Difluorophenyl)amino)-2-oxoacetamido)cyclopentane-1-carboxamido)-5-oxo-6-(2,3,5,6-tetrafluorophenoxy)hexanoic acid (62-A, Example 14): A mixture of compound 61-3 (0.178 g, 0.257 mmol, 1.0 equiv.) and 10% Pd/C (50 mg, 50% wet) in tetrahydrofuran (15 mL) was hydrogenated @ 22 psi for 2 hours. The reaction mixture was filtered through Celite, which was washed with tetrahydrofuran (25 mL). The filtrate was concentrated under reduced pressure. The residue was purified on an InterChim automated chromatography system (Sorbtech silica gel column, 12 g), eluting with a gradient of 0 to 5% methanol in dichloromethane to give an oily solid. The residue was dissolved in acetonitrile and water, frozen at −78° C. and lyophilized to dryness to give compound 62-A, (Example 14) (85 mg, 55% yield) as a white solid, (Mass Spec. m/z=604.2 (M+H).

Example 15

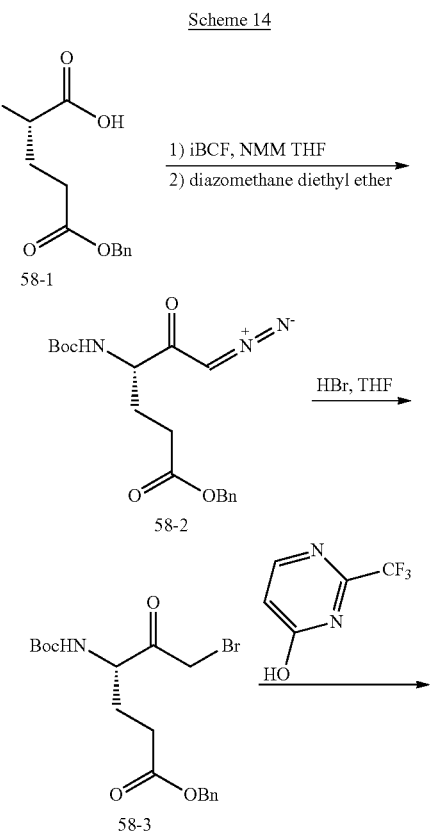

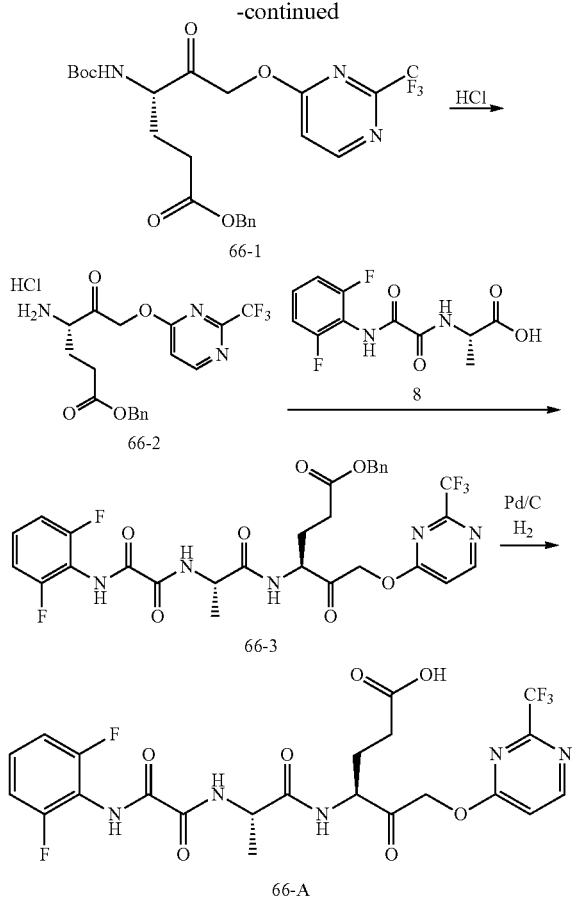

Benzyl (S)-6-bromo-4-((tert-butoxycarbonyl)amino)-5-oxohexanoate (58-3): Isobutyl chloroformate (5.84 mL, 45.0 mmol, 1.5 equiv.) was added dropwise to a solution of (S)-5-(benzyloxy)-2-((tert-butoxycarbonyl)amino)-5-oxopentanoic acid (58-1) (10.12 g, 30.0 mmol, 1 equiv.) and N-methylmorpholine (5.28 mL, 48 mmol, 1.6 equiv.) in THF (100 mL) at −10° C. After stirring at −10° C. for 20 minutes, the reaction was filtered through celite and concentrated under reduced pressure to give the mixed anhydride (12.7 g) as a colorless oil, which was used subsequently.

Diazomethane preparation: A solution of N-methyl-N'-nitroso-p-toluenesulfon-amide (Diazald®, 19.28 g, 90.0 mmol, 1 equiv.) in diethyl ether (66 mL) was added through an addition funnel to a mixture of potassium hydroxide (15.12 g, 270 mmol, 3 equiv.) in ethanol (30 mL) and water (26 mL) in an oil bath at 65° C. The receiving flask to collect the ethereal solution of diazomethane was cooled in an ice-bath and the Diazald® solution was added at such a rate as that allowed for a dropwise distillation into the receiving flask. When all of the Diazald® solution had been added, additional diethyl ether (10 mL) was added through the addition funnel until the distillate was clear (no remaining diazomethane). After cooling to room temperature, the mixture in the distillation flask was quenched slowly with acetic acid until the yellow color disappeared.

A solution of freshly prepared mixed anhydride above (12.7 g, 29.0 mmol, 1 equiv.) in diethyl ether (110 mL) was placed in a clear-seal joint flask and cooled to 0° C. in an ice bath. The freshly prepared diazomethane ethereal solution (~90.0 mmol, 3 equiv.) was added through an addition funnel dropwise while keeping it cold. The resulting mixture was stirred at 0° C. for 15 minutes, warmed to room temperature and stirred for 30 minutes. The reaction was cooled to 0° C. Meanwhile a mixture of 48% aqueous HBr (24 mL, 210.0 mmol, 7 equiv.) and acetic acid (24.0 mL) was cooled to 0° C. and added to the above reaction mixture slowly at 0° C. The mixture was stirred at 0° C. for 15 minutes, warmed to room temperature and stirred for 30 minutes. The mixture was diluted with diethyl ether (120 mL), washed with water (3×120 mL), dried over sodium sulfate, filtered and concentrated under reduced pressure. The residue was purified on an InterChim automated chromatography system (220 g SorbTech silica gel column), eluting with a gradient of 0 to 30% ethyl acetate in heptanes to give compound 58-3 (7.12 g, 57% yield) as a white solid.

Benzyl (S)-4-((tert-butoxycarbonyl)amino)-5-oxo-6-((2-(trifluoromethyl) pyrimidin-4-yl)oxy)hexanoate (66-1): Potassium fluoride (1.121 g, 19.29 mmol, 4 equiv.) was added to a solution of compound 58-3 (2.0 g, 4.83 mmol, 1 equiv.) and 2-(trifluoromethyl)pyrimidin-4-ol (0.871 g, 5.31 mmol, 1.1 equiv.) in DMF (20 mL). After stirring at room temperature for 20 hours, the reaction was diluted with ethyl acetate (250 mL), washed with saturated sodium bicarbonate (300 mL) and saturated brine (300 mL). The organic layer was dried over sodium sulfate (100 g), filtered and concentrated under reduced pressure. The residue was purified on an InterChim automated chromatography system (80 g SorbTech silica gel column, sample wet loaded in dichloromethane (10 mL)), eluting with a gradient of 0 to 30% ethyl acetate in heptanes to give compound 66-1 (1.805 g, 75% yield) as a colorless viscous oil.

Benzyl (S)-4-amino-5-oxo-6-((2-(trifluoromethyl)pyrimidin-4-yl)oxy) hexanoate hydrogen chloride (66-2): 4M HCl in 1,4-dioxane (1.8 mL, 7.18 mmol, 2.0 equiv.) was added dropwise to a solution of compound 66-1 (1.78 g, 3.6 mmol, 1 equiv.) in acetonitrile (70 mL) at 5° C. The mixture was warmed to room temperature and stirred for 20 hours. The mixture was concentrated under reduced pressure. Methanol (100 mL) was added and the mixture was concentrated under reduced pressure. The residue was dried under vacuum at room temperature for 1 hour. The solid was diluted with diethyl ether (2×100 mL) and decanted. The residue was dried under vacuum at room temperature for 2 hours to give compound 66-2 (1.331 g, 85% yield) as an off-white solid.

Benzyl (S)-4-((S)-2-(2-((2,6-difluorophenyl)amino)-2-oxoacetamido) propanamido)-5-oxo-6-((2-(trifluoromethyl) pyrimidin-4-yl)oxy)hexanoate (66-3): EDC.HCl (0.583 g, 3.0 mmol, 1.1 equiv.) was added to a suspension of compound 8 (0.752 g, 2.8 mmol, 1.0 equiv.) and HOAt (0.452 g, 3.32 mmol, 1.2 equiv.) in acetonitrile (25 mL). After stirring the mixture at room temperature for 10 minutes, compound 66-2 (1.2 g, 2.8 mmol, 1.0 equiv.) and triethylamine (0.771 mL, 5.53 mmol, 2.0 equiv.) were sequentially added and the mixture was stirred at room temperature for 16 hours. The reaction mixture was diluted with ethyl acetate (250 mL) and washed with saturated sodium bicarbonate (250 mL) and saturated brine (250 mL). The sodium bicarbonate layer was extracted with additional ethyl acetate (300 mL). This ethyl acetate layer was washed with the initial saturated brine solution. The combined organic layers were dried over sodium sulfate (100 g), filtered and concentrated under reduced pressure. The crude material was purified on an Interchim automated chromatography system (40 g, RediSep silica gel column, sample dry loaded using celite (4 g)), eluting with a gradient of 0 to 50% ethyl acetate in heptanes to give desired product (66-3) (1.069 g, 59% yield) as an off-white solid.

(S)-4-((S)-2-(2-((2,6-Difluorophenyl)amino)-2-oxoacetamido)propanamido)-5-oxo-6-((2-(trifluoromethyl)pyrimidin-4-yl)oxy)hexanoic acid (66-A, Example 15): A suspension of compound 66-3 (1.069 g, 1.64 mmol, 1 equiv.) and 10% palladium on carbon (110 mg, 50% wet) in tetrahydrofuran (30 mL) was hydrogenated @ 25 psi for 2.5 hours at room temperature. Analysis by LC-MS indicated 20% conversion of the starting material to product was observed. The reaction mixture was purged with nitrogen gas for 5 minutes and additional 10% palladium on carbon (110 mg, 50% wet) was added and purged with nitrogen gas for additional 5 minutes and hydrogenated @ 25 psi for additional 3 hours at room temperature. The suspension was filtered through celite (50 g). The celite bed was washed with ethyl acetate (250 mL). The filtrate was concentrated under reduced pressure and the crude material was purified on an Interchim automated chromatography system (40 g, RediSep silica gel column; sample dry loaded using celite (4 g) eluting with 0 to 10% methanol in dichloromethane to give desired compound 66-A (as two fractions 410 mg, >95.9% purity by HPLC and fraction; 235 mg, 94.8% purity by HPLC). Due to the traces amount of impurities in $^1$H-NMR, the compound 66-A (410 mg) was triturated with dichloromethane (2 mL), filtered and washed with dichloromethane (2 mL). The product was dried under vacuum at 40° C. for 16 hours to give compound 66-A, (Example 15) (0.336 g, 36% yield, 98.9% purity by HPLC) as a white solid, (Mass Spec. m/z=562.1 (M+H).

Example 16

Scheme 15

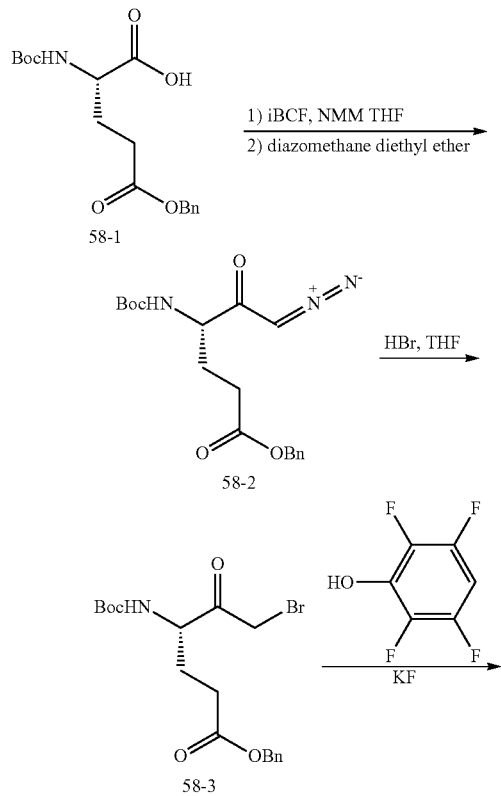

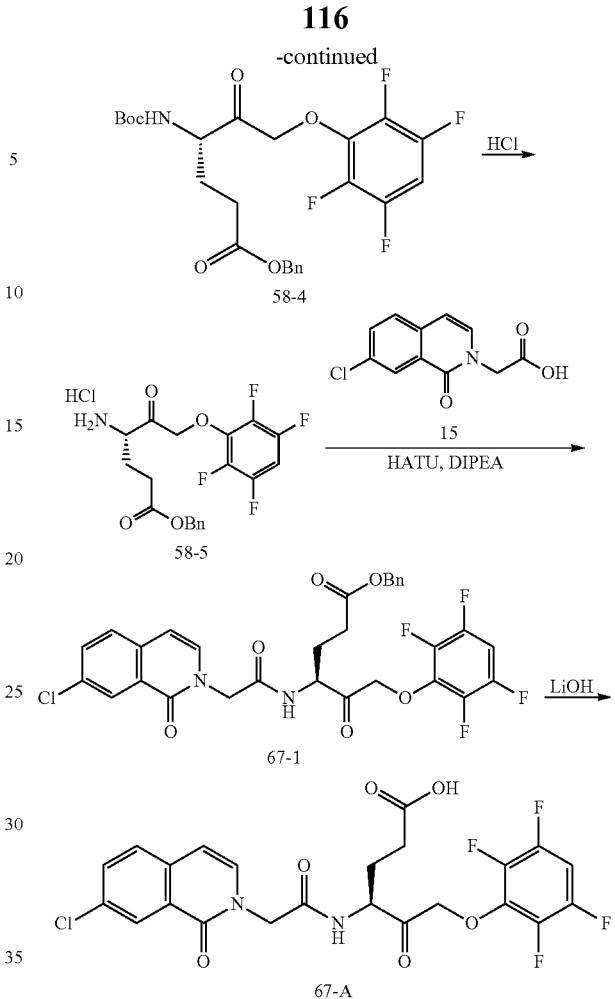

Benzyl (S)-6-bromo-4-((tert-butoxycarbonyl)amino)-5-oxohexanoate (58-3): The procedure for the preparation of compound 58-3 was shown in Scheme 14.

Benzyl (S)-4-((tert-butoxycarbonyl)amino)-5-oxo-6-(2,3,5,6-tetrafluoro phenoxy)hexanoate (58-4): Potassium fluoride (2.46 g, 44.4 mmol, 4 equiv.) was added to a solution of freshly prepared compound 58-3 (4.48 g, 10.6 mmol, 1 equiv.) and 2,3,5,6-tetrafluorophenol (1.94 g, 11.7 mmol, 1.1 equiv.) in anhydrous DMF (44 mL). After stirring at room temperature for 18 hours, the reaction was diluted with ethyl acetate (120 mL), washed with saturated sodium bicarbonate (120 mL) and saturated brine (120 mL). The organic layer was dried over sodium sulfate, filtered and concentrated under reduced pressure. The residue was purified on an InterChim automated chromatography system (120 g SorbTech silica gel column), eluting with a gradient of 0 to 25% ethyl acetate in heptanes to give compound 58-4 (3.98 g, 77% yield) as a clear liquid.

Benzyl (S)-4-amino-5-oxo-6-(2,3,5,6-tetrafluorophenoxy)hexanoate hydrochloride (58-5): 4M HCl in 1,4-dioxane (2.2 mL, 8.7 mmol, 1.2 equiv.) was added dropwise to a solution of compound 58-4 (3.6 g, 7.2 mmol, 1 equiv.) in acetonitrile (80 mL) at 0 to 5° C. The mixture was warmed to room temperature and stirred for 6.5 hours. LCMS indicated that the reaction was not complete. Additional 4M HCl in 1,4-dioxane (1.5 mL, 5.8 mmol, 0.8 equiv.) was added and the mixture was stirred for 18 hours at which time LCMS indicated that the reaction was complete. The mixture was concentrated under reduced pressure to give compound 58-5 (2.87 g, 91% yield) as an orange liquid, which was used subsequently.

Benzyl (S)-4-(2-(7-chloro-1-oxoisoquinolin-2(1H)-yl)acetamido)-5-oxo-6-(2,3,5,6-tetrafluorophenoxy)hexanoate (67-1): Hexafluorophosphate azabenzo-triazole tetramethyluronium (HATU, 0.96 g, 2.52 mmol, 1.1 equiv.) was added to a solution of compound 15 (0.54 g, 2.3 mmol, 1 equiv.) in dimethylformamide (10 mL) at room temperature. After stirring at room temperature for 10 minutes, compound 58-5 (1.0 g, 2.29 mmol, 1 equiv.) and N,N-diisopropylethylamine (1.2 mL, 6.87 mmol, 3 equiv.) were sequentially added. After stirring at room temperature for 18 hours, the reaction mixture was diluted with ethyl acetate (80 mL). The organic layer was washed with water (2×40 mL), dried over sodium sulfate, filtered and concentrated under reduced pressure. The crude material was purified on an Interchim automated chromatography system (80 g SorbTech silica gel column), eluting with a gradient of 0 to 50% ethyl acetate in heptanes. After concentrating the fractions under reduced pressure, the resulting solid was dried under vacuum at room temperature for 3 hours to give compound 67-1 (0.79 g, 56% yield) as an off-white solid.

(S)-4-(2-(7-Chloro-1-oxoisoquinolin-2(1H)-yl)acetamido)-5-oxo-6-(2,3,5,6-tetrafluorophenoxy)hexanoic acid (67-A, Example 16): 1M Lithium hydroxide (0.64 mL, 0.64 mmol, 0.95 equiv.) was added to a solution of compound 67-1 (0.42 g, 0.67 mmol, 1 equiv.) in the mixture of 1,4-dioxane (12 mL) and water (3 mL) at 0° C. and stirred for 10 minutes. The reaction mixture was concentrated under reduced pressure at room temperature. The residue was diluted with water (5 mL) and extracted with diethyl ether (15 mL) to remove any organic impurities. The aqueous layer was adjusted to pH 3 with 1N HCl (~1.0 mL) and extracted with ethyl acetate (3×50 mL). The combined organic layers were dried over sodium sulfate, filtered and concentrated under reduced pressure. The crude product was dissolved in the mixture of dichloromethane (7 mL) and methanol (1 mL), adsorbed onto silica gel (10 g) and purified on an Interchim automated system (40 g RediSepRf silica gel column), eluting with a gradient of 0 to 8% methanol in dichloromethane. After concentrating the fractions under reduced pressure, the resulting solid was dried under vacuum at room temperature for 4 hours to give compound 67-A, (Example 16) (0.30 g, 86% yield, 97.3% purity by HPLC) as a white solid, (Mass Spec. m/z=529.1 (M+H).

Examples 17-42

Scheme 16

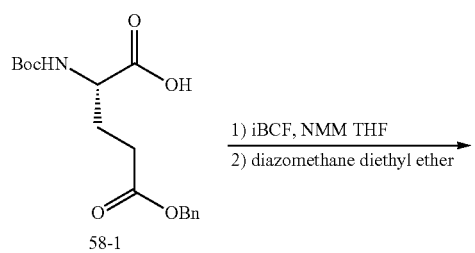

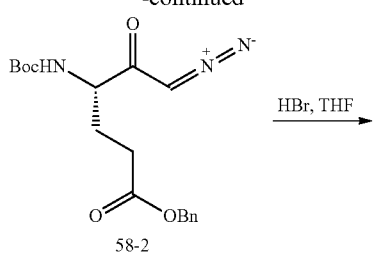

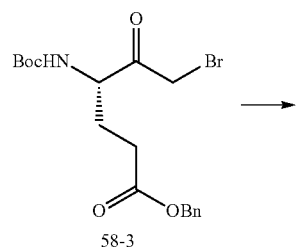

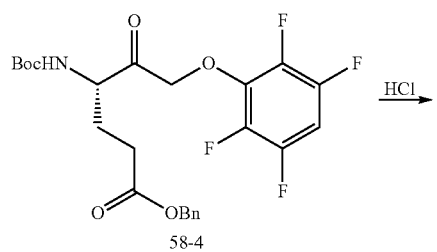

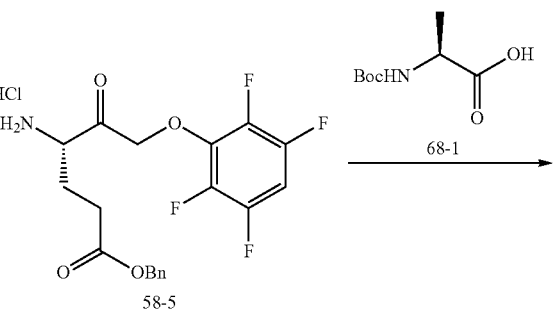

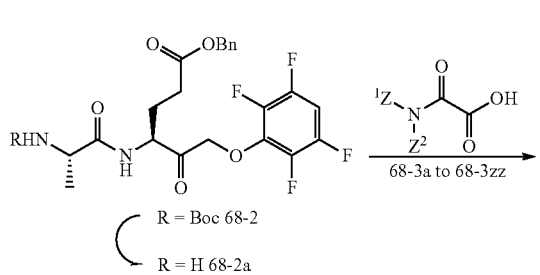

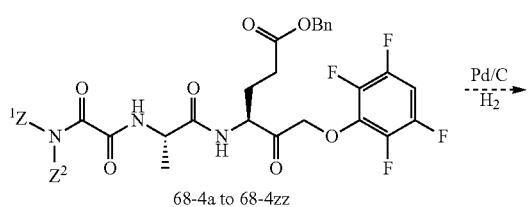

68-4a to 68-4zz

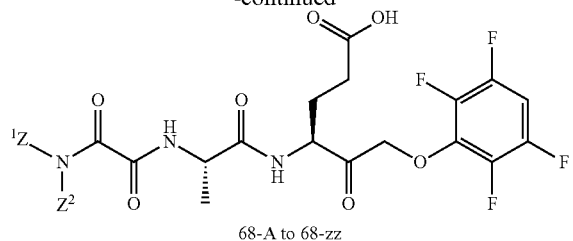

68-A to 68-zz

Compounds 68-A through 68-ZZ were prepared by the process outlined in the above scheme.

| | | | | |
|---|---|---|---|---|
| 68-A Ex. 17 | 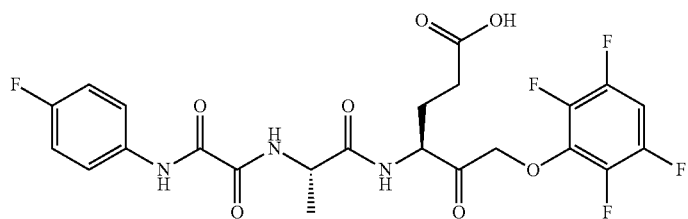 [SMILES: C[C@H](NC(=O)C(=O)Nc1ccc(F)cc1)C(=O)N[C@@H](CCC(=O)O)C(=O)COc1c(F)c(F)cc(F)c1F] | | m/z = 546.2 (M + H) | (S)-4-((S)-2-(2-((4-fluorophenyl)amino)-2-oxoacetamido)propanamido)-5-oxo-6-(2,3,5,6-tetrafluorophenoxy)hexanoic acid |
| 68-B Ex. 18 | 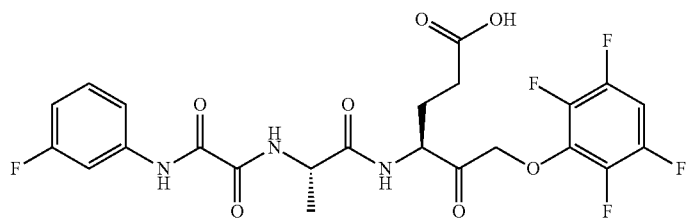 [SMILES: C[C@H](NC(=O)C(=O)Nc1cccc(F)c1)C(=O)N[C@@H](CCC(=O)O)C(=O)COc1c(F)c(F)cc(F)c1F] | | m/z = 546.2 (M + H) | (S)-4-((S)-2-(2-((3fluorophenyl)amino)-2-oxoacetamido)propanamido)-5-oxo-6-(2,3,5,6-tetrafluorophenoxy)hexanoic acid |
| 68-C Ex. 19 | 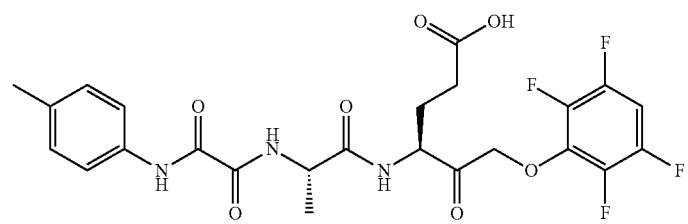 [SMILES: Cc1ccc(NC(=O)C(=O)N[C@@H](C)C(=O)N[C@@H](CCC(=O)O)C(=O)COc2c(F)c(F)cc(F)c2F)cc1] | | m/z = 542.2 (M + H) | (S)-4-((S)-2-(2-((4-methylphenyl)amino)-2-oxoacetamido)propanamido)-5-oxo-6-(2,3,5,6-tetrafluorophenoxy)hexanoic acid |
| 68-D Ex. 20 | 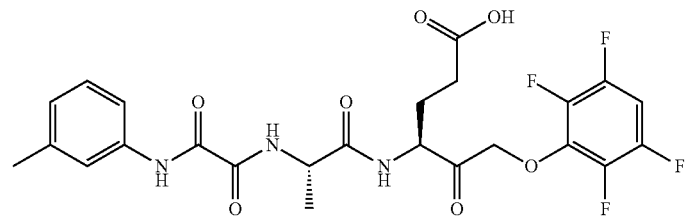 [SMILES: Cc1cccc(NC(=O)C(=O)N[C@@H](C)C(=O)N[C@@H](CCC(=O)O)C(=O)COc2c(F)c(F)cc(F)c2F)c1] | | m/z = 542.2 (M + H) | (S)-4-((S)-2-(2-((3-methylphenyl)amino)-2-oxoacetamido)propanamido)-5-oxo-6-(2,3,5,6-tetrafluorophenoxy)hexanoic acid |
| 68-E Ex. 21 | 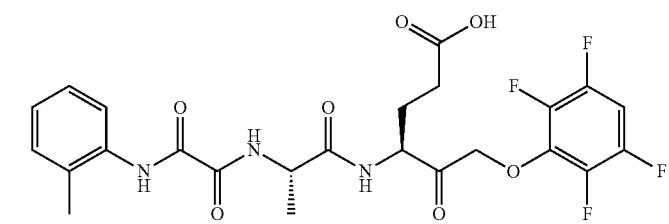 [SMILES: Cc1ccccc1NC(=O)C(=O)N[C@@H](C)C(=O)N[C@@H](CCC(=O)O)C(=O)COc1c(F)c(F)cc(F)c1F] | | m/z = 542.2 (M + H) | (S)-4-((S)-2-(2-((2-methylphenyl)amino)-2-oxoacetamido)propanamido)-5-oxo-6-(2,3,5,6-tetrafluorophenoxy)hexanoic acid |

-continued

| | | | |
|---|---|---|---|
| 68-F<br>Ex. 22 | 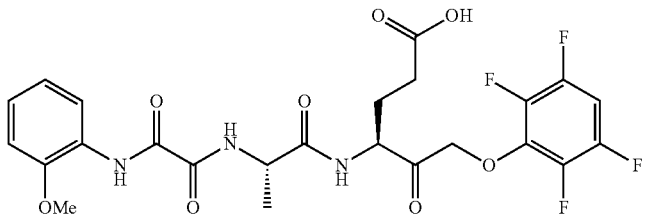 [SMILES: COc1ccccc1NC(=O)C(=O)N[C@@H](C)C(=O)N[C@@H](CCC(=O)O)C(=O)COc1c(F)c(F)cc(F)c1F] | m/z = 558.2<br>(M + H) | (S)-4-((S)-2-(2-((2-methyoxyphenyl)amino)-2-oxoacetamido)propanamido)-5-oxo-6-(2,3,5,6-tetrafluorophenoxy)hexanoic acid |
| 68-G<br>Ex. 23 | 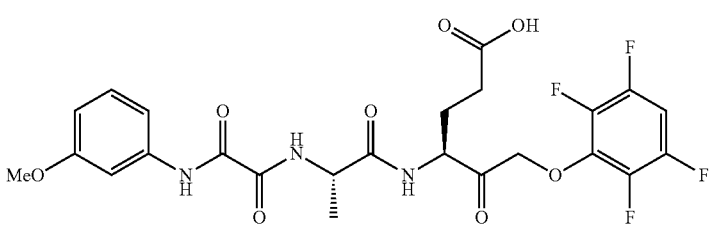 [SMILES: COc1cccc(NC(=O)C(=O)N[C@@H](C)C(=O)N[C@@H](CCC(=O)O)C(=O)COc2c(F)c(F)cc(F)c2F)c1] | m/z = 558.2<br>(M + H) | (S)-4-((S)-2-(2-((3-methyoxyphenyl)amino)-2-oxoacetamido)propanamido)-5-oxo-6-(2,3,5,6-tetrafluorophenoxy)hexanoic acid |
| 68-H<br>Ex. 24 | 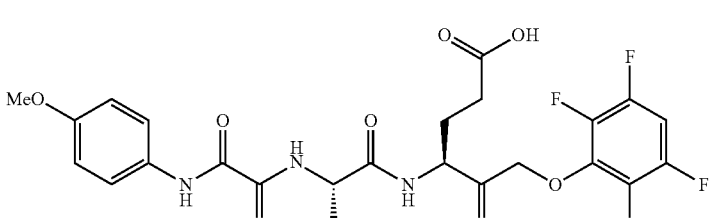 | m/z = 558.2<br>(M + H) | (S)-4-((S)-2-(2-((4-methyoxyphenyl)amino)-2-oxoacetamido)propanamido)-5-oxo-6-(2,3,5,6-tetrafluorophenoxy)hexanoic acid |
| 68-I<br>Ex. 25 | 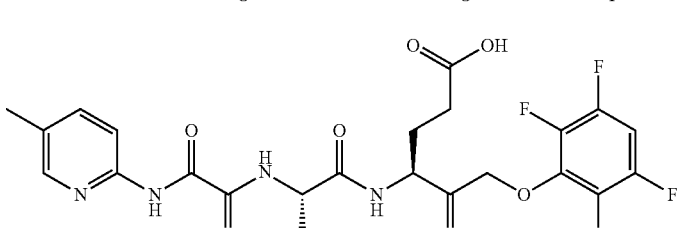 | m/z = 543.2<br>(M + H) | (S)-4-((S)-2-(2(4(5-methylpyridin-2-yl)amino)-2-oxoacetamido)propanamido)-5-oxo-6-(2,3,5,6-tetrafluorophenoxy)hexanoic acid |
| 68-J<br>Ex. 26 | 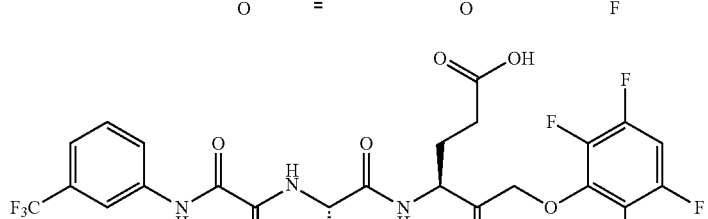 | m/z = 596.1<br>(M + H) | (S)-5-oxo-4-((S)-2-(2-oxo-2-((3-(trifluoromethyl)phenyl)amino)acetamido)propanamido)-6-(2,3,5,6-tetrafluorophenoxy)hexanoic acid |
| 68-K<br>Ex. 27 | 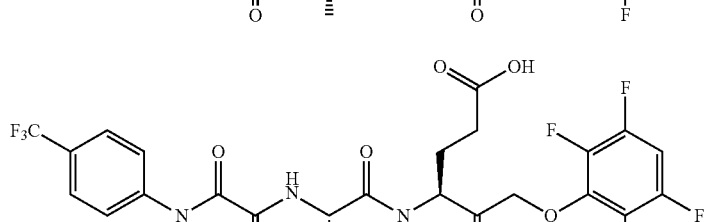 | m/z = 596.1<br>(M + H) | (S)-5-oxo-4-((S)-2-(2-oxo-2-((4-(trifluoromethyl)phenyl)amino)acetamido)propanamido)-6-(2,3,5,6-tetrafluorophenoxy)hexanoic acid |
| 68-L<br>Ex. 28 | 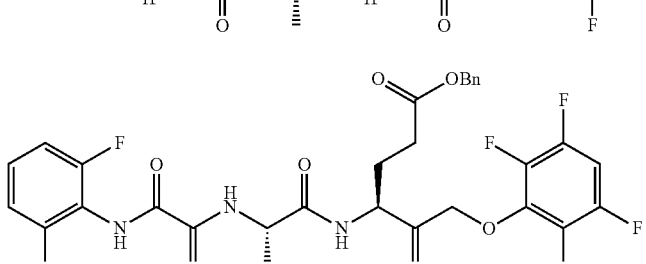 | m/z = 654.2<br>(M + H) | benzyl(S)-4-((S)-2-(2-((2,6-difluorophenyl)amino)-2-oxoacetamido)propanamido)-5-oxo-6-(2,3,5,6-tetrafluorophenoxy)hexanoate |

-continued

| | | | |
|---|---|---|---|
| 68-M Ex. 29 | 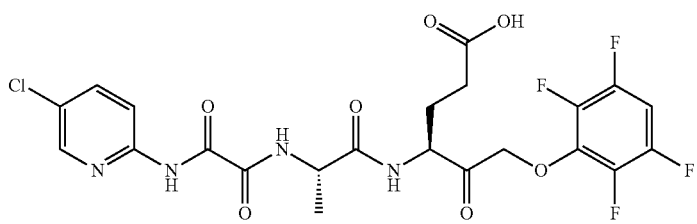 [SMILES: C[C@H](NC(=O)C(=O)Nc1ccc(Cl)cn1)C(=O)N[C@@H](CCC(=O)O)C(=O)COc1c(F)c(F)cc(F)c1F] | m/z = 563.1 (M + H) | (S)-4-((S)-2-(2-((5-chloropyridin-2-yl)amino)-2-oxoacetamido)propanamido)-5-oxo-6-(2,3,5,6-tetrafluorophenoxy)hexanoic acid |
| 68-N Ex. 30 | 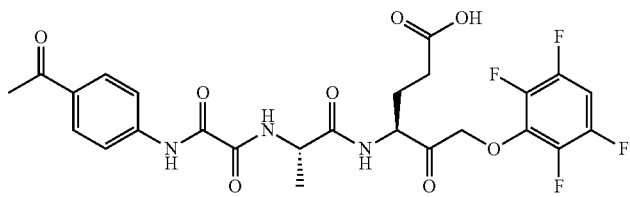 [SMILES: CC(=O)c1ccc(NC(=O)C(=O)N[C@@H](C)C(=O)N[C@@H](CCC(=O)O)C(=O)COc2c(F)c(F)cc(F)c2F)cc1] | m/z = 570.2 (M + H) | (S)-4-((S)-2-(2-((4-acetylphenyl)amino)-2-oxoacetamido)propanamido)-5-oxo-6-(2,3,5,6-tetrafluorophenoxy)hexanoic acid |
| 68-O Ex. 31 | 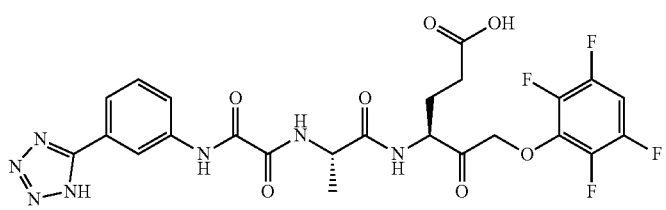 [SMILES: C[C@H](NC(=O)C(=O)Nc1cccc(-c2nnn[nH]2)c1)C(=O)N[C@@H](CCC(=O)O)C(=O)COc1c(F)c(F)cc(F)c1F] | m/z = 596.2 (M + H) | (S)-4-((S)-2-(2-((3-(1H-tetrazol-5-yl)phenyl)amino)-2-oxoacetamido)propanamido)-5-oxo-6-(2,3,5,6-tetrafluorophenoxy)hexanoic acid |
| 68-P Ex. 32 | 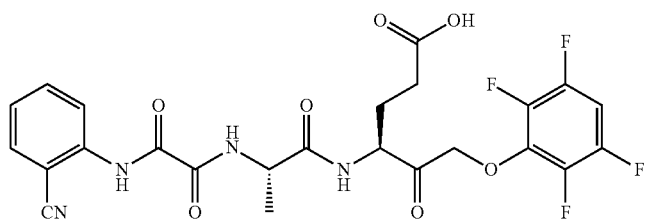 [SMILES: C[C@H](NC(=O)C(=O)Nc1ccccc1C#N)C(=O)N[C@@H](CCC(=O)O)C(=O)COc1c(F)c(F)cc(F)c1F] | m/z = 553.1 (M + H) | (S)-4-((S)-2-(2-((2-cyanophenyl)amino)-2-oxoacetamido)propanamido)-5-oxo-6-(2,3,5,6-tetrafluorophenoxy)hexanoic acid |
| 68-Q Ex. 33 | 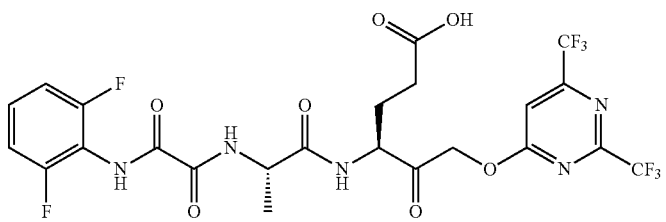 [SMILES: C[C@H](NC(=O)C(=O)Nc1c(F)cccc1F)C(=O)N[C@@H](CCC(=O)O)C(=O)COc1cc(C(F)(F)F)nc(C(F)(F)F)n1] | m/z = 630 (M + H) | (S)-6-((2,6-bis(trifluoromethyl)pyrimidin-4-yl)oxy)-4-((S)-2-(2-((2,6-difluorophenyl)amino)-2-oxoacetamido)propanamido)-5-oxohexanoic acid |
| 68-R Ex. 34 | 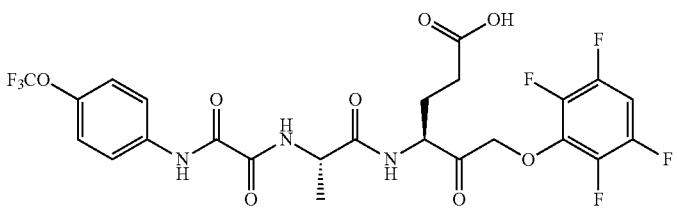 [SMILES: C[C@H](NC(=O)C(=O)Nc1ccc(OC(F)(F)F)cc1)C(=O)N[C@@H](CCC(=O)O)C(=O)COc1c(F)c(F)cc(F)c1F] | m/z = 612.1 (M + H) | (S)-5-oxo-4-((S)-2-(2-oxo-2-((4-(trifluoromethoxy)phenyl)amino)acetamido)propanamido)-6-(2,3,5,6-tetrafluorophenoxy) hexanoic acid |
| 68-S Ex. 35 | 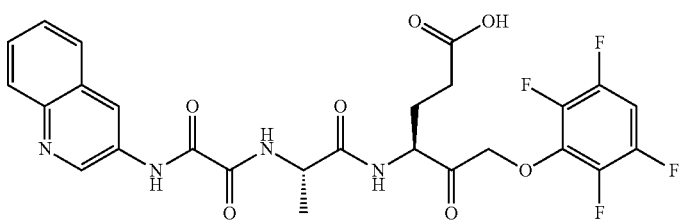 [SMILES: C[C@H](NC(=O)C(=O)Nc1cnc2ccccc2c1)C(=O)N[C@@H](CCC(=O)O)C(=O)COc1c(F)c(F)cc(F)c1F] | m/z = 579.1 (M + H) | (S)-5-oxo-4-((S)-2-(2-oxo-2-(quinolin-3-ylamino)acetamido) propanamido)-6-(2,3,5,6-tetrafluorophenoxy)hexanoic acid |

| | | | |
|---|---|---|---|
| 68-T Ex. 25 | (structure) | m/z = 578.2 (M + H) | (S)-4-((S)-2-(2-(naphthalen-1-ylamino)-2-oxoacetamido)propanamido)-5-oxo-6-(2,3,5,6-tetrafluorophenoxy)hexanoic acid |
| 68-U Ex. 36 | (structure) | m/z = 579.1 (M + H) | (S)-5-oxo-4-((S)-2-(2-oxo-2-(quinolin-8-ylamino)acetamido)propanamido)-6-(2,3,5,6-tetrafluorophenoxy)hexanoic acid |
| 68-V Ex. 37 | (structure) | m/z = 529.1 (M + H) | (S)-5-oxo-4-((S)-2-(2-oxo-2-(pyridin-4-ylamino)acetamido)propanamido)-6-(2,3,5,6-tetrafluorophenoxy)hexanoic acid |
| 68-W Ex. 38 | (structure) | m/z = 564.1 (M + H) | (R)-4-((S)-2-(2-((2,6-difluorophenyl)amino)-2-oxoacetamido)propanamido)-5-oxo-6-(2,3,5,6-tetrafluorophenoxy)hexanoic acid |
| 68-X Ex. 39 | (structure) | m/z = 529.1 (M + H) | (S)-5-oxo-4-((S)-2-(2-oxo-2-(pyridin-2-ylamino)acetamido)propanamido)-6-(2,3,5,6-tetrafluorophenoxy)hexanoic acid |
| 68-Y Ex. 40 | (structure) | m/z = 529.1 (M + H) | (S)-5-oxo-4-((S)-2-(2-oxo-2-(pyridin-3-ylamino)acetamido)propanamido)-6-(2,3,5,6-tetrafluorophenoxy)hexanoic acid |
| 68-Z Ex. 41 | (structure) | m/z = 558 (M + H) | (S)-4-((S)-2-(2-((4,6-dimethylpyrimidin-2-yl)amino)-2-oxoacetamido)propanamido)-5-oxo-6-(2,3,5,6-tetrafluorophenoxy)hexanoic acid |

| 68-ZZ Ex. 42 | 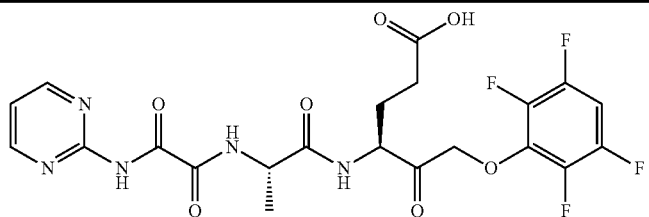 | m/z = 530.1 (M + H) | (S)-5-oxo-4-((S)-2-(2-oxo-2-(pyrimidin-2-ylamino)acetamido)propanamido)-6-(2,3,5,6-tetrafluorophenoxy)hexanoic acid |
Example 43
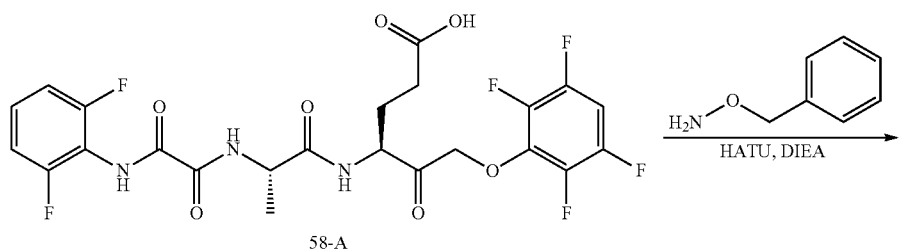
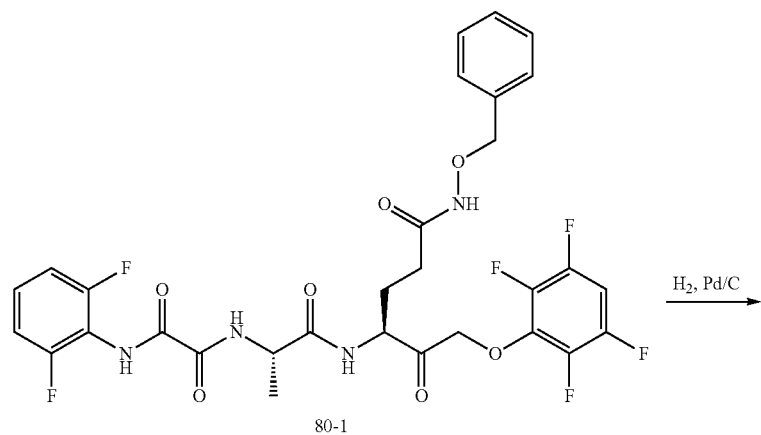
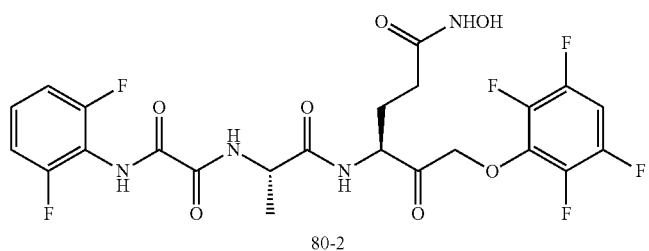

N¹—((S)-1-(((S)-6-((Benzyloxy)amino)-2,6-dioxo-1-(2,3,5,6-tetrafluorophenoxy)hexan-3-yl)amino)-1-oxopropan-2-yl)-N²-(2,6 difluorophenyl)oxalamide: 80-1

Diisopropylethylamine (0.47 ml, 0.34 g, 2.66 mmol, 3.0 equiv) was added dropwise to a solution of compound 58-A (0.50 g, 0.89 mmol, 1.0 equiv) and O-benzylhydroxylamine (0.17 g, 1.06 mmol, 1.2 equiv) in DMF (15 ml) at 0° C. HATU (1.24 g, 1.95 mmol, 1.5 equiv) was added portionwise and the reaction mixture gradually warmed up to room temperature overnight. LC-MS analysis indicated that the reaction was complete. The reaction mixture was poured into saturated sodium bicarbonate (100 mL) and extracted with ethyl acetate (2×70 mL). The combined organic layers were washed with 10% lithium chloride (100 mL), saturated brine (100 mL), dried over sodium sulfate and concentrated under reduced pressure. The crude product was purified on a Büchi automatic chromatography system (40 g SorbTech silica gel column), eluting with a gradient of 30 to 60% ethyl acetate in heptanes to give 80-1 (0.44 g, 74% yield) as a white solid, (Mass Spec. m/z=669.2 (M+H).

N¹-(2,6-difluorophenyl)-N²—((S)-1-(((S)-6-(hydroxyamino)-2,6-dioxo-1-(2,3,5,6-tetrafluorophenoxy)hexan-3-yl)amino)-1-oxopropan-2-yl)oxalamide 80-2. 80-1 (0.44 g, 0.65 mmol, 1.0 equiv) and 10% palladium on carbon (88 mg, 50% wet) in THF (20 ml) was hydrogenated at 25 psi for 2 hours. Upon completion, the reaction mixture was filtered through Celite (15 g) which was washed with THF (120 mL). The filtrate was concentrated under reduced pressure. The crude product was purified on a Büchi automatic chromatography system (40 g SorbTech silica gel column), eluting with a gradient of 0 to 5% methanol in dichloromethane to give 80-2 (0.32 g, 85% yield, 90% purity) as a yellow solid. The product was further purified on a Büchi automatic chromatography system (30 g RediSep Rf Gold Reversed-phase C18 column), eluting with a gradient of 0 to 30% acetonitrile in water to give 80.2 (0.18 g, 48% yield, 95% purity) as an off-white solid, (Mass Spec. m/z=579.2 (M+H).

Example 44

Assay for the Inhibition of Caspase Enzyme Activity and Determination of $IC_{50}$ Values Human caspases were purchased from Enzo Biosciences and used according to the manufacturer's instructions. An exemplary caspase assay, for Caspase-1, is provided below:

Caspase-1 Assay

Caspase-1 was diluted to 10 U/μl in assay buffer consisting of 50 mM HEPES, pH 7.4, 100 mM NaCl, 0.1% CHAPS, 1 mM EDTA, 10% glycerol and 10 mM DTT.

Reaction Conditions:

45 μl of assay buffer was added into ½ volume microtiter plate. The plate was allowed to equilibrate to assay temperature. 5 μl of Caspase-1 (10 U/μl) was added to each appropriate well. Two 2 blank wells containing assay buffer alone without Caspase-1 were included on the plate.

The reaction was started by the addition of 50 μl Ac-YVAD-pNA substrate, for a final substrate concentration of 200 M. The reaction was continuously monitored at 405 nm. The data was graphed as $OD_{405\,nm}$ vs time, and the slope was determined over the linear portion of the curve. The rates in OD/min were converted to substrate/min using an extinction coefficient for p-nitroaniline of 10,500M-1 cm-1, and were adjusted for pathlength of sample.

Enzymatic assays were conducted for Caspase-3, 6 and 7 activity according to the manufacture's instructions. Caspase enzyme inhibition $IC_{50}$ data for selected compounds as prepared according to methods described herein is presented below.

TABLE 1

| Example | Caspase 1 | Caspase 3 | Caspase 6 | Caspase 7 |
|---|---|---|---|---|
| IDN-7314 | A | A | A | A |
| 1 | B | D | D | D |
| 2 | B | D | D | D |
| 3 | C | D | D | D |
| 4 | B | D | D | D |
| 5 | C | D | D | D |
| 6 | A | D | D | D |
| 7 | B | D | D | D |
| 8 | C | D | D | D |
| 9 | A | D | D | D |
| 10 | A | D | D | D |
| 11 | A | D | D | C |
| 12 | A | D | D | D |
| 13 | B | D | D | D |
| 14 | A | C | C | C |
| 15 | A | D | D | D |
| 16 | A | D | D | D |
| 17 | A | D | D | D |
| 18 | A | D | D | D |
| 19 | A | D | D | D |
| 20 | A | D | D | D |
| 21 | A | D | D | D |
| 22 | A | D | D | D |
| 23 | A | D | D | D |
| 24 | A | D | D | D |
| 25 | A | D | D | D |
| 26 | A | D | D | D |
| 27 | A | D | D | D |
| 28 | A | D | D | D |
| 29 | A | D | D | D |
| 30 | A | D | D | D |
| 31 | A | D | D | D |
| 32 | A | D | D | D |
| 33 | A | D | D | D |
| 34 | A | D | D | D |
| 35 | A | D | D | D |
| 36 | A | D | D | D |
| 37 | A | D | D | D |
| 38 | A | D | D | D |
| 39 | A | D | D | D |
| 40 | A | D | D | D |
| 41 | A | D | D | D |
| 42 | A | D | D | D |

KEY:
A ≤ 10 nM;
B > 10 nM ≤ 100 nM;
C > 100 nM < 1000 nM;
D ≥ 1000 nM

Example 45

Assay for the Activity and Selectivity Determination in Cell-Based Models

Compounds in the present invention were tested in THP-1 cells, a human monocyte cell line, to assess the inhibition of the inflammatory cytokine IL-1β. THP-1 cells (ATCC TIB-202) were grown in culture and seeded in 96 well plates at a concentration of 200,000 cells per well with a total volume of 150 μL. Plated cells were incubated overnight at 37 degrees C. under an atmosphere of 5% $CO_2$. Media was removed from cells which were washed with PBS. Test compounds were diluted in DMSO stock solution and serially diluted appropriately for initial screening and $IC_{50}$ determinations. LPS in serum free media (140 μL of 1 μg/μL) was added to each well to stimulate IL-1β production. IL-1β was measured by ELISA assay kit (R&D Systems) per the manufacturers instructions. The pan caspase inhibitor, IDN-7314, was included in cell-based screening and $IC_{50}$ assays as a reference compound.

Table 2 below provides selected THP 1 screening data at 10 micromolar.

TABLE 2

| Example | Percent Inhibition of IL1-β |
| --- | --- |
| IDN-7314 | A |
| 1 | B |
| 2 | B |
| 3 | C |
| 4 | B |
| 5 | C |
| 6 | A |
| 7 | B |
| 8 | C |
| 9 | A |
| 10 | A |
| 11 | A |
| 12 | A |
| 13 | B |
| 14 | A |
| 15 | A |
| 16 | A |
| 17 | A |
| 18 | A |
| 19 | A |
| 20 | A |

KEY:
A > 90%;
B ≤ 90% > 50%;
C ≤ 50% > 25%

$IC_{50}$ values for the inhibition of IL-1β in THP 1 cells were determined from dose response studies. An example of a dose response study in THP 1 cells is shown in FIG. 1.

Compounds of the present invention were evaluated in Jurkat cells, a human T-lymphocyte cell line, to evaluate compounds ability to inhibit apoptotic cell death. Jurkat cells, Clone E6-1 (ATCC TIB-152) were grown in culture maintain a cell density between 0.5-2 million cells/mL. Cells were tested for viability and countion with typan blue stain before use. Test compounds were addes to 96 well plates and Jurkat cells were added at a concentration of approximately 100,000 cells per well and mixed thoroughly by action of pipetting. Plated cells were incubated for 1 hour at 37 degrees C. under an atmosphere of 5% $CO_2$. Anti-Fas antibody was added and mixed by pipet action. Plates were incubated for 20 hours at 37 degrees C. under an atmosphere of 5% $CO_2$. 10 microliters of thawed WST-8 solution was added to each well and incubated for 4 hours. Absorbance was measured at 450 nM and control reading at 630 nM using a SpectraMax ID5 plate reader. Apoptotic cell death is executed by caspases 3, 7 and 6. Compounds that lack activity against these caspases will not prevent the death of Jurkat cells and is a functional test of selectivity for inflammatory over apoptotic caspases.

Table 3 lists data of selected examples screened at a concentration of 10 micromolar.

A pan-caspase inhibitor, IDN-7314, a potent inhibitor of both the inflammatory and apoptotic caspases, was included as a reference compound in this cell-based assay of apoptosis.

TABLE 3

| Example | % Prevention of Fas - induced Jurkat cell apoptosis at 10 micromolar |
| --- | --- |
| IDN-7314 | A |
| 1 | D |
| 2 | D |
| 3 | D |
| 4 | D |
| 5 | D |
| 6 | D |
| 7 | D |
| 8 | D |
| 9 | D |
| 10 | D |
| 11 | D |
| 12 | D |
| 13 | D |
| 14 | D |
| 15 | D |
| 16 | D |
| 17 | D |
| 18 | D |
| 19 | D |
| 20 | D |

KEY:
A > 90%;
B ≤ 90% > 50%;
C ≤ 50% > 25%;
D ≤ 10%

$IC_{50}$ values to protect against Fas induced apoptosis and improve survival of Jurkat cells were determined from dose response studies. An example of a dose response study to Fas induced apoptosis in Jurkat cells is shown in FIG. 2.

Example 46

Assay for the Activity in In Vivo Models of Inflammation and Cytokine Production Compounds of the present invention were tested in a mouse in vivo model of peritoneal inflammation (peritonitis). Mice were treated with intraperotonial injection of bacterial endotoxin, (LPS). After 1 hour, test compounds were administered by IP injection. After an additional hour, adenosine triphosphate (ATP) was administered by IP injection to further induce the production of the inflammatory cytokines, IL-1β and IL 18. After 0.5 hours, peritoneal lavage fluid was collected and analyzed for IL-1β and IL 18. An inhibitor of the NLRP 3 inflammasome, MCC950, was administered by IP injection and included as a reference test compound. The compound of Example 6 of the present invention afforded statistically significant inhibition of the in vivo production of both IL-1β and IL 18. IL18 levels were determined by a commercially available ELISA kit following the manufacture's instructions FIG. 3.

Example 47

Assay for the Activity in In Vivo Models Gastrointestinal Disease: Ulcerative Colitis Compounds of the present invention were tested by oral administration in a rodent model of ulcerative colitis (UC). Ulcerative colitis was induced in Sprague-Dawley rats by instillation of 48 mg/kg trinitrobenzene disulfonic acid, (TNBS), through the rectum. Testing included 4 active treatment groups and one vehicle control group.

Effect of TNBS-Induced UC in Vehicle Treated Control Group, (Group 1):

Rats were administered of 0.5% vehicle carboxy methylcellulose, (CMC), twice daily starting 24 hours after the instillation of TNBS. This resulted in an 17% weight loss by DAY 7, relative to DAY 0 weights in the control group.

At the termination of the study on DAY 7, the average colon weight in the diseased rats was 5.904±2.208 g, the average colon length was 11.0±1.4 cm and the average distal colon width was 3.1±1.0 cm. Severe adhesions involving multiple intestinal loops, severe stricture resulting in proximal colon distension, ulcers of 6.4±0.4 cm in length, and colonic wall thickness of 3.5±0.8 mm combined to yield an overall colonic score of 11.5±0.8 in the diseased rats. Histological evaluation of the distal colon section revealed subacute inflammation of the mucosa, submucosa, and less frequently, colon wall and serosa; mucosal necrosis/gland loss; erosions; submucosa edema; and epithelial hyperplasia. Subacute inflammation (sub/mucosal and transmural/serosal were graded separately) was characterized by infiltration and aggregation of neutrophils, eosinophils, lymphocytes, plasma cells, and macrophages. Mucosal necrosis was characterized by damage to, necrosis of, or complete loss of colonic glands. Erosions were characterized by coagulative necrosis or loss of surface epithelium superficial to the muscularis mucosae. Submucosal edema was characterized by expansion of the submucosa by clear space or pale eosinophilic fluid, variably accompanied by dilation of lymphatic vessels and similar edematous expansion of the lamina propria. Epithelial hyperplasia was characterized by elongation of colonic glands and increased numbers of epithelial mitotic figures.

Effect of Therapeutic Treatment with Positive Control: Prednisolone (Group 2):

Once daily oral administration of 10 mg/kg prednisolone starting 24 hours after the instillation of 48 mg/kg TNBS through the rectum resulted in improved animal health by DAY 4 as reflected by increased body weight. All measured colon parameters were significantly improved resulting in a statistically significant 67% reduction in the overall colonic score and an average 40% inhibition of the histological parameters.

Effect of Therapeutic Treatment with the Compound of Example 6 (Groups 3-5):

Twice daily oral administration of the compound of Example 6 suspension in 0.5% CMC had a statistically significant effect on animal health, as determined by effect on animal weights, at all dose levels, Groups 3-5. The lowest dose (Group 3, 10 mg/kg/dose) had body weights significantly improved beginning on DAY 4. The mid-dose group (Group 4, 30 mg/kg/dose) and high dose group (Group 5, 100 mg/kg/dose) had statistically significantly improved body weights starting on DAY 5, as shown in Table 4 and FIG. 4.

All dose groups achieved statistically significant improvement in overall colonic score. The mid dose (Group 4, 30 mg/kg/dose) resulted in the best improvement in gross colon parameters (40% reduction in overall colonic score), Table 4 and FIG. 4.

All dose groups achieved statistically significant improvement of SUM scores of colon histological parameters, see, Table 4 and FIG. 4.

TABLE 4

Effect of disease and treatment on average weight loss

| Group | Statistic | STUDY DAY | | | | | | | | | |
|---|---|---|---|---|---|---|---|---|---|---|---|
| | | −5 | −1 | 0 | 1 | 2 | 3 | 4 | 5 | 6 | 7 |
| 1 (TNBS) | Mean | 222 | 251 | 236 | 231 | 220 | 211 | 205 | 202 | 199 | 195 |
| | SD | 6 | 10 | 10 | 12 | 13 | 13 | 14 | 13 | 12 | 13 |
| 2 Prednis | Mean | 222 | 249 | 235 | 232 | 221 | 223 | 223 | 227 | 227 | 229 |
| | SD | 5 | 11 | 10 | 10 | 12 | 17 | 19 | 22 | 24 | 23 |
| | p-value | 1.00 | 0.72 | 0.89 | 0.77 | 0.94 | 0.10 | 0.03 | 0.006 | 0.004 | 0.0008 |
| 3 10 mpk | Mean | 222 | 256 | 241 | 236 | 223 | 218 | 218 | 222 | 227 | 228 |
| | SD | 5 | 10 | 9 | 8 | 10 | 12 | 12 | 15 | 21 | 24 |
| | p-value | 1.00 | 0.25 | 0.19 | 0.27 | 0.59 | 0.22 | 0.05 | 0.004 | 0.002 | 0.001 |
| 4 30 mpk | Mean | 222 | 248 | 234 | 228 | 215 | 214 | 216 | 218 | 220 | 223 |
| | SD | 5 | 4 | 3 | 4 | 9 | 16 | 23 | 26 | 32 | 35 |
| | p-value | 1.00 | 0.41 | 0.57 | 0.46 | 0.31 | 0.70 | 0.21 | 0.09 | 0.07 | 0.03 |
| 5 100 mpk | Mean | 222 | 246 | 232 | 231 | 219 | 213 | 217 | 220 | 222 | 225 |
| | SD | 5 | 11 | 11 | 11 | 13 | 18 | 21 | 24 | 27 | 28 |
| | p-value | 1.00 | 0.38 | 0.40 | 0.98 | 0.80 | 0.78 | 0.17 | 0.05 | 0.02 | 0.01 |

Significance (p-value) vs Group 1 was calculated by Student's t-Test.

TABLE 5

Effect of disease and treatment on average colon histology:

| Group | Statistic | Subacute Inflammation, Mucosal/ Submucosal | Necrosis, Mucosal/ Gland Loss | Erosion/ Ulceration | Edema, Submucosal | Hyperplasia, Epithelial | Subacute Inflammation, Transmural/ Serosal | SUM Score |
|---|---|---|---|---|---|---|---|---|
| 1 | Mean | 4.7 | 5.0 | 5.0 | 3.6 | 5.0 | 4.4 | 27.7 |
| | SD | 0.9 | 0.0 | 0.0 | 1.3 | 0.0 | 1.3 | 2.2 |
| 2 | Mean | 3.5 | 2.9 | 2.9 | 2.3 | 2.9 | 2.8 | 16.3 |
| | SD | 1.3 | 1.6 | 1.6 | 0.8 | 1.3 | 1.6 | 5.9 |
| | p-value | 0.03 | 0.0006 | 0.0006 | 0.01 | $7 \times 10^{-5}$ | 0.02 | $2 \times 10^{-5}$ |

TABLE 5-continued

Effect of disease and treatment on average colon histology:

| Group | Statistic | Subacute Inflammation, Mucosal/ Submucosal | Necrosis, Mucosal/ Gland Loss | Erosion/ Ulceration | Edema, Submucosal | Hyperplasia, Epithelial | Subacute Inflammation, Transmural/ Serosal | SUM Score |
|---|---|---|---|---|---|---|---|---|
| 3 | Mean | 4.3 | 4.0 | 4.0 | 3.2 | 3.4 | 3.9 | 19.3 |
|   | SD | 0.8 | 1.2 | 1.2 | 1.4 | 1.8 | 1.3 | 3.4 |
|   | p-value | 0.33 | 0.01 | 0.01 | 0.51 | 0.01 | 0.39 | $4 \times 10^{-6}$ |
| 4 | Mean | 3.9 | 3.4 | 3.4 | 2.6 | 3.1 | 3.2 | 17.6 |
|   | SD | 1.4 | 2.0 | 2.0 | 0.8 | 1.8 | 1.5 | 7.2 |
|   | p-value | 0.16 | 0.02 | 0.02 | 0.05 | 0.004 | 0.07 | 0.0005 |
| 5 | Mean | 3.9 | 3.6 | 3.6 | 3.0 | 3.0 | 3.4 | 17.5 |
|   | SD | 1.7 | 1.8 | 1.8 | 1.4 | 1.9 | 2.0 | 7.4 |
|   | p-value | 0.20 | 0.02 | 0.02 | 0.33 | 0.004 | 0.19 | 0.0006 |

It is understood that the foregoing detailed description and accompanying examples are merely illustrative and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations and/or methods of use provided herein, can be made without departing from the spirit and scope thereof. U.S. patents and publications referenced herein are incorporated by reference.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

What is claimed is:

1. A compound selected from
$N^1$—((S)-1-(((S)-5-(Benzyloxy)-2-oxo-1-(2,3,5,6-tetrafluorophenoxy)pentan-3-yl)amino)-1-oxopropan-2-yl)-$N^2$-(2,6-difluorophenyl)oxalamide;
$N^1$-(2,6-Difluorophenyl)-$N^2$—((S)-1-(((S)-5-hydroxy-2-oxo-1-(2,3,5,6-tetrafluorophenoxy)pentan-3-yl)amino)-1-oxopropan-2-yl)oxalamide;
$N^1$—((S)-1-(((S)-5-((4-Chlorobenzyl)oxy)-2-oxo-1-(2,3,5,6-tetrafluorophenoxy)pentan-3-yl)amino)-1-oxopropan-2-yl)-$N^2$-(2,6-difluorophenyl)oxalamide;
$N^1$-(2,6-difluorophenyl)-$N^2$—((S)-1-oxo-1-(((S)-2-oxo-1-(2,3,5,6-tetrafluorophenoxy)-5-(thiophen-3-ylmethoxy)pentan-3-yl)amino)propan-2-yl)oxalamide;
$N^1$-(2,6-Difluorophenyl)-$N^2$—((S)-1-(((S)-5-methoxy-2-oxo-1-(2,3,5,6-tetrafluorophenoxy)pentan-3-yl)amino)-1-oxopropan-2-yl)oxalamide;
(S)-4-((S)-2-(2-((2,6-Difluorophenyl)amino)-2-oxoacetamido)propanamido)-5-oxo-6-(2,3,5,6-tetrafluorophenoxy)hexanoic acid;
(S)-3-((S)-2-(2-((2,6-Difluorophenyl)amino)-2-oxoacetamido)propanamido)-4-oxo-5-(2,3,5,6-tetrafluorophenoxy)pentyl phenyl carbonate;
(S)-3-((S)-2-(2-((2,6-Difluorophenyl)amino)-2-oxoacetamido)propanamido)-4-oxo-5-(2,3,5,6-tetrafluorophenoxy)pentyl benzoate;
(S)-4-(2-(2-(2-((2,6-difluorophenyl)amino)-2-oxoacetamido)acetamido)-5-oxo-6-(2,3,5,6-tetrafluorophenoxy)hexanoic acid;
(S)-6-(3,5-bis(trifluoromethyl)phenoxy)-4-((S)-2-(2-((2,6-difluorophenyl)amino)-2-oxoacetamido)propanamido)-5-oxohexanoic acid;
(S)-4-((S)-2-(2-((2-(tert-Butyl)phenyl)amino)-2-oxoacetamido)propanamido)-5-oxo-6-(2,3,5,6-tetrafluorophenoxy)hexanoic acid;
(S)-4-(2-(2-((2,6-Difluorophenyl)amino)-2-oxoacetamido)-2-methylpropanamido)-5-oxo-6-(2,3,5,6-tetrafluorophenoxy)hexanoic acid;
(S)-5-((S)-2-(2-((2,6-Difluorophenyl)amino)-2-oxoacetamido)propanamido)-6-oxo-7-(2,3,5,6-tetrafluorophenoxy)heptanoic acid;
(S)-4-(1-(2-((2,6-Difluorophenyl)amino)-2-oxoacetamido)cyclopentane-1-carboxamido)-5-oxo-6-(2,3,5,6-tetrafluorophenoxy)hexanoic acid;
(S)-4-((S)-2-(2-((2,6-Difluorophenyl)amino)-2-oxoacetamido)propanamido)-5-oxo-6-((2-(trifluoromethyl)pyrimidin-4-yl)oxy)hexanoic acid;
(S)-4-(2-(7-Chloro-1-oxoisoquinolin-2(1H)-yl)acetamido)-5-oxo-6-(2,3,5,6-tetrafluorophenoxy)hexanoic acid;
(S)-4-((S)-2-(2-((4-fluorophenyl)amino)-2-oxoacetamido)propanamido)-5-oxo-6-(2,3,5,6-tetrafluorophenoxy)hexanoic acid;
(S)-4-((S)-2-(2-((3-fluorophenyl)amino)-2-oxoacetamido)propanamido)-5-oxo-6-(2,3,5,6-tetrafluorophenoxy)hexanoic acid;
(S)-4-((S)-2-(2-((4-methylphenyl)amino)-2-oxoacetamido)propanamido)-5-oxo-6-(2,3,5,6-tetrafluorophenoxy)hexanoic acid;
(S)-4-((S)-2-(2-((3-methylphenyl)amino)-2-oxoacetamido)propanamido)-5-oxo-6-(2,3,5,6-tetrafluorophenoxy)hexanoic acid;
(S)-4-((S)-2-(2-((2-methylphenyl)amino)-2-oxoacetamido)propanamido)-5-oxo-6-(2,3,5,6-tetrafluorophenoxy)hexanoic acid;
(S)-4-((S)-2-(2-((2-methyoxyphenyl)amino)-2-oxoacetamido)propanamido)-5-oxo-6-(2,3,5,6-tetrafluorophenoxy)hexanoic acid;
(S)-4-((S)-2-(2-((3-methyoxyphenyl)amino)-2-oxoacetamido)propanamido)-5-oxo-6-(2,3,5,6-tetrafluorophenoxy)hexanoic acid;
(S)-4-((S)-2-(2-((4-methyoxyphenyl)amino)-2-oxoacetamido)propanamido)-5-oxo-6-(2,3,5,6-tetrafluorophenoxy)hexanoic acid;
(S)-4-((S)-2-(2-((5-methylpyridin-2-yl)amino)-2-oxoacetamido)propanamido)-5-oxo-6-(2,3,5,6-tetrafluorophenoxy)hexanoic acid;

(S)-5-oxo-4-((S)-2-(2-oxo-2-((3-(trifluoromethyl)phenyl)amino)acetamido)propanamido)-6-(2,3,5,6-tetrafluorophenoxy)hexanoic acid;

(S)-5-oxo-4-((S)-2-(2-oxo-2-((4-(trifluoromethyl)phenyl)amino)acetamido)propanamido)-6-(2,3,5,6-tetrafluorophenoxy)hexanoic acid;

benzyl (S)-4-((S)-2-(2-((2,6-difluorophenyl)amino)-2-oxoacetamido)propanamido)-5-oxo-6-(2,3,5,6-tetrafluorophenoxy)hexanoate;

(S)-4-((S)-2-(2-((5-chloropyridin-2-yl)amino)-2-oxoacetamido)propanamido)-5-oxo-6-(2,3,5,6-tetrafluorophenoxy)hexanoic acid;

(S)-4-((S)-2-(2-((4-acetylphenyl)amino)-2-oxoacetamido)propanamido)-5-oxo-6-(2,3,5,6-tetrafluorophenoxy)hexanoic acid;

(S)-4-((S)-2-(2-((3-(1H-tetrazol-5-yl)phenyl)amino)-2-oxoacetamido)propanamido)-5-oxo-6-(2,3,5,6-tetrafluorophenoxy)hexanoic acid;

(S)-4-((S)-2-(2-((2-cyanophenyl)amino)-2-oxoacetamido)propanamido)-5-oxo-6-(2,3,5,6-tetrafluorophenoxy)hexanoic acid;

(S)-6-((2,6-bis(trifluoromethyl)pyrimidin-4-yl)oxy)-4-((S)-2-(2-((2,6-difluorophenyl)amino)-2-oxoacetamido)propanamido)-5-oxohexanoic acid;

(S)-5-oxo-4-((S)-2-(2-oxo-2-((4-(trifluoromethoxy)phenyl)amino)acetamido)propanamido)-6-(2,3,5,6-tetrafluorophenoxy)hexanoic acid;

(S)-5-oxo-4-((S)-2-(2-oxo-2-(quinolin-3-ylamino)acetamido)propanamido)-6-(2,3,5,6-tetrafluorophenoxy)hexanoic acid;

(S)-4-((S)-2-(2-(naphthalen-1-ylamino)-2-oxoacetamido)propanamido)-5-oxo-6-(2,3,5,6-tetrafluorophenoxy)hexanoic acid;

(S)-5-oxo-4-((S)-2-(2-oxo-2-(quinolin-8-ylamino)acetamido)propanamido)-6-(2,3,5,6-tetrafluorophenoxy)hexanoic acid;

(S)-5-oxo-4-((S)-2-(2-oxo-2-(pyridin-4-ylamino)acetamido)propanamido)-6-(2,3,5,6-tetrafluorophenoxy)hexanoic acid;

(R)-4-((S)-2-(2-((2,6-difluorophenyl)amino)-2-oxoacetamido)propanamido)-5-oxo-6-(2,3,5,6-tetrafluorophenoxy)hexanoic acid;

(S)-5-oxo-4-((S)-2-(2-oxo-2-(pyridin-2-ylamino)acetamido)propanamido)-6-(2,3,5,6-tetrafluorophenoxy)hexanoic acid;

(S)-5-oxo-4-((S)-2-(2-oxo-2-(pyridin-3-ylamino)acetamido)propanamido)-6-(2,3,5,6-tetrafluorophenoxy)hexanoic acid;

(S)-4-((S)-2-(2-((4,6-dimethylpyrimidin-2-yl)amino)-2-oxoacetamido)propanamido)-5-oxo-6-(2,3,5,6-tetrafluorophenoxy)hexanoic acid;

(S)-5-oxo-4-((S)-2-(2-oxo-2-(pyrimidin-2-ylamino)acetamido)propanamido)-6-(2,3,5,6-tetrafluorophenoxy)hexanoic acid; and $N^1$-(2,6-difluorophenyl)-$N^2$—((S)-1-(((S)-6-(hydroxyamino)-2,6-dioxo-1-(2,3,5,6-tetrafluorophenoxy)hexan-3-yl)amino)-1-oxopropan-2-yl)oxalamide.

2. A pharmaceutical composition comprising the compound of claim 1 and a pharmaceutically acceptable carrier.

3. A method of treating a disease comprising administering a therapeutically effective amount of the compound of claim 1, wherein the disease is selected from gastrointestinal disease, respiratory disease, cardiovascular disease, dermatological disease, rheumatological diseases, kidney disease, autoimmune disease, CNS disease, inflammatory disease, liver disease, cancer and ophthalmological disease.

\* \* \* \* \*